(12) United States Patent
Stafford et al.

(10) Patent No.: US 11,708,413 B2
(45) Date of Patent: Jul. 25, 2023

(54) ANTI-CD74 ANTIBODY CONJUGATES, COMPOSITIONS COMPRISING ANTI-CD74 ANTIBODY CONJUGATES AND METHODS OF USING ANTI-CD74 ANTIBODY CONJUGATES

(71) Applicant: SUTRO BIOPHARMA, INC., South San Francisco, CA (US)

(72) Inventors: Ryan Stafford, Emeryville, CA (US); Alice Yam, Tiburon, CA (US); Avinash Gill, Emeryville, CA (US); Kalyani Penta, Palo Alto, CA (US); Xiaofan Li, Fremont, CA (US); Aaron Sato, Burlingame, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 517 days.

(21) Appl. No.: 16/072,778

(22) PCT Filed: Jan. 27, 2017

(86) PCT No.: PCT/US2017/015503
§ 371 (c)(1),
(2) Date: Jul. 25, 2018

(87) PCT Pub. No.: WO2017/132617
PCT Pub. Date: Aug. 3, 2017

(65) Prior Publication Data
US 2019/0144546 A1 May 16, 2019

Related U.S. Application Data
(60) Provisional application No. 62/287,824, filed on Jan. 27, 2016.

(51) Int. Cl.
| A61K 39/00 | (2006.01) |
| C07K 16/28 | (2006.01) |
| A61K 47/68 | (2017.01) |
| A61P 35/00 | (2006.01) |

(52) U.S. Cl.
CPC ...... *C07K 16/2833* (2013.01); *A61K 47/6803* (2017.08); *A61K 47/6811* (2017.08); *A61K 47/6831* (2017.08); *A61K 47/6867* (2017.08); *A61P 35/00* (2018.01)

(58) Field of Classification Search
CPC ............ C07K 16/2833; A61K 47/6803; A61K 47/6811; A61P 35/00
See application file for complete search history.

(56) References Cited

U.S. PATENT DOCUMENTS

| 4,542,225 A | 9/1985 | Blattler et al. |
| 4,618,492 A | 10/1986 | Blattler et al. |
| 4,625,014 A | 11/1986 | Senter et al. |
| 4,671,958 A | 6/1987 | Rodwell et al. |
| 4,816,567 A | 3/1989 | Cabilly et al. |
| 5,204,244 A | 4/1993 | Fell et al. |
| 5,229,275 A | 7/1993 | Goroff |
| 5,500,362 A | 3/1996 | Robinson et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,643,575 A | 7/1997 | Martinez et al. |
| 5,693,761 A | 12/1997 | Queen et al. |
| 5,693,762 A | 12/1997 | Queen et al. |
| 5,821,337 A | 10/1998 | Carter et al. |
| 5,869,644 A | 2/1999 | Shortle et al. |
| 5,932,462 A | 8/1999 | Harris et al. |
| 6,180,370 B1 | 1/2001 | Queen et al. |
| 6,339,142 B1 | 1/2002 | Basey et al. |
| 7,026,440 B2 | 4/2006 | Bentley et al. |
| 7,045,337 B2 | 5/2006 | Schultz et al. |
| 7,083,970 B2 | 8/2006 | Schultz et al. |
| 7,338,789 B2 | 3/2008 | Swartz et al. |
| 7,632,924 B2 | 12/2009 | Cho et al. |
| 7,659,241 B2 | 2/2010 | Senter et al. |
| 7,736,653 B2 | 6/2010 | Kim et al. |
| 7,887,809 B1 | 2/2011 | Garen et al. |
| 8,008,443 B2 | 8/2011 | Dall'Acqua et al. |
| 8,008,453 B2 | 8/2011 | Gegg et al. |

(Continued)

FOREIGN PATENT DOCUMENTS

| CN | 102627615 A | 8/2012 |
| CN | 106146663 A | 11/2016 |

(Continued)

OTHER PUBLICATIONS

Almagro & Fransson, Frontiers in Bioscience 2008; 13:1619-33 (Year: 2008).*
Martin et al, Leukemia & Lymphoma, vol. 56 p. 3065 (2015) (Year: 2015).*
Geneve et al Monoclonal Antibodies in Immunodiagnosis and Immunotherapy vol. 33 p. 221 (2014) (Year: 2014).*
Brown et al (J. Immunol. May 1996; 156(9):3285-3291 (Year: 1996).*
Johnson et al, Cancer Treatment Reviews vol. 2 p. 1 (1975). (Year: 1975).*
Balmana et al. Ann Oncol 2009; 20(supp 4):iv19-2 (Year: 2009).*
Kataja et al., Ann Oncol 2009; 20(sup 4): iv10-14 (Year: 2009).*

(Continued)

*Primary Examiner* — Sheela J. Huff
(74) *Attorney, Agent, or Firm* — Squire Patton Boggs (US) LLP

(57) ABSTRACT

Provided herein are antibody conjugates with binding specificity for CD74 and compositions comprising the antibody conjugates, including pharmaceutical compositions, methods of producing the conjugates, and methods of using the conjugates and compositions for therapy.

29 Claims, 12 Drawing Sheets

Specification includes a Sequence Listing.

(56) References Cited

U.S. PATENT DOCUMENTS

| | | | |
|---|---|---|---|
| 8,124,094 B2 | 2/2012 | Kim et al. | |
| 8,216,804 B2 | 7/2012 | Schultz et al. | |
| 8,258,082 B2 | 9/2012 | Ladner | |
| 8,618,257 B2 | 12/2013 | Sheffer et al. | |
| 8,691,730 B2 | 4/2014 | Vasquez et al. | |
| 8,715,958 B2 | 5/2014 | Goerke et al. | |
| 8,937,161 B2 | 1/2015 | Mao et al. | |
| 9,670,521 B2 | 6/2017 | Grabstein et al. | |
| 9,738,724 B2* | 8/2017 | Thanos | C07K 16/00 |
| 9,764,039 B2* | 9/2017 | Thanos | C12N 15/09 |
| 10,669,347 B2 | 6/2020 | Thanos et al. | |
| 10,975,150 B2* | 4/2021 | Penta | C07K 16/2833 |
| 2003/0082575 A1 | 5/2003 | Schultz et al. | |
| 2003/0108885 A1 | 7/2003 | Schultz et al. | |
| 2003/0143596 A1 | 7/2003 | Bentley et al. | |
| 2004/0219203 A1 | 11/2004 | Griffiths et al. | |
| 2005/0260711 A1 | 11/2005 | Datta et al. | |
| 2006/0074225 A1 | 4/2006 | Chamberlain et al. | |
| 2007/0148170 A1 | 6/2007 | Desjarlais et al. | |
| 2008/0050374 A1 | 2/2008 | Cho et al. | |
| 2008/0085277 A1 | 4/2008 | Cho et al. | |
| 2008/0233611 A1 | 9/2008 | Schultz et al. | |
| 2008/0317670 A1 | 12/2008 | Miao et al. | |
| 2009/0035836 A1 | 2/2009 | Datta et al. | |
| 2009/0093405 A1 | 4/2009 | Wallen, III et al. | |
| 2009/0110662 A1 | 4/2009 | Breitenkamp et al. | |
| 2009/0117100 A1 | 5/2009 | Mao et al. | |
| 2009/0258420 A1 | 10/2009 | van Vlijmen et al. | |
| 2010/0093082 A1 | 4/2010 | Tian et al. | |
| 2010/0098630 A1 | 4/2010 | Miao | |
| 2011/0033378 A1 | 2/2011 | Dimasi et al. | |
| 2012/0077948 A1 | 3/2012 | Nguyen et al. | |
| 2012/0100140 A1 | 4/2012 | Reyes et al. | |
| 2014/0046030 A1 | 2/2014 | Thanos et al. | |
| 2014/0051836 A1 | 2/2014 | Thanos et al. | |
| 2014/0066598 A1 | 3/2014 | Stafford et al. | |
| 2014/0093495 A1* | 4/2014 | Hampl | C07K 16/30 424/133.1 |
| 2014/0127209 A1 | 5/2014 | Grabstein et al. | |
| 2015/0017187 A1 | 1/2015 | Thanos et al. | |
| 2016/0257709 A1 | 9/2016 | Kline et al. | |
| 2017/0173151 A1 | 6/2017 | Verploegen et al. | |
| 2017/0253656 A1 | 9/2017 | Penta et al. | |
| 2019/0144546 A1 | 5/2019 | Stafford et al. | |
| 2020/0207859 A1 | 7/2020 | Molina | |
| 2020/0283543 A1 | 9/2020 | Thanos et al. | |

FOREIGN PATENT DOCUMENTS

| | | | |
|---|---|---|---|
| EP | | 953639 * | 4/1998 |
| RU | | 2349343 C2 | 3/2009 |
| WO | WO 2002/085923 A3 | | 10/2002 |
| WO | WO 2003/074679 A2 | | 9/2003 |
| WO | WO 2004/016778 A1 | | 2/2004 |
| WO | WO 2005/047337 A1 | | 5/2005 |
| WO | WO 2005/100402 | | 10/2005 |
| WO | WO 2005/100402 A1 | | 10/2005 |
| WO | WO 2006/029879 | | 3/2006 |
| WO | WO 2006/029879 A2 | | 3/2006 |
| WO | WO 2006/069246 A2 | | 6/2006 |
| WO | WO 2006/116260 A2 | | 11/2006 |
| WO | WO 2007/041635 A2 | | 4/2007 |
| WO | WO 2007/130453 | | 11/2007 |
| WO | WO 2008/030558 A2 | | 3/2008 |
| WO | WO 2008/030612 A2 | | 3/2008 |
| WO | WO 2008/066583 A2 | | 6/2008 |
| WO | WO 2008/134761 A2 | | 11/2008 |
| WO | WO 2009/052249 A1 | | 4/2009 |
| WO | WO 2010/006214 A1 | | 1/2010 |
| WO | WO 2010/051056 A2 | | 5/2010 |
| WO | WO 2010/139948 A2 | | 12/2010 |
| WO | WO 2012/032181 A2 | | 3/2012 |
| WO | WO 2012/104344 A1 | | 8/2012 |
| WO | WO 2013/068874 A1 | | 5/2013 |
| WO | WO 2013/093809 A1 | | 6/2013 |
| WO | WO 2013/185115 A1 | | 12/2013 |
| WO | WO 2014/004639 A1 | | 1/2014 |
| WO | WO 2014/036492 A1 | | 3/2014 |
| WO | WO 2014/065860 A1 | | 5/2014 |
| WO | WO 2014/128221 A1 | | 8/2014 |
| WO | WO 2016/014434 * | | 1/2016 |
| WO | WO 2016/081748 * | | 5/2016 |
| WO | WO 2016/123582 A1 | | 8/2016 |
| WO | WO 2017/197241 A1 | | 11/2017 |
| WO | WO 2018/187074 A1 | | 10/2018 |

OTHER PUBLICATIONS

Nelson et al., Ann. Intern Med. 2009; 151:727-737 (Year: 2009).*
Casset et al., "A peptide mimetic of an anti-CD4 monoclonal antibody by rational design", Biochemical and Biophysical Research Communications, 2003, vol. 307, pp. 198-205.
Colman, P.M., "Effects of amino acid sequence changes on antibody-antigen interactions", Research in Immunology, 1994, vol. 145, pp. 33-36.
MacCallum et al., "Antibody-antigen Interactions: Contact Analysis and Binding Site Topography", J. Mol. Biol., 1996, vol. 262, pp. 732-745.
Pascalis et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology, 2002, vol. 169, pp. 3076-3084.
Paul, E. W., Fundamental Immunology, $3^{rd}$ Edition, 1993, pp. 292-295.
Rudikoff et al., "Single amino acid substitution altering antigen-binding specificity", Proc. Natl. Acad. Sci. USA, Mar. 1982, vol. 79, pp. 1979-1983.
H. Sakahara et al., Effect of DPTA Conjugation on the Antigen Binding Activity and Biodistribution of Monoclonal Antibodies Against α-Fetoprotein, J Nucl Med, Jul. 1985, vol. 26, pp. 750-755.
Lockard J.S. et al., "Efficacy and toxicity of the solvent polyethylene glycol 400 in monkey model", Epilepsia, 1979, vol. 20, No. 1, pp. 77-84 (see Abstract).
Vajdos F.F. et al., "Comprehensive Functional Maps of the Antigenbinding Site of an Anti-ErbB2 Antibody Obtained with Shotgun Scanning Mutagenesis", J.Mol. Biol., 2002, vol. 320, pp. 415-428 (see p. 416).
Axup et al., "Synthesis of site-specific antibody-drug conjugates using unnatural amino acids" (2012) Proc. Nat. Acad. Sci. USA 109(40):16101-16106.
Balog et al., "Synthesis of new 2,2,5,5-Tetramethyl-2,5-dihydro-1H-pyrrol-1-yloxyl Radicals and 2-Substituted-2,5,5-trimethylpyrrolidin-1-yloxyl Radicals Based α-Amino Acids" (2004) SYNLETT 14:2591-2593.
Bazewicz et al., "Expanding the Utility of 4-Cyano-L-Phenylalanine As a Vibrational Reporter of Protein Environments" (2012) J. Phys. Chem. B 116:10824-10831.
Caldas et al., "Humanization of the anti-CD18 antibody 6.7: An unexpected effect of a framework residue in binding to antigen," Molecular Immunology, (2003), vol. 39, pp. 941-952.
Carter, "Introduction to current and future protein therapeutics: A protein engineering perspective" Experimental Cell Research (2011) 317(9):1261-1269.
Chen et al., "N-Benzylpyroglutamyl-L-phenylalanine Derivatives as VCAM/VLA-4 Antagonists" (2000) Bioorg. & Med. Chem. Let. 10:729-733.
Chien et al., "Significant structural and functional change of an antigen-binding site by a distant amino acid substitution: Proposal of a structural mechanism," Proc. Natl. Acad. Sci. USA, (Jul. 1989), vol. 86, pp. 5532-5536.
Chin et al., "Addition of p-azido-L-phenylalanine to the genetic code of Escherichia coli" (2002), J. Am. Chem. Soc. 124:9026-9027.
Chin et al., "An Expanded Eukaryotic Genetic Code", (2003) Science 301:964-967.

(56) References Cited

OTHER PUBLICATIONS

Database WPI Week Oct. 2013 Thomson Scientific, London, GB; AN 2012-P98574 CN 102 627 615 A (Univ Lanzhou) Aug. 8, 2012.
Delgado et al., "The uses and properties of PEG-linked proteins" (1992) Critical Reviews in Therapeutic Drug Carrier Systems 9:249-304.
Gerber et al., The antibody-drug conjugate: an enabling modality for natural product-based cancer therapeutics (2013) Nat. Prod. Rep. 30:625-639.
Giusti et al., "Somatic diversification of S107 from an antiphosphocholine to an anti-DNA autoantibody is due to a single base change in its heavy chain variable region," Proc. Natl. Acad. Sci. USA, (May 1987), vol. 84, pp. 2926-2930.
Golay et al., "Mechanism of action of therapeutic monoclonal antibodies: Promises and pitfalls of in vitro and in vivo assays," Archives of Biochemistry and Biophysics, (2012), vol. 526, pp. 146-153.
Harris, "Laboratory synthesis of polyethylene glycol derivatives" (1985) Macronol. Chem. Phys. C25:325-373.
Hutchins et al., "Site-Specific Coupling and Sterically Controlled Formation of Multimeric Antibody Fab Fragments with Unnatural Amino Acids", Journal of Molecular Biology, 2011, pp. 595-603.
Jeong et al., Site-Specific $^{99m}$Tc-Labeling of Antibody Using Dihydrazinophthalazine (DHZ) Conjugation to Fc Region of Heavy Chain (2004) Arch Pharm Res 27:961-967.
Johansson et al., Azide- and Alkyne-Derivatised α-Amino Acids (2012) Eur. J. Org. Chem. 23:4267-4281.
Jubala et al., "CD20 Expression in Normal Canine B Cells and in Canine non-Hodgkin Lymphoma," Vet Pathol, (2005), vol. 42, pp. 468-476.
Kaneko et al., Optimizing Therapeutic Antibody Function (2011) Biodrugs 25:1-11.
Kazane et al., Self-Assembled Antibody Multimers through Peptide Nucleic Acid Conjugation (2013), J. Am. Chem. Soc. 135:340-346.
Kazane et al., Site-specific DNA-antibody conjugates for specific and sensitive immuno-PCR (2012) PNAS 109:3731-3736.
Kiick et al., "Incorporation of azides into recombinant proteins for chemoselective modification by the Staudinger ligation" (2002) Proc. Nat. Acad. Sci. USA 99:19-24.
Liu et al., "Protein evolution with an expanded genetic code" (2008) PNAS 105:17688-17693.
Lund et al, "Multiple interactions of IgG with its core oligosaccharide can modulate recognition by complement and human Fc gamma receptor I and influence the synthesis of its oligosaccharide chains", The Journal of Immunology, 1996, vol. 157, pp. 4963-4969.
Nguyen et al., "Genetic Encoding and Labeling of Aliphatic Azides and Alkynes in Recombinant Proteins via a Pyrrolysyl-tRNA Synthetase/ tRNA$_{CUA}$ Pair and Click Chemistry" (2009) J. Am. Chem. Soc. 131:8720-8721.
Patel et al., "Cell-free production of Gaussia princeps luciferase— antibody fragment bioconjugates for ex vivo detection of tumor cells", (2009) Biochemical and Biophysical Research Communications, 390:971-976.
Reichert, "Antibody-based therapeutics to watch in 2011" (2011) mABS 3(1):76-99.
Santi et al., "Predictable and tunable half-life extension of therapeutic agents by controlled chemical release from macromolecular conjugates" (2012) PNAS 109(16):6211-6216.
Saxon et al., "Cell surface engineering by a modified Staudinger reaction", (2000) Science 287:2007-2010.
Schmidt et al., "A Need for Speed: Genetic Encoding of Rapid Cycloaddition Chemistries for Protein Labelling in Living Cells", (2012) ChemBioChem 13:1553-1557.
Schroeder et al., "Structure and function of immunoglobulins", J Allergy Clin Immunol, Feb. 2010, pp. S41-S52.
Scouten, "A survey of enzyme coupling techniquesMethods in Enzymology" (1987) Methods in Enzymology 135:30-65.

Seitchik et al., "Genetically Encoded Tetrazine Amino Acid Directs Rapid Site-Specific in Vivo Bioorthogonal Ligation with trans-Cyclooctenes", (2012) J. Am. Chem. Soc. 134:2898-2901.
Strohl W., "Optimization of Fc-mediated effector functions of monoclonal antibodies", (2009) Current Opinion in Biotechnology 20:685-691.
Strop et al., "Location Matters: Cite of Conjugation Modulates Stability and Pharmacokinetics of Antibody Drug Conjugates" (2013) Chem. & Biol. 20:161-167.
Vidarsson et al., "IgG subclasses and allotypes: from structure to effector functions", Frontiers in Immunology; Oct. 2014; vol. 5, article 520, 17 pages.
Wang et al., "Bioconjugation by copper(I)-catalyzed azide-alkyne [3+2] cycloaddition", (2003) J. Am. Chem. Soc. 125:3192-3193.
Wang et al., "Expanding the Genetic Code for Biological Studies", Chemistry & Biology 16, Mar. 27, 2009, pp. 323-336.
Winkler et al., "Changing the Antigen Binding Specificity by Single Point Mutations of an Anti-p24 (HIV-1) Antibody," The Journal of Immunology, (2000), vol. 165, pp. 4505-4514.
Wong et al., "Chemical crosslinking and the stabilization of proteins and enzymes" (1992) Enzyme Microb. Technol. 14:866-874.
Wu et al., "Humanization of a Murine Monoclonal Antibody by Simultaneous Optimization of Framework and CDR Residues", J. MoL Biol. (1999) 294, pp. 151-162.
Young et al., "An Evolved Aminoacyl-tRNA Synthetase with Atypical Polysubstrate Specificity" (2011) Biochem. 50:1894-1900.
Zalevsky et al., "Enhanced antibody half-life improves in vivo activity", (2010) Nature Biotechnology 28:157-159.
Zalipsky, "Functionalized poly(ethylene glycol) for preparation of biologically relevant conjugates", (1995) Bioconjug. Chem. 6:150-165.
Invitation To Pay Additional Fees And, Where Applicable, Protest Fee dated Oct. 28, 2015 for Application No. PCT/US2015/041192, 8 pages.
International Search Report and Written Opinion dated Jan. 21, 2016 for Application No. PCT/US2015/041192, 17 pages.
International Search Report and Written Opinion of the International Searching Authority of PCT/US2018/043633 dated Oct. 9, 2018, 14 pages.
Berkova et al., "Milatuzumab—apromising new immunotherapeutic agent", Expert Opinion on Investigational Drugs, Informa Healthcare, United Kingdom, Jan. 1, 2010, vol. 19, No. 1, pp. 141-149.
Borghese et al., "CD74: An emerging opportunity as a therapeutic target in cancer and autoimmune disease", Expert Opin. Ther. Targets, 2011, vol. 15, No. 3, pp. 237-251.
Brüggemann et al., "Comparison Of The Effector Functions of Human Immunoglobulins Using a Matched Set Of Chimeric Antibodies", J. Exp. Med., Nov. 1987, vol. 166, pp. 1351-1361.
Brüggemann et al., "Designer Mice: The Production of Human Antibody Repertoires in Transgenic Animals", Year Immunol. Basel, Karger, 1993, vol. 7, pp. 33-40.
Burton eta al., "CD74 is expressed by multiple myeloma and is a promising target for therapy", Clinical Cancer Research, The American Association For Cancer Research, US, Oct. 1, 2004, vol. 10, No. 19, pp. 6606-6611.
Carter et al. "High Level Escherichia Col/ Expression And Production Of A Bivalent Humanized Antibody Fragment", Biotechnology, Feb. 1992, vol. 10, pp. 163-167.
Christian et al., "The combination of milatuzumab, a humanized anti-CD74 antibody, and veltuzumab, a humanized anti-CD20 antibody, demonstrates activity in patients with relapsed and refractory B-cell non-Hodgkin lymphoma", British Journal of Haematology, vol. 169, No. 5, Jun. 1, 2015, pp. 701-710, XP55468495.
Claesson et al., "cDNA clone for the human invariant γ chain of class II histocompatibility antigens and its implications for the protein structure", Proc. Natl. Acad. Sci. U.S.A., Dec. 1983, vol. 80, pp. 7395-7399.
Clynes et al. "Fc receptors are required in passive and active immunity to melanoma", Proc. Natl. Acad. Sci. U.S.A., Jan. 1998, vol. 95, pp. 652-656.
Cragg et al., "Antibody specificity controls in vivo effector mechanisms of anti-CD20 reagents", Blood, 2004, vol. 103, pp. 2738-2743.

(56) References Cited

OTHER PUBLICATIONS

Cragg et al., "Complement-mediated lysis by anti-CD20 mAb correlates with segregation into lipid rafts", Blood, 2003, vol. 101, pp. 1045-1052.
Cresswell, "Assembly, Transport, and Function of MHC Class II Molecules", Ann. Rev. Immunol., 1994, vol. 12, pp. 259-293.
Dreir et al., "Ribosome Display: A Technology for Selecting and Evolving Proteins from Large Libraries", Methods in Molecular Biology, 2011, vol. 687, pp. 283-306.
Gazzano-Santoro et al., "A non-radioactive complement-dependent cytotoxicity assay for anti-CD20 monoclonal antibody", Journal of Immunological Methods, 1996, vol. 202, pp. 163-171.
Gore et al., "Macrophage Migration Inhibitory Factor Induces B Cell Survival by Activation of a CD74-CD44 Receptor Complex", Journal Of Biological Chemistry, Feb. 1, 2008, vol. 283, No. 5, pp. 2784-2792.
Govindan et al., "Milatuzumab-SN-38 Conjugates for the Treatment of CD74+Cancers", Molecular Cancer Therapeutics, vol. 12, No. 6, Jun. 1, 2013, pp. 968-978, XP55280453.
Gupta et al., "Dual-targeting immunotherapy of lymphoma: potent cytotoxicity of anti-CD20/CD74 bispecific antibodies in mantle cell and other lymphomas", Blood, American Society of Hematology, US, vol. 119, No. 16, May 19, 2012, pp. 3767-3778, XP002675543.
Hanes et al., "In vitro selection and evolution of functional proteins by using ribosome display", Proc. Natl. Acad. Sci. U.S.A., May 1997, vol. 94, pp. 4937-4942.
Heckman et al., "Gene splicing and mutagenesis by PCR-driven overlap extension", Nature Protocols, 2007, vol. 2, No. 4, pp. 924-932.
Hellström et al., "Antitumor effects of L6, an IgG2a antibody that reacts with most human carcinomas", Proc. Natl. Acad. Sci. U.S.A., Sep. 1986, vol. 83, pp. 7059-7063.
Hellström et al., "Strong antitumor activities of IgG3 antibodies to a human melanoma-associated ganglioside", Proc. Natl. Acad. Sci. U.S.A., Mar. 1985, vol. 82, pp. 1499-1502.
Hofman et al., "Gene expression profiling in human gastric mucosa infected with Helicobacter pylori", Modern Pathology, 2007, vol. 20, pp. 974-989.
Hoogenboom et al., By-passing Immunisation Human Antibodies from Synthetic Repertoires of Germline $V_H$ Gene Segments Rearranged in Vitro, J. Mol. Biol., 1991, vol. 227, pp. 381-388.
Jakobovits et al., "Analysis of homozygous mutant chimeric mice: Deletion of the immunoglobulin heavy-chain joining region blocks B-cell development and antibody production", Proc. Natl. Acad. Sci. U.S.A., Mar. 1993, vol. 90, pp. 2551-2555.
Jakobovits et al., "Germ-line transmission and expression of a human-derived yeast artificial chromosome", Nature, Mar. 18, 1993, vol. 362, pp. 255-258.
Köhler et al., "Continuous cultures of fused cells secreting antibody of predefined specificity", Nature, Aug. 7, 1975, vol. 256, pp. 495-497.
Kozbor et al., "A Human Hybrid Myeloma For Production Of Human Monoclonal Antibodies", Journal of Immunology, Dec. 1984, vol. 133, No. 6, pp. 3001-3005.
Kudo et al., "Structure of the human gene encoding the Invariant 7-chain of class II histocompatibility Antigens", Nucleic Acids Research, 1985, vol. 13, No. 24, pp. 8827-8841.
Marks et al., "By-passing Immunization Human Antibodies from V-gene Libraries Displayed on Phage", J. Mol. Biol., 1991, vol. 222, pp. 581-597.
Martin et al., "Phase I study of the anti-CD74 monoclonal antibody milatuzumab (hLL1) in patients with previously treated B-cell lymphomas", Leukemia and Lymphoma, vol. 56, No. 11, May 12, 2015, pp. 3065-3070, XP55510788.
Pawlak-Byczkowska et al., "Two New Monoclonal Antibodies, Epb-1 And Epb-2, Reactive with Human Lymphoma", Cancer Research, American Association For Cancer Research, US, Aug. 15, 1989, vol. 49, No. 16, pp. 4568-4577.
Petkova et al., "Enhanced half-life of genetically engineered human IgG1 antibodies in a humanized FcRn mouse model: Potential application in humorally mediated autoimmune disease", International Immunology, 2006, vol. 18, No. 12, pp. 1759-1769.
Queen et al., "A humanized antibody that binds to the interleukin 2 receptor", Proc. Natl. Acad. Sci. U.S.A., Dec. 1989, vol. 86, pp. 10029-10033.
Rader et al., "A phage display approach for rapid antibody humanization: Designed combinatorial V gene libraries", Proc. Nat. Acad. Sci. U.S.A., Jul. 1998, vol. 95, pp. 8910-8915.
Ravetch et al., "Fc receptors", Annual Review of Immunology, 1991, vol. 9, pp. 457-492.
Stafford et al., "In vitro Fab display: A cell-free system for IgG discovery", Protein Engineering, Design & Selection, 2014, vol. 27, No. 4, pp. 97-109.
Starlets et al., "Cell-surface CD74 initiates a signaling cascade leading to cell proliferation and survival", Blood, 2006, vol. 107, pp. 4807-4816.
Stein et al., "Antiproliferative activity of a humanized anti-CD74 monoclonal antibody, hLL1, on B-cell Malignancies", Blood, Dec. 1, 2004, vol. 104, No. 12, pp. 3705-3711.
Steinberger et al., "Generation and Characterization of a Recombinant Human CCR5-specific Antibody", J. Biol. Chem., Nov. 17, 2000, vol. 275, No. 46, pp. 36073-36078.
Vera et al., "Upregulation of Macrophage Migration Inhibitory Factor (MIF) and CD74, Receptor for MIF, in Rat Bladder During Persistent Cyclophosphamide-Induced Inflammation", Experimental Biology and Medicine, 2008, vol. 233, pp. 620-626.
Wang et al. "Functional Characterization of an scFv-Fc Antibody that Immunotherapeutically Targets the Common Cancer Cell Surface Proteoglycan CSPG4", Cancer Res., Dec. 15, 2011, vol. 71, No. 24, pp. 7410-7422.
Winter et al., "Man-made antibodies", Nature, 1991, vol. 349, pp. 293-299.
Yin et al., "Aglycosylated antibodies and antibody fragments produced in a scalable in vitro transcription-translation system", mAbs, Mar./Apr. 2012, vol. 4, No. 2, pp. 217-225.
Zawada et al., "Microscale to Manufacturing Scale-up of Cell-Free Cytokine Production—A New Approach for Shortening Protein Production Development Timelines", Biotechnology and Bioengineering, Jul. 2011, vol. 108, No. 7, pp. 1570-1578.
Zhang et al., "Effect of CD74 on the prognosis of patients with resectable pancreatic cancer", Hepatobiliary Pancreat. Dis. Int., Feb. 15, 2014, vol. 13, No. 1, pp. 81-86.
International Search Report and Written Opinion of PCT/US2017/015503 dated May 2, 2017, 15 pages.
Armitage et al., "New Approach to Classifying Non-Hodgkin's Lymphomas: Clinical Features of the Major Histological Subtypes", Journal of Clinical Oncology (1998), 16, pp. 2780-2795 (Aug. 1998).
Chatterjee et al., "A Versatile Platform for Single- and Multiple-Unnatural Amino Acid Mutagenesis in *Escherichia coli*", Biochemistry, vol. 52, No. 10, Mar. 12, 2013, pp. 1828-1837.
Ducry et al., "Antibody-Drug Conjugates: Linking Cytotoxic Payloads to Monoclonal Antibodies", Bioconjugate Chem, 2010, 21, pp. 5-13.
Edwards et al., "The Remarkable Flexibility of the Human Antibody Repertoire; Isolation of Over One Thousand Different Antibodies to a Single Protein, BLyS" J Mol Biol., 334(1), 2003, pp. 103-118.
Griffiths et al., "Cure of SCID Mice Bearing Human B-Lymphoma Xenografts by an Anti-CD74 Antibody-Anthracycline Drug Conjugate", Clinical Cancer Research, 9, pp. 6567-6571 (Dec. 15, 2003).
Grimm et al., "Ribosome Display Selection of a Murine $IgG_1$ Fab Binding Affibody Molecule Allowing Species Selective Recovery of Monoclonal Antibodies", Mol Biotechnol, 2011, 48:263-276; DOI 10.1007/s12033-010-9367-1.
Junutula et al., "Rapid identification of reactive cysteine residues for site-specific labeling of antibody-Fabs", Journal of Immunological Methods, Elsevier Science Publishers B.V., Amsterdam, NL, vol. 332, No. 1-2, Jan. 14, 2008, pp. 41-52, XP022527824.
Junutula et al., "Site-specific conjugation of a cytotoxic drug to an antibody improves the therapeutic index", Nature Biotechnology, Nature Publishing Group, United States, vol. 26, No. 8, Aug. 1, 2008, pp. 925-932, XP002727747.

(56) References Cited

OTHER PUBLICATIONS

Karver et al., "Bioorthogonal Reaction Pairs Enable Simultaneous, Selective, Multi-Target Imaging", Angew Chen Int Ed Engl., 51(4), pp. 920-922 (Jan. 2012).

Lang et al., "Cellular Incorporation of Unnatural Amino Acids and Bioorthogonal Labeling of Proteins", Chemical Reviews, vol. 114, No. 9, May 14, 2014, pp. 4764-4806.

Li, Liang et al., "Progress in Antibody Drug Conjugates Studies", Chin Med Biotechnol, vol. 9, No. 4, Aug. 2014; DOI:10.3969/cmba.j.issn.1673-713X.2014.04.011; along with the English translation.

Lloyd et al., "Modelling the human immune response: performance of a 10" human antibody repertoire against a broad panel of therapeutically relevant antigens", Protein Engineering, Design & Selection, 2009, vol. 22, pp. 159-168.

Lu et al., "On the evolution of the standard amino-acid alphabet", Genome Biology 2006, vol. 7, No. 1, 2006, p. 102.

Ong et al., "Cell surface expression and metabolism of major histocompatibility complex class II invariant chain (CD74) by diverse cell lines", Immunology (1999), 98, pp. 296-302, (Jun. 4, 1999).

Stancovski et al., PNAS 88: 8691-8695, 1991.

Tsuchikama et al., "Antibody-drug conjugates: recent advances in conjugation and linker chemistries", Protein & Cell, 9(1), 2018, pp. 33-46.

Wu et al., "An Analysis of the Sequences of the Variable Regions of Bence Jones Proteins and Myeloma Light Chains and their Implications for Antibody Complementarity" J. Exp. Med. 132(2): 211-250; Aug. 1, 1970.

Zhao et al., "High frequency of CD74 expression in lymphomas: implications for targeted therapy using a novel anti-CD74-drug conjugate", J Pathol Clin Res; Jan. 2019; 5: pp. 12-24; DOI: 10.1002/cjp2.114.

Zimmerman et al., "Production of Site-Specific Antibody-Drug Conjugates Using Optimized Non-Natural Amino Acids in a Cell-Free Expression System", Bioconjugate Chemistry, vol. 25, pp. 351-361 (2014).

\* cited by examiner

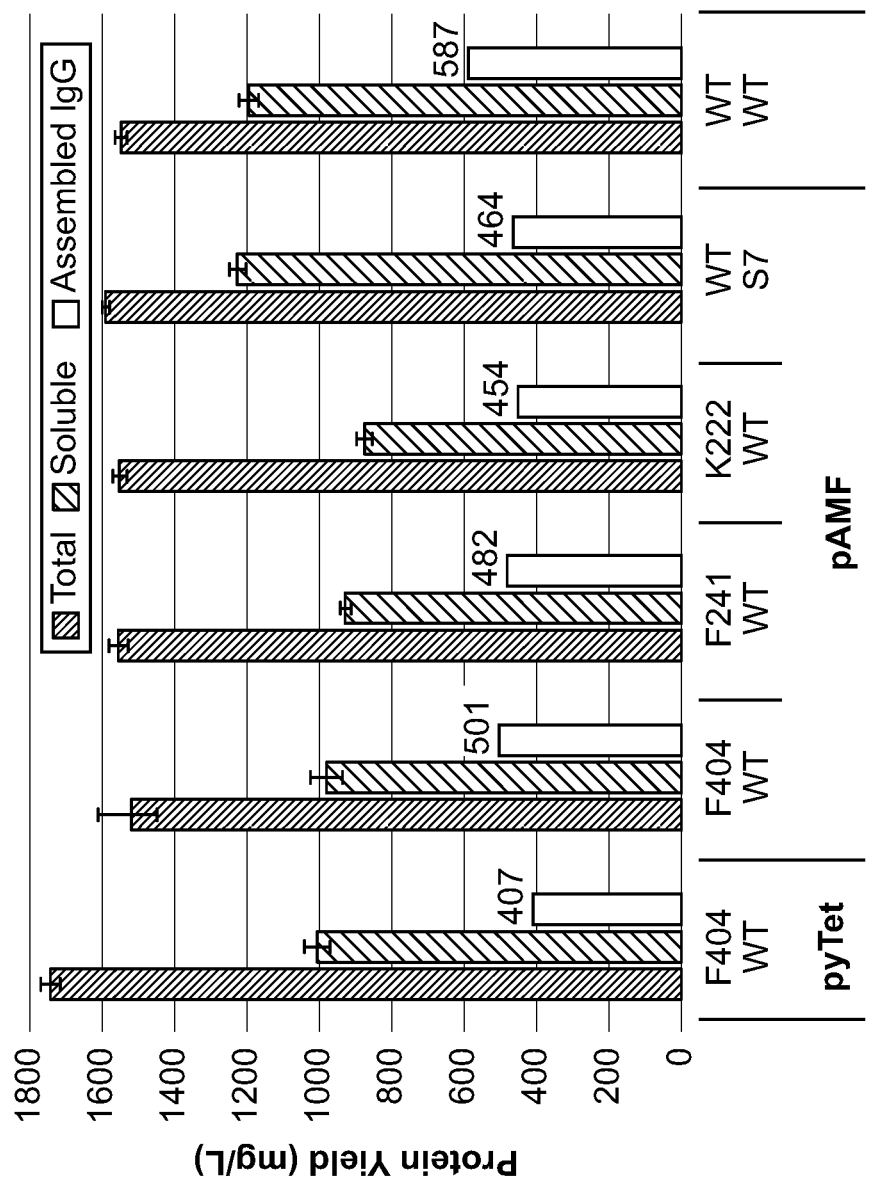

SEQUENCE LISTING

```
<160> NUMBER OF SEQ ID NOS: 320

<210> SEQ ID NO 1
<211> LENGTH: 7
<212> TYPE: PRT
<213> ORGANISM: Artificial Sequence
<220> FEATURE:
<223> OTHER INFORMATION: Synthetic: 1251-B08, CDR-H1, Chothia

<400> SEQUENCE: 1

Gly Phe Asn Phe Ser Asp Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic: 1193-C08, CDR-H1, Chothia

<400> SEQUENCE: 2

Gly Phe Thr Phe Asn Asn Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic: 1193-E06b, CDR-H1, Chothia

<400> SEQUENCE: 3

Gly Phe Thr Phe Asn Asn Thr
1               5

<210> SEQ ID NO 4
```

```
<211> LENGTH: 7
<212> TYPE: PRT
<213> ORGANISM: Artificial Sequence
<220> FEATURE:
<223> OTHER INFORMATION: Synthetic: 1193-H04b, CDR-H1, Chothia

<400> SEQUENCE: 4

Gly Phe Thr Phe Thr Ser Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: 1198-A01, CDR-H1, Chothia

<400> SEQUENCE: 5

Gly Phe Thr Phe Ser Asp Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic: 1198-B10, CDR-H1, Chothia

<400> SEQUENCE: 6

Gly Phe Asn Ile Ser Gly Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic: 1198-D03, CDR-H1, Chothia

<400> SEQUENCE: 7

Gly Phe Asn Ile Asn Asn Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 1198-D04, CDR-H1, Chothia

<400> SEQUENCE: 8

Gly Phe Asn Ile Asn Asn Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic: 1251-A02, CDR-H1, Chothia

<400> SEQUENCE: 9

Gly Phe Ala Phe Ser Asp His
1               5

<210> SEQ ID NO 10
<211> LENGTH: 7
```

```
<212> TYPE: PRT
<213> ORGANISM: Artificial Sequence
<220> FEATURE:
<223> OTHER INFORMATION: Synthetic: 1251-A03, CDR-H1, Chothia

<400> SEQUENCE: 10

Gly Phe Ala Phe Ser Asp His
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: 1251-A06, CDR-H1, Chothia

<400> SEQUENCE: 11

Gly Phe Asp Phe Ser Ser Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: 1193-B06, CDR-H1, Chothia

<400> SEQUENCE: 12

Gly Phe Thr Phe Thr Gly Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: 1251-B09, CDR-H1, Chothia

<400> SEQUENCE: 13

Gly Phe Asn Phe Ser Asp Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 1251-B10, CDR-H1, Chothia

<400> SEQUENCE: 14

Gly Phe Asn Phe Ser Ser His
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: 1251-C03, CDR-H1, Chothia

<400> SEQUENCE: 15

Gly Phe Asn Phe Ser Ser Tyr
1               5

<210> SEQ ID NO 16
<211> LENGTH: 7
<212> TYPE: PRT
```

```
<213> ORGANISM: Artificial Sequence
<220> FEATURE:
<223> OTHER INFORMATION: Synthetic: 1251-D02, CDR-H1, Chothia

<400> SEQUENCE: 16

Gly Phe Ser Phe Ala Ser His
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: 1251-D06, CDR-H1, Chothia

<400> SEQUENCE: 17

Gly Phe Ser Phe Gly Ser Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic: 1251-D09, CDR-H1, Chothia

<400> SEQUENCE: 18

Gly Phe Ser Phe Ser Ser Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: 1251-E06, CDR-H1, Chothia

<400> SEQUENCE: 19

Gly Phe Thr Phe Asp Ser Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: 1251-F06, CDR-H1, Chothia

<400> SEQUENCE: 20

Gly Phe Thr Phe Ser Ser Phe
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: 1251-F07, CDR-H1, Chothia

<400> SEQUENCE: 21

Gly Phe Thr Phe Ser Ser His
1               5

<210> SEQ ID NO 22
<211> LENGTH: 7
<212> TYPE: PRT
<213> ORGANISM: Artificial Sequence
```

```
<220> FEATURE:
<223> OTHER INFORMATION: Synthetic: 1251-G02, CDR-H1, Chothia

<400> SEQUENCE: 22

Gly Phe Thr Phe Ser Ser Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: 1445-A03, CDR-H1, Chothia

<400> SEQUENCE: 23

Gly Phe Asn Ile Ser Gly Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: 1445-B09, CDR-H1, Chothia

<400> SEQUENCE: 24

Gly Phe Asn Ile Thr Gly Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: 1447-D11, CDR-H1, Chothia

<400> SEQUENCE: 25

Gly Phe Thr Phe Asn Asn Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic: 1447-E08, CDR-H1, Chothia

<400> SEQUENCE: 26

Gly Phe Thr Phe Asn Asp Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic: 1447-F11, CDR-H1, Chothia

<400> SEQUENCE: 27

Gly Phe Thr Phe Asp Asn Thr
1               5

<210> SEQ ID NO 28
<211> LENGTH: 7
<212> TYPE: PRT
<213> ORGANISM: Artificial Sequence
<220> FEATURE:
```

<223> OTHER INFORMATION: Synthetic: 1447-G01, CDR-H1, Chothia

<400> SEQUENCE: 28

Gly Phe Thr Phe Asn Thr Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic: VH11-[19], CDR-H1, Chothia

<400> SEQUENCE: 29

Gly Phe Thr Phe Ser Ser Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic: VH5-[7], CDR-H1, Chothia

<400> SEQUENCE: 30

Gly Phe Thr Phe Ser Ser Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic: VH6-[11], CDR-H1, Chothia

<400> SEQUENCE: 31

Gly Phe Thr Phe Ser Ser Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic: VH8-[15], CDR-H1, Chothia

<400> SEQUENCE: 32

Gly Phe Thr Phe Ser Ser Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic: 1251-B08, CDR-H1, Kabat

<400> SEQUENCE: 33

Asp Tyr Gly Met His
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: 1193-C08, CDR-H1, Kabat

```
<400> SEQUENCE: 34

Asn Asn Trp Met Ser
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic: 1193-E06b, CDR-H1, Kabat

<400> SEQUENCE: 35

Asn Thr Asp Met Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic: 1193-H04b, CDR-H1, Kabat

<400> SEQUENCE: 36

Ser Ser Trp Met Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic: 1198-A01, CDR-H1, Kabat

<400> SEQUENCE: 37

Asp Tyr Asp Met Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic: 1198-B10, CDR-H1, Kabat

<400> SEQUENCE: 38

Gly Ser Trp Ile His
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic: 1198-D03, CDR-H1, Kabat

<400> SEQUENCE: 39

Asn Tyr Asp Ile His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic: 1198-D04, CDR-H1, Kabat
```

```
<400> SEQUENCE: 40

Asn Tyr Asp Ile His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 1251-A02, CDR-H1, Kabat

<400> SEQUENCE: 41

Asp His Gly Met His
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic: 1251-A03, CDR-H1, Kabat

<400> SEQUENCE: 42

Asp His Gly Met His
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic: 1251-A06, CDR-H1, Kabat

<400> SEQUENCE: 43

Ser Tyr Gly Met His
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic: 1193-B06, CDR-H1, Kabat

<400> SEQUENCE: 44

Gly Asn Trp Met Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic: 1251-B09, CDR-H1, Kabat

<400> SEQUENCE: 45

Asp Tyr Gly Met His
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic: 1251-B10, CDR-H1, Kabat

<400> SEQUENCE: 46
```

```
Ser His Gly Met His
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic: 1251-C03, CDR-H1, Kabat

<400> SEQUENCE: 47

Ser Tyr Gly Met His
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic: 1251-D02, CDR-H1, Kabat

<400> SEQUENCE: 48

Ser His Gly Met His
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic: 1251-D06, CDR-H1, Kabat

<400> SEQUENCE: 49

Ser Tyr Gly Met His
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic: 1251-D09, CDR-H1, Kabat

<400> SEQUENCE: 50

Ser Tyr Gly Met His
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic: 1251-E06, CDR-H1, Kabat

<400> SEQUENCE: 51

Ser Tyr Gly Met His
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic: 1251-F06, CDR-H1, Kabat

<400> SEQUENCE: 52
```

```
Ser Phe Gly Met His
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic: 1251-F07, CDR-H1, Kabat

<400> SEQUENCE: 53

Ser His Gly Met His
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic: 1251-G02, CDR-H1, Kabat

<400> SEQUENCE: 54

Ser Tyr Gly Met His
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic: 1445-A03, CDR-H1, Kabat

<400> SEQUENCE: 55

Gly Tyr Tyr Ile His
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic: 1445-B09, CDR-H1, Kabat

<400> SEQUENCE: 56

Gly Thr Gly Ile His
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic: 1447-D11, CDR-H1, Kabat

<400> SEQUENCE: 57

Asn Thr Asp Met Ser
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic: 1447-E08, CDR-H1, Kabat

<400> SEQUENCE: 58

Asp Thr Asp Met Ser
```

```
<210> SEQ ID NO 59
<211> LENGTH: 5
<212> TYPE: PRT
<213> ORGANISM: Artificial Sequence
<220> FEATURE:
<223> OTHER INFORMATION: Synthetic: 1447-F11, CDR-H1, Kabat

<400> SEQUENCE: 59

Asn Thr Asp Met Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic: 1447-G01, CDR-H1, Kabat

<400> SEQUENCE: 60

Thr Ser Asp Met Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic: VH11-[19], CDR-H1, Kabat

<400> SEQUENCE: 61

Ser Tyr Gly Met His
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic: VH5-[7], CDR-H1, Kabat

<400> SEQUENCE: 62

Ser Tyr Ala Met His
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic: VH6-[11], CDR-H1, Kabat

<400> SEQUENCE: 63

Ser Tyr Ala Met His
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic: VH8-[15], CDR-H1, Kabat

<400> SEQUENCE: 64

Ser Tyr Ala Met His
1               5
```

```
<210> SEQ ID NO 65
<211> LENGTH: 6
<212> TYPE: PRT
<213> ORGANISM: Artificial Sequence
<220> FEATURE:
<223> OTHER INFORMATION: Synthetic: 1251-B08, CDR-H2, Chothia

<400> SEQUENCE: 65

Trp Tyr Asp Gly Ser Ile
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic: 1193-C08, CDR-H2, Chothia

<400> SEQUENCE: 66

Asn Gly Asp Asp Gly Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic: 1193-E06b, CDR-H2, Chothia

<400> SEQUENCE: 67

Asn Gly Ser Gly Gly Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic: 1193-H04b, CDR-H2, Chothia

<400> SEQUENCE: 68

Asn Gly Tyr Asn Gly Ile
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic: 1198-A01, CDR-H2, Chothia

<400> SEQUENCE: 69

Ala Gln Asp Gly Ser Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic: 1198-B10, CDR-H2, Chothia

<400> SEQUENCE: 70

Tyr Pro Asp Asp Gly Asp
1               5
```

```
<210> SEQ ID NO 71
<211> LENGTH: 6
<212> TYPE: PRT
<213> ORGANISM: Artificial Sequence
<220> FEATURE:
<223> OTHER INFORMATION: Synthetic: 1198-D03, CDR-H2, Chothia

<400> SEQUENCE: 71

Asp Pro Tyr Asn Gly Ala
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic: 1198-D04, CDR-H2, Chothia

<400> SEQUENCE: 72

Asp Pro Tyr Asn Gly Thr
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic: 1251-A02, CDR-H2, Chothia

<400> SEQUENCE: 73

Trp Tyr Asp Gly Ser His
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic: 1251-A03, CDR-H2, Chothia

<400> SEQUENCE: 74

Trp Tyr Asp Gly Ser His
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic: 1251-A06, CDR-H2, Chothia

<400> SEQUENCE: 75

Trp Asp Asp Gly Ser Asp
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic: 1193-B06, CDR-H2, Chothia

<400> SEQUENCE: 76

Tyr Gly Thr Ser Gly Ala
1               5
```

```
<210> SEQ ID NO 77
<211> LENGTH: 6
<212> TYPE: PRT
<213> ORGANISM: Artificial Sequence
<220> FEATURE:
<223> OTHER INFORMATION: Synthetic: 1251-B09, CDR-H2, Chothia

<400> SEQUENCE: 77

Trp Tyr Asp Gly Ser Arg
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic: 1251-B10, CDR-H2, Chothia

<400> SEQUENCE: 78

Trp His Asp Gly Ser Asp
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic: 1251-C03, CDR-H2, Chothia

<400> SEQUENCE: 79

Trp Tyr Asp Gly Ser Ile
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic: 1251-D02, CDR-H2, Chothia

<400> SEQUENCE: 80

Trp Asp Asp Gly Ser Asp
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic: 1251-D06, CDR-H2, Chothia

<400> SEQUENCE: 81

Trp Tyr Asp Gly Ser Lys
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic: 1251-D09, CDR-H2, Chothia

<400> SEQUENCE: 82

Trp Tyr Asp Ala Ser Ile
1               5

<210> SEQ ID NO 83
```

```
<211> LENGTH: 6
<212> TYPE: PRT
<213> ORGANISM: Artificial Sequence
<220> FEATURE:
<223> OTHER INFORMATION: Synthetic: 1251-E06, CDR-H2, Chothia

<400> SEQUENCE: 83

Trp Tyr Asp Gly Ser Asn
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic: 1251-F06, CDR-H2, Chothia

<400> SEQUENCE: 84

Trp Tyr Asp Gly Ser Asn
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic: 1251-F07, CDR-H2, Chothia

<400> SEQUENCE: 85

Trp Asp Asp Gly Ser Asn
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic: 1251-G02, CDR-H2, Chothia

<400> SEQUENCE: 86

Trp His Asp Gly Ser Lys
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic: 1445-A03, CDR-H2, Chothia

<400> SEQUENCE: 87

Ser Pro Thr Gly Gly Tyr
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic: 1445-B09, CDR-H2, Chothia

<400> SEQUENCE: 88

Thr Pro Tyr Asn Gly Thr
1               5

<210> SEQ ID NO 89
<211> LENGTH: 6
```

```
<212> TYPE: PRT
<213> ORGANISM: Artificial Sequence
<220> FEATURE:
<223> OTHER INFORMATION: Synthetic: 1447-D11, CDR-H2, Chothia

<400> SEQUENCE: 89

Asn Gly Ser Gly Gly Ser
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic: 1447-E08, CDR-H2, Chothia

<400> SEQUENCE: 90

Asn Gly Ala Gly Gly Ala
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic: 1447-F11, CDR-H2, Chothia

<400> SEQUENCE: 91

Asn Gly Ser Gly Gly Val
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic: 1447-G01, CDR-H2, Chothia

<400> SEQUENCE: 92

Asn Gly Ser Gly Gly Ala
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic: VH11-[19], CDR-H2, Chothia

<400> SEQUENCE: 93

Trp Tyr Asp Gly Ser Asn
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic: VH5-[7], CDR-H2, Chothia

<400> SEQUENCE: 94

Ser Tyr Asp Gly Ser Asn
1               5

<210> SEQ ID NO 95
<211> LENGTH: 6
<212> TYPE: PRT
```

```
<213> ORGANISM: Artificial Sequence
<220> FEATURE:
<223> OTHER INFORMATION: Synthetic: VH6-[11], CDR-H2, Chothia

<400> SEQUENCE: 95

Ser Tyr Asp Gly Ser Ile
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic: VH8-[15], CDR-H2, Chothia

<400> SEQUENCE: 96

Ser Tyr Asp Gly Ser Asn
1               5

<210> SEQ ID NO 97
<211> LENGTH: 17
<212> TYPE: PRT
<213> ORGANISM: Artificial Sequence
<220> FEATURE:
<223> OTHER INFORMATION: Synthetic: 1251-B08, CDR-H2, Kabat

<400> SEQUENCE: 97

Val Ile Trp Tyr Asp Gly Ser Ile Ser Tyr Tyr Ala Asp Ser Val Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic: 1193-C08, CDR-H2, Kabat

<400> SEQUENCE: 98

Ile Ile Asn Gly Asp Asp Gly Tyr Thr Tyr Tyr Ala Asp Arg Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic: 1193-E06b, CDR-H2, Kabat

<400> SEQUENCE: 99

Ile Ile Asn Gly Ser Gly Gly Ala Thr Asn Tyr Ala Asp Ser Val Lys
1               5                   10                  15

Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic: 1193-H04b, CDR-H2, Kabat

<400> SEQUENCE: 100

Ile Ile Asn Gly Tyr Asn Gly Ile Thr Tyr Tyr Ala Asp Ser Val Lys
1               5                   10                  15
```

```
<210> SEQ ID NO 101
<211> LENGTH: 17
<212> TYPE: PRT
<213> ORGANISM: Artificial Sequence
<220> FEATURE:
<223> OTHER INFORMATION: Synthetic: 1198-A01, CDR-H2, Kabat

<400> SEQUENCE: 101

Phe Ile Ala Gln Asp Gly Ser Tyr Lys Tyr Tyr Val Asp Ser Val Lys
1               5                   10                  15
Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic: 1198-B10, CDR-H2, Kabat

<400> SEQUENCE: 102

Tyr Ile Tyr Pro Asp Asp Gly Asp Thr Tyr Tyr Ala Asp Ser Val Lys
1               5                   10                  15
Gly

<210> SEQ ID NO 103
<211> LENGTH: 17
<212> TYPE: PRT
<213> ORGANISM: Artificial Sequence
<220> FEATURE:
<223> OTHER INFORMATION: Synthetic: 1198-D03, CDR-H2, Kabat

<400> SEQUENCE: 103

Asn Ile Asp Pro Tyr Asn Gly Ala Thr Tyr Tyr Ala Asp Ser Val Lys
1               5                   10                  15
Gly

<210> SEQ ID NO 104
<211> LENGTH: 17
<212> TYPE: PRT
<213> ORGANISM: Artificial Sequence
<220> FEATURE:
<223> OTHER INFORMATION: Synthetic: 1198-D04, CDR-H2, Kabat

<400> SEQUENCE: 104

Asn Ile Asp Pro Tyr Asn Gly Thr Thr Tyr Tyr Ala Asp Ser Val Lys
1               5                   10                  15
Gly

<210> SEQ ID NO 105
<211> LENGTH: 17
<212> TYPE: PRT
<213> ORGANISM: Artificial Sequence
<220> FEATURE:
<223> OTHER INFORMATION: Synthetic: 1251-A02, CDR-H2, Kabat

<400> SEQUENCE: 105

Val Ile Trp Tyr Asp Gly Ser His Lys Ile Tyr Ala Asp Ser Val Lys
1               5                   10                  15
Gly
```

```
<210> SEQ ID NO 106
<211> LENGTH: 17
<212> TYPE: PRT
<213> ORGANISM: Artificial Sequence
<220> FEATURE:
<223> OTHER INFORMATION: Synthetic: 1251-A03, CDR-H2, Kabat

<400> SEQUENCE: 106

Val Ile Trp Tyr Asp Gly Ser His Lys Ile Tyr Ala Asp Ser Val Lys
1               5                   10                  15

Gly

<210> SEQ ID NO 107
<211> LENGTH: 17
<212> TYPE: PRT
<213> ORGANISM: Artificial Sequence
<220> FEATURE:
<223> OTHER INFORMATION: Synthetic: 1251-A06, CDR-H2, Kabat

<400> SEQUENCE: 107

Val Ile Trp Asp Asp Gly Ser Asp Arg Tyr Tyr Ala Asp Ser Val Lys
1               5                   10                  15

Gly

<210> SEQ ID NO 108
<211> LENGTH: 17
<212> TYPE: PRT
<213> ORGANISM: Artificial Sequence
<220> FEATURE:
<223> OTHER INFORMATION: Synthetic: 1193-B06, CDR-H2, Kabat

<400> SEQUENCE: 108

Ile Ile Tyr Gly Thr Ser Gly Ala Thr Tyr Tyr Ala Asp Ser Val Lys
1               5                   10                  15

Gly

<210> SEQ ID NO 109
<211> LENGTH: 17
<212> TYPE: PRT
<213> ORGANISM: Artificial Sequence
<220> FEATURE:
<223> OTHER INFORMATION: Synthetic: 1251-B09, CDR-H2, Kabat

<400> SEQUENCE: 109

Val Thr Trp Tyr Asp Gly Ser Arg Glu Tyr Tyr Ala Asp Ser Val Lys
1               5                   10                  15

Gly

<210> SEQ ID NO 110
<211> LENGTH: 17
<212> TYPE: PRT
<213> ORGANISM: Artificial Sequence
<220> FEATURE:
<223> OTHER INFORMATION: Synthetic: 1251-B10, CDR-H2, Kabat

<400> SEQUENCE: 110

Val Ile Trp His Asp Gly Ser Asp Lys Tyr Tyr Ala Asp Ser Val Lys
1               5                   10                  15

Gly

<210> SEQ ID NO 111
<211> LENGTH: 17
<212> TYPE: PRT
<213> ORGANISM: Artificial Sequence
```

```
<220> FEATURE:
<223> OTHER INFORMATION: Synthetic: 1251-C03, CDR-H2, Kabat

<400> SEQUENCE: 111

Val Ile Trp Tyr Asp Gly Ser Ile Lys Asn Tyr Ala Asp Ser Val Lys
1               5                   10                  15
Gly

<210> SEQ ID NO 112
<211> LENGTH: 17
<212> TYPE: PRT
<213> ORGANISM: Artificial Sequence
<220> FEATURE:
<223> OTHER INFORMATION: Synthetic: 1251-D02, CDR-H2, Kabat

<400> SEQUENCE: 112

Val Ile Trp Asp Asp Gly Ser Asp Arg Tyr Tyr Ala Asp Ser Val Lys
1               5                   10                  15
Gly

<210> SEQ ID NO 113
<211> LENGTH: 17
<212> TYPE: PRT
<213> ORGANISM: Artificial Sequence
<220> FEATURE:
<223> OTHER INFORMATION: Synthetic: 1251-D06, CDR-H2, Kabat

<400> SEQUENCE: 113

Val Val Trp Tyr Asp Gly Ser Lys Thr Ile Tyr Ala Asp Ser Val Lys
1               5                   10                  15
Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic: 1251-D09, CDR-H2, Kabat

<400> SEQUENCE: 114

Val Ile Trp Tyr Asp Ala Ser Ile Arg Lys Tyr Ala Gly Ser Val Lys
1               5                   10                  15
Gly

<210> SEQ ID NO 115
<211> LENGTH: 17
<212> TYPE: PRT
<213> ORGANISM: Artificial Sequence
<220> FEATURE:
<223> OTHER INFORMATION: Synthetic: 1251-E06, CDR-H2, Kabat

<400> SEQUENCE: 115

Val Ile Trp Tyr Asp Gly Ser Asn Lys Val Tyr Ala Asp Ser Val Lys
1               5                   10                  15
Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic: 1251-F06, CDR-H2, Kabat

<400> SEQUENCE: 116
```

Val Ile Trp Tyr Asp Gly Ser Asn Glu Tyr Tyr Ala Asp Ser Val Lys
1               5                   10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Synthetic: 1251-F07, CDR-H2, Kabat

<400> SEQUENCE: 117

Val Ile Trp Asp Asp Gly Ser Asn Glu Val Tyr Ala Asp Ser Val Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic: 1251-G02, CDR-H2, Kabat

<400> SEQUENCE: 118

Val Ile Trp His Asp Gly Ser Lys Asp Tyr Tyr Ala Asp Ser Val Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic: 1445-A03, CDR-H2, Kabat

<400> SEQUENCE: 119

Glu Ile Ser Pro Thr Gly Gly Tyr Thr Tyr Tyr Ala Asp Ser Val Lys
1               5                   10                  15

Gly

<210> SEQ ID NO 120
<211> LENGTH: 17
<212> TYPE: PRT
<213> ORGANISM: Artificial Sequence
<220> FEATURE:
<223> OTHER INFORMATION: Synthetic: 1445-B09, CDR-H2, Kabat

<400> SEQUENCE: 120

Ile Ile Thr Pro Tyr Asn Gly Thr Thr Asn Tyr Ala Asp Ser Val Lys
1               5                   10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: Synthetic: 1447-D11, CDR-H2, Kabat

<400> SEQUENCE: 121

Val Ile Asn Gly Ser Gly Gly Ser Ser Asn Tyr Ala Asp Ser Val Lys
1               5                   10                  15

<210> SEQ ID NO 122
<211> LENGTH: 17
<212> TYPE: PRT
<213> ORGANISM: Artificial Sequence
<220> FEATURE:
<223> OTHER INFORMATION: Synthetic: 1447-E08, CDR-H2, Kabat

<400> SEQUENCE: 122

Met Ile Asn Gly Ala Gly Gly Ala Ser Phe Tyr Ala Asp Ser Val Arg
1               5                   10                  15
Gly

<210> SEQ ID NO 123
<211> LENGTH: 17
<212> TYPE: PRT
<213> ORGANISM: Artificial Sequence
<220> FEATURE:
<223> OTHER INFORMATION: Synthetic: 1447-F11, CDR-H2, Kabat

<400> SEQUENCE: 123

Ile Ile Asn Gly Ser Gly Gly Val Thr Asn Tyr Ala Asp Ser Val Arg
1               5                   10                  15
Gly

<210> SEQ ID NO 124
<211> LENGTH: 17
<212> TYPE: PRT
<213> ORGANISM: Artificial Sequence
<220> FEATURE:
<223> OTHER INFORMATION: Synthetic: 1447-G01, CDR-H2, Kabat

<400> SEQUENCE: 124

Ile Ile Asn Gly Ser Gly Gly Ala Thr Asn Tyr Ala Asp Ser Val Lys
1               5                   10                  15
Gly

<210> SEQ ID NO 125
<211> LENGTH: 17
<212> TYPE: PRT
<213> ORGANISM: Artificial Sequence
<220> FEATURE:
<223> OTHER INFORMATION: Synthetic: VH11-[19], CDR-H2, Kabat

<400> SEQUENCE: 125

Val Ile Trp Tyr Asp Gly Ser Asn Lys Tyr Tyr Ala Asp Ser Val Lys
1               5                   10                  15
Gly

<210> SEQ ID NO 126
<211> LENGTH: 17
<212> TYPE: PRT
<213> ORGANISM: Artificial Sequence
<220> FEATURE:
<223> OTHER INFORMATION: Synthetic: VH5-[7], CDR-H2, Kabat

<400> SEQUENCE: 126

Val Ile Ser Tyr Asp Gly Ser Asn Lys Tyr Tyr Ala Asp Ser Val Lys
1               5                   10                  15
Gly

<210> SEQ ID NO 127

<210> SEQ ID NO 127
<211> LENGTH: 17
<212> TYPE: PRT
<213> ORGANISM: Artificial Sequence
<220> FEATURE:
<223> OTHER INFORMATION: Synthetic: VH6-[11], CDR-H2, Kabat

<400> SEQUENCE: 127

Val Ile Ser Tyr Asp Gly Ser Ile Lys Tyr Tyr Ala Asp Ser Val Lys
1               5                   10                  15
Gly

<210> SEQ ID NO 128
<211> LENGTH: 17
<212> TYPE: PRT
<213> ORGANISM: Artificial Sequence
<220> FEATURE:
<223> OTHER INFORMATION: Synthetic: VH8-[15], CDR-H2, Kabat

<400> SEQUENCE: 128

Val Ile Ser Tyr Asp Gly Ser Asn Lys Tyr Tyr Ala Asp Ser Val Lys
1               5                   10                  15
Gly

<210> SEQ ID NO 129
<211> LENGTH: 14
<212> TYPE: PRT
<213> ORGANISM: Artificial Sequence
<220> FEATURE:
<223> OTHER INFORMATION: Synthetic: 1251-B08, CDR-H3, K/C

<400> SEQUENCE: 129

Gly Gly Thr Val Glu His Gly Ala Val Tyr Gly Thr Asp Val
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic: 1193-C08, CDR-H3, K/C

<400> SEQUENCE: 130

Val Ala Leu Gly Arg Pro Arg Arg Phe Asp Tyr
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic: 1193-E06b, CDR-H3, K/C

<400> SEQUENCE: 131

Phe Glu Asn Glu Trp Glu Val Ser Met Asp Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic: 1193-H04b, CDR-H3, K/C

<400> SEQUENCE: 132

Pro Ser Ala Pro Gly Ala Arg Arg Phe Asp Tyr
1               5                   10

```
<210> SEQ ID NO 133
<211> LENGTH: 11
<212> TYPE: PRT
<213> ORGANISM: Artificial Sequence
<220> FEATURE:
<223> OTHER INFORMATION: Synthetic: 1198-A01, CDR-H3, K/C

<400> SEQUENCE: 133

Ser Lys Leu Phe Arg Ala Gly Gln Phe Asp Tyr
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic: 1198-B10, CDR-H3, K/C

<400> SEQUENCE: 134

Glu Gly Ser His Asn Leu Asp Lys Met Asp Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic: 1198-D03, CDR-H3, K/C

<400> SEQUENCE: 135

Val Leu Trp Gly Phe Trp Ala Pro Phe Asp Tyr
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic: 1198-D04, CDR-H3, K/C

<400> SEQUENCE: 136

Val Pro Trp Gly Phe Trp Ala Pro Phe Asp Tyr
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthetic: 1251-A02, CDR-H3, K/C

<400> SEQUENCE: 137

Gly Gly Ser Leu Ala Gly Gly Ala Val Tyr Gly Thr Asp Val
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic: 1251-A03, CDR-H3, K/C

<400> SEQUENCE: 138

Gly Gly Ser Leu Ala Gly Gly Ala Val Tyr Gly Thr Asp Val
1               5                   10
```

<210> SEQ ID NO 139
<211> LENGTH: 14
<212> TYPE: PRT
<213> ORGANISM: Artificial Sequence
<220> FEATURE:
<223> OTHER INFORMATION: Synthetic: 1251-A06, CDR-H3, K/C

<400> SEQUENCE: 139

Gly Gly Thr Arg Val Leu Gly Ala Ile His Gly Thr Asp Val
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic: 1193-B06, CDR-H3, K/C

<400> SEQUENCE: 140

Pro Ser Met Ser Gly Ser Arg Gly Phe Asp Tyr
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic: 1251-B09, CDR-H3, K/C

<400> SEQUENCE: 141

Gly Gly Thr Leu Val His Gly Ala Leu Tyr Gly Asn Asp Val
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Synthetic: 1251-B10, CDR-H3, K/C

<400> SEQUENCE: 142

Gly Gly Thr Arg Val Leu Gly Ala Val Tyr Gly Leu Asp Val
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Synthetic: 1251-C03, CDR-H3, K/C

<400> SEQUENCE: 143

Gly Gly Ala Leu Met Arg Gly Glu Phe Ser Gly His Asp Val
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic: 1251-D02, CDR-H3, K/C

<400> SEQUENCE: 144

Gly Gly Thr Arg Val Leu Gly Ala Ile His Gly Thr Asp Val
1               5                   10

```
<210> SEQ ID NO 145
<211> LENGTH: 14
<212> TYPE: PRT
<213> ORGANISM: Artificial Sequence
<220> FEATURE:
<223> OTHER INFORMATION: Synthetic: 1251-D06, CDR-H3, K/C

<400> SEQUENCE: 145

Gly Gly Thr Leu Val Arg Gly Ala Val Tyr Gly Leu Asp Val
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthetic: 1251-D09, CDR-H3, K/C

<400> SEQUENCE: 146

Gly Gly Thr Val Glu Arg Gly Ala Ile Tyr Gly Thr Asp Val
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthetic: 1251-E06, CDR-H3, K/C

<400> SEQUENCE: 147

Gly Gly Met Val Gly Gln Gly Ala Met Phe Gly Leu Asp Val
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic: 1251-F06, CDR-H3, K/C

<400> SEQUENCE: 148

Gly Gly Ser Leu Val Thr Arg Gly Val Tyr Gly Leu Asp Val
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Synthetic: 1251-F07, CDR-H3, K/C

<400> SEQUENCE: 149

Gly Gly Thr Arg Ile Arg Gly Leu Arg Tyr Gly Thr Asp Val
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Synthetic: 1251-G02, CDR-H3, K/C

<400> SEQUENCE: 150

Gly Gly Gln Leu Asp His Gly Ala Ile Tyr Gly Leu Asp Val
1               5                   10

<210> SEQ ID NO 151
```

```
<211> LENGTH: 12
<212> TYPE: PRT
<213> ORGANISM: Artificial Sequence
<220> FEATURE:
<223> OTHER INFORMATION: Synthetic: 1445-A03, CDR-H3, K/C

<400> SEQUENCE: 151

Glu His Gly Leu Val Tyr Gly Gln Pro Met Asp Tyr
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic: 1445-B09, CDR-H3, K/C

<400> SEQUENCE: 152

Gly Gly Tyr Gly Tyr Tyr Tyr Pro Pro Phe Asp Tyr
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Synthetic: 1447-D11, CDR-H3, K/C

<400> SEQUENCE: 153

Tyr Glu Thr Glu Trp Glu Val Ser Leu Asp Tyr
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthetic: 1447-E08, CDR-H3, K/C

<400> SEQUENCE: 154

Phe Glu Asn Gln Trp Glu Val Thr Phe Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic: 1447-F11, CDR-H3, K/C

<400> SEQUENCE: 155

Tyr Glu Ser Glu Trp Glu Val Ser Leu Asp Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthetic: 1447-G01, CDR-H3, K/C

<400> SEQUENCE: 156

Tyr Glu Asn Glu Met Glu Val Ser Met Asp Tyr
1               5                   10

<210> SEQ ID NO 157
<211> LENGTH: 14
```

```
<212> TYPE: PRT
<213> ORGANISM: Artificial Sequence
<220> FEATURE:
<223> OTHER INFORMATION: Synthetic: VH11-[19], CDR-H3, K/C

<400> SEQUENCE: 157

Gly Gly Thr Leu Val Arg Gly Ala Met Tyr Gly Thr Asp Val
1               5                   10

<210> SEQ ID NO 158
<211> LENGTH: 15
<212> TYPE: PRT
<213> ORGANISM: Artificial Sequence
<220> FEATURE:
<223> OTHER INFORMATION: Synthetic: VH5-[7], CDR-H3, K/C

<400> SEQUENCE: 158

Gly Arg Tyr Tyr Gly Ser Gly Ser Tyr Ser Ser Tyr Phe Asp Tyr
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic: VH6-[11], CDR-H3, K/C

<400> SEQUENCE: 159

Gly Arg Glu Ile Thr Ser Gln Asn Ile Val Ile Leu Leu Asp Tyr
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic: VH8-[15], CDR-H3, K/C

<400> SEQUENCE: 160

Gly Arg Glu Ile Thr Ser Gln Asn Ile Val Ile Leu Leu Asp Tyr
1               5                   10                  15

<210> SEQ ID NO 161
<211> LENGTH: 11
<212> TYPE: PRT
<213> ORGANISM: Artificial Sequence
<220> FEATURE:
<223> OTHER INFORMATION: Synthetic: 1337-A09, CDR-L1, K/C

<400> SEQUENCE: 161

Arg Ala Ser Gln Gly Ile Gly Ser Trp Leu Ala
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic: 1193-C08, CDR-L1, K/C

<400> SEQUENCE: 162

Arg Ala Ser Gln Ser Val Ser Ser Asn Tyr Leu Ala
1               5                   10

<210> SEQ ID NO 163
<211> LENGTH: 12
<212> TYPE: PRT
```

<213> ORGANISM: Artificial Sequence
<220> FEATURE:
<223> OTHER INFORMATION: Synthetic: 1193-E06b, CDR-L1, K/C

<400> SEQUENCE: 163

Arg Ala Ser Gln Ser Val Ser Ser Ser Tyr Leu Ala
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic: 1193-H04b, CDR-L1, K/C

<400> SEQUENCE: 164

Arg Ala Ser Gln Ser Val Ser Ser Ser Tyr Leu Ala
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic: 1275-C10, CDR-L1, K/C

<400> SEQUENCE: 165

Arg Ala Ser Gln Gly Val Ser Ser Trp Leu Ala
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic: 1275-D01, CDR-L1, K/C

<400> SEQUENCE: 166

Arg Ala Ser Gln Gly Ile Gly Arg Trp Leu Ala
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic: 1275-D10, CDR-L1, K/C

<400> SEQUENCE: 167

Arg Ala Ser Gln Gly Val Phe Ser Trp Leu Ala
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic: 1275-G02, CDR-L1, K/C

<400> SEQUENCE: 168

Arg Ala Ser Gln Gly Leu Gly Ser Phe Leu Ala
1               5                   10

<210> SEQ ID NO 169
<211> LENGTH: 11
<212> TYPE: PRT
<213> ORGANISM: Artificial Sequence

```
<220> FEATURE:
<223> OTHER INFORMATION: Synthetic: 1337-A04, CDR-L1, K/C

<400> SEQUENCE: 169

Arg Ala Ser Gln Asp Ile Gly Arg Trp Val Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic: 1337-A05, CDR-L1, K/C

<400> SEQUENCE: 170

Arg Ala Ser Gln Gly Ile Gly Arg Trp Val Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic: 1337-A06, CDR-L1, K/C

<400> SEQUENCE: 171

Arg Ala Ser Gln Asp Ile Gly Ser Trp Val Ala
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Synthetic: 1337-A07, CDR-L1, K/C

<400> SEQUENCE: 172

Arg Ala Ser Gln Gly Ile Ser Ser Trp Val Ala
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Synthetic: 1337-A08, CDR-L1, K/C

<400> SEQUENCE: 173

Arg Ala Ser Gln Asp Ile Gly Ser Trp Val Ala
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic: 1193-B06, CDR-L1, K/C

<400> SEQUENCE: 174

Arg Ala Gly Gln Ser Val Ser Ser Ser Tyr Leu Ala
1               5                   10

<210> SEQ ID NO 175
<211> LENGTH: 11
<212> TYPE: PRT
<213> ORGANISM: Artificial Sequence
<220> FEATURE:
```

<223> OTHER INFORMATION: Synthetic: 1337-A10, CDR-L1, K/C

<400> SEQUENCE: 175

Arg Ala Ser Gln Gly Ile Ser Ser Trp Val Ala
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic: 1447-D11, CDR-L1, K/C

<400> SEQUENCE: 176

Arg Ala Ser Gln Ser Val Ser Ser Ser Tyr Leu Ala
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Synthetic: 1447-E08, CDR-L1, K/C

<400> SEQUENCE: 177

Arg Ala Ser Gln Arg Val Ala Gly Ile Asp Leu Ser
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Synthetic: 1447-F11, CDR-L1, K/C

<400> SEQUENCE: 178

Arg Ala Ser Gln Ser Val Tyr Arg Ser Tyr Leu Ala
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetic: 1447-G01, CDR-L1, K/C

<400> SEQUENCE: 179

Arg Ala Ser Gln Ser Val Ser Ser Arg Glu Leu Gly
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic: VL-5[23] & VL6-[26], CDR-L1, K/C

<400> SEQUENCE: 180

Arg Ala Ser Gln Gly Ile Ser Ser Trp Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Synthetic: 1337-A09, CDR-L2, K/C

```
<400> SEQUENCE: 181

Ala Ala Asp Arg Leu Gln Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic: 1193-C08, CDR-L2, K/C

<400> SEQUENCE: 182

Gly Ala Ser Ser Arg Ala Thr
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic: 1193-E06b, CDR-L2, K/C

<400> SEQUENCE: 183

Gly Ala Ser Ser Arg Ala Thr
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic: 1193-H04b, CDR-L2, K/C

<400> SEQUENCE: 184

Gly Ala Ser Ser Arg Ala Thr
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic: 1275-C10, CDR-L2, K/C

<400> SEQUENCE: 185

Ser Ala Arg Tyr Leu Gln Ser
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic: 1275-D01, CDR-L2, K/C

<400> SEQUENCE: 186

Gly Arg Ser Ser Leu Gln Ser
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic: 1275-D10, CDR-L2, K/C
```

```
<400> SEQUENCE: 187

Asn Ala Thr Gln Leu Gln Ser
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic: 1275-G02, CDR-L2, K/C

<400> SEQUENCE: 188

Leu Gly Asn Leu Leu Gln Ile
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic: 1337-A04, CDR-L2, K/C

<400> SEQUENCE: 189

Gly Ala Ser Ser Leu Gln Ser
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic: 1337-A05, CDR-L2, K/C

<400> SEQUENCE: 190

Gly Ala Asp Arg Leu Gln Ser
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic: 1337-A06, CDR-L2, K/C

<400> SEQUENCE: 191

Gly Ala Asp Arg Leu Gln Ser
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic: 1337-A07, CDR-L2, K/C

<400> SEQUENCE: 192

Gly Ala Ser Arg Leu Gln Ser
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic: 1337-A08, CDR-L2, K/C

<400> SEQUENCE: 193
```

```
Ala Ser Asp Ser Leu Gln Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic: 1193-B06, CDR-L2, K/C

<400> SEQUENCE: 194

Gly Ala Ser Ser Arg Ala Thr
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic: 1337-A10, CDR-L2, K/C

<400> SEQUENCE: 195

Gly Ser Ser Arg Leu Gln Ser
1               5

<210> SEQ ID NO 196
<211> LENGTH: 7
<212> TYPE: PRT
<213> ORGANISM: Artificial Sequence
<220> FEATURE:
<223> OTHER INFORMATION: Synthetic: 1447-D11, CDR-L2, K/C

<400> SEQUENCE: 196

Gly Ala Ser Ser Arg Ala Thr
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic: 1447-E08, CDR-L2, K/C

<400> SEQUENCE: 197

Gly Ala Ser Ser Arg Ala Thr
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic: 1447-F11, CDR-L2, K/C

<400> SEQUENCE: 198

Gly Ala Ser Ser Arg Ala Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic: 1447-G01, CDR-L2, K/C

<400> SEQUENCE: 199
```

Gly Ala Ser Ser Arg Ala Thr
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic: VL-5[23] & VL6-[26], CDR-L2, K/C

<400> SEQUENCE: 200

Ala Ala Ser Ser Leu Gln Ser
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic: 1337-A09, CDR-L3, K/C

<400> SEQUENCE: 201

Gln Gln Tyr His Thr Tyr Pro Leu Thr
1               5

<210> SEQ ID NO 202
<211> LENGTH: 9
<212> TYPE: PRT
<213> ORGANISM: Artificial Sequence
<220> FEATURE:
<223> OTHER INFORMATION: Synthetic: 1193-C08, CDR-L3, K/C

<400> SEQUENCE: 202

Gln Gln His Tyr Thr Thr Pro Pro Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic: 1193-E06b, CDR-L3, K/C

<400> SEQUENCE: 203

Gln Gln His Tyr Thr Thr Pro Pro Thr
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic: 1193-H04b, CDR-L3, K/C

<400> SEQUENCE: 204

Gln Gln His Tyr Thr Thr Pro Pro Thr
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic: 1275-C10, CDR-L3, K/C

<400> SEQUENCE: 205

Gln Gln Tyr Asn Leu Tyr Pro Leu Thr

```
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic: 1275-D01, CDR-L3, K/C

<400> SEQUENCE: 206

Gln Gln Tyr Asn Ile Tyr Pro Leu Thr
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic: 1275-D10, CDR-L3, K/C

<400> SEQUENCE: 207

Gln Gln Tyr Tyr Tyr Tyr Pro Leu Thr
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic: 1275-G02, CDR-L3, K/C

<400> SEQUENCE: 208

Gln Gln Tyr Asn Ala Tyr Pro Leu Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic: 1337-A04, CDR-L3, K/C

<400> SEQUENCE: 209

Gln Gln Tyr Asn Thr Tyr Pro Leu Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic: 1337-A05, CDR-L3, K/C

<400> SEQUENCE: 210

Gln Gln Tyr Asn Ser Tyr Pro Leu Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic: 1337-A06, CDR-L3, K/C

<400> SEQUENCE: 211

Gln Gln Tyr Asn Ser Tyr Pro Leu Thr
1               5
```

```
<210> SEQ ID NO 212
<211> LENGTH: 9
<212> TYPE: PRT
<213> ORGANISM: Artificial Sequence
<220> FEATURE:
<223> OTHER INFORMATION: Synthetic: 1337-A07, CDR-L3, K/C

<400> SEQUENCE: 212

Gln Gln Tyr His Thr Tyr Pro Leu Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic: 1337-A08, CDR-L3, K/C

<400> SEQUENCE: 213

Gln Gln Tyr Asn Ser Tyr Pro Leu Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic: 1193-B06, CDR-L3, K/C

<400> SEQUENCE: 214

Gln Gln His Tyr Thr Thr Pro Pro Thr
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic: 1337-A10, CDR-L3, K/C

<400> SEQUENCE: 215

Gln Gln Tyr Asn Thr Tyr Pro Leu Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic: 1447-D11, CDR-L3, K/C

<400> SEQUENCE: 216

Gln His Asn Gln Pro Thr Pro Pro Thr
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic: 1447-E08, CDR-L3, K/C

<400> SEQUENCE: 217

Gln Gln His Asn Thr Thr Pro Pro Thr
1               5
```

```
<210> SEQ ID NO 218
<211> LENGTH: 9
<212> TYPE: PRT
<213> ORGANISM: Artificial Sequence
<220> FEATURE:
<223> OTHER INFORMATION: Synthetic: 1447-F11, CDR-L3, K/C

<400> SEQUENCE: 218

Gln Gln His Gln Thr Ala Pro Pro Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic: 1447-G01, CDR-L3, K/C

<400> SEQUENCE: 219

Gln Gln Gln Cys Ser Trp Pro Pro Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic: VL-5[23] & VL6-[26], CDR-L3, K/C

<400> SEQUENCE: 220

Gln Gln Tyr Asn Ser Tyr Pro Leu Thr
1               5

<210> SEQ ID NO 221
<211> LENGTH: 243
<212> TYPE: PRT
<213> ORGANISM: Artificial Sequence
<220> FEATURE:
<223> OTHER INFORMATION: Synthetic: 1193-B06, scFv

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Met Ser Trp Val Arg Gln Ala Pro Gly Lys Gly Leu Glu Trp Val
        35                  40                  45

Gly Ile Ile Tyr Gly Thr Ser Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Met Ser Gly Ser Arg Gly Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160
```

Gly Gln Ser Val Ser Ser Ser Tyr Leu Ala Trp Tyr Gln Gln Lys Pro
            165                 170                 175

Gly Gln Ala Pro Arg Leu Leu Ile Tyr Gly Ala Ser Ser Arg Ala Thr
        180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Tyr Thr Thr Pro Pro Thr Phe Gly Gln Gly Thr Lys Val
225                 230                 235                 240

Glu Ile Lys

<210> SEQ ID NO 222
<211> LENGTH: 243
<212> TYPE: PRT
<213> ORGANISM: Artificial Sequence
<220> FEATURE:
<223> OTHER INFORMATION: Synthetic: 1193-C08, scFv

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Asn
            20                  25                  30

Trp Met Ser Trp Val Arg Gln Ala Pro Gly Lys Gly Leu Glu Trp Val
        35                  40                  45

Gly Ile Ile Asn Gly Asp Asp Gly Tyr Thr Tyr Tyr Ala Asp Arg Val
    50                  55                  60

Lys Gly Arg Phe Thr Ile Ile Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Leu Gly Arg Pro Arg Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Thr Pro Gly Glu Arg Ala Thr Leu Ser Cys Arg Ala
145                 150                 155                 160

Ser Gln Ser Val Ser Ser Asn Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Met Tyr Tyr Cys
    210                 215                 220

Gln Gln His Tyr Thr Thr Pro Pro Thr Phe Gly Gln Gly Thr Lys Val
225                 230                 235                 240

Glu Ile Lys

<210> SEQ ID NO 223
<211> LENGTH: 243
<212> TYPE: PRT
<213> ORGANISM: Artificial Sequence
<220> FEATURE:
<223> OTHER INFORMATION: Synthetic: 1193-E06b, scFv

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Glu Trp Glu Val Ser Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Tyr Thr Thr Pro Pro Thr Phe Gly Gln Gly Thr Lys Val
225                 230                 235                 240

Glu Ile Lys

<210> SEQ ID NO 224
<211> LENGTH: 242
<212> TYPE: PRT
<213> ORGANISM: Artificial Sequence
<220> FEATURE:
<223> OTHER INFORMATION: Synthetic: 1193-H04b, scFv

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
            20                  25                  30

Trp Met Ser Trp Val Arg Gln Ala Pro Gly Lys Gly Leu Glu Trp Val
        35                  40                  45

Gly Ile Ile Asn Gly Tyr Asn Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Pro Ser Ala Pro Gly Ala Arg Arg Phe Asp Tyr Trp Gly Gln
            100                 105                 110

Gly Thr Leu Val Thr Val Ser Gly Gly Gly Ser Gly Gly Gly
            115                 120                 125

Gly Ser Gly Gly Gly Ser Glu Ile Val Leu Thr Gln Ser Pro Gly
        130                 135                 140

Thr Leu Ser Leu Ser Pro Gly Glu Ala Thr Leu Ser Cys Arg Ala Ser
145                 150                 155                 160

Gln Ser Val Ser Ser Tyr Leu Ala Trp Tyr Gln Gln Arg Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
            210                 215                 220

Gln His Tyr Thr Thr Pro Pro Thr Phe Gly Gln Gly Thr Lys Val Glu
225                 230                 235                 240

Ile Lys

<210> SEQ ID NO 225
<211> LENGTH: 243
<212> TYPE: PRT
<213> ORGANISM: Artificial Sequence
<220> FEATURE:
<223> OTHER INFORMATION: Synthetic: 1447-D11, scFv

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
            20                  25                  30

Asp Met Ser Trp Val Arg Gln Ala Pro Gly Lys Gly Leu Glu Trp Val
        35                  40                  45

Gly Val Ile Asn Gly Ser Gly Ser Ser Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Thr Glu Trp Glu Val Ser Leu Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Leu Thr Gln Ser Pro Gly
        130                 135                 140

Thr Leu Ser Leu Ser Pro Gly Glu Arg Ala Thr Leu Ser Cys Arg Ala
145                 150                 155                 160

Ser Gln Ser Val Ser Ser Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
            195                 200                 205
```

```
Leu Thr Ile Ser Arg Leu Glu Pro Glu Asp Phe Ala Val Tyr Tyr Cys
        210                 215                 220

Gln His Asn Gln Pro Thr Pro Pro Thr Phe Gly Gln Gly Thr Lys Val
225                 230                 235                 240

Glu Ile Lys

<210> SEQ ID NO 226
<211> LENGTH: 243
<212> TYPE: PRT
<213> ORGANISM: Artificial Sequence
<220> FEATURE:
<223> OTHER INFORMATION: Synthetic: 1447-E08, scFv

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Thr
            20                  25                  30

Asp Met Ser Trp Val Arg Gln Ala Pro Gly Lys Gly Leu Glu Trp Val
        35                  40                  45

Gly Met Ile Asn Gly Ala Gly Gly Ala Ser Phe Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Gln Trp Glu Val Thr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Arg Val Ala Gly Ile Asp Leu Ser Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln His Asn Thr Thr Pro Pro Thr Phe Gly Gln Gly Thr Lys Val
225                 230                 235                 240

Glu Ile Lys

<210> SEQ ID NO 227
<211> LENGTH: 243
<212> TYPE: PRT
<213> ORGANISM: Artificial Sequence
<220> FEATURE:
<223> OTHER INFORMATION: Synthetic: 1447-F11, scFv

<400> SEQUENCE: 227

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Asp Asn Thr
```

```
                    20                  25                  30
Asp Met Ser Trp Val Arg Gln Ala Pro Gly Lys Gly Leu Glu Trp Val
            35                  40                  45

Gly Ile Ile Asn Gly Ser Gly Val Thr Asn Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Ser Glu Trp Glu Val Ser Leu Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Glu Ile Val Leu Thr Gln Ser Pro Gly
        130                 135                 140

Thr Leu Ser Leu Ser Pro Gly Glu Arg Ala Thr Leu Ser Cys Arg Ala
145                 150                 155                 160

Ser Gln Ser Val Tyr Arg Ser Tyr Leu Ala Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
            195                 200                 205

Leu Thr Ile Ser Arg Leu Glu Pro Glu Asp Phe Ala Val Tyr Tyr Cys
        210                 215                 220

Gln Gln His Gln Thr Ala Pro Pro Thr Phe Gly Gln Gly Thr Lys Val
225                 230                 235                 240

Glu Ile Lys

<210> SEQ ID NO 228
<211> LENGTH: 243
<212> TYPE: PRT
<213> ORGANISM: Artificial Sequence
<220> FEATURE:
<223> OTHER INFORMATION: Synthetic: 1447-G01, scFv

<400> SEQUENCE: 228

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ser
            20                  25                  30

Asp Met Ser Trp Val Arg Gln Ala Pro Gly Lys Gly Leu Glu Trp Val
            35                  40                  45

Gly Ile Ile Asn Gly Ser Gly Gly Ala Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Asn Glu Met Glu Val Ser Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Leu Thr Gln Ser Pro Gly
        130                 135                 140
```

Thr Leu Ser Leu Ser Pro Gly Glu Arg Ala Thr Leu Ser Cys Arg Ala
145                 150                 155                 160

Ser Gln Ser Val Ser Ser Arg Glu Leu Gly Trp Tyr Gln Gln Lys Pro
            165                 170                 175

Gly Gln Ala Pro Arg Leu Leu Ile Tyr Gly Ala Ser Ser Arg Ala Thr
        180                 185                 190

Gly Ile Pro Asp Arg Phe Ser Gly Ser Gly Ser Gly Thr Asp Phe Thr
    195                 200                 205

Leu Thr Ile Ser Arg Leu Glu Pro Glu Asp Phe Ala Val Tyr Tyr Cys
210                 215                 220

Gln Gln Gln Cys Ser Trp Pro Pro Thr Phe Gly Gln Gly Thr Lys Val
225                 230                 235                 240

Glu Ile Lys

<210> SEQ ID NO 229
<211> LENGTH: 483
<212> TYPE: PRT
<213> ORGANISM: Artificial Sequence
<220> FEATURE:
<223> OTHER INFORMATION: Synthetic: 1251-B08-g_1337-A09-g scFv-Fc,
      scFv-Fc

<400> SEQUENCE: 229

Gln Val Gln Leu Val Glu Ser Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Thr Val Glu His Gly Ala Val Tyr Gly Thr Asp Val
        100                 105                 110

Trp Gly Gln Gly Thr Thr Val Thr Val Ser Ser Gly Gly Gly Gly Ser
    115                 120                 125

Gly Gly Gly Gly Ser Gly Gly Gly Ser Asp Ile Gln Met Thr Gln
130                 135                 140

Ser Pro Ser Ser Val Ser Ala Ser Val Gly Asp Arg Val Thr Ile Thr
145                 150                 155                 160

Cys Arg Ala Ser Gln Gly Ile Gly Ser Trp Leu Ala Trp Tyr Gln Gln
            165                 170                 175

Lys Pro Gly Lys Ala Pro Lys Leu Leu Ile Tyr Ala Ala Asp Arg Leu
        180                 185                 190

Gln Ser Gly Val Pro Ser Arg Phe Ser Gly Ser Gly Ser Gly Thr Asp
    195                 200                 205

Phe Thr Leu Thr Ile Ser Ser Leu Gln Pro Glu Asp Phe Ala Thr Tyr
210                 215                 220

Tyr Cys Gln Gln Tyr His Thr Tyr Pro Leu Thr Phe Gly Gly Gly Thr
225                 230                 235                 240

Lys Val Glu Ile Lys Ala Ala Gly Ser Asp Gln Glu Pro Lys Ser Ser
            245                 250                 255

Asp Lys Thr His Thr Cys Pro Pro Cys Ser Ala Pro Glu Leu Leu Gly
                260                 265                 270

Gly Ser Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 230
<211> LENGTH: 120
<212> TYPE: PRT
<213> ORGANISM: Artificial Sequence
<220> FEATURE:
<223> OTHER INFORMATION: Synthetic: 1198-A01, VH

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Gly Phe Ile Ala Gln Asp Gly Ser Tyr Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Leu Phe Arg Ala Gly Gln Phe Asp Tyr Trp Gly Gln
            100                 105                 110

Gly Thr Leu Val Thr Val Ser Ser
        115                 120

```
<210> SEQ ID NO 231
<211> LENGTH: 120
<212> TYPE: PRT
<213> ORGANISM: Artificial Sequence
<220> FEATURE:
<223> OTHER INFORMATION: Synthetic: 1198-B10, VH

<400> SEQUENCE: 231

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser Gly Ser
             20                  25                  30

Trp Ile His Trp Val Arg Gln Ala Pro Gly Lys Gly Leu Glu Trp Val
         35                  40                  45

Gly Tyr Ile Tyr Pro Asp Asp Gly Asp Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ser His Asn Leu Asp Lys Met Asp Tyr Trp Gly Gln
            100                 105                 110

Gly Thr Leu Val Thr Val Ser Ser
        115                 120

<210> SEQ ID NO 232
<211> LENGTH: 120
<212> TYPE: PRT
<213> ORGANISM: Artificial Sequence
<220> FEATURE:
<223> OTHER INFORMATION: Synthetic: 1198-D03, VH

<400> SEQUENCE: 232

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Asn Asn Tyr
             20                  25                  30

Asp Ile His Trp Val Arg Gln Ala Pro Gly Lys Gly Leu Glu Trp Val
         35                  40                  45

Ala Asn Ile Asp Pro Tyr Asn Gly Ala Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Val Leu Trp Gly Phe Trp Ala Pro Phe Asp Tyr Trp Gly Gln
            100                 105                 110

Gly Thr Leu Val Thr Val Ser Ser
        115                 120

<210> SEQ ID NO 233
<211> LENGTH: 120
<212> TYPE: PRT
<213> ORGANISM: Artificial Sequence
<220> FEATURE:
<223> OTHER INFORMATION: Synthetic: 1198-D04, VH

<400> SEQUENCE: 233

Glu Val Gln Leu Val Glu Ser Gly Gly Gly Leu Val Gln Pro Gly Gly
```

```
            1               5                  10                 15
Ser Leu Arg Leu Ser Cys Ala Ala Ser Gly Phe Asn Ile Asn Asn Tyr
            20                 25                 30

Asp Ile His Trp Val Arg Gln Ala Pro Gly Lys Gly Leu Glu Trp Val
            35                 40                 45

Ala Asn Ile Asp Pro Tyr Asn Gly Thr Thr Tyr Ala Asp Ser Val
        50                 55                 60

Lys Gly Arg Phe Thr Ile Ser Asp Thr Ser Lys Asn Thr Ala Tyr
65                 70                 75                 80

Leu Gln Met Asn Ser Leu Arg Ala Glu Asp Thr Ala Val Tyr Tyr Cys
            85                 90                 95

Ala Arg Val Pro Trp Gly Phe Trp Ala Pro Phe Asp Tyr Trp Gly Gln
            100                105                110

Gly Thr Leu Val Thr Val Ser Ser
            115                120

<210> SEQ ID NO 234
<211> LENGTH: 123
<212> TYPE: PRT
<213> ORGANISM: Artificial Sequence
<220> FEATURE:
<223> OTHER INFORMATION: Synthetic: 1251-A02, VH

<400> SEQUENCE: 234

Gln Val Gln Leu Val Glu Ser Gly Gly Gly Val Val Gln Pro Gly Arg
1               5                  10                 15

Ser Leu Arg Leu Ser Cys Ala Ala Ser Gly Phe Ala Phe Ser Asp His
            20                 25                 30

Gly Met His Trp Val Arg Gln Ala Pro Asp Lys Gly Leu Glu Trp Val
            35                 40                 45

Ala Val Ile Trp Tyr Asp Gly Ser His Lys Ile Tyr Ala Asp Ser Val
        50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
            85                 90                 95

Ala Arg Gly Gly Ser Leu Ala Gly Gly Ala Val Tyr Gly Thr Asp Val
            100                105                110

Trp Gly Gln Gly Thr Thr Val Thr Val Ser Ser
            115                120

<210> SEQ ID NO 235
<211> LENGTH: 123
<212> TYPE: PRT
<213> ORGANISM: Artificial Sequence
<220> FEATURE:
<223> OTHER INFORMATION: Synthetic: 1251-A03, VH

<400> SEQUENCE: 235

Gln Val Gln Leu Val Glu Ser Gly Gly Gly Val Val Gln Pro Gly Arg
1               5                  10                 15

Ser Leu Arg Leu Ser Cys Ala Ala Ser Gly Phe Ala Phe Ser Asp His
            20                 25                 30

Gly Met His Trp Val Arg Gln Ala Pro Asp Lys Gly Leu Glu Trp Val
            35                 40                 45

Ala Val Ile Trp Tyr Asp Gly Ser His Lys Ile Tyr Ala Asp Ser Val
        50                 55                 60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ser Leu Ala Gly Ala Val Tyr Gly Thr Asp Val
            100                 105                 110

Trp Gly Gln Gly Thr Thr Val Thr Val Ser Ser
            115                 120
```

<210> SEQ ID NO 236
<211> LENGTH: 123
<212> TYPE: PRT
<213> ORGANISM: Artificial Sequence
<220> FEATURE:
<223> OTHER INFORMATION: Synthetic: 1251-B08-g, VH

<400> SEQUENCE: 236

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Asn Phe Ser Asp Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Ile Ser Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Thr Val Glu His Gly Ala Val Tyr Gly Thr Asp Val
            100                 105                 110

Trp Gly Gln Gly Thr Thr Val Thr Val Ser Ser
            115                 120
```

<210> SEQ ID NO 237
<211> LENGTH: 123
<212> TYPE: PRT
<213> ORGANISM: Artificial Sequence
<220> FEATURE:
<223> OTHER INFORMATION: Synthetic: 1251-A06-g, VH

<400> SEQUENCE: 237

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Asp Phe Ser Ser Tyr
                 20                  25                  30

Gly Met His Trp Val Arg Gln Ala Pro Gly Lys Gly Leu Glu Trp Val
             35                  40                  45

Ala Val Ile Trp Asp Asp Gly Ser Asp Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
            115                 120
```

<210> SEQ ID NO 238
<211> LENGTH: 123
<212> TYPE: PRT
<213> ORGANISM: Artificial Sequence
<220> FEATURE:
<223> OTHER INFORMATION: Synthetic: 1251-B08, VH

<400> SEQUENCE: 238

Gln Val Gln Leu Val Glu Ser Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Ile Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Val Glu His Gly Ala Val Tyr Gly Thr Asp Val
            100                 105                 110

Trp Gly Gln Gly Ala Thr Val Thr Val Ser Ser
        115                 120

<210> SEQ ID NO 239
<211> LENGTH: 123
<212> TYPE: PRT
<213> ORGANISM: Artificial Sequence
<220> FEATURE:
<223> OTHER INFORMATION: Synthetic: 1251-A06, VH

<400> SEQUENCE: 239

Gln Val Gln Leu Val Glu Ser Gly Gly Val Val Gln Pro Gly Arg
1               5                   10                  15

Ser Leu Arg Leu Ser Cys Ala Ala Ser Gly Phe Asp Phe Ser Ser Tyr
            20                  25                  30

Gly Met His Trp Val Arg Gln Ala Pro Asp Lys Gly Leu Glu Trp Val
        35                  40                  45

Ala Val Ile Trp Asp Asp Gly Ser Asp Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
        115                 120

<210> SEQ ID NO 240
<211> LENGTH: 123
<212> TYPE: PRT
<213> ORGANISM: Artificial Sequence
<220> FEATURE:
<223> OTHER INFORMATION: Synthetic: 1251-B09, VH

<400> SEQUENCE: 240

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Asp Tyr
            20                  25                  30

Gly Met His Trp Val Arg Gln Ala Pro Asp Lys Gly Leu Glu Trp Val
        35                  40                  45

Ala Val Thr Trp Tyr Asp Gly Ser Arg Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val His Gly Ala Leu Tyr Gly Asn Asp Val
            100                 105                 110

Trp Gly Gln Gly Thr Thr Val Thr Val Ser Ser
        115                 120

<210> SEQ ID NO 241
<211> LENGTH: 123
<212> TYPE: PRT
<213> ORGANISM: Artificial Sequence
<220> FEATURE:
<223> OTHER INFORMATION: Synthetic: 1251-B10, VH

<400> SEQUENCE: 241

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Ser His
            20                  25                  30

Gly Met His Trp Val Arg Gln Ala Pro Asp Lys Gly Leu Glu Trp Val
        35                  40                  45

Ala Val Ile Trp His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Val Leu Gly Ala Val Tyr Gly Leu Asp Val
            100                 105                 110

Trp Gly Gln Gly Thr Thr Val Thr Val Ser Ser
        115                 120

<210> SEQ ID NO 242
<211> LENGTH: 123
<212> TYPE: PRT
<213> ORGANISM: Artificial Sequence
<220> FEATURE:
<223> OTHER INFORMATION: Synthetic: 1251-C03, VH

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Ile Lys Asn Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ala Leu Met Arg Gly Glu Phe Ser Gly His Asp Val
            100                 105                 110

Trp Gly Gln Gly Thr Thr Val Thr Val Ser Ser
            115                 120
```

<210> SEQ ID NO 243
<211> LENGTH: 123
<212> TYPE: PRT
<213> ORGANISM: Artificial Sequence
<220> FEATURE:
<223> OTHER INFORMATION: Synthetic: 1251-D02, VH

<400> SEQUENCE: 243

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Ser Phe Ala Ser His
                 20                  25                  30

Gly Met His Trp Val Arg Gln Ala Pro Asp Lys Gly Leu Glu Trp Val
             35                  40                  45

Ala Val Ile Trp Asp Asp Gly Ser Asp Arg Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Thr Arg Val Leu Gly Ala Ile His Gly Thr Asp Val
            100                 105                 110

Trp Gly Gln Gly Thr Thr Val Thr Val Ser Ser
            115                 120
```

<210> SEQ ID NO 244
<211> LENGTH: 123
<212> TYPE: PRT
<213> ORGANISM: Artificial Sequence
<220> FEATURE:
<223> OTHER INFORMATION: Synthetic: 1251-D06, VH

<400> SEQUENCE: 244

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Ser Phe Gly Ser Tyr
                 20                  25                  30

Gly Met His Trp Val Arg Gln Ala Pro Asp Lys Gly Leu Glu Trp Val
             35                  40                  45

Ala Val Val Trp Tyr Asp Gly Ser Lys Thr Ile Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Thr Leu Val Arg Gly Ala Val Tyr Gly Leu Asp Val
            100                 105                 110

Trp Gly Gln Gly Thr Thr Val Thr Val Ser Ser
```

<210> SEQ ID NO 245
<211> LENGTH: 123
<212> TYPE: PRT
<213> ORGANISM: Artificial Sequence
<220> FEATURE:
<223> OTHER INFORMATION: Synthetic: 1251-D09, VH

<400> SEQUENCE: 245

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Ala Ser Ile Arg Lys Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Val Glu Arg Gly Ala Ile Tyr Gly Thr Asp Val
            100                 105                 110

Trp Gly Gln Gly Thr Thr Val Thr Val Ser Ser
        115                 120

<210> SEQ ID NO 246
<211> LENGTH: 123
<212> TYPE: PRT
<213> ORGANISM: Artificial Sequence
<220> FEATURE:
<223> OTHER INFORMATION: Synthetic: 1251-E06, VH

<400> SEQUENCE: 246

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Lys Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Met Val Gly Gln Gly Ala Met Phe Gly Leu Asp Val
            100                 105                 110

Trp Gly Gln Gly Thr Thr Val Thr Val Ser Ser
        115                 120

<210> SEQ ID NO 247
<211> LENGTH: 123
<212> TYPE: PRT
<213> ORGANISM: Artificial Sequence
<220> FEATURE:
<223> OTHER INFORMATION: Synthetic: 1251-F06, VH

<400> SEQUENCE: 247

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Val Thr Arg Gly Val Tyr Gly Leu Asp Val
            100                 105                 110

Trp Gly Gln Gly Thr Thr Val Thr Val Ser Ser
        115                 120
```

<210> SEQ ID NO 248
<211> LENGTH: 123
<212> TYPE: PRT
<213> ORGANISM: Artificial Sequence
<220> FEATURE:
<223> OTHER INFORMATION: Synthetic: 1251-F07, VH

<400> SEQUENCE: 248

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Asp Lys Gly Leu Glu Trp Val
        35                  40                  45

Ala Val Ile Trp Asp Asp Gly Ser Asn Glu Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Arg Ile Arg Gly Leu Arg Tyr Gly Thr Asp Val
            100                 105                 110

Trp Gly Gln Gly Thr Thr Val Thr Val Ser Ser
        115                 120
```

<210> SEQ ID NO 249
<211> LENGTH: 123
<212> TYPE: PRT
<213> ORGANISM: Artificial Sequence
<220> FEATURE:
<223> OTHER INFORMATION: Synthetic: 1251-G02, VH

<400> SEQUENCE: 249

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Ile Trp His Asp Gly Ser Lys Asp Tyr Tyr Ala Asp Ser Val
```

```
                   50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Gly Gly Gln Leu Asp His Gly Ala Ile Tyr Gly Leu Asp Val
                100                 105                 110

Trp Gly Gln Gly Thr Thr Val Thr Val Ser Ser
            115                 120

<210> SEQ ID NO 250
<211> LENGTH: 121
<212> TYPE: PRT
<213> ORGANISM: Artificial Sequence
<220> FEATURE:
<223> OTHER INFORMATION: Synthetic: 1445-A03, VH

<400> SEQUENCE: 250

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser Gly Tyr
                20                  25                  30

Tyr Ile His Trp Val Arg Gln Ala Pro Gly Lys Gly Leu Glu Trp Val
            35                  40                  45

Ala Glu Ile Ser Pro Thr Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu His Gly Leu Val Tyr Gly Gln Pro Met Asp Tyr Trp Gly
                100                 105                 110

Gln Gly Thr Leu Val Thr Val Ser Ser
            115                 120

<210> SEQ ID NO 251
<211> LENGTH: 121
<212> TYPE: PRT
<213> ORGANISM: Artificial Sequence
<220> FEATURE:
<223> OTHER INFORMATION: Synthetic: 1445-B09, VH

<400> SEQUENCE: 251

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Thr Gly Thr
                20                  25                  30

Gly Ile His Trp Val Arg Gln Ala Pro Gly Lys Gly Leu Glu Trp Val
            35                  40                  45

Gly Ile Ile Thr Pro Tyr Asn Gly Thr Thr Asn Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Gly Tyr Tyr Tyr Pro Pro Phe Asp Tyr Trp Gly
                100                 105                 110
```

```
Gln Gly Thr Leu Val Thr Val Ser Ser
        115                 120
```

<210> SEQ ID NO 252
<211> LENGTH: 123
<212> TYPE: PRT
<213> ORGANISM: Artificial Sequence
<220> FEATURE:
<223> OTHER INFORMATION: Synthetic: VH11-[19], VH

<400> SEQUENCE: 252

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val Arg Gly Ala Met Tyr Gly Thr Asp Val
            100                 105                 110

Trp Gly Gln Gly Thr Thr Val Thr Val Ser Ser
        115                 120
```

<210> SEQ ID NO 253
<211> LENGTH: 124
<212> TYPE: PRT
<213> ORGANISM: Artificial Sequence
<220> FEATURE:
<223> OTHER INFORMATION: Synthetic: VH5-[7], VH

<400> SEQUENCE: 253

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Arg Tyr Tyr Gly Ser Gly Ser Tyr Ser Ser Tyr Phe Asp
            100                 105                 110

Tyr Trp Gly Gln Gly Thr Leu Val Thr Val Ser Ser
        115                 120
```

<210> SEQ ID NO 254
<211> LENGTH: 124
<212> TYPE: PRT
<213> ORGANISM: Artificial Sequence
<220> FEATURE:
<223> OTHER INFORMATION: Synthetic: VH6-[11], VH

```
<400> SEQUENCE: 254

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Ile Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Ser
            115                 120

<210> SEQ ID NO 255
<211> LENGTH: 124
<212> TYPE: PRT
<213> ORGANISM: Artificial Sequence
<220> FEATURE:
<223> OTHER INFORMATION: Synthetic: VH8-[15], VH

<400> SEQUENCE: 255

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Ser Ser
            115                 120

<210> SEQ ID NO 256
<211> LENGTH: 107
<212> TYPE: PRT
<213> ORGANISM: Artificial Sequence
<220> FEATURE:
<223> OTHER INFORMATION: Synthetic: 1337-A09-g, VL

<400> SEQUENCE: 256

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Gly Ser Trp
                20                  25                  30

Leu Ala Trp Tyr Gln Gln Lys Pro Gly Lys Ala Pro Lys Leu Leu Ile
            35                  40                  45
```

```
Tyr Ala Ala Asp Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105
```

```
<210> SEQ ID NO 257
<211> LENGTH: 107
<212> TYPE: PRT
<213> ORGANISM: Artificial Sequence
<220> FEATURE:
<223> OTHER INFORMATION: Synthetic: 1275-C10-g, VL

<400> SEQUENCE: 257

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Gly Lys Ala Pro Lys Leu Leu Ile
        35                  40                  45

Tyr Ser Ala Arg Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Leu
                85                  90                  95

Thr Phe Gly Gly Gly Thr Lys Val Glu Ile Lys
            100                 105
```

```
<210> SEQ ID NO 258
<211> LENGTH: 107
<212> TYPE: PRT
<213> ORGANISM: Artificial Sequence
<220> FEATURE:
<223> OTHER INFORMATION: Synthetic: 1275-D01, VL

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Arg Trp
            20                  25                  30

Leu Ala Trp Tyr Gln Gln Lys Pro Glu Lys Ala Pro Lys Ser Leu Ile
        35                  40                  45

Tyr Gly Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gly Gly Thr Lys Val Glu Ile Lys
            100                 105
```

```
<210> SEQ ID NO 259
<211> LENGTH: 107
<212> TYPE: PRT
<213> ORGANISM: Artificial Sequence
```

```
<220> FEATURE:
<223> OTHER INFORMATION: Synthetic: 1275-D10, VL

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Phe Ser Trp
            20                  25                  30

Leu Ala Trp Tyr Gln Gln Lys Pro Glu Lys Ala Pro Lys Ser Leu Ile
        35                  40                  45

Tyr Asn Ala Thr Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Leu
                85                  90                  95

Thr Phe Gly Gly Gly Thr Lys Val Glu Ile Lys
            100                 105

<210> SEQ ID NO 260
<211> LENGTH: 107
<212> TYPE: PRT
<213> ORGANISM: Artificial Sequence
<220> FEATURE:
<223> OTHER INFORMATION: Synthetic: 1275-G02, VL

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Leu Gly Ser Phe
            20                  25                  30

Leu Ala Trp Tyr Gln Gln Lys Pro Glu Lys Ala Pro Lys Ser Leu Ile
        35                  40                  45

Tyr Leu Gly Asn Leu Leu Gln Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ala Tyr Pro Leu
                85                  90                  95

Thr Phe Gly Gly Gly Thr Lys Val Glu Ile Lys
            100                 105

<210> SEQ ID NO 261
<211> LENGTH: 107
<212> TYPE: PRT
<213> ORGANISM: Artificial Sequence
<220> FEATURE:
<223> OTHER INFORMATION: Synthetic: 1337-A04, VL

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Arg Trp
            20                  25                  30

Val Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Thr Tyr Pro Leu
                 85                  90                  95

Thr Phe Gly Gly Gly Thr Lys Val Glu Ile Lys
            100                 105

<210> SEQ ID NO 262
<211> LENGTH: 107
<212> TYPE: PRT
<213> ORGANISM: Artificial Sequence
<220> FEATURE:
<223> OTHER INFORMATION: Synthetic: 1337-A05, VL

<400> SEQUENCE: 262

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Gly Arg Trp
                 20                  25                  30

Val Ala Trp Tyr Gln Gln Lys Pro Glu Lys Ala Pro Lys Ser Leu Ile
             35                  40                  45

Tyr Gly Ala Asp Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 263
<211> LENGTH: 107
<212> TYPE: PRT
<213> ORGANISM: Artificial Sequence
<220> FEATURE:
<223> OTHER INFORMATION: Synthetic: 1337-A06, VL

<400> SEQUENCE: 263

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Ser Trp
                 20                  25                  30

Val Ala Trp Tyr Gln Gln Lys Pro Glu Lys Ala Pro Lys Ser Leu Ile
             35                  40                  45

Tyr Gly Ala Asp Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 264
<211> LENGTH: 107
<212> TYPE: PRT
<213> ORGANISM: Artificial Sequence
<220> FEATURE:
<223> OTHER INFORMATION: Synthetic: 1337-A07-g, VL
```

-continued

<400> SEQUENCE: 264

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105

<210> SEQ ID NO 265
<211> LENGTH: 107
<212> TYPE: PRT
<213> ORGANISM: Artificial Sequence
<220> FEATURE:
<223> OTHER INFORMATION: Synthetic: 1337-A07, VL

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Glu Lys Ala Pro Lys Ser Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
                85                  90                  95

Thr Phe Gly Gly Gly Thr Lys Val Glu Ile Lys
            100                 105

<210> SEQ ID NO 266
<211> LENGTH: 107
<212> TYPE: PRT
<213> ORGANISM: Artificial Sequence
<220> FEATURE:
<223> OTHER INFORMATION: Synthetic: 1337-A08, VL

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Trp
            20                  25                  30

Val Ala Trp Tyr Gln Gln Lys Pro Glu Lys Ala Pro Lys Ser Leu Ile
        35                  40                  45

Tyr Ala Ser Asp Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
            85                  90                  95

Thr Phe Gly Gly Gly Thr Lys Val Glu Ile Lys
            100                 105

<210> SEQ ID NO 267
<211> LENGTH: 107
<212> TYPE: PRT
<213> ORGANISM: Artificial Sequence
<220> FEATURE:
<223> OTHER INFORMATION: Synthetic: 1337-A09, VL

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Glu Lys Ala Pro Lys Ser Leu Ile
        35                  40                  45

Tyr Ala Ala Asp Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Thr Tyr Pro Leu
            85                  90                  95

Thr Phe Gly Gly Gly Thr Lys Val Glu Ile Lys
            100                 105

<210> SEQ ID NO 268
<211> LENGTH: 107
<212> TYPE: PRT
<213> ORGANISM: Artificial Sequence
<220> FEATURE:
<223> OTHER INFORMATION: Synthetic: 1275-C10, VL

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Glu Lys Ala Pro Lys Ser Leu Ile
        35                  40                  45

Tyr Ser Ala Arg Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Leu
            85                  90                  95

Thr Phe Gly Gly Gly Thr Lys Val Glu Ile Lys
            100                 105

<210> SEQ ID NO 269
<211> LENGTH: 107
<212> TYPE: PRT
<213> ORGANISM: Artificial Sequence
<220> FEATURE:
<223> OTHER INFORMATION: Synthetic: 1337-A10, VL

<400> SEQUENCE: 269

Asp Ile Gln Met Thr Gln Ser Pro Ser Ser Leu Ser Ala Ser Val Gly

```
                1               5                  10                 15
Asp Arg Val Thr Ile Thr Cys Arg Ala Ser Gln Gly Ile Ser Ser Trp
                    20                  25                 30

Val Ala Trp Tyr Gln Gln Lys Pro Glu Lys Ala Pro Lys Ser Leu Ile
            35                  40                 45

Tyr Gly Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                    85                  90                  95

Thr Phe Gly Gly Gly Thr Lys Val Glu Ile Lys
                100                 105

<210> SEQ ID NO 270
<211> LENGTH: 107
<212> TYPE: PRT
<213> ORGANISM: Artificial Sequence
<220> FEATURE:
<223> OTHER INFORMATION: Synthetic: 1337-A10-g, VL

<400> SEQUENCE: 270

Asp Ile Gln Met Thr Gln Ser Pro Ser Ser Val Ser Ala Ser Val Gly
1               5                  10                 15

Asp Arg Val Thr Ile Thr Cys Arg Ala Ser Gln Gly Ile Ser Ser Trp
                    20                  25                 30

Val Ala Trp Tyr Gln Gln Lys Pro Gly Lys Ala Pro Lys Leu Leu Ile
            35                  40                 45

Tyr Gly Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                    85                  90                  95

Thr Phe Gly Gly Gly Thr Lys Val Glu Ile Lys
                100                 105

<210> SEQ ID NO 271
<211> LENGTH: 107
<212> TYPE: PRT
<213> ORGANISM: Artificial Sequence
<220> FEATURE:
<223> OTHER INFORMATION: Synthetic: VL5-[23], VL

<400> SEQUENCE: 271

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Gly Ile Ser Ser Trp
                    20                  25                 30

Leu Ala Trp Phe Gln Gln Lys Pro Glu Lys Ala Pro Lys Ser Leu Ile
            35                  40                 45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                    85                  90                  95
```

```
Thr Phe Gly Gly Gly Thr Lys Val Glu Ile Lys
            100                 105

<210> SEQ ID NO 272
<211> LENGTH: 107
<212> TYPE: PRT
<213> ORGANISM: Artificial Sequence
<220> FEATURE:
<223> OTHER INFORMATION: Synthetic: VL6-[26], VL

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 273
<211> LENGTH: 120
<212> TYPE: PRT
<213> ORGANISM: Artificial Sequence
<220> FEATURE:
<223> OTHER INFORMATION: Synthetic: 1193-B06, VH

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Met Ser Trp Val Arg Gln Ala Pro Gly Lys Gly Leu Glu Trp Val
        35                  40                  45

Gly Ile Ile Tyr Gly Thr Ser Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Met Ser Gly Ser Arg Gly Phe Asp Tyr Trp Gly Gln
            100                 105                 110

Gly Thr Leu Val Thr Val Ser Ser
        115                 120

<210> SEQ ID NO 274
<211> LENGTH: 120
<212> TYPE: PRT
<213> ORGANISM: Artificial Sequence
<220> FEATURE:
<223> OTHER INFORMATION: Synthetic: 1193-C08, VH

<400> SEQUENCE: 274

Glu Val Gln Leu Leu Glu Ser Gly Gly Gly Leu Val Gln Pro Gly Gly
1               5                   10                  15
```

```
                1               5                  10                 15
Ser Leu Arg Leu Ser Cys Ala Ala Ser Gly Phe Thr Phe Asn Asn Asn
                20                  25                  30

Trp Met Ser Trp Val Arg Gln Ala Pro Gly Lys Gly Leu Glu Trp Val
        35                  40                  45

Gly Ile Ile Asn Gly Asp Asp Gly Tyr Thr Tyr Tyr Ala Asp Arg Val
        50                  55                  60

Lys Gly Arg Phe Thr Ile Ile Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Leu Gly Arg Pro Arg Arg Phe Asp Tyr Trp Gly Gln
                100                 105                 110

Gly Thr Leu Val Thr Val Ser Ser
                115                 120

<210> SEQ ID NO 275
<211> LENGTH: 120
<212> TYPE: PRT
<213> ORGANISM: Artificial Sequence
<220> FEATURE:
<223> OTHER INFORMATION: Synthetic: 1193-E06b, VH

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Thr
                20                  25                  30

Asp Met Ser Trp Val Arg Gln Ala Pro Gly Lys Gly Leu Glu Trp Val
        35                  40                  45

Gly Ile Ile Asn Gly Ser Gly Gly Ala Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Glu Asn Glu Trp Glu Val Ser Met Asp Tyr Trp Gly Gln
                100                 105                 110

Gly Thr Leu Val Thr Val Ser Ser
                115                 120

<210> SEQ ID NO 276
<211> LENGTH: 120
<212> TYPE: PRT
<213> ORGANISM: Artificial Sequence
<220> FEATURE:
<223> OTHER INFORMATION: Synthetic: 1193-H04b, VH

<400> SEQUENCE: 276

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
                20                  25                  30

Trp Met Ser Trp Val Arg Gln Ala Pro Gly Lys Gly Leu Glu Trp Val
        35                  40                  45

Gly Ile Ile Asn Gly Tyr Asn Gly Ile Thr Tyr Tyr Ala Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Ser Ala Pro Gly Ala Arg Arg Phe Asp Tyr Trp Gly Gln
            100                 105                 110

Gly Thr Leu Val Thr Val Ser Ser
        115                 120
```

<210> SEQ ID NO 277
<211> LENGTH: 120
<212> TYPE: PRT
<213> ORGANISM: Artificial Sequence
<220> FEATURE:
<223> OTHER INFORMATION: Synthetic: 1447-D11, VH

<400> SEQUENCE: 277

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Thr
             20                  25                  30

Asp Met Ser Trp Val Arg Gln Ala Pro Gly Lys Gly Leu Glu Trp Val
         35                  40                  45

Gly Val Ile Asn Gly Ser Gly Gly Ser Ser Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Glu Thr Glu Trp Glu Val Ser Leu Asp Tyr Trp Gly Gln
            100                 105                 110

Gly Thr Leu Val Thr Val Ser Ser
        115                 120
```

<210> SEQ ID NO 278
<211> LENGTH: 120
<212> TYPE: PRT
<213> ORGANISM: Artificial Sequence
<220> FEATURE:
<223> OTHER INFORMATION: Synthetic: 1447-E08, VH

<400> SEQUENCE: 278

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asp Thr
             20                  25                  30

Asp Met Ser Trp Val Arg Gln Ala Pro Gly Lys Gly Leu Glu Trp Val
         35                  40                  45

Gly Met Ile Asn Gly Ala Gly Gly Ala Ser Phe Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Glu Asn Gln Trp Glu Val Thr Phe Asp Tyr Trp Gly Gln
            100                 105                 110

Gly Thr Leu Val Thr Val Ser Ser
        115                 120
```

<210> SEQ ID NO 279
<211> LENGTH: 120
<212> TYPE: PRT
<213> ORGANISM: Artificial Sequence
<220> FEATURE:
<223> OTHER INFORMATION: Synthetic: 1447-F11, VH

<400> SEQUENCE: 279

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Asp Asn Thr
            20                  25                  30

Asp Met Ser Trp Val Arg Gln Ala Pro Gly Lys Gly Leu Glu Trp Val
        35                  40                  45

Gly Ile Ile Asn Gly Ser Gly Val Thr Asn Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Ser Glu Trp Glu Val Ser Leu Asp Tyr Trp Gly Gln
            100                 105                 110

Gly Thr Leu Val Thr Val Ser Ser
        115                 120

<210> SEQ ID NO 280
<211> LENGTH: 120
<212> TYPE: PRT
<213> ORGANISM: Artificial Sequence
<220> FEATURE:
<223> OTHER INFORMATION: Synthetic: 1447-G01, VH

<400> SEQUENCE: 280

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Ser
            20                  25                  30

Asp Met Ser Trp Val Arg Gln Ala Pro Gly Lys Gly Leu Glu Trp Val
        35                  40                  45

Gly Ile Ile Asn Gly Ser Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Glu Asn Glu Met Glu Val Ser Met Asp Tyr Trp Gly Gln
            100                 105                 110

Gly Thr Leu Val Thr Val Ser Ser
        115                 120

<210> SEQ ID NO 281
<211> LENGTH: 108
<212> TYPE: PRT
<213> ORGANISM: Artificial Sequence
<220> FEATURE:
<223> OTHER INFORMATION: Synthetic: 1193-B06, VL

<400> SEQUENCE: 281

```
Glu Ile Val Leu Thr Gln Ser Pro Gly Thr Leu Ser Leu Ser Pro Gly
1               5                   10                  15

Glu Arg Ala Thr Leu Ser Cys Arg Ala Gly Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys
            100                 105
```

<210> SEQ ID NO 282
<211> LENGTH: 108
<212> TYPE: PRT
<213> ORGANISM: Artificial Sequence
<220> FEATURE:
<223> OTHER INFORMATION: Synthetic: 1193-C08, VL

<400> SEQUENCE: 282

```
Glu Ile Val Leu Thr Gln Ser Pro Gly Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys Gln Gln His Tyr Thr Thr Pro
                85                  90                  95

Pro Thr Phe Gly Gln Gly Thr Lys Val Glu Ile Lys
            100                 105
```

<210> SEQ ID NO 283
<211> LENGTH: 108
<212> TYPE: PRT
<213> ORGANISM: Artificial Sequence
<220> FEATURE:
<223> OTHER INFORMATION: Synthetic: 1193-E06b, VL

<400> SEQUENCE: 283

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Tyr Thr Thr Pro
                85                  90                  95
```

```
Pro Thr Phe Gly Gln Gly Thr Lys Val Glu Ile Lys
            100                 105
```

<210> SEQ ID NO 284
<211> LENGTH: 107
<212> TYPE: PRT
<213> ORGANISM: Artificial Sequence
<220> FEATURE:
<223> OTHER INFORMATION: Synthetic: 1193-H04b, VL

<400> SEQUENCE: 284

```
Glu Ile Val Leu Thr Gln Ser Pro Gly Thr Leu Ser Leu Ser Pro Gly
1               5                   10                  15

Glu Ala Thr Leu Ser Cys Arg Ala Ser Gln Ser Val Ser Ser Ser Tyr
            20                  25                  30

Leu Ala Trp Tyr Gln Gln Arg Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 285
<211> LENGTH: 108
<212> TYPE: PRT
<213> ORGANISM: Artificial Sequence
<220> FEATURE:
<223> OTHER INFORMATION: Synthetic: 1447-D11, VL

<400> SEQUENCE: 285

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Asn Gln Pro Thr Pro
                85                  90                  95

Pro Thr Phe Gly Gln Gly Thr Lys Val Glu Ile Lys
            100                 105
```

<210> SEQ ID NO 286
<211> LENGTH: 108
<212> TYPE: PRT
<213> ORGANISM: Artificial Sequence
<220> FEATURE:
<223> OTHER INFORMATION: Synthetic: 1447-E08, VL

<400> SEQUENCE: 286

```
Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Arg Val Ala Gly Ile
            20                  25                  30

Asp Leu Ser Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asn Thr Thr Pro
                85                  90                  95

Pro Thr Phe Gly Gln Gly Thr Lys Val Glu Ile Lys
            100                 105

<210> SEQ ID NO 287
<211> LENGTH: 108
<212> TYPE: PRT
<213> ORGANISM: Artificial Sequence
<220> FEATURE:
<223> OTHER INFORMATION: Synthetic: 1447-F11, VL

<400> SEQUENCE: 287

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gln Thr Ala Pro
                85                  90                  95

Pro Thr Phe Gly Gln Gly Thr Lys Val Glu Ile Lys
            100                 105

<210> SEQ ID NO 288
<211> LENGTH: 108
<212> TYPE: PRT
<213> ORGANISM: Artificial Sequence
<220> FEATURE:
<223> OTHER INFORMATION: Synthetic: 1447-G01, VL

<400> SEQUENCE: 288

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Glu Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gln Cys Ser Trp Pro
                85                  90                  95

Pro Thr Phe Gly Gln Gly Thr Lys Val Glu Ile Lys
            100                 105
```

<210> SEQ ID NO 289
<211> LENGTH: 238
<212> TYPE: PRT
<213> ORGANISM: Artificial Sequence
<220> FEATURE:
<223> OTHER INFORMATION: Synthetic: IgG1 Fc from scFv-Fc

<400> SEQUENCE: 289

Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 290
<211> LENGTH: 107
<212> TYPE: PRT
<213> ORGANISM: Artificial Sequence
<220> FEATURE:
<223> OTHER INFORMATION: Synthetic: Trastuzumab LC, LC

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro

```
                65                  70                  75                  80
Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys
            100                 105

<210> SEQ ID NO 291
<211> LENGTH: 454
<212> TYPE: PRT
<213> ORGANISM: Artificial Sequence
<220> FEATURE:
<223> OTHER INFORMATION: Synthetic: 1251-A06-(wt), HC

<400> SEQUENCE: 291

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asp Phe Ser Ser
            20                  25                  30

Tyr Gly Met His Trp Val Arg Gln Ala Pro Asp Lys Gly Leu Glu Trp
        35                  40                  45

Val Ala Val Ile Trp Asp Asp Gly Ser Asp Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Ile His Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Glu Asp Tyr Phe Pro Glu Pro
145                 150                 155                 160

Ala Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
```

```
              325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
            405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Lys
            450

<210> SEQ ID NO 292
<211> LENGTH: 454
<212> TYPE: PRT
<213> ORGANISM: Artificial Sequence
<220> FEATURE:
<223> OTHER INFORMATION: Synthetic: 1251-A06-(g), HC

<400> SEQUENCE: 292

Met Gln Val Gln Leu Val Glu Ser Gly Gly Gly Val Val Gln Pro Gly
1               5                   10                  15
Arg Ser Leu Arg Leu Ser Cys Ala Ala Ser Gly Phe Asp Phe Ser Ser
            20                  25                  30
Tyr Gly Met His Trp Val Arg Gln Ala Pro Gly Lys Gly Leu Glu Trp
            35                  40                  45
Val Ala Val Ile Trp Asp Asp Gly Ser Asp Arg Tyr Tyr Ala Asp Ser
            50                  55                  60
Val Lys Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
            85                  90                  95
Cys Ala Arg Gly Gly Thr Arg Val Leu Gly Ala Ile His Gly Thr Asp
            100                 105                 110
Val Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
            130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
            165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Lys Val Glu Pro
            210                 215                 220
Lys Ser Cys Asp Lys Thr His Thr Cys Pro Pro Cys Pro Ala Pro Glu
```

-continued

```
               225                 230                 235                 240
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
        450

<210> SEQ ID NO 293
<211> LENGTH: 454
<212> TYPE: PRT
<213> ORGANISM: Artificial Sequence
<220> FEATURE:
<223> OTHER INFORMATION: Synthetic: 1251-B08-(wt), HC

<400> SEQUENCE: 293

Met Gln Val Gln Leu Val Glu Ser Gly Gly Val Val Gln Pro Gly
1               5                   10                  15

Arg Ser Leu Arg Leu Ser Cys Ala Ala Ser Gly Phe Asn Phe Ser Asp
                20                  25                  30

Tyr Gly Met His Trp Val Arg Gln Ala Pro Asp Lys Gly Leu Glu Trp
            35                  40                  45

Val Ala Val Ile Trp Tyr Asp Gly Ser Ile Ser Tyr Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Val Glu His Gly Ala Val Tyr Gly Thr Asp
                100                 105                 110

Val Trp Gly Gln Gly Ala Thr Val Thr Val Ser Ser Ala Ser Thr Lys
            115                 120                 125

Gly Pro Ser Val Phe Pro Leu Ala Pro Ser Ser Lys Ser Thr Ser Gly
```

```
            130                 135                 140
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 294
<211> LENGTH: 454
<212> TYPE: PRT
<213> ORGANISM: Artificial Sequence
<220> FEATURE:
<223> OTHER INFORMATION: Synthetic: 1251-B08-(g), HC

<400> SEQUENCE: 294

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Asp
            20                  25                  30

Tyr Gly Met His Trp Val Arg Gln Ala Pro Gly Lys Gly Leu Glu Trp
```

```
                    35                  40                  45
Val Ala Val Ile Trp Tyr Asp Gly Ser Ile Ser Tyr Tyr Ala Asp Ser
 50                  55                  60
Val Lys Gly Arg Phe Thr Ile Ser Arg Asp Asn Ser Lys Asn Thr Leu
 65                  70                  75                  80
Tyr Leu Gln Met Asn Ser Leu Arg Ala Glu Asp Thr Ala Val Tyr Tyr
                 85                  90                  95
Cys Ala Arg Gly Gly Thr Val Glu His Gly Ala Val Tyr Gly Thr Asp
                100                 105                 110
Val Trp Gly Gln Gly Thr Thr Val Thr Val Ser Ser Ala Ser Thr Lys
                115                 120                 125
Gly Pro Ser Val Phe Pro Leu Ala Pro Ser Ser Lys Ser Thr Ser Gly
                130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
                195                 200                 205
Val Asn His Lys Pro Ser Asn Thr Lys Val Asp Lys Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
                275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
                355                 360                 365
Gln Val Ser Leu Thr Cys Leu Val Lys Gly Phe Tyr Pro Ser Asp Ile
                370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
                435                 440                 445
Ser Leu Ser Pro Gly Lys
                450
```

-continued

```
<210> SEQ ID NO 295
<211> LENGTH: 215
<212> TYPE: PRT
<213> ORGANISM: Artificial Sequence
<220> FEATURE:
<223> OTHER INFORMATION: Synthetic: 1275-C10-(wt), LC

<400> SEQUENCE: 295

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Val Ser Ser
            20                  25                  30

Trp Leu Ala Trp Tyr Gln Gln Lys Pro Glu Lys Ala Pro Lys Ser Leu
        35                  40                  45

Ile Tyr Ser Ala Arg Tyr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Leu Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 296
<211> LENGTH: 215
<212> TYPE: PRT
<213> ORGANISM: Artificial Sequence
<220> FEATURE:
<223> OTHER INFORMATION: Synthetic: 1275-C10-(g), LC

<400> SEQUENCE: 296

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Val Ser Ser
            20                  25                  30

Trp Leu Ala Trp Tyr Gln Gln Lys Pro Gly Lys Ala Pro Lys Leu Leu
        35                  40                  45

Ile Tyr Ser Ala Arg Tyr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Leu Tyr Pro
```

```
                85                  90                  95
Leu Thr Phe Gly Gly Gly Thr Lys Val Glu Ile Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
                195                 200                 205
Ser Phe Asn Arg Gly Glu Cys
                210                 215
```

<210> SEQ ID NO 297
<211> LENGTH: 215
<212> TYPE: PRT
<213> ORGANISM: Artificial Sequence
<220> FEATURE:
<223> OTHER INFORMATION: Synthetic: 1337-A07-(wt), LC

<400> SEQUENCE: 297

```
Met Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Gly Ile Ser Ser
                20                  25                  30
Trp Val Ala Trp Tyr Gln Gln Lys Pro Glu Lys Ala Pro Lys Ser Leu
            35                  40                  45
Ile Tyr Gly Ala Ser Arg Leu Gln Ser Gly Val Pro Ser Arg Phe Ser
        50                  55                  60
Gly Ser Gly Ser Gly Thr Asp Phe Thr Leu Thr Ile Ser Ser Leu Gln
65                  70                  75                  80
Pro Glu Asp Phe Ala Thr Tyr Tyr Cys Gln Gln Tyr His Thr Tyr Pro
                85                  90                  95
Leu Thr Phe Gly Gly Gly Thr Lys Val Glu Ile Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
                195                 200                 205
Ser Phe Asn Arg Gly Glu Cys
                210                 215
```

```
<210> SEQ ID NO 298
<211> LENGTH: 215
<212> TYPE: PRT
<213> ORGANISM: Artificial Sequence
<220> FEATURE:
<223> OTHER INFORMATION: Synthetic: 1337-A07-(g), LC

<400> SEQUENCE: 298
```

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Gly Lys Ala Pro Lys Leu Leu
        35                  40                  45

Ile Tyr Gly Ala Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 299
<211> LENGTH: 215
<212> TYPE: PRT
<213> ORGANISM: Artificial Sequence
<220> FEATURE:
<223> OTHER INFORMATION: Synthetic: 1337-A09-(wt), LC

<400> SEQUENCE: 299
```

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Gly Ser
            20                  25                  30

Trp Leu Ala Trp Tyr Gln Gln Lys Pro Glu Lys Ala Pro Lys Ser Leu
        35                  40                  45

Ile Tyr Ala Ala Asp Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

-continued

```
Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 300
<211> LENGTH: 215
<212> TYPE: PRT
<213> ORGANISM: Artificial Sequence
<220> FEATURE:
<223> OTHER INFORMATION: Synthetic: 1337-A09-(g), LC

<400> SEQUENCE: 300

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Gly Ser
            20                  25                  30

Trp Leu Ala Trp Tyr Gln Gln Lys Pro Gly Lys Ala Pro Lys Leu Leu
        35                  40                  45

Ile Tyr Ala Ala Asp Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr His Thr Tyr Pro
                85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 301
<211> LENGTH: 215
```

```
<212> TYPE: PRT
<213> ORGANISM: Artificial Sequence
<220> FEATURE:
<223> OTHER INFORMATION: Synthetic: 1337-A10-(wt), LC

<400> SEQUENCE: 301
```

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Glu Lys Ala Pro Lys Ser Leu
        35                  40                  45

Ile Tyr Gly Ser Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Thr Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 302
<211> LENGTH: 215
<212> TYPE: PRT
<213> ORGANISM: Artificial Sequence
<220> FEATURE:
<223> OTHER INFORMATION: Synthetic: 1337-A10-(g), LC

<400> SEQUENCE: 302
```

Met Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
            20                  25                  30

Trp Val Ala Trp Tyr Gln Gln Lys Pro Gly Lys Ala Pro Lys Leu Leu
        35                  40                  45

Ile Tyr Gly Ser Ser Arg Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Thr Tyr Pro
                85                  90                  95

Leu Thr Phe Gly Gly Gly Thr Lys Val Glu Ile Lys Arg Thr Val Ala
            100                 105                 110

```
Ala Pro Ser Val Phe Ile Phe Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 303
<211> LENGTH: 9
<212> TYPE: PRT
<213> ORGANISM: Artificial Sequence
<220> FEATURE:
<223> OTHER INFORMATION: Synthetic: C-term His Tag, Tag

<400> SEQUENCE: 303

Gly Gly Ser His His His His His
1               5

<210> SEQ ID NO 304
<211> LENGTH: 330
<212> TYPE: PRT
<213> ORGANISM: Artificial Sequence
<220> FEATURE:
<223> OTHER INFORMATION: Synthetic: HC Constant

<400> SEQUENCE: 304

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                180             185             190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 305
<211> LENGTH: 107
<212> TYPE: PRT
<213> ORGANISM: Artificial Sequence
<220> FEATURE:
<223> OTHER INFORMATION: Synthetic: LC Constant

<400> SEQUENCE: 305

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 306
<211> LENGTH: 454
<212> TYPE: PRT
<213> ORGANISM: Artificial Sequence
<220> FEATURE:
<223> OTHER INFORMATION: Synthetic: 1251-A03, HC

<400> SEQUENCE: 306

Met Gln Val Gln Leu Val Glu Ser Gly Gly Val Val Gln Pro Gly
1               5                   10                  15

Arg Ser Leu Arg Leu Ser Cys Ala Ala Ser Gly Phe Ala Phe Ser Asp
            20                  25                  30

His Gly Met His Trp Val Arg Gln Ala Pro Asp Lys Gly Leu Glu Trp
        35                  40                  45
```

```
Val Ala Val Ile Trp Tyr Asp Gly Ser His Lys Ile Tyr Ala Asp Ser
 50                  55                  60
Val Lys Gly Arg Phe Thr Ile Ser Arg Asp Asn Ser Lys Asn Thr Leu
 65                  70                  75                  80
Tyr Leu Gln Met Asn Ser Leu Arg Ala Glu Asp Thr Ala Val Tyr Tyr
                 85                  90                  95
Cys Ala Arg Gly Gly Ser Leu Ala Gly Gly Ala Val Tyr Gly Thr Asp
            100                 105                 110
Val Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Arg Thr Tyr Ile Cys Asn
            195                 200                 205
Val Asn His Lys Pro Ser Asn Thr Lys Val Asp Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
            290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Lys
450
```

<210> SEQ ID NO 307
<211> LENGTH: 454
<212> TYPE: PRT
<213> ORGANISM: Artificial Sequence
<220> FEATURE:
<223> OTHER INFORMATION: Synthetic: 1251-B09, HC

<400> SEQUENCE: 307

```
Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Asp
            20                  25                  30

Tyr Gly Met His Trp Val Arg Gln Ala Pro Asp Lys Gly Leu Glu Trp
        35                  40                  45

Val Ala Val Thr Trp Tyr Asp Gly Ser Arg Glu Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Leu Val His Gly Ala Leu Tyr Gly Asn Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
```

```
                    370                 375                 380
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
                450

<210> SEQ ID NO 308
<211> LENGTH: 454
<212> TYPE: PRT
<213> ORGANISM: Artificial Sequence
<220> FEATURE:
<223> OTHER INFORMATION: Synthetic: 1251-B10, HC

<400> SEQUENCE: 308

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asn Phe Ser Ser
                20                  25                  30

His Gly Met His Trp Val Arg Gln Ala Pro Asp Lys Gly Leu Glu Trp
                35                  40                  45

Val Ala Val Ile Trp His Asp Gly Ser Asp Lys Tyr Tyr Ala Asp Ser
            50                  55                  60

Val Lys Gly Arg Phe Thr Ile Ser Arg Asp Asn Ser Lys Asn Thr Leu
65              70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Val Tyr Gly Leu Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
```

```
                275                 280                 285
Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 309
<211> LENGTH: 238
<212> TYPE: PRT
<213> ORGANISM: Artificial Sequence
<220> FEATURE:
<223> OTHER INFORMATION: Synthetic: Fc Constant, Fc Constant

<400> SEQUENCE: 309

Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
```

```
                180                 185                 190
Gly Ser Phe Phe Leu Tyr Ser Lys Leu Thr Val Asp Lys Ser Arg Trp
            195                 200                 205

Gln Gln Gly Asn Val Phe Ser Cys Ser Val Met His Glu Ala Leu His
            210                 215                 220

Asn His Tyr Thr Gln Lys Ser Leu Ser Leu Ser Pro Gly Lys
225                 230                 235

<210> SEQ ID NO 310
<211> LENGTH: 454
<212> TYPE: PRT
<213> ORGANISM: Artificial Sequence
<220> FEATURE:
<223> OTHER INFORMATION: Synthetic: 1251-A06 HC, HC

<400> SEQUENCE: 310

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Asp Phe Ser Ser
            20                  25                  30

Tyr Gly Met His Trp Val Arg Gln Ala Pro Asp Lys Gly Leu Glu Trp
        35                  40                  45

Val Ala Val Ile Trp Asp Asp Gly Ser Asp Arg Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Val Leu Gly Ala Ile His Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
```

```
                305                 310                 315                 320
Leu Asn Gly Lys Glu Tyr Lys Cys Lys Val Ser Asn Lys Ala Leu Pro
                    325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 311
<211> LENGTH: 454
<212> TYPE: PRT
<213> ORGANISM: Artificial Sequence
<220> FEATURE:
<223> OTHER INFORMATION: Synthetic: 1251-F07 HC, HC

<400> SEQUENCE: 311

Met Gln Val Gln Leu Val Glu Ser Gly Gly Val Val Gln Pro Gly
1               5                   10                  15

Arg Ser Leu Arg Leu Ser Cys Ala Ala Ser Gly Phe Thr Phe Ser Ser
                20                  25                  30

His Gly Met His Trp Val Arg Gln Ala Pro Asp Lys Gly Leu Glu Trp
            35                  40                  45

Val Ala Val Ile Trp Asp Asp Gly Ser Asn Glu Val Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Thr Arg Ile Arg Gly Leu Arg Tyr Gly Thr Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
```

```
                 210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 312
<211> LENGTH: 14
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (3)..(3)
<223> OTHER INFORMATION: X is T, S, Q, M, or A
<220> FEATURE:
<221> NAME/KEY: misc_feature
<222> LOCATION: (4)..(4)
<223> OTHER INFORMATION: X is R, L, or V
<220> FEATURE:
<221> NAME/KEY: misc_feature
<222> LOCATION: (5)..(5)
<223> OTHER INFORMATION: X is V, E, A, G, I, D, or M
<220> FEATURE:
<221> NAME/KEY: misc_feature
<222> LOCATION: (6)..(6)
<223> OTHER INFORMATION: X is R, L, H, G, Q, or T
<220> FEATURE:
<221> NAME/KEY: misc_feature
<222> LOCATION: (7)..(7)
<223> OTHER INFORMATION: X is G or R
<220> FEATURE:
<221> NAME/KEY: misc_feature
<222> LOCATION: (8)..(8)
<223> OTHER INFORMATION: X is A, L, E, or G
<220> FEATURE:
```

```
<221> NAME/KEY: misc_feature
<222> LOCATION: (9)..(9)
<223> OTHER INFORMATION: X is V, I, M, F, R, or L
<220> FEATURE:
<221> NAME/KEY: misc_feature
<222> LOCATION: (10)..(10)
<223> OTHER INFORMATION: X is Y, H, F, or S
<220> FEATURE:
<221> NAME/KEY: misc_feature
<222> LOCATION: (12)..(12)
<223> OTHER INFORMATION: X is T, L, H, or N

<400> SEQUENCE: 312

Gly Gly Xaa Xaa Xaa Xaa Xaa Xaa Xaa Xaa Gly Xaa Asp Val
1               5                   10

<210> SEQ ID NO 313
<211> LENGTH: 6
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(1)
<223> OTHER INFORMATION: X is W or S
<220> FEATURE:
<221> NAME/KEY: misc_feature
<222> LOCATION: (2)..(2)
<223> OTHER INFORMATION: X is Y, D, or H
<220> FEATURE:
<221> NAME/KEY: misc_feature
<222> LOCATION: (4)..(4)
<223> OTHER INFORMATION: X is G or A
<220> FEATURE:
<221> NAME/KEY: misc_feature
<222> LOCATION: (6)..(6)
<223> OTHER INFORMATION: X is N, I, D, H, K, or R

<400> SEQUENCE: 313

Xaa Xaa Asp Xaa Ser Xaa
1               5

<210> SEQ ID NO 314
<211> LENGTH: 7
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (3)..(3)
<223> OTHER INFORMATION: X is T, N, S, A, or D
<220> FEATURE:
<221> NAME/KEY: misc_feature
<222> LOCATION: (5)..(5)
<223> OTHER INFORMATION: X is S, G, D, or A
<220> FEATURE:
<221> NAME/KEY: misc_feature
<222> LOCATION: (6)..(6)
<223> OTHER INFORMATION: X is S or D
<220> FEATURE:
<221> NAME/KEY: misc_feature
<222> LOCATION: (7)..(7)
<223> OTHER INFORMATION: X is Y, H, or F

<400> SEQUENCE: 314

Gly Phe Xaa Phe Xaa Xaa Xaa
1               5

<210> SEQ ID NO 315
<211> LENGTH: 17
<212> TYPE: PRT
```

<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (2)..(2)
<223> OTHER INFORMATION: X is I, T, or V
<220> FEATURE:
<221> NAME/KEY: misc_feature
<222> LOCATION: (3)..(3)
<223> OTHER INFORMATION: X is W or S
<220> FEATURE:
<221> NAME/KEY: misc_feature
<222> LOCATION: (4)..(4)
<223> OTHER INFORMATION: X is Y, D, or H
<220> FEATURE:
<221> NAME/KEY: misc_feature
<222> LOCATION: (6)..(6)
<223> OTHER INFORMATION: X is G or A
<220> FEATURE:
<221> NAME/KEY: misc_feature
<222> LOCATION: (8)..(8)
<223> OTHER INFORMATION: X is N, I , D, H, K, or R
<220> FEATURE:
<221> NAME/KEY: misc_feature
<222> LOCATION: (9)..(9)
<223> OTHER INFORMATION: X is K, E, R, S, T, or D
<220> FEATURE:
<221> NAME/KEY: misc_feature
<222> LOCATION: (10)..(10)
<223> OTHER INFORMATION: X is Y, I, V, K, or N
<220> FEATURE:
<221> NAME/KEY: misc_feature
<222> LOCATION: (13)..(13)
<223> OTHER INFORMATION: X is D or G

<400> SEQUENCE: 315

Val Xaa Xaa Xaa Asp Xaa Ser Xaa Xaa Xaa Tyr Ala Xaa Ser Val Lys
1               5                   10                  15

Gly

<210> SEQ ID NO 316
<211> LENGTH: 17
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (2)..(2)
<223> OTHER INFORMATION: X is I, T, or V
<220> FEATURE:
<221> NAME/KEY: misc_feature
<222> LOCATION: (4)..(4)
<223> OTHER INFORMATION: X is Y, D, or H
<220> FEATURE:
<221> NAME/KEY: misc_feature
<222> LOCATION: (6)..(6)
<223> OTHER INFORMATION: X is G or A
<220> FEATURE:
<221> NAME/KEY: misc_feature
<222> LOCATION: (8)..(8)
<223> OTHER INFORMATION: X is N, I , D, H, K, or R
<220> FEATURE:
<221> NAME/KEY: misc_feature
<222> LOCATION: (9)..(9)
<223> OTHER INFORMATION: X is K, E, R, S, T, or D
<220> FEATURE:
<221> NAME/KEY: misc_feature
<222> LOCATION: (10)..(10)
<223> OTHER INFORMATION: X is Y, I, V, K, or N
<220> FEATURE:
<221> NAME/KEY: misc_feature
<222> LOCATION: (13)..(13)
<223> OTHER INFORMATION: X is D or G

```
<400> SEQUENCE: 316

Val Xaa Trp Xaa Asp Xaa Ser Xaa Xaa Xaa Tyr Ala Xaa Ser Val Lys
1               5                   10                  15

Gly

<210> SEQ ID NO 317
<211> LENGTH: 5
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(1)
<223> OTHER INFORMATION: X is S or D
<220> FEATURE:
<221> NAME/KEY: misc_feature
<222> LOCATION: (2)..(2)
<223> OTHER INFORMATION: X is Y, H, or F
<220> FEATURE:
<221> NAME/KEY: misc_feature
<222> LOCATION: (3)..(3)
<223> OTHER INFORMATION: X is G or A

<400> SEQUENCE: 317

Xaa Xaa Xaa Met His
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (2)..(2)
<223> OTHER INFORMATION: X is Q or H
<220> FEATURE:
<221> NAME/KEY: misc_feature
<222> LOCATION: (3)..(3)
<223> OTHER INFORMATION: X is Y, H, Q, or N
<220> FEATURE:
<221> NAME/KEY: misc_feature
<222> LOCATION: (4)..(4)
<223> OTHER INFORMATION: X is N, Y, Q, H, or C
<220> FEATURE:
<221> NAME/KEY: misc_feature
<222> LOCATION: (5)..(5)
<223> OTHER INFORMATION: X is T, S, I, Y, P, L, or A
<220> FEATURE:
<221> NAME/KEY: misc_feature
<222> LOCATION: (6)..(6)
<223> OTHER INFORMATION: X is Y, T, W, or A
<220> FEATURE:
<221> NAME/KEY: misc_feature
<222> LOCATION: (8)..(8)
<223> OTHER INFORMATION: X is L or P

<400> SEQUENCE: 318

Gln Xaa Xaa Xaa Xaa Xaa Pro Xaa Thr
1               5

<210> SEQ ID NO 319
<211> LENGTH: 7
<212> TYPE: PRT
<213> ORGANISM: Artificial Sequence
```

```
<220> FEATURE:
<223> OTHER INFORMATION: Synthetic: consensus sequence
<220> FEATURE:
<221> NAME/KEY: misc_feature
<222> LOCATION: (1)..(1)
<223> OTHER INFORMATION: X is G, A, L, S, or N
<220> FEATURE:
<221> NAME/KEY: misc_feature
<222> LOCATION: (2)..(2)
<223> OTHER INFORMATION: X is A, S, G, or R
<220> FEATURE:
<221> NAME/KEY: misc_feature
<222> LOCATION: (3)..(3)
<223> OTHER INFORMATION: X is S, D, T, N, or R
<220> FEATURE:
<221> NAME/KEY: misc_feature
<222> LOCATION: (4)..(4)
<223> OTHER INFORMATION: X is S, R, Y, Q, or L
<220> FEATURE:
<221> NAME/KEY: misc_feature
<222> LOCATION: (5)..(5)
<223> OTHER INFORMATION: X is L or R
<220> FEATURE:
<221> NAME/KEY: misc_feature
<222> LOCATION: (6)..(6)
<223> OTHER INFORMATION: X is Q or A
<220> FEATURE:
<221> NAME/KEY: misc_feature
<222> LOCATION: (7)..(7)
<223> OTHER INFORMATION: X is S, T, or I

<400> SEQUENCE: 319

Xaa Xaa Xaa Xaa Xaa Xaa Xaa
1               5

<210> SEQ ID NO 320
<211> LENGTH: 12
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (3)..(3)
<223> OTHER INFORMATION: X is S or G
<220> FEATURE:
<221> NAME/KEY: misc_feature
<222> LOCATION: (5)..(5)
<223> OTHER INFORMATION: X is G, S, D, or R
<220> FEATURE:
<221> NAME/KEY: misc_feature
<222> LOCATION: (6)..(6)
<223> OTHER INFORMATION: X is V, I, or L
<220> FEATURE:
<221> NAME/KEY: misc_feature
<222> LOCATION: (7)..(7)
<223> OTHER INFORMATION: X is S, G, F, A, or Y
<220> FEATURE:
<221> NAME/KEY: misc_feature
<222> LOCATION: (8)..(8)
<223> OTHER INFORMATION: X is S, R, or G
<220> FEATURE:
<221> NAME/KEY: misc_feature
<222> LOCATION: (9)..(9)
<223> OTHER INFORMATION: X is S, I, N, R, or nothing (ie, not present)
<220> FEATURE:
<221> NAME/KEY: misc_feature
<222> LOCATION: (10)..(10)
<223> OTHER INFORMATION: X is W, Y, F, E, or D
<220> FEATURE:
<221> NAME/KEY: misc_feature
<222> LOCATION: (11)..(11)
<223> OTHER INFORMATION: X is L or V
<220> FEATURE:
<221> NAME/KEY: misc_feature
<222> LOCATION: (12)..(12)
<223> OTHER INFORMATION: X is A, S, or G
```

<400> SEQUENCE: 320

Arg Ala Xaa Gln Xaa Xaa Xaa Xaa Xaa Xaa Xaa Xaa
1               5                   10

ANTI-CD74 ANTIBODY CONJUGATES, COMPOSITIONS COMPRISING ANTI-CD74 ANTIBODY CONJUGATES AND METHODS OF USING ANTI-CD74 ANTIBODY CONJUGATES

CROSS-REFERENCE TO RELATED APPLICATION

This application is a filing under 35 U.S.C. § 371 of International Patent Application No. PCT/US2017/015503, filed Jan. 27, 2017, which claims the benefit of U.S. Provisional Patent Application No. 62/287,824, filed Jan. 27, 2016. Each of the foregoing applications is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "108843 00152 ST25.txt," created Jun. 6, 2020, and is 197 kilobytes in size. The sequence listing contained in this .txt file is part of the specification and is incorporated herein by reference in its entirety. Please insert the Sequence Listing, enclosed herewith, immediately after the Abstract.

FIELD

Provided herein are antibody conjugates with binding specificity for CD74 and compositions comprising the antibody conjugates, including pharmaceutical compositions, methods of producing the conjugates, and methods of using the conjugates and compositions for therapy. The conjugates and compositions are useful in methods of treatment and prevention of cell proliferation and cancer, methods of detection of cell proliferation and cancer, and methods of diagnosis of cell proliferation and cancer. The conjugates and compositions are also useful in methods of treatment, prevention, detection, and diagnosis of autoimmune diseases, infectious diseases, and inflammatory conditions.

BACKGROUND

Human leukocyte antigen (HLA) class II histocompatibility antigen gamma chain (also known as HLA-DR antigens-associated invariant chain or CD74 (Cluster of Differentiation 74)) is a protein that is involved in the formation and transport of major histocompatibility complex (MHC) class II protein. See Claesson et al., *Proc. Natl. Acad. Sci. U.S.A.*, 1983, 80:7395-7399; Kudo et al., *Nucleic Acids Res.*, 1985, 13:8827-8841; and Cresswell, *Ann. Rev. Immunol.*, 1994, 12:259-291.

One function of CD74 is to regulate peptide loading onto MHC class II heterodimers in intracellular compartments, to prevent MHC class II from binding cellular peptides. The full range of functionality of cell surface-expressed CD74 is not yet known. However, studies have demonstrated that CD74 is a receptor for the pro-inflammatory cytokine macrophage migration inhibitory factor (MIF). Binding of MIF to CD74 activates downstream signaling through the MAPK and Akt pathways and promotes cell proliferation and survival. See Gore et al., *J Biol. Chem.*, 2008, 283:2784-2792; and Starlets et al., *Blood*, 2006, 107:4807-4816.

Upregulation of CD74 expression has been observed in cancers and autoimmune disease (Borghese et al., *Exp. Op.* *Ther. Targets*, 2011, 15:237-251), as well as in infection (Hofman et al., *Modern Pathology*, 2007, 20:974-989) and inflammatory conditions (Vera et al., *Exp. Biol. & Med.*, 2008, 233:620-626). CD74 is known to be expressed at moderate to high levels on a variety of hematological tumors including B-cell lymphoma, leukemia, and multiple myeloma. Burton et al., *Clin. Cancer Res.*, 2004, 10:6606-6611. CD74 expression is also known to be a key factor associated with the progression of pancreatic cancer. Zhang et al., *Hepatobiliary Pancreat. Dis. Int.*, 2014, 13:81-86.

In view of the role of CD74 in multiple disease processes, there is a need for improved methods of modulating the interaction of CD74 with its ligands and the downstream signaling processes activated by CD74. Moreover, given the upregulation of CD74 in several diseases, there is also a need for therapeutics that specifically target cells and tissues overexpressing CD74. Antibody conjugates to CD74 could be used to deliver therapeutic or diagnostic payload moieties to target cells expressing CD74 for the treatment or diagnosis of such diseases.

SUMMARY

In one aspect, provided herein are antibody conjugates that selectively bind CD74. The antibody conjugates comprise an antibody that binds CD74 linked to one or more payload moieties. The antibody can be linked to the payload directly by a covalent bond or indirectly by way of a linker. CD74 antibodies are described in detail herein, as are useful payload moieties, and useful linkers.

In another aspect, provided are compositions comprising the antibody conjugates. In some embodiments, the compositions are pharmaceutical compositions. Any suitable pharmaceutical composition may be used. In some embodiments, the pharmaceutical composition is a composition for parenteral administration. In a further aspect, provided herein are kits comprising the antibody conjugates or pharmaceutical compositions.

In another aspect, provide herein are methods of using the anti-CD74 antibody conjugates. In some embodiments, the methods are methods of delivering one or more payload moieties to a target cell or tissue expressing CD74. In some embodiments, the methods are methods of treatment. In some embodiments, the methods are diagnostic methods. In some embodiments, the methods are analytical methods. In some embodiments, the antibody conjugates are used to treat a disease or condition. In some aspects, the disease or condition is selected from a cancer, an autoimmune disease, an infectious disease, or an inflammatory condition. In some aspects, the disease or condition is a B-cell lymphoma. In some aspects, the disease or condition is non-Hodgkin's lymphoma. In some aspects, the disease or condition is leukemia. In some aspects, the disease or condition is pancreatic cancer. In some aspects, the disease or condition is multiple myeloma.

BRIEF DESCRIPTION OF THE DRAWINGS

FIG. 2A provides protein yield of antibodies expressed according to an example herein.

DETAILED DESCRIPTION

1. Definitions

Figure 1:
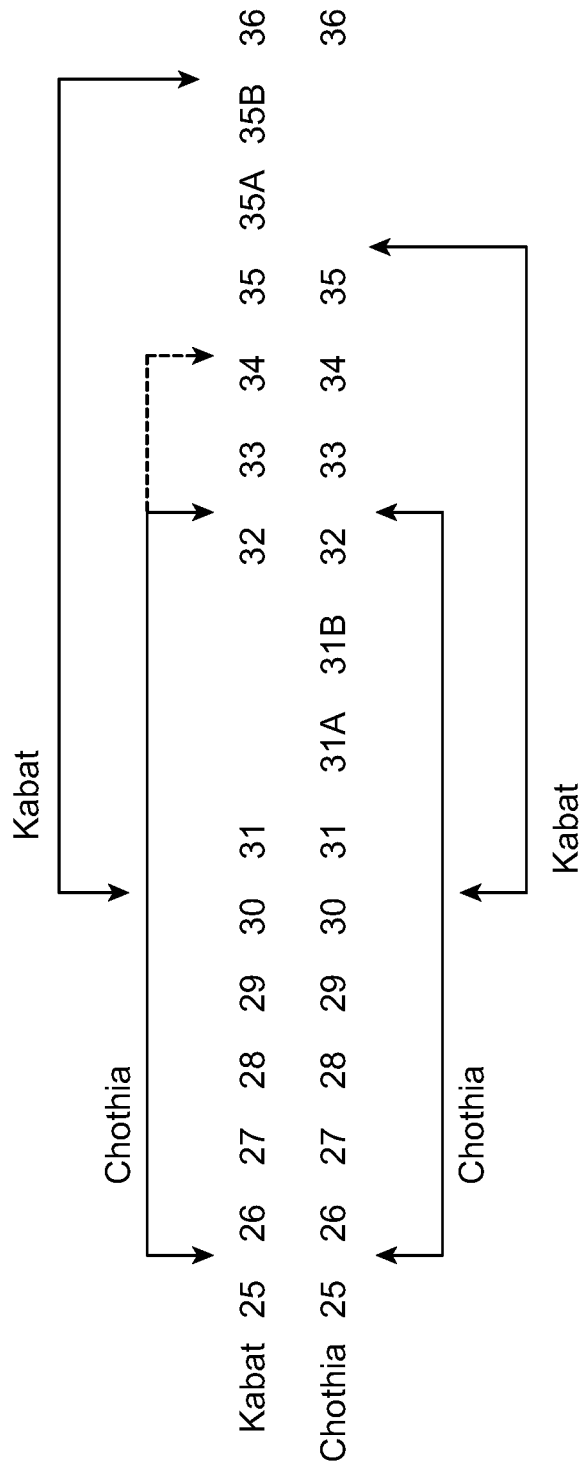
FIG. 1 provides a comparison of the Kabat and Chothia numbering systems for CDR-H1. See Martin A. C. R. (2010). Protein Sequence and Structure Analysis of Antibody Variable Domains. In R. Kontermann & S. Dubel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term about indicates the designated value±10%, ±5% or ±1%. In certain embodiments, the term about indicates the designated value±one standard deviation of that value.

The terms "CD74" and "CD74 antigen" are used interchangeably herein. Unless specified otherwise, the terms include any variants, isoforms and species homologs of human CD74 that are naturally expressed by cells, or that are expressed by cells transfected with a CD74 gene.

At least four human isoforms of CD74 are known to exist, including p43, p41, p35 and p33. Borghese et al., *Expert Opin. Ther. Targets*, 2011, 15:237-251, incorporated by reference in its entirety. These isoforms result from alternative transcript splicing and two translation start sites.

p43 (also known as CD74 isoform 1, isoform a, or "long"; see UniProt entry P04233-1 and NCBI Reference Sequence NP 001020330, each incorporated by reference in its entirety) contains 296 amino acids, with residues 73-296 forming the extracellular portion. Protein constructs of CD74 having the extracellular part of isoform 1 are herein referred to as "variant 1" or "CD74v1."

p35 (also known as CD74 isoform 2, isoform b or "short"; see UniProt entry P04233-2 and NCBI Reference Sequence NP 004346, each incorporated by reference in its entirety) lacks residues 209-272 from the extracellular domain due to alternative splicing. Protein constructs of CD74 having the extracellular part of isoform 2 are herein referred to as "variant 2" or "CD74v2."

p41 and p33 arise from an alternative translation start site (48 nucleotides/16 amino acids downstream) leading to variants lacking the endoplasmic reticulum (ER) retention signal that is present within the eliminated 16 amino acids, but having extracellular domain that is identical to p43 and p35, respectively.

The sequence of another isoform (known as isoform 3 and isoform c), in which residues 148-160 are replaced and residues 161-296 are lacking, is provided in NP 001020329.

The sequences of cynomolgus CD74 homologs are provided in, e.g., NCBI Reference Sequence: XP-001099491.2 and NCBI Reference Sequence: XP-002804624.1.

The term "immunoglobulin" refers to a class of structurally related proteins generally consisting of two pairs of polypeptide chains, one pair of light (L) chains and one pair of heavy (H) chains. In an intact immunoglobulin, all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes monoclonal antibody conjugates, polyclonal antibody conjugates, intact antibody conjugates, and antibody fragments. Antibody conjugates comprise at least one antigen-binding domain. One example of an antigen-binding domain is an antigen binding domain formed by a $V_H$-$V_L$ dimer. A "CD74 antibody," "anti-CD74 antibody," "CD74 Ab," "CD74-specific antibody" or "anti-CD74 Ab" is an antibody, as described herein, which binds specifically to the antigen CD74.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes. FIG. 1 provides a comparison of the Kabat and Chothia numbering schemes for CDR-H1. See Martin (2010), supra.

Unless otherwise specified, the numbering scheme used for identification of a particular CDR herein is the Kabat/Chothia numbering scheme. Where these two numbering schemes diverge, the numbering scheme is specified as either Kabat or Chothia.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" or "EU index" is generally used when referring to a residue in an antibody heavy chain constant region (e.g., the EU index reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by papain digestion of a full-length antibody.

"F(ab')$_2$" fragments contain two Fab' fragments joined, near the hinge region, by disulfide bonds. F(ab')$_2$ fragments may be generated, for example, by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety. "scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain is an IgG1 Fc domain (e.g., SEQ ID NO: 289).

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Affinity can be determined, for example, using surface plasmon resonance (SPR) technology, such as a Biacore® instrument.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen (e.g., CD74). In one exemplary assay, CD74 is coated on a plate and allowed to bind a first antibody, after which a second, labeled antibody is added. If the presence of the first antibody reduces binding of the second antibody, then the antibodies compete. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to CD74 variants with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), or CLUSTALW software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the following groups of amino acids are considered conservative substitutions for one another.

| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

| Group 1 | A, S, and T |
| Group 2 | D and E |
| Group 3 | N and Q |
| Group 4 | R and K |
| Group 5 | I, L, and M |
| Group 6 | F, Y, and W |

| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The term "conjugate" or "antibody conjugate" refers to an antibody linked to one or more payload moieties. The antibody can be any antibody described herein. The payload can be any payload described herein. The antibody can be directly linked to the payload via a covalent bond, or the antibody can be linked to the payload indirectly via a linker. Typically, the linker is covalently bonded to the antibody and also covalently bonded to the payload. The term "antibody drug conjugate" or "ADC" refers to a conjugate wherein at least one payload is a therapeutic moiety such as a drug.

The term "payload" refers to a molecular moiety that can be conjugated to an antibody. In particular embodiments, payloads are selected from the group consisting of therapeutic moieties and labelling moieties.

The term "linker" refers to a molecular moiety that is capable of forming at least two covalent bonds. Typically, a linker is capable of forming at least one covalent bond to an antibody and at least another covalent bond to a payload. In certain embodiments, a linker can form more than one covalent bond to an antibody. In certain embodiments, a linker can form more than one covalent bond to a payload or can form covalent bonds to more than one payload. After a linker forms a bond to an antibody, or a payload, or both, the remaining structure, i.e. the residue of the linker after one or more covalent bonds are formed, may still be referred to as a "linker" herein. The term "linker precursor" refers to a linker having one or more reactive groups capable of forming a covalent bond with an antibody or payload, or both.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the term "therapeutically effective amount" or "effective amount" refers to an amount of an antibody or composition that when administered to a subject is effective to prevent or ameliorate a disease or the progression of the disease, or result in amelioration of symptoms.

As used herein, the term "inhibits growth" (e.g. referring to cells, such as tumor cells) is intended to include any measurable decrease in cell growth (e.g., tumor cell growth) when contacted with a CD74 antibody, as compared to the growth of the same cells not in contact with a CD74 antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

As used herein, the term "subject" means a mammalian subject. Exemplary subjects include, but are not limited to humans, monkeys, dogs, cats, mice, rats, cows, horses, goats and sheep. In certain embodiments, the subject is a human. In some embodiments, the subject has cancer, an inflammatory disease or condition, or an autoimmune disease or condition, that can be treated with an antibody provided herein. In some embodiments, the subject is a human that has or is suspected to have cancer, antiinflammatory disease or condition, or an autoimmune disease or condition.

In some chemical structures illustrated herein, certain substituents, chemical groups, and atoms are depicted with a curvy/wavy line (e.g.,

)

that intersects a bond or bonds to indicate the atom through which the substituents, chemical groups, and atoms are bonded. For example, in some structures, such as but not limited to

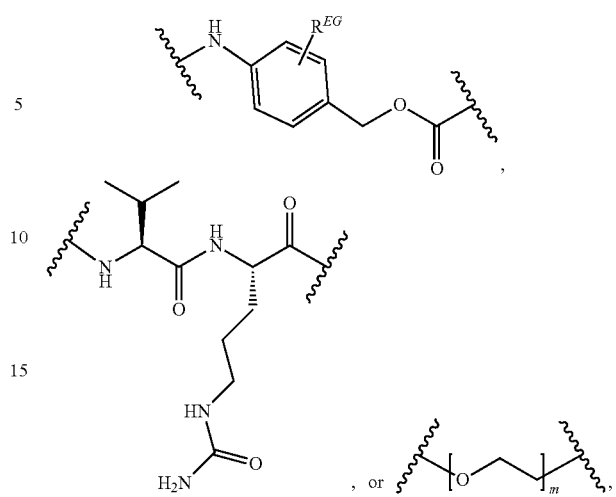

this curvy/wavy line indicates the atoms in the backbone of a conjugate or linker-payload structure to which the illustrated chemical entity is bonded. In some structures, such as but not limited to

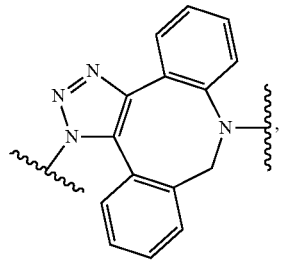 [SMILES: *N1Cc2ccccc2-c2c(nnn2*)-c2ccccc21]

this curvy/wavy line indicates the atoms in the antibody or antibody fragment as well as the atoms in the backbone of a conjugate or linker-payload structure to which the illustrated chemical entity is bonded.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Conjugates

Provided herein are conjugates of antibodies to CD74. The conjugates comprise an antibody to CD74 covalently linked directly or indirectly, via a linker, to a payload. In certain embodiments, the antibody is linked to one payload. In further embodiments, the antibody is linked to more than one payload. In certain embodiments, the antibody is linked to two, three, four, five, six, seven, eight, or more payloads.

The payload can be any payload deemed useful by the practitioner of skill. In certain embodiments, the payload is a therapeutic moiety. In certain embodiments, the payload is a diagnostic moiety, e.g. a label. Useful payloads are described in the sections and examples below.

The linker can be any linker capable of forming at least one bond to the antibody and at least one bond to a payload. Useful linkers are described the sections and examples below.

In the conjugates provided herein, the antibody can be any antibody with binding specificity for CD74. The CD74 can be from any species. In certain embodiments, the CD74 is a vertebrate CD74. In certain embodiments, the CD74 is a mammalian CD74. In certain embodiments, the CD74 is human CD74. In certain embodiments, the CD74 is mouse CD74. In certain embodiments, the CD74 is cynomolgus CD74.

In certain embodiments, the antibody to CD74 competes with an antibody described herein for binding. In certain embodiments, the antibody to CD74 binds to the same epitope as an antibody described herein.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, sFv, etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair). In certain embodiments, the antibody to CD74 is milatuzumab.

In certain embodiments, the antibody of the conjugate comprises any of the amino acid sequences of the antibodies described above. In certain embodiments, the antibody comprises any of the amino acid sequences above with up to 10 conservative amino acid substitutions. In certain embodiments, the antibody comprises any of the amino acid sequences above with up to 9 conservative amino acid substitutions. In certain embodiments, the antibody comprises any of the amino acid sequences above with up to 8 conservative amino acid substitutions. In certain embodiments, the antibody comprises any of the amino acid sequences above with up to 7 conservative amino acid substitutions. In certain embodiments, the antibody comprises any of the amino acid sequences above with up to 6 conservative amino acid substitutions. In certain embodiments, the antibody comprises any of the amino acid sequences above with up to 5 conservative amino acid substitutions. In certain embodiments, the antibody comprises any of the amino acid sequences above with up to 4 conservative amino acid substitutions. In certain embodiments, the antibody comprises any of the amino acid sequences above with up to 3 conservative amino acid substitutions. In certain embodiments, the antibody comprises any of the amino acid sequences above with up to 2 conservative amino acid substitutions. In certain embodiments, the antibody comprises any of the amino acid sequences above with up to 1 conservative amino acid substitution.

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Further reactive groups are described in the sections and examples below.

In further embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

The non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

In certain embodiments, the antibodies provided herein comprise one or more non-natural amino acids at one or more positions selected from the group consisting of heavy chain or light chain residues HC-F404, HC-K121, HC-Y180, HC-F241, HC-221, LC-T22, LC-S7, LC-N152, LC-K42, LC-E161, LC-D170, HC-S136, HC-S25, HC-A40, HC-K119, HC-S190, HC-K222, HC-R19, HC-Y52, or HC-S70 according to the Kabat or Chothia or EU numbering scheme, or a post-translationally modified variant thereof. In these designations, HC indicates a heavy chain residue, and LC indicates a light chain residue.

In certain embodiments, provided herein are conjugates according to Formula (C1) or (C2):

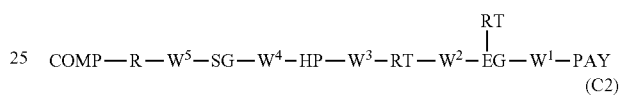

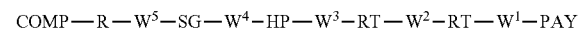

or a pharmaceutically acceptable salt, solvate, stereoisomer, regioisomer, or tautomer thereof, wherein:

COMP is a residue of an anti-CD74 antibody;

PAY is a payload moiety;

$W^1$, $W^2$, $W^3$, $W^4$, and $W^5$ are each independently a single bond, absent, or a divalent attaching group;

EG is absent, or an eliminator group;

each RT is a release trigger group, in the backbone of Formula (C1) or (C2) or bonded to EG, wherein each RT is optional;

HP is a single bond, absent, or a divalent hydrophilic group;

SG is a single bond, absent, or a divalent spacer group; and

R is hydrogen, a terminal conjugating group, or a divalent residue of a terminal conjugating group.

Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise —C(O)—, —O—, —C(O)NH—, —C(O)NH-alkyl-, —OC(O)NH—, —SC(O)NH—, —NH—, —NH-alkyl-, —N(CH$_3$)CH$_2$CH$_2$N(CH$_3$)—, —S—, —S—S—, —OCH$_2$CH$_2$O—, or the reverse (e.g. —NHC(O)—) thereof, or a combination thereof.

Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

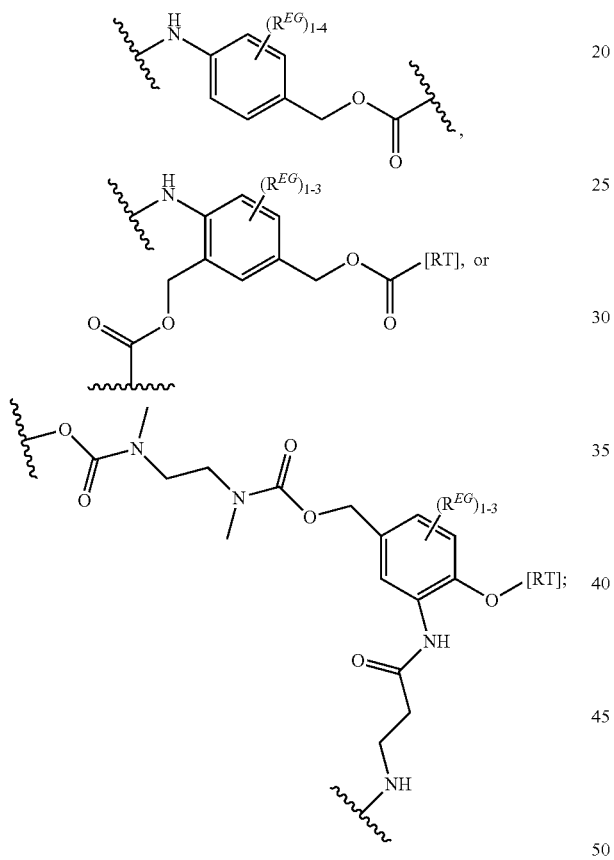

wherein $R^{EG}$ is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the second and third structures, those of skill will recognize that EG is bonded to an RT that is not within the backbone of formula (C1) as indicated in the above description of formula (C1). In some embodiments, $R^{EG}$ is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —NO$_2$, —CN, fluoro, bromo, and chloro. In certain embodiments, the eliminator group is

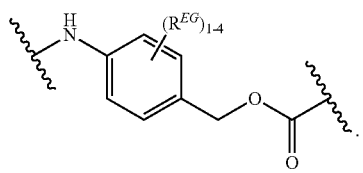

In certain embodiments, the eliminator group is

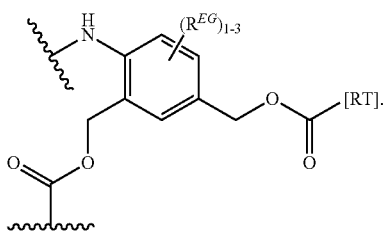

In certain embodiments, the eliminator group is

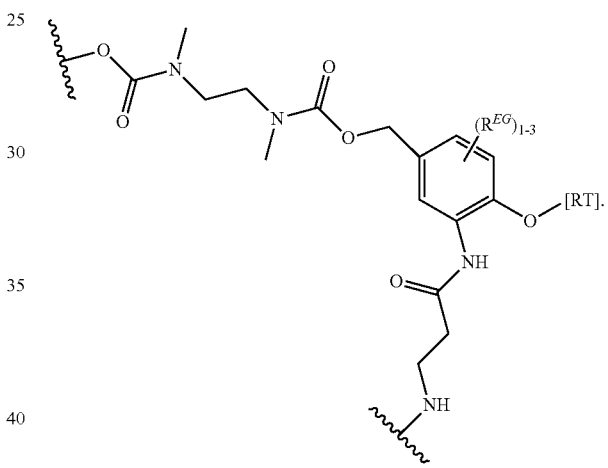

Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiment, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

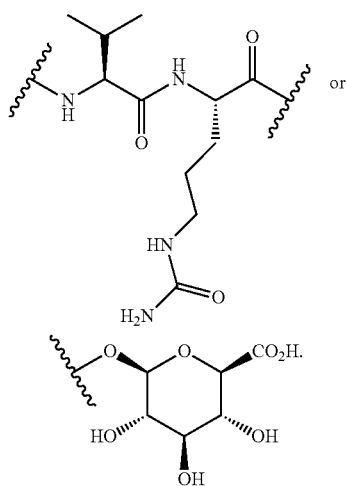 or

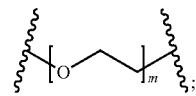

wherein m is an integer from 1 to 12, optionally 1 to 4, optionally 2 to 4.

In some embodiments, the hydrophilic group is a divalent poly(ethylene glycol) having the following formula:

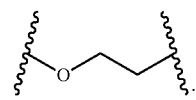

Those of skill will recognize that the first structure is divalent and can be bonded within the backbone of Formula (C1) or as depicted in Formula (C2), and that the second structure is monovalent and can be bonded to EG as depicted in formula (C1) above.

In certain embodiments, the release trigger group is

In some other embodiments, the hydrophilic group is a divalent poly(ethylene glycol) having the following formula:

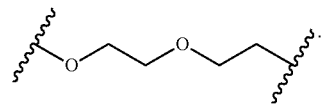 [SMILES: *CCOCCO*]

In other embodiments, the hydrophilic group is a divalent poly(ethylene glycol) having the following formula:

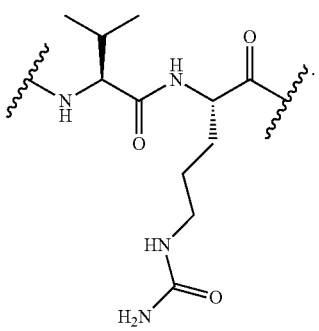

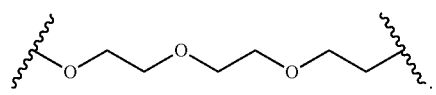 [SMILES: *CCOCCOCCO*]

In other embodiments, the hydrophilic group is a divalent poly(ethylene glycol) having the following formula:

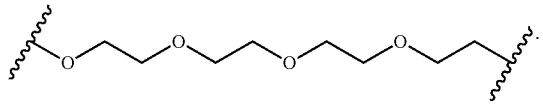 [SMILES: *CCOCCOCCOCCO*]

In certain embodiments, the release trigger group is

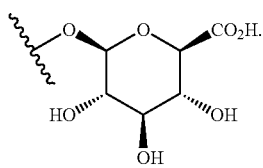

Spacer Groups

Spacer groups facilitate spacing of the conjugating group from the other groups of the compounds described herein. This spacing can lead to more efficient conjugation of the compounds described herein to a second compound. The spacer group can also stabilize the conjugating group.

In certain embodiments, the spacer group is designated SP herein. Useful spacer groups include those described herein. In certain embodiments, the spacer group is:

Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

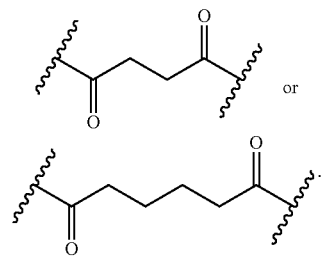

In certain embodiments, the spacer group, $W^4$, and the hydrophilic group combine to form a divalent poly(ethylene glycol) according to the formula:

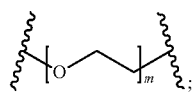

wherein m is an integer from 1 to 12, optionally 1 to 4, optionally 2 to 4.

In some embodiments, the SP is

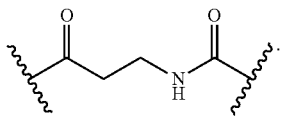

In some embodiments, the divalent poly(ethylene glycol) has the following formula:

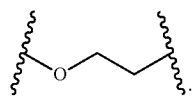

In some other embodiments, the divalent poly(ethylene glycol) has the following formula:

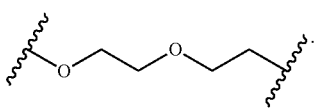 [SMILES: *CCOCCO*]

In other embodiments, the divalent poly(ethylene glycol) has the following formula:

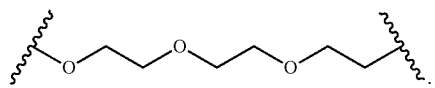 [SMILES: *CCOCCOCCO*]

In other embodiments, the divalent poly(ethylene glycol) has the following formula:

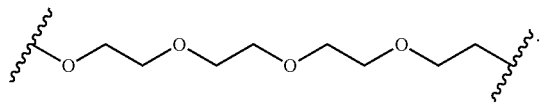 [SMILES: *CCOCCOCCOCCO*]

Conjugating Groups and Residues Thereof

Conjugating groups facilitate conjugation of the compounds described herein to a second compound, such as a targeting moiety. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

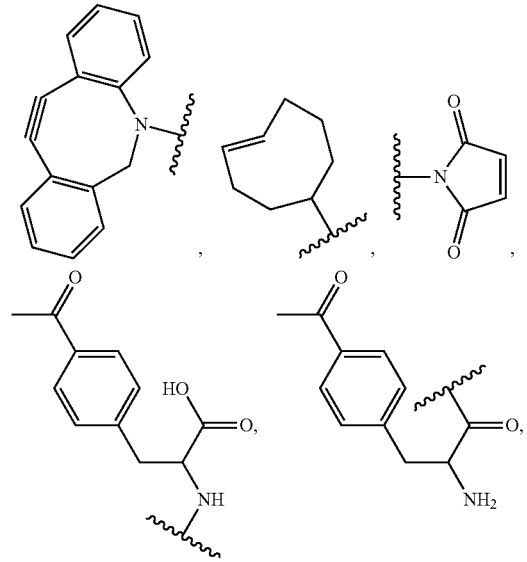

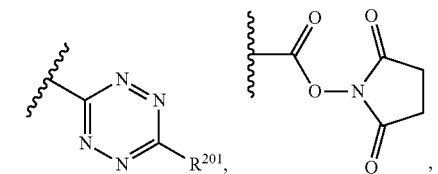

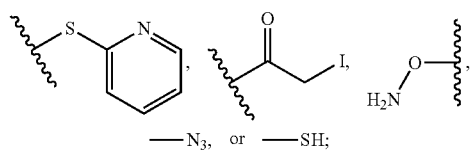

—$N_3$, or —SH;

wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a [3+2] alkyne-azide cycloaddition reaction, the divalent residue of the conjugating group is:

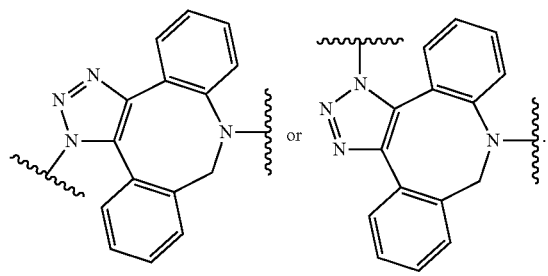 [SMILES: *N1Cc2ccccc2-c2c(nnn2*)-c2ccccc21 ; *N1Cc2ccccc2-c2nnn(*)c2-c2ccccc21]

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

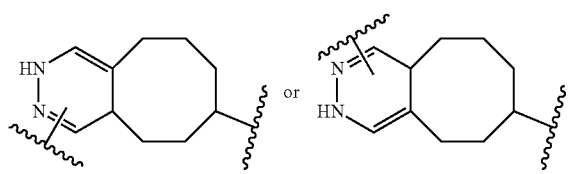

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

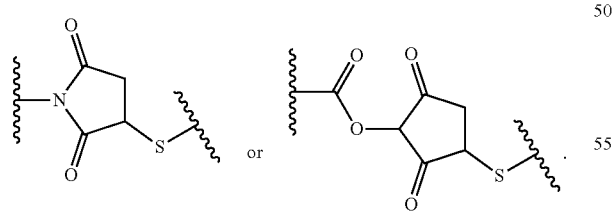

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

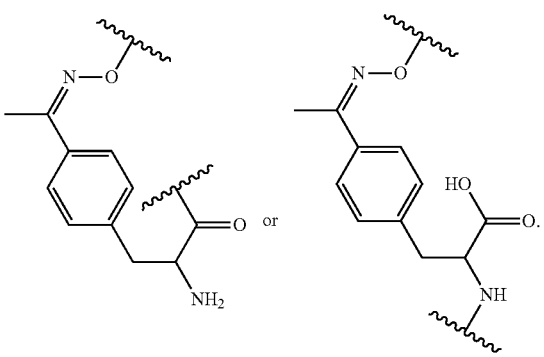 [SMILES: *O/N=C(/C)c1ccc(CC(N)C(*)=O)cc1 ; *NC(Cc1ccc(/C(C)=N\O*)cc1)C(=O)O]

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

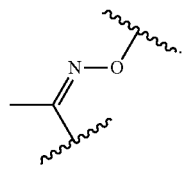 [SMILES: *O/N=C(\*)C]

In an embodiment, provided herein is a conjugate according to Formula (C1) or (C2) or a pharmaceutically acceptable salt, solvate, stereoisomer, or tautomer thereof; wherein EG comprises phenylene, carboxylene, amine, or a combination thereof. In an embodiment, provided herein is a conjugate according to Formula (C1) or (C2), or a pharmaceutically acceptable salt, solvate, stereoisomer, or tautomer thereof; wherein EG is:

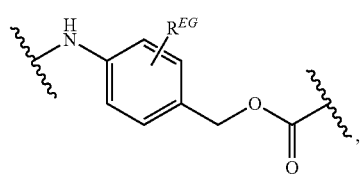

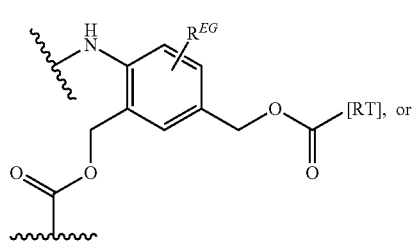

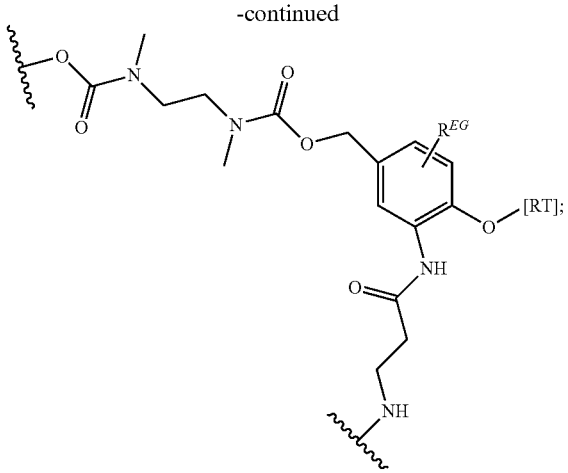

wherein R^{EG} is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four R^{EG} groups. In the second and third structures, those of skill will recognize that EG is bonded to an RT that is not within the backbone of Formula C1 as indicated in the above description of Formula C1. In some embodiments, R^{EG} is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, R^{EG} is selected from the group consisting of hydrogen, —NO$_2$, —CN, fluoro, bromo, and chloro.

In an embodiment, provided herein is a conjugate according to Formula (C1) or (C2), or a pharmaceutically acceptable salt, solvate, stereoisomer, or tautomer thereof; wherein RT comprises a residue of a natural or non-natural amino acid or a residue of a sugar. In an embodiment, provided herein is a conjugate according to Formula (C1) or (C2), or a pharmaceutically acceptable salt, solvate, stereoisomer, or tautomer thereof; wherein RT is:

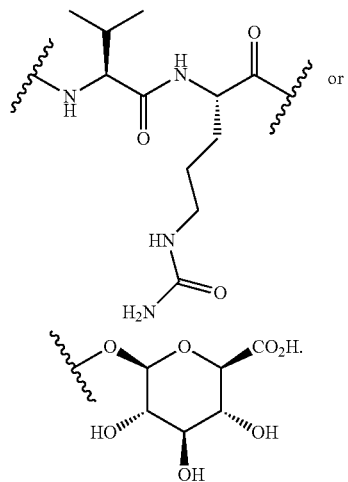

Those of skill will recognize that the first structure is divalent and can be bonded within the backbone as depicted in Formula (C2), and that the second structure is monovalent and can be bonded to EG as depicted in Formula (C1) above.

In an embodiment, provided herein is a conjugate according to Formula (C1) or (C2), or a pharmaceutically acceptable salt, solvate, stereoisomer, or tautomer thereof; wherein HP comprises poly(ethylene glycol). In an embodiment, provided herein is a conjugate according to Formula (C1) or (C2), or a pharmaceutically acceptable salt, solvate, stereoisomer, or tautomer thereof; wherein HP is:

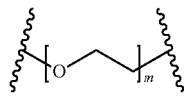

wherein m is an integer from 1 to 12.

In an embodiment, provided herein is a conjugate according to Formula (C1) or (C2), or a pharmaceutically acceptable salt, solvate, stereoisomer, or tautomer thereof; wherein SG comprises $C_1$-$C_{10}$ alkylene, $C_4$-$C_6$ alkylene, carbonylene, or combination thereof. In an embodiment, provided herein is a conjugate according to Formula (C1) or (C2), or a pharmaceutically acceptable salt, solvate, stereoisomer, or tautomer thereof; wherein SG is:

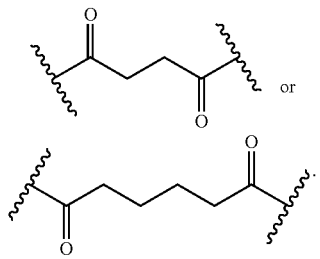

In an embodiment, provided herein is a conjugate according to Formula (C1) or (C2), or a pharmaceutically acceptable salt, solvate, stereoisomer, or tautomer thereof; wherein $W^1$, $W^2$, $W^3$, $W^4$, and $W^5$ are each independently a single bond, absent, or comprise a divalent ketone, divalent ester, divalent ether, divalent amide, divalent amine, alkylene, arylene, sulfide, disulfide, carbonylene, or a combination thereof. In an embodiment, provided herein is a conjugate according to Formula (C1) or (C2), or a pharmaceutically acceptable salt, solvate, stereoisomer, or tautomer thereof; wherein $W^1$, $W^2$, $W^3$, $W^4$, and $W^5$ are each independently a single bond, absent, or comprise —C(O)—, —O—, —C(O)NH—, —C(O)NH-alkyl-, —OC(O)NH—, —SC(O)NH—, —NH—, —NH-alkyl-, —N(CH$_3$)CH$_2$CH$_2$N(CH$_3$)—, —S—, —S—S—, —OCH$_2$CH$_2$O—, or a combination thereof.

In an embodiment, provided herein is a conjugate according to Formula (C1) or (C2), or a pharmaceutically acceptable salt, solvate, stereoisomer, or tautomer thereof; wherein R comprises a triazole ring. In an embodiment, provided herein is a conjugate according to Formula (C1) or (C2), or a pharmaceutically acceptable salt, solvate, stereoisomer, or tautomer thereof; wherein R is a triazole ring or fused cyclic group comprising a triazole ring. In an embodiment, provided herein is a conjugate according to Formula (C1) or (C2), or a pharmaceutically acceptable salt, solvate, stereoisomer, or tautomer thereof; wherein R is:

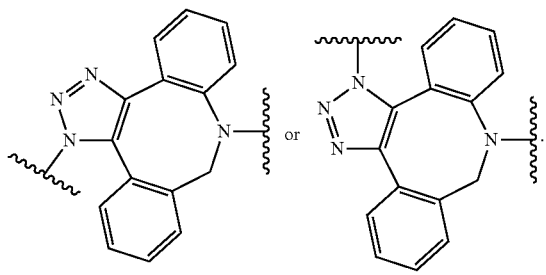 [SMILES: *N1Cc2ccccc2-c2c(nnn2*)-c2ccccc21 ; *N1Cc2ccccc2-c2nnn(*)c2-c2ccccc21] or 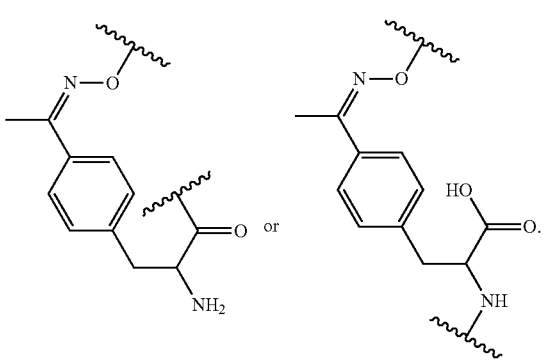 [SMILES: *O/N=C(/C)c1ccc(CC(N)C(*)=O)cc1 ; *NC(Cc1ccc(/C(C)=N\O*)cc1)C(=O)O]

In an embodiment, provided herein is a conjugate according to Formula (C1) or (C2), or a pharmaceutically acceptable salt, solvate, stereoisomer, or tautomer thereof; wherein R comprises a fused bicyclic ring having at least two adjacent nitrogen atoms in the ring. In an embodiment, provided herein is a conjugate according to Formula (C1) or (C2), or a pharmaceutically acceptable salt, solvate, stereoisomer, or tautomer thereof; wherein R is:

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R is:

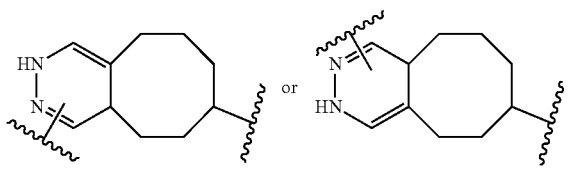 or 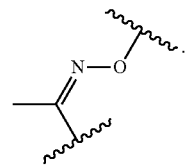 [SMILES: *O/N=C(\*)C].

In an embodiment, provided herein is a conjugate according to Formula (C1) or (C2), or a pharmaceutically acceptable salt, solvate, stereoisomer, or tautomer thereof; wherein R comprises a sulfur linkage. In an embodiment, provided herein is a conjugate according to Formula (C1) or (C2), or a pharmaceutically acceptable salt, solvate, stereoisomer, or tautomer thereof; wherein R is:

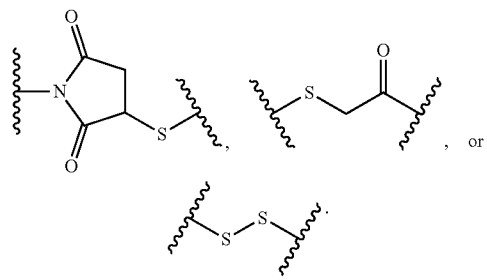

In an embodiment, provided herein is a conjugate according to Formula (C1) or (C2), or a pharmaceutically acceptable salt, solvate, stereoisomer, or tautomer thereof; wherein R comprises a divalent residue of a non-natural amino acid. In an embodiment, provided herein is a conjugate according to Formula (C1) or (C2), or a pharmaceutically acceptable salt, solvate, stereoisomer, or tautomer thereof; wherein R is:

In an embodiment, provided herein is a conjugate according to Formula (C1) or (C2), or a pharmaceutically acceptable salt, solvate, stereoisomer, or tautomer thereof; wherein R is:

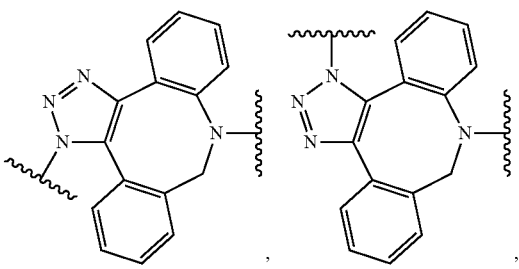,

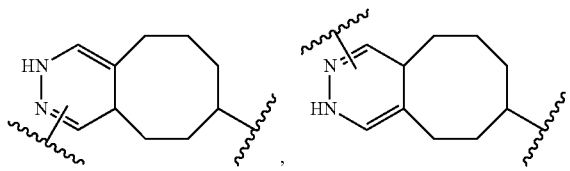,

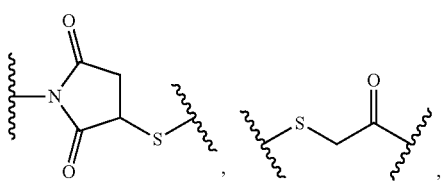,

-continued

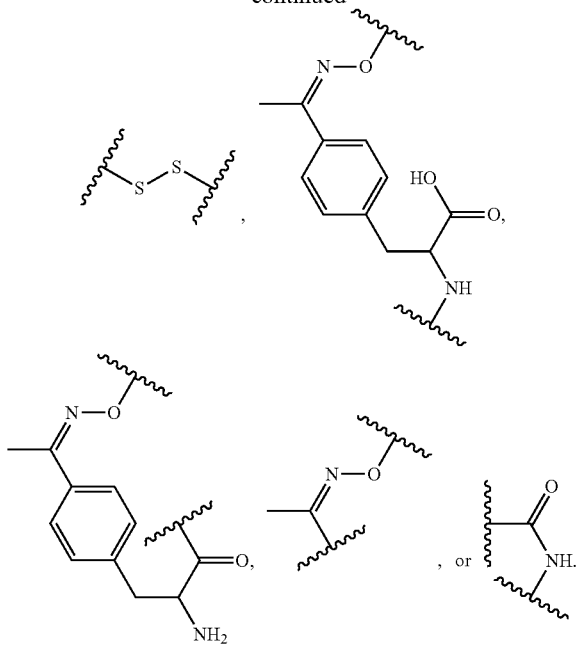

In an embodiment, provided herein is a compound according to Formula (C1) or (C2), or a pharmaceutically acceptable salt, solvate, stereoisomer, or tautomer thereof; wherein COMP is a residue of any compound known to be useful for conjugation to a payload, described herein, and an optional linker, described herein. In an embodiment, provided herein is a compound according to Formula (C1) or (C2), or a pharmaceutically acceptable salt, solvate, stereoisomer, or tautomer thereof, wherein COMP is a residue of an antibody chain.

In an aspect, provided herein is an antibody conjugate comprising payload, described herein, and an optional linker, described herein, linked to an anti-CD74 antibody, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

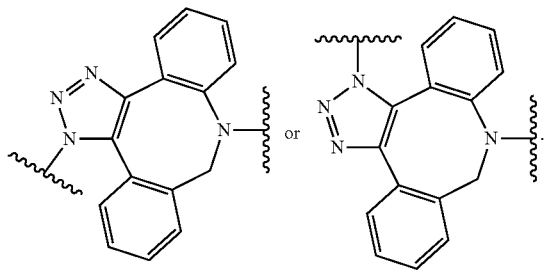 [SMILES: *N1Cc2ccccc2-c2c(nnn2*)-c2ccccc21 ; *N1Cc2ccccc2-c2nnn(*)c2-c2ccccc21]

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

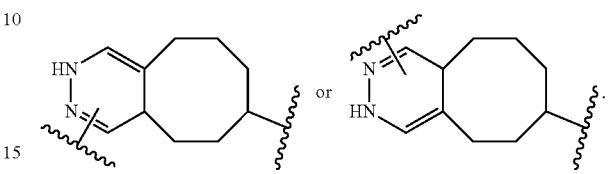

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

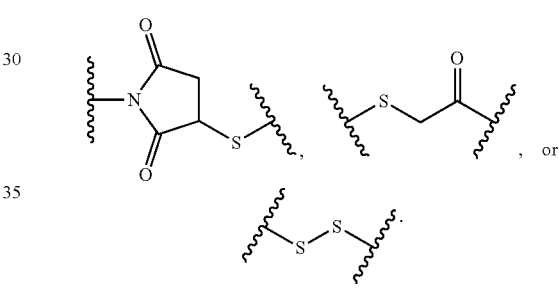

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

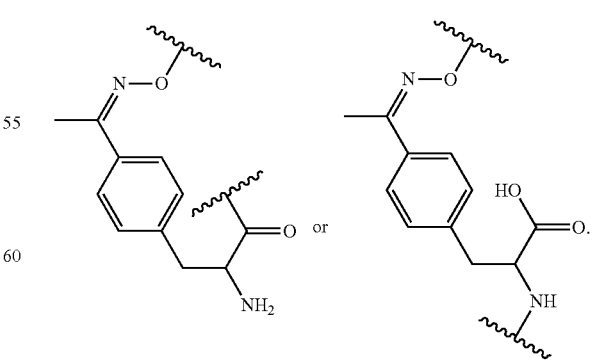

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises an oxime linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

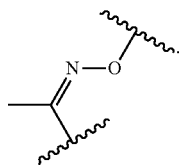 [SMILES: *O/N=C(\*)C]

In an aspect, provided herein is an antibody conjugate comprising a payload, described herein, and an optional linker, described herein, linked to an antibody according to Formula (C1) or (C2), or a pharmaceutically acceptable salt, solvate, stereoisomer, or tautomer thereof, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

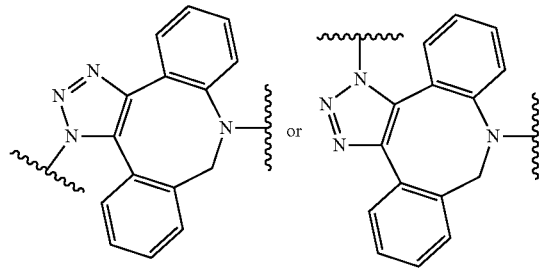

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

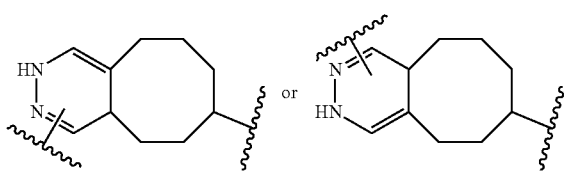

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

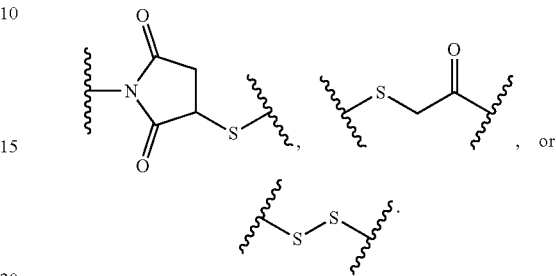

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

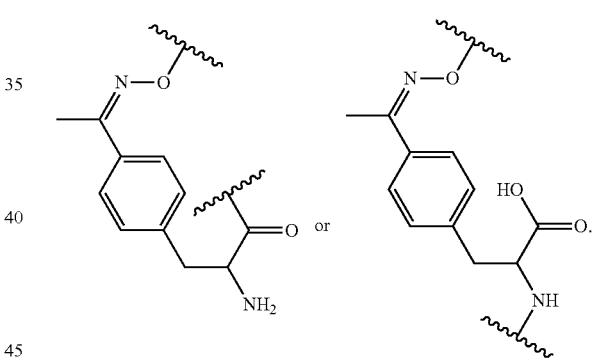

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises an oxime linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

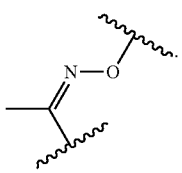 [SMILES: *O/N=C(\*)C]

In an aspect, provided herein is an antibody conjugate comprising a payload, described herein, and an optional linker, described herein, linked to an antibody chain according to Formula (C1) or (C2), or a pharmaceutically acceptable salt, solvate, stereoisomer, or tautomer thereof, wherein COMP is a residue of the antibody chain. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

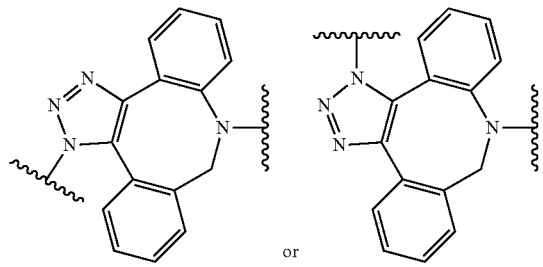

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

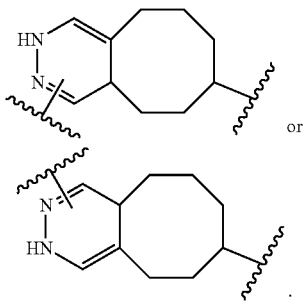

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

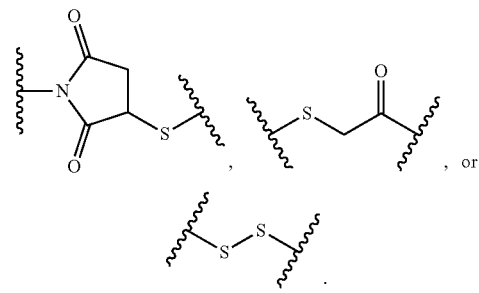

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

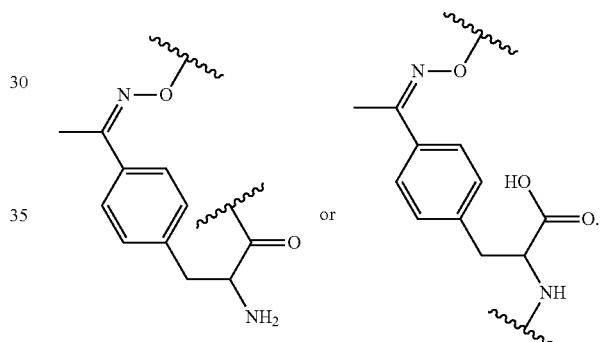

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises an oxime linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

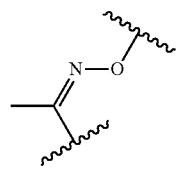

In an embodiment, provided herein is a conjugate according to any of the following formulas, where COMP indicates a residue of the anti-CD74 antibody and PAY indicates a payload moiety:

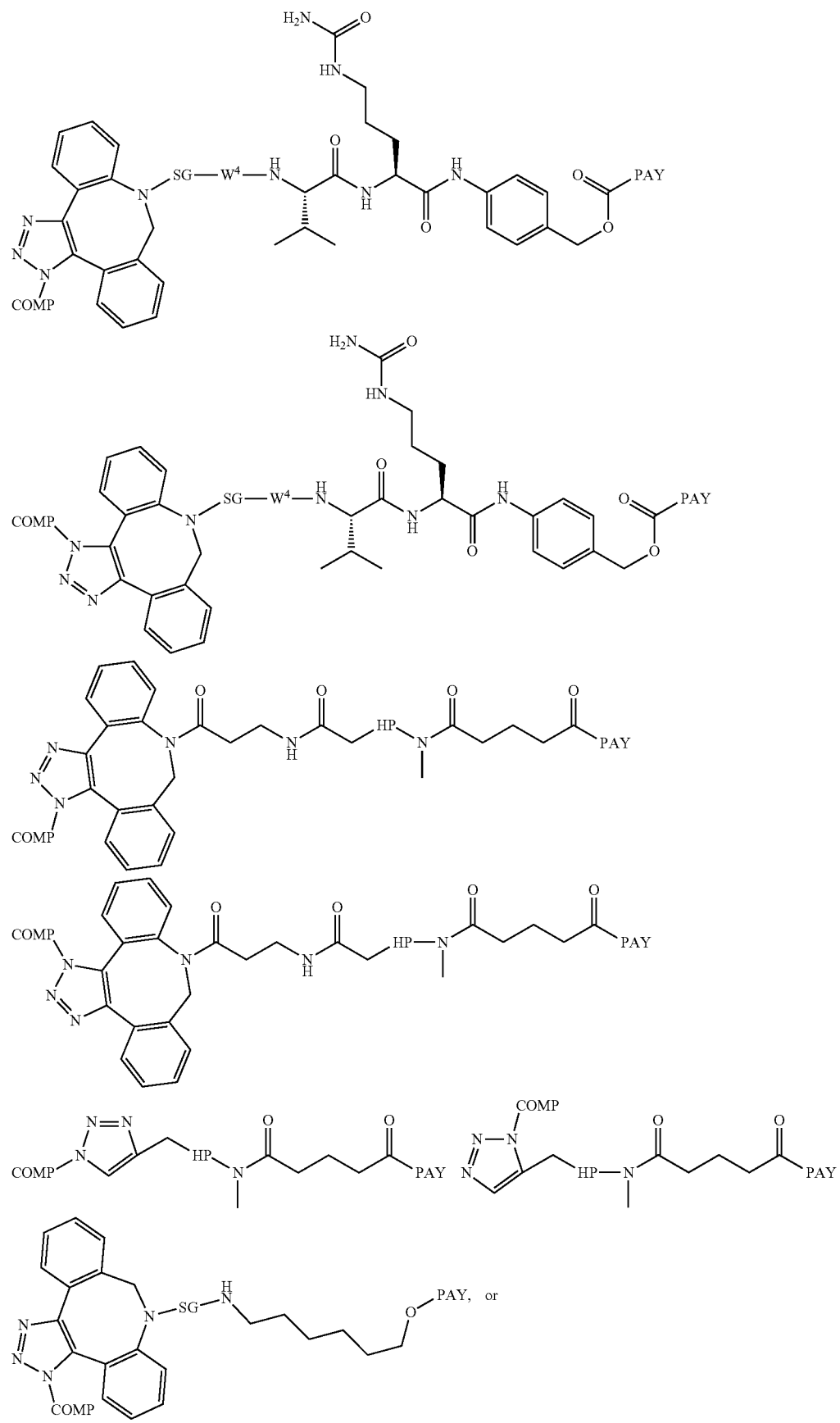

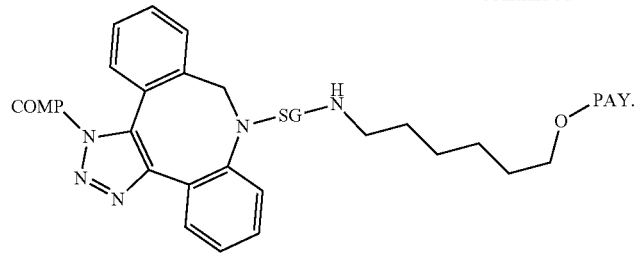
In an embodiment, provided herein is a conjugate according to any of the following formulas, where COMP indicates a residue of the anti-CD74 antibody and PAY indicates a payload moiety:
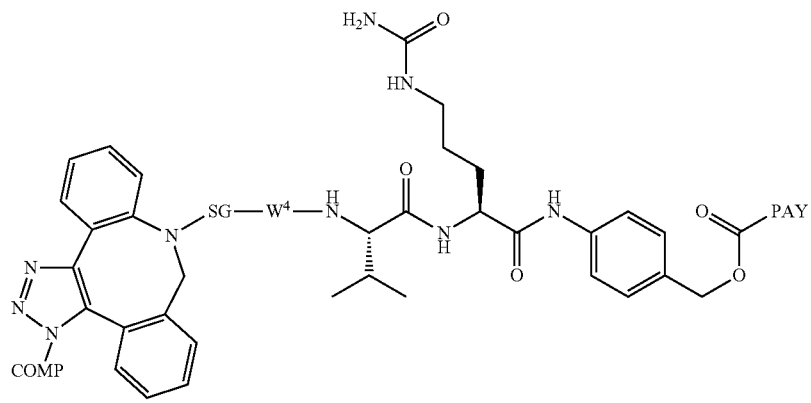
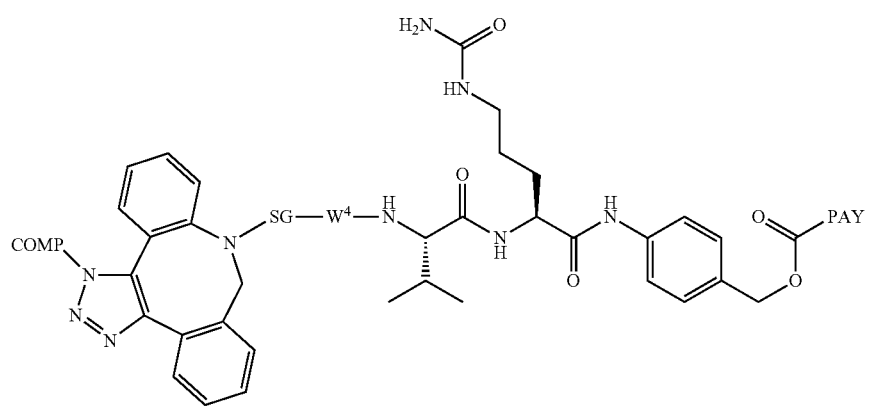
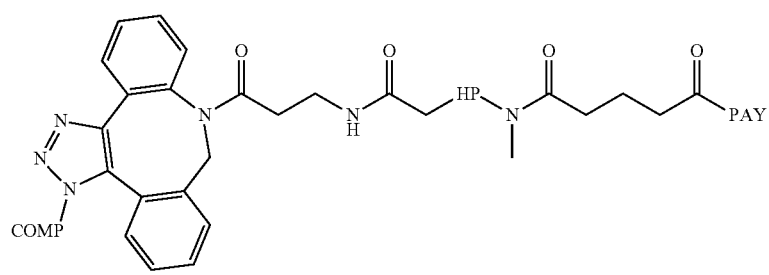

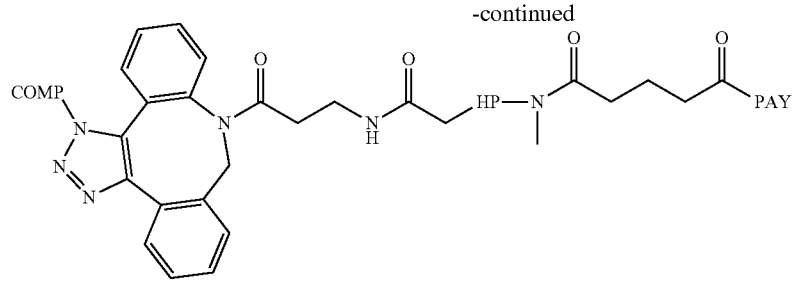

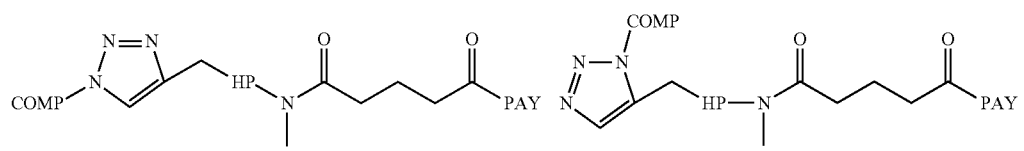

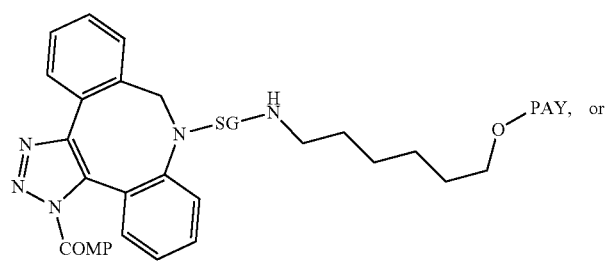

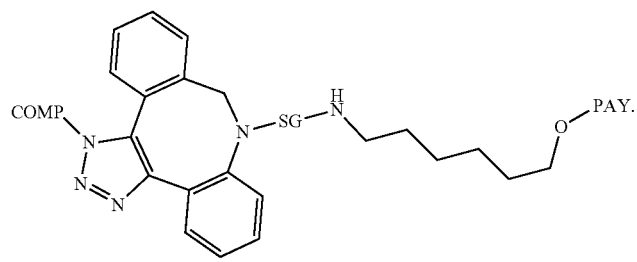

In an embodiment, provided herein is a conjugate according to any of the following formulas, where COMP indicates a residue of the anti-CD74 antibody and PAY indicates a payload moiety:

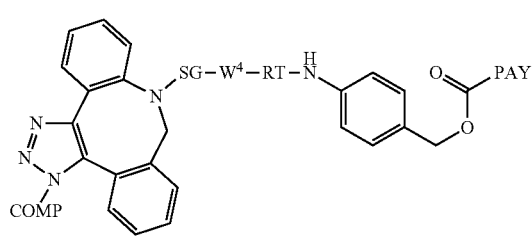

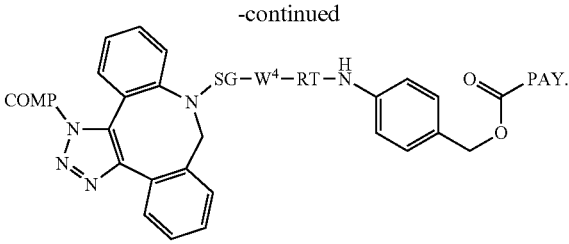

In an embodiment, provided herein is a conjugate according to any of the following formulas, where COMP indicates a residue of the anti-CD74 antibody and PAY indicates a payload moiety:

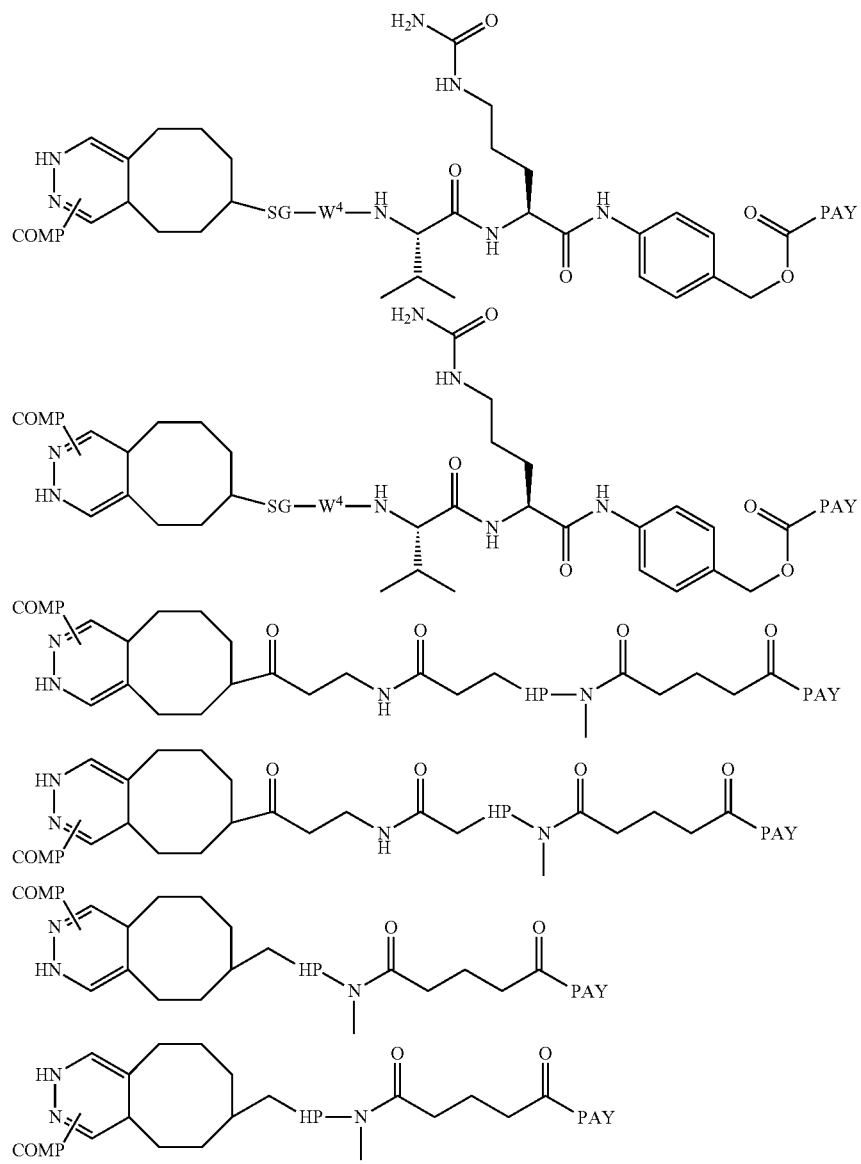
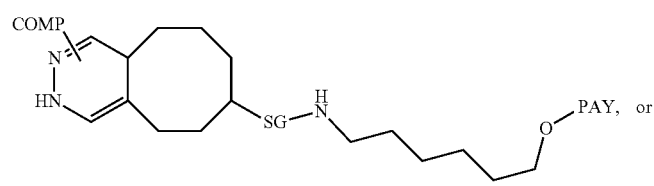
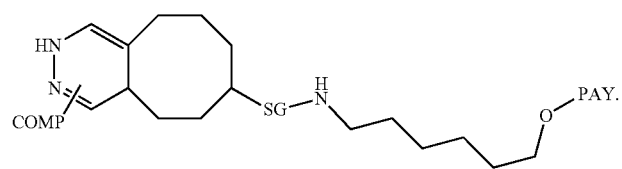

In an embodiment, provided herein is a conjugate according to any of Formulas 101a-104b, where COMP indicates a residue of the anti-CD74 antibody and PAY indicates a payload moiety:
(101a)
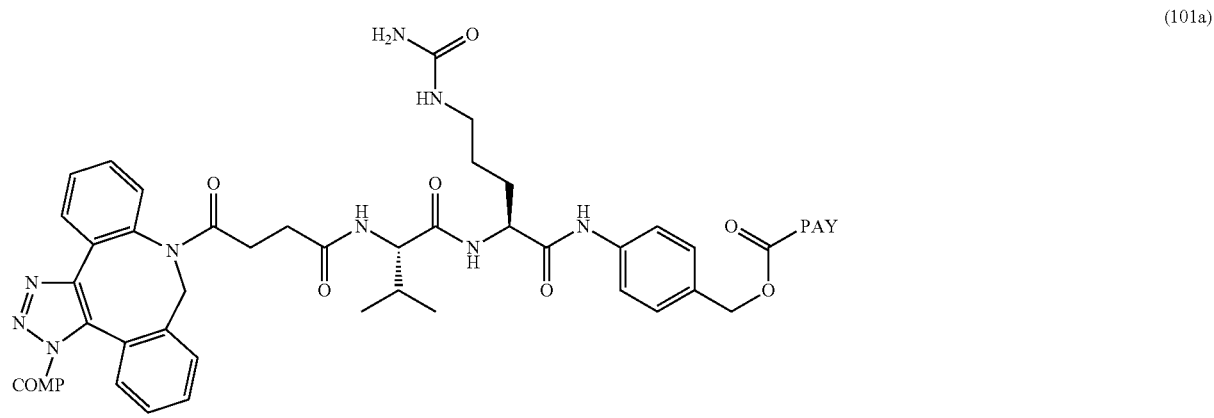
(101b)
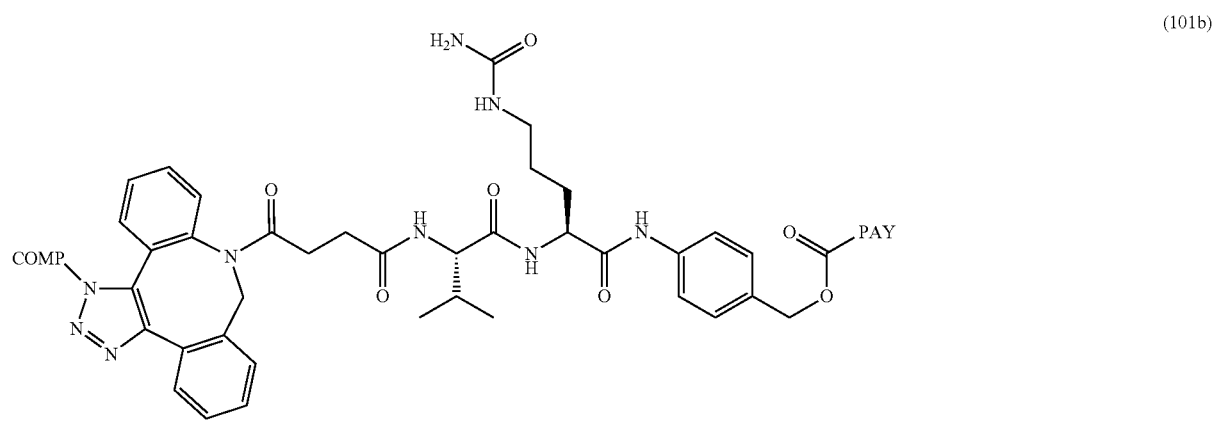
(102a)
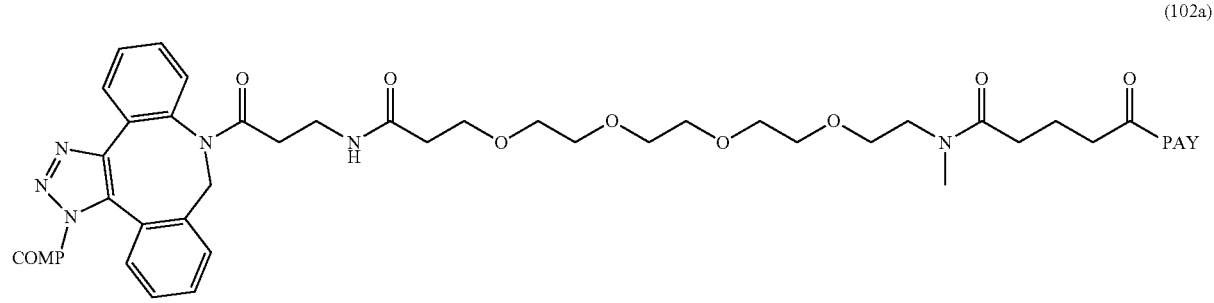
(102b)
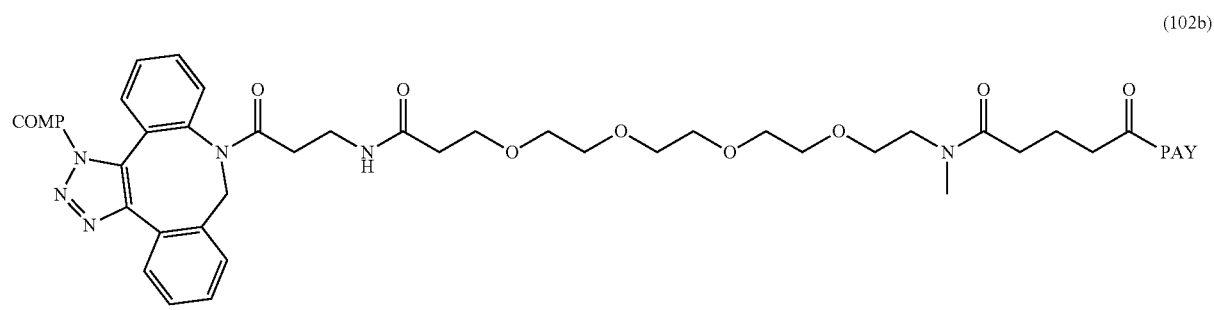
(103a)
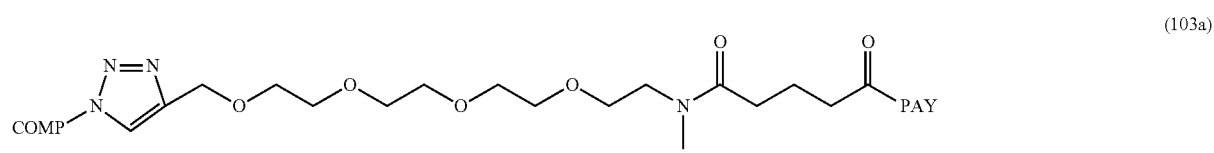

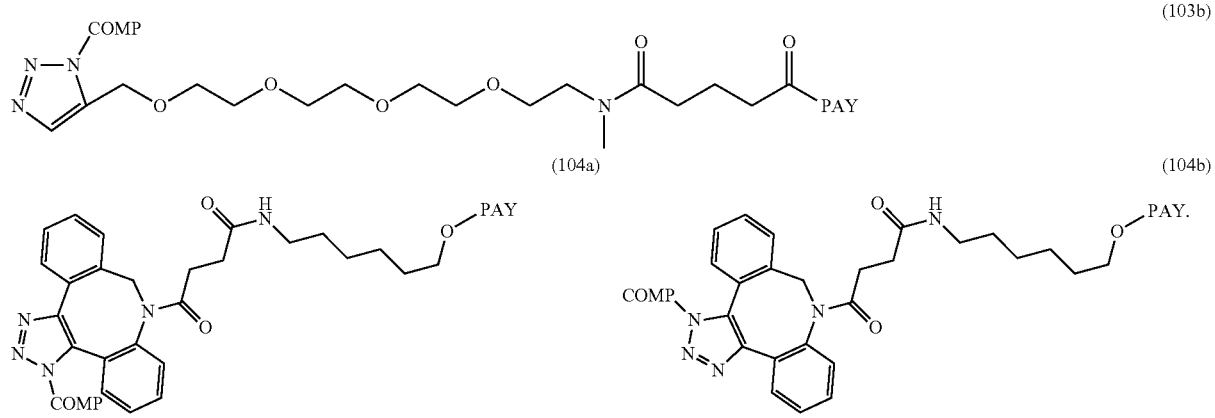

In particular embodiments, provided herein are anti-CD74 conjugates according to any of Formulas 101a-104b wherein COMP indicates a non-natural amino acid residue according to Formula (30), below. In particular embodiments, provided herein are anti-CD74 conjugates according to any of Formulas 101a-104b wherein COMP indicates a non-natural amino acid residue according to Formula (30), below, at heavy chain position 404 according to the EU numbering system. In particular embodiments, provided herein are anti-CD74 conjugates according to any of Formulas 101a-104b wherein COMP indicates a non-natural amino acid residue according to Formula (30), below, at heavy chain position 241 according to the EU numbering system. In particular embodiments, provided herein are anti-CD74 conjugates according to any of Formulas 101a-104b wherein COMP indicates a non-natural amino acid residue according to Formula (30), below, at heavy chain position 222 according to the EU numbering system. In particular embodiments, provided herein are anti-CD74 conjugates according to any of Formulas 101a-104b wherein COMP indicates a non-natural amino acid residue according to Formula (30), below, at light chain position 7 according to the Kabat or Chothia numbering system. In certain embodiments, PAY is selected from the group consisting of maytansine, hemiasterlin, amanitin, monomethyl auristatin F (MMAF), and monomethyl auristatin E (MMAE). In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

In particular embodiments, provided herein are anti-CD74 conjugates according to any of Formulas 101a-104b wherein COMP indicates a non-natural amino acid residue according to Formula (56), below. In particular embodiments, provided herein are anti-CD74 conjugates according to any of Formulas 101a-104b wherein COMP indicates a non-natural amino acid residue according to Formula (56), below, at heavy chain position 404 according to the EU numbering system. In particular embodiments, provided herein are anti-CD74 conjugates according to any of Formulas 101a-104b wherein COMP indicates a non-natural amino acid residue according to Formula (56), below, at heavy chain position 241 according to the EU numbering system. In particular embodiments, provided herein are anti-CD74 conjugates according to any of Formulas 101a-104b wherein COMP indicates a non-natural amino acid residue according to Formula (56), below, at heavy chain position 222 according to the EU numbering system. In particular embodiments, provided herein are anti-CD74 conjugates according to any of Formulas 101a-104b wherein COMP indicates a non-natural amino acid residue according to Formula (56), below, at light chain position 7 according to the Kabat or Chothia numbering system. In certain embodiments, PAY is selected from the group consisting of maytansine, hemiasterlin, amanitin, MMAF, and MMAE. In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

In particular embodiments, provided herein are anti-CD74 conjugates according to any of Formulas 101a-104b wherein COMP indicates a non-natural amino acid residue of para-azido-L-phenylalanine. In particular embodiments, provided herein are anti-CD74 conjugates according to any of Formulas 101a-104b wherein COMP indicates the non-natural amino acid residue para-azido-phenylalanine at heavy chain position 404 according to the EU numbering system. In particular embodiments, provided herein are anti-CD74 conjugates according to any of Formulas 101a-104b wherein COMP indicates the non-natural amino acid residue para-azido-L-phenylalanine at heavy chain position 241 according to the EU numbering system. In particular embodiments, provided herein are anti-CD74 conjugates according to any of Formulas 101a-104b wherein COMP indicates the non-natural amino acid residue para-azido-L-phenylalanine at heavy chain position 222 according to the EU numbering system. In particular embodiments, provided herein are anti-CD74 conjugates according to any of Formulas 101a-104b wherein COMP indicates the non-natural amino acid residue para-azido-L-phenylalanine at light chain position 7 according to the Kabat or Chothia numbering system. In certain embodiments, PAY is selected from the group consisting of maytansine, hemiasterlin, amanitin, MMAF, and MMAE. In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

3. Payloads

The molecular payload can be any molecular entity that one of skill in the art might desire to conjugate to the polypeptide. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the polypeptide to its target. In certain embodiments, the payload is a cytotoxic moiety. In such embodiments, the antibody conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, an antibody conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

Useful drug payloads include any cytotoxic, cytostatic or immunomodulatory agent. Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP (auristatin phenylalanine phenylenediamine), MMAF (monomethyl auristatin F), and MMAE (monomethyl auristatin E). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscamet, or trifluridine.

In other embodiments, the payload is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN), tretinoin, uracil mustard, valrubicin, vinblastine, vincristine, vinorelbine or zoledronate.

In some embodiments, the payload is an immunomodulatory agent. The immunomodulatory agent can be, for example, gangcyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, indomethacin, ketoprofen, nabumetone, sulindac, tenoxicam and tolmetin.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, camosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Other useful drug payloads include chemical compounds useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780, 386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is an antibody or an antibody fragment. In certain embodiments, the payload antibody or fragment can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibody and antibody fragments recognized by those of skill in the art, and variants thereof. Exemplary fragments include but are not limited to Fv, Fc, Fab, and $(Fab')_2$, single chain Fv (scFv), diabodies, triabodies, tetrabodies, bifunctional hybrid polypeptides, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: $XO-(CH_2CH_2O)_n-CH_2CH_2-Y$ where n is 2 to 10,000, X is H or a terminal modification, including but not limited to, a $C_{1-4}$ alkyl, and Y is the attachment point to the polypeptide.

In some cases, a PEG terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester, and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the PEG molecule is available for reaction with the antibody. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: -PEG-CO$_2$—PEG-+H$_2$O→PEG-CO$_2$H+HO-PEG- It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly suitable. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described herein are contemplated as being suitable for use.

In some embodiments the polymer derivatives are "multi-functional", meaning that the polymer backbone has at least two termini, and possibly as many as about 300 termini, functionalized or activated with a functional group. Multi-functional polymer derivatives include, but are not limited to, linear polymers having two termini, each terminus being bonded to a functional group which may be the same or different.

4. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarlyene, and substituted heteroarylene. In certain embodiments, the linker is $C_{1-10}$ alkylene or $C_{1-10}$ heteroalkylene. In some embodiments, the $C_{1-10}$ heteroalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of: N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl)cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly).

In some embodiments, a linker comprises a self-immolative spacer. In certain embodiments, the self-immolative spacer comprises p-aminobenzyl. In certain embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. 55:5867). Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as val-cit-PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

5. Antibody Specificity

The conjugates comprise antibodies that selectively bind human CD74. In some aspects, the antibody selectively binds to human CD74 isoform 1. In some aspects, the antibody selectively binds to human CD74 isoform 2. In some aspects, the antibody may selectively bind to more than one CD74 isoform, for example, both human CD74 isoforms 1 and 2. In some aspects, the antibody may selectively bind to one or more CD74 isoforms with the same extracellular domain as isoforms 1 and 2, such as p41 and p33, respectively.

In some embodiments, the antibody binds to homologs of human CD74. In some aspects, the antibody binds to a homolog of human CD74 from a species selected from monkeys, dogs, cats, mice, rats, cows, horses, goats or sheep. In some aspects, the homolog is a cynomolgus monkey homolog.

In some embodiments, the antibodies have higher melting temperatures than other anti-CD74 antibodies. In some aspects, the Tm2 of the antibody is higher than other anti-CD74 antibodies. The Tm2 represents the melting temperature of the Fab domain of an IgG. A higher Tm2 therefore promotes stability of the antibody binding site. Such improved stability can lead to better stability of the antibody during storage, as well as improved yield during manufacturing.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with a conservative amino acid substitution.

In some embodiments, the antibody has one or more CDRs having particular lengths, in terms of the number of amino acid residues. In some aspects, the Chothia CDR-H1 of the antibody is seven residues in length. In some embodiments, the Kabat CDR-H1 of the antibody is five residues in length. In some aspects, the Chothia CDR-H2 of the antibody is six residues in length. In some embodiments, the Kabat CDR-H2 of the antibody is seventeen residues in length. In some aspects, the Chothia/Kabat CDR-H3 of the antibody is eleven residues in length. In some aspects, the Chothia/Kabat CDR-H3 of the antibody is twelve residues in length. In some aspects, the Chothia/Kabat CDR-H3 of the antibody is thirteen residues in length. In some aspects, the Chothia/Kabat CDR-H3 of the antibody is fourteen residues in length. In some aspects, the Chothia/Kabat CDR-H3 of the antibody is fifteen residues in length. In some aspects, the Chothia/Kabat CDR-H3 of the antibody is more than fifteen residues in length. In some aspects, the Chothia/Kabat CDR-H3 of the antibody is up to twenty-five residues in length.

In some aspects, the Kabat/Chothia CDR-L1 of the antibody is eleven residues in length. In some aspects, the Kabat/Chothia CDR-L1 of the antibody is twelve residues in length. In some aspects, the Kabat/Chothia CDR-L2 of the antibody is seven residues in length. In some aspects, the Kabat/Chothia CDR-L3 of the antibody is nine residues in length.

In some embodiments, the antibody comprises a light chain. In some aspects, the light chain is selected from a kappa light chain and a lambda light chain.

In some embodiments, the antibody comprises a heavy chain. In some aspects, the heavy chain is selected from IgA, IgD, IgE, IgG, and IgM. In some aspects, the heavy chain is selected from IgG1, IgG2, IgG3, IgG4, IgA1, and IgA2.

In some embodiments, the antibody is an antibody fragment. In some aspects, the antibody fragment is selected from an Fv fragment, a Fab fragment, a F(ab')$_2$ fragment, a Fab' fragment, an scFv (sFv) fragment, and an scFv-Fc fragment.

In some embodiments, the antibody is a monoclonal antibody.

In some embodiments, the antibody is a chimeric, humanized, or human antibody.

In some embodiments, the antibody is an affinity matured antibody. In some aspects, the antibody is an affinity matured antibody derived from an illustrative sequence provided in this disclosure.

In some embodiments, the antibody is internalized by a cell after binding.

In some embodiments, the antibody inhibits the binding of CD74 to its ligands. In some aspects, the antibody inhibits the binding of CD74 to macrophage migration inhibitory factor (MIF).

In some embodiments, the antibody is one that is described in WO2016/014434 A2, which is incorporated herein by reference in its entirety.

5.1. CDR-H3 Sequences

In some embodiments, the antibody comprises a CDR-H3 sequence comprising, consisting of, or consisting essentially of a sequence selected from SEQ ID NOs: 129-160. In some aspects, the antibody comprises a CDR-H3 sequence comprising, consisting of, or consisting essentially of SEQ ID NO: 129. In some aspects, the antibody comprises a CDR-H3 sequence comprising, consisting of, or consisting essentially of SEQ ID NO: 130. In some aspects, the antibody comprises a CDR-H3 sequence comprising, consisting of, or consisting essentially of SEQ ID NO: 131. In some aspects, the antibody comprises a CDR-H3 sequence comprising, consisting of, or consisting essentially of SEQ ID NO: 132. In some aspects, the antibody comprises a CDR-H3 sequence comprising, consisting of, or consisting essentially of SEQ ID NO: 133. In some aspects, the antibody comprises a CDR-H3 sequence comprising, consisting of, or consisting essentially of SEQ ID NO: 134. In some aspects, the antibody comprises a CDR-H3 sequence comprising, consisting of, or consisting essentially of SEQ ID NO: 135. In some aspects, the antibody comprises a CDR-H3 sequence comprising, consisting of, or consisting essentially of SEQ ID NO: 136. In some aspects, the antibody comprises a CDR-H3 sequence comprising, consisting of, or consisting essentially of SEQ ID NO: 137. In some aspects, the antibody comprises a CDR-H3 sequence comprising, consisting of, or consisting essentially of SEQ ID NO: 138. In some aspects, the antibody comprises a CDR-H3 sequence comprising, consisting of, or consisting essentially of SEQ ID NO: 139. In some aspects, the antibody comprises a CDR-H3 sequence comprising, consisting of, or consisting essentially of SEQ ID NO: 140. In some aspects, the antibody comprises a CDR-H3 sequence comprising, consisting of, or consisting essentially of SEQ ID NO: 141. In some aspects, the antibody comprises a CDR-H3 sequence comprising, consisting of, or consisting essentially of SEQ ID NO: 142. In some aspects, the antibody comprises a CDR-H3 sequence comprising, consisting of, or consisting essentially of SEQ ID NO: 143. In some aspects, the antibody comprises a CDR-H3 sequence comprising, consisting of, or consisting essentially of SEQ ID NO: 144. In some aspects, the antibody comprises a CDR-H3 sequence comprising, consisting of, or consisting essentially of SEQ ID NO: 145. In some aspects, the antibody comprises a CDR-H3 sequence comprising, consisting of, or consisting essentially of SEQ ID NO: 146. In some aspects, the antibody comprises a CDR-H3 sequence comprising, consisting of, or consisting essentially of SEQ ID NO: 147. In some aspects, the antibody comprises a CDR-H3 sequence comprising, consisting of, or consisting essentially of SEQ ID NO: 148. In some aspects, the antibody comprises a CDR-H3 sequence comprising, consisting of, or consisting essentially of SEQ ID NO: 149. In some aspects, the antibody comprises a CDR-H3 sequence comprising, consisting of, or consisting essentially of SEQ ID NO: 150. In some aspects, the antibody comprises a CDR-H3 sequence comprising, consisting of, or consisting essentially of SEQ ID NO: 151. In some aspects, the antibody comprises a CDR-H3 sequence comprising, consisting of, or consisting essentially of SEQ ID NO: 152. In some aspects, the antibody comprises a CDR-H3 sequence comprising, consisting of, or consisting essentially of SEQ ID NO: 153. In some aspects, the antibody comprises a CDR-H3 sequence comprising, consisting of, or consisting essentially of SEQ ID NO: 154. In some aspects, the antibody comprises a CDR-H3 sequence comprising, consisting of, or consisting essentially of SEQ ID NO: 155. In some aspects, the antibody comprises a CDR-H3 sequence comprising, consisting of, or consisting essentially of SEQ ID NO: 156. In some aspects, the antibody comprises a CDR-H3 sequence comprising, consisting of, or consisting essentially of SEQ ID NO: 157. In some aspects, the antibody comprises a CDR-H3 sequence comprising, consisting of, or consisting essentially of SEQ ID NO: 158. In some aspects, the antibody comprises a CDR-H3 sequence comprising, consisting of, or consisting essentially of SEQ ID NO: 159. In some aspects, the antibody comprises a CDR-H3 sequence comprising, consisting of, or consisting essentially of SEQ ID NO: 160.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-H3 sequence does not comprise, consist of, or consist essentially of a sequence selected from SEQ ID NOs: 157-160. In some aspects, the CDR-H3 sequence does not comprise, consist of, or consist essentially of SEQ ID NO: 157. In some aspects, the CDR-H3 sequence does not comprise, consist of, or consist essentially of SEQ ID NO: 158. In some aspects, the CDR-H3 sequence does not comprise, consist of, or consist essentially of SEQ ID NO: 159. In some aspects, the CDR-H3 sequence does not comprise, consist of, or consist essentially of SEQ ID NO: 160.

5.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof.

5.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

5.2.1.1. Kabat CDR-H3

In some embodiments, the antibody comprises a $V_H$ sequence comprising a Kabat CDR-H3 sequence comprising, consisting of, or consisting essentially of a sequence selected from SEQ ID NOs: 129-156. In some aspects, the antibody comprises a $V_H$ sequence comprising a Kabat CDR-H3 sequence comprising, consisting of, or consisting essentially of SEQ ID NO: 129. In some aspects, the antibody comprises a $V_H$ sequence comprising a Kabat CDR-H3 sequence comprising, consisting of, or consisting essentially of SEQ ID NO: 130. In some aspects, the antibody comprises a $V_H$ sequence comprising a Kabat CDR-H3 sequence comprising, consisting of, or consisting essentially of SEQ ID NO: 131. In some aspects, the antibody comprises a $V_H$ sequence comprising a Kabat CDR-H3 sequence comprising, consisting of, or consisting essentially of SEQ ID NO: 132. In some aspects, the antibody comprises a $V_H$ sequence comprising a Kabat CDR-H3 sequence comprising, consisting of, or consisting essentially of SEQ ID NO: 133. In some aspects, the antibody comprises a $V_H$ sequence comprising a Kabat CDR-H3 sequence comprising, consisting of, or consisting essentially of SEQ ID NO: 134. In some aspects, the antibody comprises a $V_H$ sequence comprising a Kabat CDR-H3 sequence comprising, consisting of, or consisting essentially of SEQ ID NO: 135. In some aspects, the antibody comprises a $V_H$ sequence comprising a Kabat CDR-H3 sequence comprising, consisting of, or consisting essentially of SEQ ID NO: 136. In some aspects, the antibody comprises a $V_H$ sequence comprising a Kabat CDR-H3 sequence comprising, consisting of, or consisting essentially of SEQ ID NO: 137. In some aspects, the antibody comprises a $V_H$ sequence comprising a Kabat CDR-H3 sequence comprising, consisting of, or consisting essentially of SEQ ID NO: 138. In some aspects, the antibody comprises a $V_H$ sequence comprising a Kabat CDR-H3 sequence comprising, consisting of, or consisting essentially of SEQ ID NO: 139. In some aspects, the antibody comprises a $V_H$ sequence comprising a Kabat CDR-H3 sequence comprising, consisting of, or consisting essentially of SEQ ID NO: 140. In some aspects, the antibody comprises a $V_H$ sequence comprising a Kabat CDR-H3 sequence comprising, consisting of, or consisting essentially of SEQ ID NO: 141. In some aspects, the antibody comprises a $V_H$ sequence comprising a Kabat CDR-H3 sequence comprising, consisting of, or consisting essentially of SEQ ID NO: 142. In some aspects, the antibody comprises a $V_H$ sequence comprising a Kabat CDR-H3 sequence comprising, consisting of, or consisting essentially of SEQ ID NO: 143. In some aspects, the antibody comprises a $V_H$ sequence comprising a Kabat CDR-H3 sequence comprising, consisting of, or consisting essentially of SEQ ID NO: 144. In some aspects, the antibody comprises a $V_H$ sequence comprising a Kabat CDR-H3 sequence comprising, consisting of, or consisting essentially of SEQ ID NO: 145. In some aspects, the antibody comprises a $V_H$ sequence comprising a Kabat CDR-H3 sequence comprising, consisting of, or consisting essentially of SEQ ID NO: 146. In some aspects, the antibody comprises a $V_H$ sequence comprising a Kabat CDR-H3 sequence comprising, consisting of, or consisting essentially of SEQ ID NO: 147. In some aspects, the antibody comprises a $V_H$ sequence comprising a Kabat CDR-H3 sequence comprising, consisting of, or consisting essentially of SEQ ID NO: 148. In some aspects, the antibody comprises a $V_H$ sequence comprising a Kabat CDR-H3 sequence comprising, consisting of, or consisting essentially of SEQ ID NO: 149. In some aspects, the antibody comprises a $V_H$ sequence comprising a Kabat CDR-H3 sequence comprising, consisting of, or consisting essentially of SEQ ID NO: 150. In some aspects, the antibody comprises a $V_H$ sequence comprising a Kabat CDR-H3 sequence comprising, consisting of, or consisting essentially of SEQ ID NO: 151. In some aspects, the antibody comprises a $V_H$ sequence comprising a Kabat CDR-H3 sequence comprising, consisting of, or consisting essentially of SEQ ID NO: 152. In some aspects, the antibody comprises a $V_H$ sequence comprising a Kabat CDR-H3 sequence comprising, consisting of, or consisting essentially of SEQ ID NO: 153. In some aspects, the antibody comprises a $V_H$ sequence comprising a Kabat CDR-H3 sequence comprising, consisting of, or consisting essentially of SEQ ID NO: 154. In some aspects, the antibody comprises a $V_H$ sequence comprising a Kabat CDR-H3 sequence comprising, consisting of, or consisting essentially of SEQ ID NO: 155. In some aspects, the antibody comprises a $V_H$ sequence comprising a Kabat CDR-H3 sequence comprising, consisting of, or consisting essentially of SEQ ID NO: 156.

5.2.1.2. Kabat CDR-H2

In some embodiments, the antibody comprises a $V_H$ sequence comprising a Kabat CDR-H2 sequence comprising, consisting of, or consisting essentially of a sequence selected from SEQ ID NOs: 97-124. In some aspects, the antibody comprises a $V_H$ sequence comprising a Kabat CDR-H2 sequence comprising, consisting of, or consisting essentially of SEQ ID NO: 97. In some aspects, the antibody comprises a $V_H$ sequence comprising a Kabat CDR-H2 sequence comprising, consisting of, or consisting essentially of SEQ ID NO: 98. In some aspects, the antibody comprises a $V_H$ sequence comprising a Kabat CDR-H2 sequence comprising, consisting of, or consisting essentially of SEQ ID NO: 99. In some aspects, the antibody comprises a $V_H$ sequence comprising a Kabat CDR-H2 sequence comprising, consisting of, or consisting essentially of SEQ ID NO: 100. In some aspects, the antibody comprises a $V_H$ sequence comprising a Kabat CDR-H2 sequence comprising, consisting of, or consisting essentially of SEQ ID NO: 101. In some aspects, the antibody comprises a $V_H$ sequence comprising a Kabat CDR-H2 sequence comprising, consisting of, or consisting essentially of SEQ ID NO: 102. In some aspects, the antibody comprises a $V_H$ sequence comprising a Kabat CDR-H2 sequence comprising, consisting of, or consisting essentially of SEQ ID NO: 103. In some aspects, the antibody comprises a $V_H$ sequence comprising a Kabat CDR-H2 sequence comprising, consisting of, or consisting essentially of SEQ ID NO: 104. In some aspects, the antibody comprises a $V_H$ sequence comprising a Kabat CDR-H2 sequence comprising, consisting of, or consisting essentially of SEQ ID NO: 105. In some aspects, the antibody comprises a $V_H$ sequence comprising a Kabat CDR-H2 sequence comprising, consisting of, or consisting essentially of SEQ ID NO: 106. In some aspects, the antibody comprises a $V_H$ sequence comprising a Kabat CDR-H2 sequence comprising, consisting of, or consisting essentially of SEQ ID NO: 107. In some aspects, the antibody comprises a $V_H$ sequence comprising a Kabat CDR-H2 sequence comprising, consisting of, or consisting essentially of SEQ ID NO: 108. In some aspects, the antibody comprises a $V_H$ sequence comprising a Kabat CDR-H2 sequence comprising, consisting of, or consisting essentially of SEQ ID NO: 109. In some aspects, the antibody comprises a $V_H$ sequence comprising a Kabat CDR-H2 sequence comprising, consisting of, or consisting essentially of SEQ ID NO: 110. In some aspects, the antibody comprises a $V_H$ sequence comprising a Kabat CDR-H2 sequence comprising, consisting of, or consisting essentially of SEQ ID NO: 111. In some aspects, the antibody comprises a $V_H$ sequence comprising a Kabat CDR-H2 sequence comprising, consisting of, or consisting essentially of SEQ ID NO: 112. In some aspects, the antibody comprises a $V_H$ sequence comprising a Kabat CDR-H2 sequence comprising, consisting of, or consisting essentially of SEQ ID NO: 113. In some aspects, the antibody comprises a $V_H$ sequence comprising a Kabat CDR-H2 sequence comprising, consisting of, or consisting essentially of SEQ ID NO: 114. In some aspects, the antibody comprises a $V_H$ sequence comprising a Kabat CDR-H2 sequence comprising, consisting of, or consisting essentially of SEQ ID NO: 115. In some aspects, the antibody comprises a $V_H$ sequence comprising a Kabat CDR-H2 sequence comprising, consisting of, or consisting essentially of SEQ ID NO: 116. In some aspects, the antibody comprises a $V_H$ sequence comprising a Kabat CDR-H2 sequence comprising, consisting of, or consisting essentially of SEQ ID NO: 117. In some aspects, the antibody comprises a $V_H$ sequence comprising a Kabat CDR-H2 sequence comprising, consisting of, or consisting essentially of SEQ ID NO: 118. In some aspects, the antibody comprises a $V_H$ sequence comprising a Kabat CDR-H2 sequence comprising, consisting of, or consisting essentially of SEQ ID NO: 119. In some aspects, the antibody comprises a $V_H$ sequence comprising a Kabat CDR-H2 sequence comprising, consisting of, or consisting essentially of SEQ ID NO: 120. In some aspects, the antibody comprises a $V_H$ sequence comprising a Kabat CDR-H2 sequence comprising, consisting of, or consisting essentially of SEQ ID NO: 121. In some aspects, the antibody comprises a $V_H$ sequence comprising a Kabat CDR-H2 sequence comprising, consisting of, or consisting essentially of SEQ ID NO: 122. In some aspects, the antibody comprises a $V_H$ sequence comprising a Kabat CDR-H2 sequence comprising, consisting of, or consisting essentially of SEQ ID NO: 123. In some aspects, the antibody comprises a $V_H$ sequence comprising a Kabat CDR-H2 sequence comprising, consisting of, or consisting essentially of SEQ ID NO: 124.

5.2.1.3. Kabat CDR-H1

In some embodiments, the antibody comprises a $V_H$ sequence comprising a Kabat CDR-H1 sequence comprising, consisting of, or consisting essentially of a sequence selected from SEQ ID NOs: 33-60. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34. In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36 In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a $V_H$ sequence comprising a Kabat CDR-H1 sequence comprising, consisting of, or consisting essentially of SEQ ID NO: 45. In some aspects, the antibody comprises a $V_H$ sequence comprising a Kabat CDR-H1 sequence comprising, consisting of, or consisting essentially of SEQ ID NO: 46. In some aspects, the antibody comprises a $V_H$ sequence comprising a Kabat CDR-H1 sequence comprising, consisting of, or consisting essentially of SEQ ID NO: 47. In some aspects, the antibody comprises a $V_H$ sequence comprising a Kabat CDR-H1 sequence comprising, consisting of, or consisting essentially of SEQ ID NO: 48. In some aspects, the antibody comprises a $V_H$ sequence comprising a Kabat CDR-H1 sequence comprising, consisting of, or consisting essentially of SEQ ID NO: 49. In some aspects, the antibody comprises a $V_H$ sequence comprising a Kabat CDR-H1 sequence comprising, consisting of, or consisting essentially of SEQ ID NO: 50. In some aspects, the antibody comprises a $V_H$ sequence comprising a Kabat CDR-H1 sequence comprising, consisting of, or consisting essentially of SEQ ID NO: 51. In some aspects, the antibody comprises a $V_H$ sequence comprising a Kabat CDR-H1 sequence comprising, consisting of, or consisting essentially of SEQ ID NO: 52. In some aspects, the antibody comprises a $V_H$ sequence comprising a Kabat CDR-H1 sequence comprising, consisting of, or consisting essentially of SEQ ID NO: 53. In some aspects, the antibody comprises a $V_H$ sequence comprising a Kabat CDR-H1 sequence comprising, consisting of, or consisting essentially of SEQ ID NO:

54. In some aspects, the antibody comprises a $V_H$ sequence comprising a Kabat CDR-H1 sequence comprising, consisting of, or consisting essentially of SEQ ID NO: 55. In some aspects, the antibody comprises a $V_H$ sequence comprising a Kabat CDR-H1 sequence comprising, consisting of, or consisting essentially of SEQ ID NO: 56. In some aspects, the antibody comprises a $V_H$ sequence comprising a Kabat CDR-H1 sequence comprising, consisting of, or consisting essentially of SEQ ID NO: 57. In some aspects, the antibody comprises a $V_H$ sequence comprising a Kabat CDR-H1 sequence comprising, consisting of, or consisting essentially of SEQ ID NO: 58. In some aspects, the antibody comprises a $V_H$ sequence comprising a Kabat CDR-H1 sequence comprising, consisting of, or consisting essentially of SEQ ID NO: 59. In some aspects, the antibody comprises a $V_H$ sequence comprising a Kabat CDR-H1 sequence comprising, consisting of, or consisting essentially of SEQ ID NO: 60.

5.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 129-156 and a Kabat CDR-H2 sequence comprising, consisting of, or consisting essentially of a sequence selected from SEQ ID NOs: 97-124. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 230-251 and 273-280.

5.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 129-156 and a Kabat CDR-H1 sequence comprising, consisting of, or consisting essentially of a sequence selected from SEQ ID NOs: 33-60. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 230-251 and 273-280.

5.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 33-60 and a Kabat CDR-H2 sequence comprising, consisting of, or consisting essentially of a sequence selected from SEQ ID NOs: 97-124. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 230-251 and 273-280.

5.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 33-60, a Kabat CDR-H2 sequence comprising, consisting of, or consisting essentially of a sequence selected from SEQ ID NOs: 97-124, and a Kabat CDR-H3 sequence comprising, consisting of, or consisting essentially of a sequence selected from SEQ ID NOs: 129-156. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 230-251 and 273-280.

5.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

5.2.1.9. Excluded $V_H$ Sequences Comprising Kabat CDRs

In some embodiments, the $V_H$ sequences provided herein do not comprise certain Kabat CDR-H3, CDR-H2, and/or CDR-H1 sequences.

In some aspects, the Kabat CDR-H3 sequence does not comprise, consist of, or consist essentially of a sequence selected from SEQ ID NOs: 157-160. In some aspects, the Kabat CDR-H3 sequence does not comprise, consist of, or consist essentially of SEQ ID NO: 157. In some aspects, the Kabat CDR-H3 sequence does not comprise, consist of, or consist essentially of SEQ ID NO: 158. In some aspects, the Kabat CDR-H3 sequence does not comprise, consist of, or consist essentially of SEQ ID NO: 159. In some aspects, the Kabat CDR-H3 sequence does not comprise, consist of, or consist essentially of SEQ ID NO: 160.

In some aspects, the Kabat CDR-H2 sequence does not comprise, consist of, or consist essentially of a sequence selected from SEQ ID NOs: 125-128. In some aspects, the Kabat CDR-H2 sequence does not comprise, consist of, or consist essentially of SEQ ID NO: 125. In some aspects, the Kabat CDR-H2 sequence does not comprise, consist of, or consist essentially of SEQ ID NO: 126. In some aspects, the Kabat CDR-H2 sequence does not comprise, consist of, or consist essentially of SEQ ID NO: 127. In some aspects, the Kabat CDR-H2 sequence does not comprise, consist of, or consist essentially of SEQ ID NO: 128.

In some aspects, the Kabat CDR-H1 sequence does not comprise, consist of, or consist essentially of a sequence selected from SEQ ID NOs: 61-64. In some aspects, the Kabat CDR-H1 sequence does not comprise, consist of, or consist essentially of SEQ ID NO: 61. In some aspects, the Kabat CDR-H1 sequence does not comprise, consist of, or consist essentially of SEQ ID NO: 62. In some aspects, the Kabat CDR-H1 sequence does not comprise, consist of, or consist essentially of SEQ ID NO: 63. In some aspects, the Kabat CDR-H1 sequence does not comprise, consist of, or consist essentially of SEQ ID NO: 64.

5.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

5.2.2.1. Chothia CDR-H3

In some embodiments, the antibody comprises a $V_H$ sequence comprising a Chothia CDR-H3 sequence comprising, consisting of, or consisting essentially of a sequence selected from SEQ ID NOs: 129-156. In some aspects, the antibody comprises a $V_H$ sequence comprising a Chothia CDR-H3 sequence comprising, consisting of, or consisting essentially of SEQ ID NO: 129. In some aspects, the antibody comprises a $V_H$ sequence comprising a Chothia CDR-H3 sequence comprising, consisting of, or consisting essentially of SEQ ID NO: 130. In some aspects, the antibody comprises a $V_H$ sequence comprising a Chothia CDR-H3 sequence comprising, consisting of, or consisting essentially of SEQ ID NO: 131. In some aspects, the antibody comprises a $V_H$ sequence comprising a Chothia CDR-H3 sequence comprising, consisting of, or consisting essentially of SEQ ID NO: 132. In some aspects, the antibody comprises a $V_H$ sequence comprising a Chothia CDR-H3 sequence comprising, consisting of, or consisting essentially of SEQ ID NO: 133. In some aspects, the antibody comprises a $V_H$ sequence comprising a Chothia CDR-H3 sequence comprising, consisting of, or consisting essentially of SEQ ID NO: 134. In some aspects, the antibody comprises a $V_H$ sequence comprising a Chothia CDR-H3 sequence comprising, consisting of, or consisting essentially of SEQ ID NO: 135. In some aspects, the antibody comprises a $V_H$ sequence comprising a Chothia CDR-H3 sequence comprising, consisting of, or consisting essentially of SEQ ID NO: 136. In some aspects, the antibody comprises a $V_H$ sequence comprising a Chothia CDR-H3 sequence comprising, consisting of, or consisting essentially of SEQ ID NO: 137. In some aspects, the antibody comprises a $V_H$ sequence comprising a Chothia CDR-H3 sequence comprising, consisting of, or consisting essentially of SEQ ID NO: 138. In some aspects, the antibody comprises a $V_H$ sequence comprising a Chothia CDR-H3 sequence comprising, consisting of, or consisting essentially of SEQ ID NO: 139. In some aspects, the antibody comprises a $V_H$ sequence comprising a Chothia CDR-H3 sequence comprising, consisting of, or consisting essentially of SEQ ID NO: 140. In some aspects, the antibody comprises a $V_H$ sequence comprising a Chothia CDR-H3 sequence comprising, consisting of, or consisting essentially of SEQ ID NO: 141. In some aspects, the antibody comprises a $V_H$ sequence comprising a Chothia CDR-H3 sequence comprising, consisting of, or consisting essentially of SEQ ID NO: 142. In some aspects, the antibody comprises a $V_H$ sequence comprising a Chothia CDR-H3 sequence comprising, consisting of, or consisting essentially of SEQ ID NO: 143. In some aspects, the antibody comprises a $V_H$ sequence comprising a Chothia CDR-H3 sequence comprising, consisting of, or consisting essentially of SEQ ID NO: 144. In some aspects, the antibody comprises a $V_H$ sequence comprising a Chothia CDR-H3 sequence comprising, consisting of, or consisting essentially of SEQ ID NO: 145. In some aspects, the antibody comprises a $V_H$ sequence comprising a Chothia CDR-H3 sequence comprising, consisting of, or consisting essentially of SEQ ID NO: 146. In some aspects, the antibody comprises a $V_H$ sequence comprising a Chothia CDR-H3 sequence comprising, consisting of, or consisting essentially of SEQ ID NO: 147. In some aspects, the antibody comprises a $V_H$ sequence comprising a Chothia CDR-H3 sequence comprising, consisting of, or consisting essentially of SEQ ID NO: 148. In some aspects, the antibody comprises a $V_H$ sequence comprising a Chothia CDR-H3 sequence comprising, consisting of, or consisting essentially of SEQ ID NO: 149. In some aspects, the antibody comprises a $V_H$ sequence comprising a Chothia CDR-H3 sequence comprising, consisting of, or consisting essentially of SEQ ID NO: 150. In some aspects, the antibody comprises a $V_H$ sequence comprising a Chothia CDR-H3 sequence comprising, consisting of, or consisting essentially of SEQ ID NO: 151. In some aspects, the antibody comprises a $V_H$ sequence comprising a Chothia CDR-H3 sequence comprising, consisting of, or consisting essentially of SEQ ID NO: 152. In some aspects, the antibody comprises a $V_H$ sequence comprising a Chothia CDR-H3 sequence comprising, consisting of, or consisting essentially of SEQ ID NO: 153. In some aspects, the antibody comprises a $V_H$ sequence comprising a Chothia CDR-H3 sequence comprising, consisting of, or consisting essentially of SEQ ID NO: 154. In some aspects, the antibody comprises a $V_H$ sequence comprising a Chothia CDR-H3 sequence comprising, consisting of, or consisting essentially of SEQ ID NO: 155. In some aspects, the antibody comprises a $V_H$ sequence comprising a Chothia CDR-H3 sequence comprising, consisting of, or consisting essentially of SEQ ID NO: 156.

5.2.2.2. Chothia CDR-H2

In some embodiments, the antibody comprises a $V_H$ sequence comprising a Chothia CDR-H2 sequence comprising, consisting of, or consisting essentially of a sequence selected from SEQ ID NOs: 65-92. In some aspects, the antibody comprises a $V_H$ sequence comprising a Chothia CDR-H2 sequence comprising, consisting of, or consisting essentially of SEQ ID NO: 65. In some aspects, the antibody comprises a $V_H$ sequence comprising a Chothia CDR-H2 sequence comprising, consisting of, or consisting essentially of SEQ ID NO: 66. In some aspects, the antibody comprises a $V_H$ sequence comprising a Chothia CDR-H2 sequence comprising, consisting of, or consisting essentially of SEQ ID NO: 67. In some aspects, the antibody comprises a $V_H$ sequence comprising a Chothia CDR-H2 sequence comprising, consisting of, or consisting essentially of SEQ ID NO: 68. In some aspects, the antibody comprises a $V_H$ sequence comprising a Chothia CDR-H2 sequence comprising, consisting of, or consisting essentially of SEQ ID NO: 69. In some aspects, the antibody comprises a $V_H$ sequence comprising a Chothia CDR-H2 sequence comprising, consisting of, or consisting essentially of SEQ ID NO: 70. In some aspects, the antibody comprises a $V_H$ sequence comprising a Chothia CDR-H2 sequence comprising, consisting of, or consisting essentially of SEQ ID NO: 71. In some aspects, the antibody comprises a $V_H$ sequence comprising a Chothia CDR-H2 sequence comprising, consisting of, or consisting essentially of SEQ ID NO: 72. In some aspects, the antibody comprises a $V_H$ sequence comprising a Chothia CDR-H2 sequence comprising, consisting of, or consisting essentially of SEQ ID NO: 73. In some aspects, the antibody comprises a $V_H$ sequence comprising a Chothia CDR-H2 sequence comprising, consisting of, or consisting essentially of SEQ ID NO: 74. In some aspects, the antibody comprises a $V_H$ sequence comprising a Chothia CDR-H2 sequence comprising, consisting of, or consisting essentially of SEQ ID NO: 75. In some aspects, the antibody comprises a $V_H$ sequence comprising a Chothia CDR-H2 sequence comprising, consisting of, or consisting essentially of SEQ ID NO: 76. In some aspects, the antibody comprises a $V_H$ sequence comprising a Chothia CDR-H2 sequence comprising, consisting of, or consisting essentially of SEQ ID NO: 77. In some aspects, the antibody comprises a $V_H$ sequence comprising a Chothia CDR-H2 sequence comprising, consisting of, or consisting essentially of SEQ ID NO: 78. In some aspects, the antibody comprises a $V_H$ sequence comprising a Chothia CDR-H2 sequence comprising, consisting of, or consisting essentially of SEQ ID NO: 79. In some aspects, the antibody comprises a $V_H$ sequence comprising a Chothia CDR-H2 sequence comprising, consisting of, or consisting essentially of SEQ ID NO: 80. In some aspects, the antibody comprises a $V_H$ sequence comprising a Chothia CDR-H2 sequence comprising, consisting of, or consisting essentially of SEQ ID NO: 81. In some aspects, the antibody comprises a $V_H$ sequence comprising a Chothia CDR-H2 sequence comprising, consisting of, or consisting essentially of SEQ ID NO: 82. In some aspects, the antibody comprises a $V_H$ sequence comprising a Chothia CDR-H2 sequence comprising, consisting of, or consisting essentially of SEQ ID NO: 83. In some aspects, the antibody comprises a $V_H$ sequence comprising a Chothia CDR-H2 sequence comprising, consisting of, or consisting essentially of SEQ ID NO: 84. In some aspects, the antibody comprises a $V_H$ sequence comprising a Chothia CDR-H2 sequence comprising, consisting of, or consisting essentially of SEQ ID NO: 85. In some aspects, the antibody comprises a $V_H$ sequence comprising a Chothia CDR-H2 sequence comprising, consisting of, or consisting essentially of SEQ ID NO: 86. In some aspects, the antibody comprises a $V_H$ sequence comprising a Chothia CDR-H2 sequence comprising, consisting of, or consisting essentially of SEQ ID NO: 87. In some aspects, the antibody comprises a $V_H$ sequence comprising a Chothia CDR-H2 sequence comprising, consisting of, or consisting essentially of SEQ ID NO: 88. In some aspects, the antibody comprises a $V_H$ sequence comprising a Chothia CDR-H2 sequence comprising, consisting of, or consisting essentially of SEQ ID NO: 89. In some aspects, the antibody comprises a $V_H$ sequence comprising a Chothia CDR-H2 sequence comprising, consisting of, or consisting essentially of SEQ ID NO: 90. In some aspects, the antibody comprises a $V_H$ sequence comprising a Chothia CDR-H2 sequence comprising, consisting of, or consisting essentially of SEQ ID NO: 91. In some aspects, the antibody comprises a $V_H$ sequence comprising a Chothia CDR-H2 sequence comprising, consisting of, or consisting essentially of SEQ ID NO: 92.

5.2.2.3. Chothia CDR-H1

In some embodiments, the antibody comprises a $V_H$ sequence comprising a Chothia CDR-H1 sequence comprising, consisting of, or consisting essentially of a sequence selected from SEQ ID NOs: 1-28. In some aspects, the antibody comprises a $V_H$ sequence comprising a Chothia CDR-H1 sequence comprising, consisting of, or consisting essentially of SEQ ID NO: 1. In some aspects, the antibody comprises a $V_H$ sequence comprising a Chothia CDR-H1 sequence comprising, consisting of, or consisting essentially of SEQ ID NO: 2. In some aspects, the antibody comprises a $V_H$ sequence comprising a Chothia CDR-H1 sequence comprising, consisting of, or consisting essentially of SEQ ID NO: 3. In some aspects, the antibody comprises a $V_H$ sequence comprising a Chothia CDR-H1 sequence comprising, consisting of, or consisting essentially of SEQ ID NO: 4 In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a $V_H$ sequence comprising a Chothia CDR-H1 sequence comprising, consisting of, or consisting essentially of SEQ ID NO: 24. In some aspects, the antibody comprises a $V_H$ sequence comprising a Chothia CDR-H1 sequence comprising, consisting of, or consisting essentially of SEQ ID NO: 25. In some aspects, the antibody comprises a $V_H$ sequence comprising a Chothia CDR-H1 sequence comprising, consisting of, or consisting essentially of SEQ ID NO: 26. In some aspects, the antibody comprises a $V_H$ sequence comprising a Chothia CDR-H1 sequence comprising, consisting of, or consisting essentially of SEQ ID NO: 27. In some aspects, the antibody comprises a $V_H$ sequence comprising a Chothia CDR-H1 sequence comprising, consisting of, or consisting essentially of SEQ ID NO: 28.

5.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 129-156 and a Chothia CDR-H2 sequence comprising, consisting of, or consisting essentially of a sequence selected from SEQ ID NOs: 65-92. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 230-251 and 273-280.

5.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 129-156 and a Chothia CDR-H1 sequence comprising, consisting of, or consisting essentially of a sequence selected from SEQ ID NOs: 1-28. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 230-251 and 273-280.

5.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 1-28 and a Chothia CDR-H2 sequence comprising, consisting of, or consisting essentially of a sequence selected from SEQ ID NOs: 65-92. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 230-251 and 273-280.

5.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 1-28, a Chothia CDR-H2 sequence comprising, consisting of, or consisting essentially of a sequence selected from SEQ ID NOs: 65-92, and a Chothia CDR-H3 sequence comprising, consisting of, or consisting essentially of a sequence selected from SEQ ID NOs: 129-156. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 230-251 and 273-280.

5.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

5.2.2.9. Excluded $V_H$ Sequences Comprising Chothia CDRs

In some embodiments, the $V_H$ sequences provided herein do not comprise certain Chothia CDR-H3, CDR-H2, and/or CDR-H1 sequences.

In some aspects, the Chothia CDR-H3 sequence does not comprise, consist of, or consist essentially of a sequence selected from SEQ ID NOs: 157-160. In some aspects, the Chothia CDR-H3 sequence does not comprise, consist of, or consist essentially of SEQ ID NO: 157. In some aspects, the Chothia CDR-H3 sequence does not comprise, consist of, or consist essentially of SEQ ID NO: 158. In some aspects, the Chothia CDR-H3 sequence does not comprise, consist of, or consist essentially of SEQ ID NO: 159. In some aspects, the Chothia CDR-H3 sequence does not comprise, consist of, or consist essentially of SEQ ID NO: 160.

In some aspects, the Chothia CDR-H2 sequence does not comprise, consist of, or consist essentially of a sequence selected from SEQ ID NOs: 93-96. In some aspects, the Chothia CDR-H2 sequence does not comprise, consist of, or consist essentially of SEQ ID NO: 93. In some aspects, the Chothia CDR-H2 sequence does not comprise, consist of, or consist essentially of SEQ ID NO: 94. In some aspects, the Chothia CDR-H2 sequence does not comprise, consist of, or consist essentially of SEQ ID NO: 95. In some aspects, the Chothia CDR-H2 sequence does not comprise, consist of, or consist essentially of SEQ ID NO: 96.

In some aspects, the Chothia CDR-H1 sequence does not comprise, consist of, or consist essentially of a sequence selected from SEQ ID NOs: 29-32. In some aspects, the Chothia CDR-H1 sequence does not comprise, consist of, or consist essentially of SEQ ID NO: 29. In some aspects, the Chothia CDR-H1 sequence does not comprise, consist of, or consist essentially of SEQ ID NO: 30. In some aspects, the Chothia CDR-H1 sequence does not comprise, consist of, or consist essentially of SEQ ID NO: 31. In some aspects, the Chothia CDR-H1 sequence does not comprise, consist of, or consist essentially of SEQ ID NO: 32.

5.3. $V_H$ Sequences

In some embodiments, the antibody comprises a $V_H$ sequence comprising, consisting of, or consisting essentially of a sequence selected from SEQ ID NOs: 230-251 and 273-280. In some aspects, the antibody comprises a $V_H$ sequence comprising, consisting of, or consisting essentially of SEQ ID NO: 230. In some aspects, the antibody comprises a $V_H$ sequence comprising, consisting of, or consisting essentially of SEQ ID NO: 231. In some aspects, the antibody comprises a $V_H$ sequence comprising, consisting of, or consisting essentially of SEQ ID NO: 232. In some aspects, the antibody comprises a $V_H$ sequence comprising, consisting of, or consisting essentially of SEQ ID NO: 233. In some aspects, the antibody comprises a $V_H$ sequence comprising, consisting of, or consisting essentially of SEQ ID NO: 234. In some aspects, the antibody comprises a $V_H$ sequence comprising, consisting of, or consisting essentially of SEQ ID NO: 235. In some aspects, the antibody comprises a $V_H$ sequence comprising, consisting of, or consisting essentially of SEQ ID NO: 236. In some aspects, the antibody comprises a $V_H$ sequence comprising, consisting of, or consisting essentially of SEQ ID NO: 237. In some aspects, the antibody comprises a $V_H$ sequence comprising, consisting of, or consisting essentially of SEQ ID NO: 238. In some aspects, the antibody comprises a $V_H$ sequence comprising, consisting of, or consisting essentially of SEQ ID NO: 239. In some aspects, the antibody comprises a $V_H$ sequence comprising, consisting of, or consisting essentially of SEQ ID NO: 240. In some aspects, the antibody comprises a $V_H$ sequence comprising, consisting of, or consisting essentially of SEQ ID NO: 241. In some aspects, the antibody comprises a $V_H$ sequence comprising, consisting of, or consisting essentially of SEQ ID NO: 242. In some aspects, the antibody comprises a $V_H$ sequence comprising, consisting of, or consisting essentially of SEQ ID NO: 243. In some aspects, the antibody comprises a $V_H$ sequence comprising, consisting of, or consisting essentially of SEQ ID NO: 244. In some aspects, the antibody comprises a $V_H$ sequence comprising, consisting of, or consisting essentially of SEQ ID NO: 245. In some aspects, the antibody comprises a $V_H$ sequence comprising, consisting of, or consisting essentially of SEQ ID NO: 246. In some aspects, the antibody comprises a $V_H$ sequence comprising, consisting of, or consisting essentially of SEQ ID NO: 247. In some aspects, the antibody comprises a $V_H$ sequence comprising, consisting of, or consisting essentially of SEQ ID NO: 248. In some aspects, the antibody comprises a $V_H$ sequence comprising, consisting of, or consisting essentially of SEQ ID NO: 249. In some aspects, the antibody comprises a $V_H$ sequence comprising, consisting of, or consisting essentially of SEQ ID NO: 250. In some aspects, the antibody comprises a $V_H$ sequence comprising, consisting of, or consisting essentially of SEQ ID NO: 251. In some aspects, the antibody comprises a $V_H$ sequence comprising, consisting of, or consisting essentially of SEQ ID NO: 273. In some aspects, the antibody comprises a $V_H$ sequence comprising, consisting of, or consisting essentially of SEQ ID NO: 274. In some aspects, the antibody comprises a $V_H$ sequence comprising, consisting of, or consisting essentially of SEQ ID NO: 275. In some aspects, the antibody comprises a $V_H$ sequence comprising, consisting of, or consisting essentially of SEQ ID NO: 276. In some aspects, the antibody comprises a $V_H$ sequence comprising, consisting of, or consisting essentially of SEQ ID NO: 277. In some aspects, the antibody comprises a $V_H$ sequence comprising, consisting of, or consisting essentially of SEQ ID NO: 278. In some aspects, the antibody comprises a $V_H$ sequence comprising, consisting of, or consisting essentially of SEQ ID NO: 279. In some aspects, the antibody comprises a $V_H$ sequence comprising, consisting of, or consisting essentially of SEQ ID NO: 280.

5.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure. In some aspects, the $V_H$ sequence comprises, consists of, or consists essentially of any of the illustrative $V_H$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

5.3.2. Excluded $V_H$ Sequences

In some embodiments, the $V_H$ sequences provided herein do not comprise certain $V_H$ sequences.

In some aspects, the $V_H$ sequence does not comprise, consist of, or consist essentially of a sequence selected from SEQ ID NOs: 252-255. In some aspects, the $V_H$ sequence does not comprise, consist of, or consist essentially of SEQ ID NO: 252. In some aspects, the $V_H$ sequence does not comprise, consist of, or consist essentially of SEQ ID NO: 253. In some aspects, the $V_H$ sequence does not comprise, consist of, or consist essentially of SEQ ID NO: 254. In some aspects, the $V_H$ sequence does not comprise, consist of, or consist essentially of SEQ ID NO: 255.

5.4. CDR-L3 Sequences

In some embodiments, the antibody comprises a CDR-L3 sequence comprising, consisting of, or consisting essentially of a sequence selected from SEQ ID NOs: 201-219. In some aspects, the antibody comprises a CDR-L3 sequence comprising, consisting of, or consisting essentially of SEQ ID NO: 201. In some aspects, the antibody comprises a CDR-L3 sequence comprising, consisting of, or consisting essentially of SEQ ID NO: 202. In some aspects, the antibody comprises a CDR-L3 sequence comprising, consisting of, or consisting essentially of SEQ ID NO: 203. In some aspects, the antibody comprises a CDR-L3 sequence comprising, consisting of, or consisting essentially of SEQ ID NO: 204. In some aspects, the antibody comprises a CDR-L3 sequence comprising, consisting of, or consisting essentially of SEQ ID NO: 205. In some aspects, the antibody comprises a CDR-L3 sequence comprising, consisting of, or consisting essentially of SEQ ID NO: 206. In some aspects, the antibody comprises a CDR-L3 sequence comprising, consisting of, or consisting essentially of SEQ ID NO: 207. In some aspects, the antibody comprises a CDR-L3 sequence comprising, consisting of, or consisting essentially of SEQ ID NO: 208. In some aspects, the antibody comprises a CDR-L3 sequence comprising, consisting of, or consisting essentially of SEQ ID NO: 209. In some aspects, the antibody comprises a CDR-L3 sequence comprising, consisting of, or consisting essentially of SEQ ID NO: 210. In some aspects, the antibody comprises a CDR-L3 sequence comprising, consisting of, or consisting essentially of SEQ ID NO: 211. In some aspects, the antibody comprises a CDR-L3 sequence comprising, consisting of, or consisting essentially of SEQ ID NO: 212. In some aspects, the antibody comprises a CDR-L3 sequence comprising, consisting of, or consisting essentially of SEQ ID NO: 213. In some aspects, the antibody comprises a CDR-L3 sequence comprising, consisting of, or consisting essentially of SEQ ID NO: 214. In some aspects, the antibody comprises a CDR-L3 sequence comprising, consisting of, or consisting essentially of SEQ ID NO: 215. In some aspects, the antibody comprises a CDR-L3 sequence comprising, consisting of, or consisting essentially of SEQ ID NO: 216. In some aspects, the antibody comprises a CDR-L3 sequence comprising, consisting of, or consisting essentially of SEQ ID NO: 217. In some aspects, the antibody comprises a CDR-L3 sequence comprising, consisting of, or consisting essentially of SEQ ID NO: 218. In some aspects, the antibody comprises a CDR-L3 sequence comprising, consisting of, or consisting essentially of SEQ ID NO: 219.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L3 sequence does not comprise, consist of, or consist essentially of SEQ ID NO: 220.

5.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

5.5.1. CDR-L3

In some embodiments, the antibody comprises a $V_L$ sequence comprising a CDR-L3 sequence comprising, consisting of, or consisting essentially of a sequence selected from SEQ ID NOs: 201-219. In some aspects, the antibody comprises a $V_L$ sequence comprising a CDR-L3 sequence comprising, consisting of, or consisting essentially of SEQ ID NO: 201. In some aspects, the antibody comprises a $V_L$ sequence comprising a CDR-L3 sequence comprising, consisting of, or consisting essentially of SEQ ID NO: 202. In some aspects, the antibody comprises a $V_L$ sequence comprising a CDR-L3 sequence comprising, consisting of, or consisting essentially of SEQ ID NO: 203. In some aspects, the antibody comprises a $V_L$ sequence comprising a CDR-L3 sequence comprising, consisting of, or consisting essentially of SEQ ID NO: 204. In some aspects, the antibody comprises a $V_L$ sequence comprising a CDR-L3 sequence comprising, consisting of, or consisting essentially of SEQ ID NO: 205. In some aspects, the antibody comprises a $V_L$ sequence comprising a CDR-L3 sequence comprising, consisting of, or consisting essentially of SEQ ID NO: 206. In some aspects, the antibody comprises a $V_L$ sequence comprising a CDR-L3 sequence comprising, consisting of, or consisting essentially of SEQ ID NO: 207. In some aspects, the antibody comprises a $V_L$ sequence comprising a CDR-L3 sequence comprising, consisting of, or consisting essentially of SEQ ID NO: 208. In some aspects, the antibody comprises a $V_L$ sequence comprising a CDR-L3 sequence comprising, consisting of, or consisting essentially of SEQ ID NO: 209. In some aspects, the antibody comprises a $V_L$ sequence comprising a CDR-L3 sequence comprising, consisting of, or consisting essentially of SEQ ID NO: 210. In some aspects, the antibody comprises a $V_L$ sequence comprising a CDR-L3 sequence comprising, consisting of, or consisting essentially of SEQ ID NO: 211. In some aspects, the antibody comprises a $V_L$ sequence comprising a CDR-L3 sequence comprising, consisting of, or consisting essentially of SEQ ID NO: 212. In some aspects, the antibody comprises a $V_L$ sequence comprising a CDR-L3 sequence comprising, consisting of, or consisting essentially of SEQ ID NO: 213. In some aspects, the antibody comprises a $V_L$ sequence comprising a CDR-L3 sequence comprising, consisting of, or consisting essentially of SEQ ID NO: 214. In some aspects, the antibody comprises a $V_L$ sequence comprising a CDR-L3 sequence comprising, consisting of, or consisting essentially of SEQ ID NO: 215. In some aspects, the antibody comprises a $V_L$ sequence comprising a CDR-L3 sequence comprising, consisting of, or consisting essentially of SEQ ID NO: 216. In some aspects, the antibody comprises a $V_L$ sequence comprising a CDR-L3 sequence comprising, consisting of, or consisting essentially of SEQ ID NO: 217. In some aspects, the antibody comprises a $V_L$ sequence comprising a CDR-L3 sequence comprising, consisting of, or consisting essentially of SEQ ID NO: 218. In some aspects, the antibody comprises a $V_L$ sequence comprising a CDR-L3 sequence comprising, consisting of, or consisting essentially of SEQ ID NO: 219.

5.5.2. CDR-L2

In some embodiments, the antibody comprises a $V_L$ sequence comprising a CDR-L2 sequence comprising, consisting of, or consisting essentially of a sequence selected from SEQ ID NOs: 181-199. In some aspects, the antibody comprises a $V_L$ sequence comprising a CDR-L2 sequence comprising, consisting of, or consisting essentially of SEQ ID NO: 181. In some aspects, the antibody comprises a $V_L$ sequence comprising a CDR-L2 sequence comprising, consisting of, or consisting essentially of SEQ ID NO: 182. In some aspects, the antibody comprises a $V_L$ sequence comprising a CDR-L2 sequence comprising, consisting of, or consisting essentially of SEQ ID NO: 183. In some aspects, the antibody comprises a $V_L$ sequence comprising a CDR-L2 sequence comprising, consisting of, or consisting essentially of SEQ ID NO: 184. In some aspects, the antibody comprises a $V_L$ sequence comprising a CDR-L2 sequence comprising, consisting of, or consisting essentially of SEQ ID NO: 185. In some aspects, the antibody comprises a $V_L$ sequence comprising a CDR-L2 sequence comprising, consisting of, or consisting essentially of SEQ ID NO: 186. In some aspects, the antibody comprises a $V_L$ sequence comprising a CDR-L2 sequence comprising, consisting of, or consisting essentially of SEQ ID NO: 187. In some aspects, the antibody comprises a $V_L$ sequence comprising a CDR-L2 sequence comprising, consisting of, or consisting essentially of SEQ ID NO: 188. In some aspects, the antibody comprises a $V_L$ sequence comprising a CDR-L2 sequence comprising, consisting of, or consisting essentially of SEQ ID NO: 189. In some aspects, the antibody comprises a $V_L$ sequence comprising a CDR-L2 sequence comprising, consisting of, or consisting essentially of SEQ ID NO: 190. In some aspects, the antibody comprises a $V_L$ sequence comprising a CDR-L2 sequence comprising, consisting of, or consisting essentially of SEQ ID NO: 191. In some aspects, the antibody comprises a $V_L$ sequence comprising a CDR-L2 sequence comprising, consisting of, or consisting essentially of SEQ ID NO: 192. In some aspects, the antibody comprises a $V_L$ sequence comprising a CDR-L2 sequence comprising, consisting of, or consisting essentially of SEQ ID NO: 193. In some aspects, the antibody comprises a $V_L$ sequence comprising a CDR-L2 sequence comprising, consisting of, or consisting essentially of SEQ ID NO: 194. In some aspects, the antibody comprises a $V_L$ sequence comprising a CDR-L2 sequence comprising, consisting of, or consisting essentially of SEQ ID NO: 195. In some aspects, the antibody comprises a $V_L$ sequence comprising a CDR-L2 sequence comprising, consisting of, or consisting essentially of SEQ ID NO: 196. In some aspects, the antibody comprises a $V_L$ sequence comprising a CDR-L2 sequence comprising, consisting of, or consisting essentially of SEQ ID NO: 197. In some aspects, the antibody comprises a $V_L$ sequence comprising a CDR-L2 sequence comprising, consisting of, or consisting essentially of SEQ ID NO: 198. In some aspects, the antibody comprises a $V_L$ sequence comprising a CDR-L2 sequence comprising, consisting of, or consisting essentially of SEQ ID NO: 199.

5.5.3. CDR-L1

In some embodiments, the antibody comprises a $V_L$ sequence comprising a CDR-L1 sequence comprising, consisting of, or consisting essentially of a sequence selected from SEQ ID NOs: 161-179. In some aspects, the antibody comprises a $V_L$ sequence comprising a CDR-L1 sequence comprising, consisting of, or consisting essentially of SEQ ID NO: 161. In some aspects, the antibody comprises a $V_L$ sequence comprising a CDR-L1 sequence comprising, consisting of, or consisting essentially of SEQ ID NO: 162. In some aspects, the antibody comprises a $V_L$ sequence comprising a CDR-L1 sequence comprising, consisting of, or consisting essentially of SEQ ID NO: 163. In some aspects, the antibody comprises a $V_L$ sequence comprising a CDR-L1 sequence comprising, consisting of, or consisting essentially of SEQ ID NO: 164. In some aspects, the antibody comprises a $V_L$ sequence comprising a CDR-L1 sequence comprising, consisting of, or consisting essentially of SEQ ID NO: 165. In some aspects, the antibody comprises a $V_L$ sequence comprising a CDR-L1 sequence comprising, consisting of, or consisting essentially of SEQ ID NO: 166. In some aspects, the antibody comprises a $V_L$ sequence comprising a CDR-L1 sequence comprising, consisting of, or consisting essentially of SEQ ID NO: 167. In some aspects, the antibody comprises a $V_L$ sequence comprising a CDR-L1 sequence comprising, consisting of, or consisting essentially of SEQ ID NO: 168. In some aspects, the antibody comprises a $V_L$ sequence comprising a CDR-L1 sequence comprising, consisting of, or consisting essentially of SEQ ID NO: 169. In some aspects, the antibody comprises a $V_L$ sequence comprising a CDR-L1 sequence comprising, consisting of, or consisting essentially of SEQ ID NO: 170. In some aspects, the antibody comprises a $V_L$ sequence comprising a CDR-L1 sequence comprising, consisting of, or consisting essentially of SEQ ID NO: 171. In some aspects, the antibody comprises a $V_L$ sequence comprising a CDR-L1 sequence comprising, consisting of, or consisting essentially of SEQ ID NO: 172. In some aspects, the antibody comprises a $V_L$ sequence comprising a CDR-L1 sequence comprising, consisting of, or consisting essentially of SEQ ID NO: 173. In some aspects, the antibody comprises a $V_L$ sequence comprising a CDR-L1 sequence comprising, consisting of, or consisting essentially of SEQ ID NO: 174. In some aspects, the antibody comprises a $V_L$ sequence comprising a CDR-L1 sequence comprising, consisting of, or consisting essentially of SEQ ID NO: 175. In some aspects, the antibody comprises a $V_L$ sequence comprising a CDR-L1 sequence comprising, consisting of, or consisting essentially of SEQ ID NO: 176. In some aspects, the antibody comprises a $V_L$ sequence comprising a CDR-L1 sequence comprising, consisting of, or consisting essentially of SEQ ID NO: 177. In some aspects, the antibody comprises a $V_L$ sequence comprising a CDR-L1 sequence comprising, consisting of, or consisting essentially of SEQ ID NO: 178. In some aspects, the antibody comprises a $V_L$ sequence comprising a CDR-L1 sequence comprising, consisting of, or consisting essentially of SEQ ID NO: 179.

5.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 201-219 and a CDR-L2 sequence comprising, consisting of, or consisting essentially of a sequence selected from SEQ ID NOs: 181-199. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 256-270 and 281-288.

5.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 201-219 and a CDR-L1 sequence comprising, consisting of, or consisting essentially of a sequence selected from SEQ ID NOs: 161-179. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 256-270 and 281-288.

5.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 161-179 and a CDR-L2 sequence comprising, consisting of, or consisting essentially of a sequence selected from SEQ ID NOs: 181-199. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 256-270 and 281-288.

5.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 161-179, a CDR-L2 sequence comprising, consisting of, or consisting essentially of a sequence selected from SEQ ID NOs: 181-199, and a CDR-L3 sequence comprising, consisting of, or consisting essentially of a sequence selected from SEQ ID NOs: 201-219. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 256-270 and 281-288.

5.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

5.5.9. Excluded $V_L$ Sequences Comprising CDR-Ls

In some embodiments, the $V_L$ sequences provided herein do not comprise certain CDR-L3, CDR-L2, and/or CDR-L1 sequences.

In some aspects, the CDR-L3 sequence does not comprise, consist of, or consist essentially of SEQ ID NO: 220.

In some aspects, the CDR-L2 sequence does not comprise, consist of, or consist essentially of SEQ ID NO: 200.

In some aspects, the CDR-L1 sequence does not comprise, consist of, or consist essentially of SEQ ID NO: 180.

5.6. $V_L$ Sequences

In some embodiments, the antibody comprises a $V_L$ sequence comprising, consisting of, or consisting essentially of a sequence selected from SEQ ID NOs: 256-270 and 281-288. In some aspects, the antibody comprises a $V_L$ sequence comprising, consisting of, or consisting essentially of SEQ ID NO: 256. In some aspects, the antibody comprises a $V_L$ sequence comprising, consisting of, or consisting essentially of SEQ ID NO: 257. In some aspects, the antibody comprises a $V_L$ sequence comprising, consisting of, or consisting essentially of SEQ ID NO: 258. In some aspects, the antibody comprises a $V_L$ sequence comprising, consisting of, or consisting essentially of SEQ ID NO: 259. In some aspects, the antibody comprises a $V_L$ sequence comprising, consisting of, or consisting essentially of SEQ ID NO: 260. In some aspects, the antibody comprises a $V_L$ sequence comprising, consisting of, or consisting essentially of SEQ ID NO: 261. In some aspects, the antibody comprises a $V_L$ sequence comprising, consisting of, or consisting essentially of SEQ ID NO: 262. In some aspects, the antibody comprises a $V_L$ sequence comprising, consisting of, or consisting essentially of SEQ ID NO: 263. In some aspects, the antibody comprises a $V_L$ sequence comprising, consisting of, or consisting essentially of SEQ ID NO: 264. In some aspects, the antibody comprises a $V_L$ sequence comprising, consisting of, or consisting essentially of SEQ ID NO: 265. In some aspects, the antibody comprises a $V_L$ sequence comprising, consisting of, or consisting essentially of SEQ ID NO: 266. In some aspects, the antibody comprises a $V_L$ sequence comprising, consisting of, or consisting essentially of SEQ ID NO: 267. In some aspects, the antibody comprises a $V_L$ sequence comprising, consisting of, or consisting essentially of SEQ ID NO: 268. In some aspects, the antibody comprises a $V_L$ sequence comprising, consisting of, or consisting essentially of SEQ ID NO: 269. In some aspects, the antibody comprises a $V_L$ sequence comprising, consisting of, or consisting essentially of SEQ ID NO: 270. In some aspects, the antibody comprises a $V_L$ sequence comprising, consisting of, or consisting essentially of SEQ ID NO: 281. In some aspects, the antibody comprises a $V_L$ sequence comprising, consisting of, or consisting essentially of SEQ ID NO: 282. In some aspects, the antibody comprises a $V_L$ sequence comprising, consisting of, or consisting essentially of SEQ ID NO: 283. In some aspects, the antibody comprises a $V_L$ sequence comprising, consisting of, or consisting essentially of SEQ ID NO: 284. In some aspects, the antibody comprises a $V_L$ sequence comprising, consisting of, or consisting essentially of SEQ ID NO: 285. In some aspects, the antibody comprises a $V_L$ sequence comprising, consisting of, or consisting essentially of SEQ ID NO: 286. In some aspects, the antibody comprises a $V_L$ sequence comprising, consisting of, or consisting essentially of SEQ ID NO: 287. In some aspects, the antibody comprises a $V_L$ sequence comprising, consisting of, or consisting essentially of SEQ ID NO: 288.

5.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure. In some aspects, the $V_L$ sequence comprises, consists of, or consists essentially of any of the illustrative $V_L$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

5.6.2. Excluded V$_L$ Sequences

In some embodiments, the V$_L$ sequences provided herein do not comprise certain V$_L$ sequences.

In some aspects, the V$_L$ sequence does not comprise, consist of, or consist essentially of a sequence selected from SEQ ID NOs: 271-272. In some aspects, the V$_L$ sequence does not comprise, consist of, or consist essentially of SEQ ID NO: 271. In some aspects, the V$_L$ sequence does not comprise, consist of, or consist essentially of SEQ ID NO: 272.

5.7. Pairs 5.7.1. CDR-H3–CDR-L3 Pairs

In some embodiments, the antibody comprises a CDR-H3 sequence and a CDR-L3 sequence. In some aspects, the CDR-H3 sequence is part of a V$_H$ and the CDR-L3 sequence is part of a V$_L$.

In some aspects, the CDR-H3 sequence is a CDR-H3 sequence comprising, consisting of, or consisting essentially of SEQ ID NOs: 129-156 and the CDR-L3 sequence is a CDR-L3 sequence comprising, consisting of, or consisting essentially of SEQ ID NOs: 201-219.

In some aspects, the CDR-H3 sequence is SEQ ID NO: 129, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 130, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 131, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 132, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 133, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 134, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 135, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 136, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 137, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 138, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 139, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 140, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 141, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 142, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 143, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 144, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 145, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 146, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 147, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 148, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 149, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 150, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 151, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 152, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 153, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

In some aspects, the CDR-H3 sequence is SEQ ID NO: 154, and the CDR-L3 sequence is selected from SEQ ID NOs: 201-219. In some aspects, the CDR-L3 sequence is SEQ ID NO: 201. In some aspects, the CDR-L3 sequence is SEQ ID NO: 202. In some aspects, the CDR-L3 sequence is SEQ ID NO: 203. In some aspects, the CDR-L3 sequence is SEQ ID NO: 204. In some aspects, the CDR-L3 sequence is SEQ ID NO: 205. In some aspects, the CDR-L3 sequence is SEQ ID NO: 206. In some aspects, the CDR-L3 sequence is SEQ ID NO: 207. In some aspects, the CDR-L3 sequence is SEQ ID NO: 208. In some aspects, the CDR-L3 sequence is SEQ ID NO: 209. In some aspects, the CDR-L3 sequence is SEQ ID NO: 210. In some aspects, the CDR-L3 sequence is SEQ ID NO: 211. In some aspects, the CDR-L3 sequence is SEQ ID NO: 212. In some aspects, the CDR-L3 sequence is SEQ ID NO: 213. In some aspects, the CDR-L3 sequence is SEQ ID NO: 214. In some aspects, the CDR-L3 sequence is SEQ ID NO: 215. In some aspects, the CDR-L3 sequence is SEQ ID NO: 216. In some aspects, the CDR-L3 sequence is SEQ ID NO: 217. In some aspects, the CDR-L3 sequence is SEQ ID NO: 218. In some aspects, the CDR-L3 sequence is SEQ ID NO: 219.

5.7.1.1. Variants of CDR-H3–CDR-L3 Pairs

In some embodiments, the CDR-H3–CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

5.7.1.2. Excluded CDR-H3–CDR-L3 Pairs

In some embodiments, the CDR-H3–CDR-L3 pairs provided herein do not comprise certain CDR-H3–CDR-L3 pairs.

In some aspects, the CDR-H3 sequence is not SEQ ID NO: 157, and the CDR-L3 sequence not SEQ ID NO: 220. In some aspects, the CDR-H3 sequence is not SEQ ID NO: 158, and the CDR-L3 sequence not SEQ ID NO: 220. In some aspects, the CDR-H3 sequence is not SEQ ID NO: 159, and the CDR-L3 sequence not SEQ ID NO: 220. In some aspects, the CDR-H3 sequence is not SEQ ID NO: 160, and the CDR-L3 sequence not SEQ ID NO: 220.

5.7.2. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 230-251 and 273-280, and the $V_L$ sequence is a $V_L$ sequence comprising, consisting of, or consisting essentially of SEQ ID NOs: 256-270 and 281-288.

In some aspects, the $V_H$ sequence is SEQ ID NO: 230, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 231, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 232, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 233, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 234, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 235, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 236, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 237, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 238, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 239, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 240, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 241, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 242, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 243, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 244, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 245, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 246, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 247, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 248, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 249, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 250, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 251, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 273, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 274, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 275, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 276, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 277, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 278, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 279, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

In some aspects, the $V_H$ sequence is SEQ ID NO: 280, and the $V_L$ sequence is selected from SEQ ID NOs: 256-270 and 281-288. In some aspects, the $V_L$ sequence is SEQ ID NO: 256. In some aspects, the $V_L$ sequence is SEQ ID NO: 257. In some aspects, the $V_L$ sequence is SEQ ID NO: 258. In some aspects, the $V_L$ sequence is SEQ ID NO: 259. In some aspects, the $V_L$ sequence is SEQ ID NO: 260. In some aspects, the $V_L$ sequence is SEQ ID NO: 261. In some aspects, the $V_L$ sequence is SEQ ID NO: 262. In some aspects, the $V_L$ sequence is SEQ ID NO: 263. In some aspects, the $V_L$ sequence is SEQ ID NO: 264. In some aspects, the $V_L$ sequence is SEQ ID NO: 265. In some aspects, the $V_L$ sequence is SEQ ID NO: 266. In some aspects, the $V_L$ sequence is SEQ ID NO: 267. In some aspects, the $V_L$ sequence is SEQ ID NO: 268. In some aspects, the $V_L$ sequence is SEQ ID NO: 269. In some aspects, the $V_L$ sequence is SEQ ID NO: 270. In some aspects, the $V_L$ sequence is SEQ ID NO: 281. In some aspects, the $V_L$ sequence is SEQ ID NO: 282. In some aspects, the $V_L$ sequence is SEQ ID NO: 283. In some aspects, the $V_L$ sequence is SEQ ID NO: 284. In some aspects, the $V_L$ sequence is SEQ ID NO: 285. In some aspects, the $V_L$ sequence is SEQ ID NO: 286. In some aspects, the $V_L$ sequence is SEQ ID NO: 287. In some aspects, the $V_L$ sequence is SEQ ID NO: 288.

5.7.2.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure. In some aspects, the $V_H$ sequence comprises, consists of, or consists essentially of any of the illustrative $V_H$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure. In some aspects, the $V_L$ sequence comprises, consists of, or consists essentially of any of the illustrative $V_L$ sequences provided in this disclosure, with 1-25 amino acid substitutions, 1-20 amino acid substitutions, 1-15 amino acid substitutions, 1-10 amino acid substitutions, 1-5 amino acid substitutions, 1-3 amino acid substitutions, 1-2 amino acid substitutions, or 1 amino acid substitution. In some aspects, the amino acid substitutions are conservative amino acid substitutions.

5.7.2.2. Excluded $V_H$-$V_L$ Pairs

In some embodiments, the $V_H$-$V_L$ pairs provided herein do not comprise certain $V_H$-$V_L$ pairs.

In some aspects, the $V_H$ sequence is not selected from SEQ ID NOs: 252-255, and the $V_L$ sequence is not selected from SEQ ID NOs: 271-272.

In some aspects, the $V_H$ sequence is not SEQ ID NO: 252, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 253, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 254, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

In some aspects, the $V_H$ sequence is not SEQ ID NO: 255, and the $V_L$ sequence is not selected from SEQ ID NO: 271-272. In some aspects, the $V_L$ sequence is not SEQ ID NO: 271. In some aspects, the $V_L$ sequence is not SEQ ID NO: 272.

5.7.2.3. Constant Region Sequences

In some embodiments, the antibody comprises a constant region selected from SEQ ID NOs: 304-305.

5.8. Consensus Sequences

In particular embodiments, the anti-CD74 antibody comprises one or more consensus sequences. Each consensus sequences is based, at least in part, on one or more alignments of two or more useful anti-CD74 CDR sequences provided in this disclosure. Based on such alignments, a person of skill in the art would recognize that different amino acid residues may useful in certain positions of the CDRs. Accordingly, each consensus sequence encompasses two or more useful anti-CD74 CDR sequences.

5.8.1. CDR-H3 Consensus Sequences

In some embodiments, the antibody comprises a CDR-H3 sequence defined by the consensus sequence G-G-$\alpha_3$-$\alpha_4$-$\alpha_5$-$\alpha_6$-$\alpha_7$-$\alpha_8$-$\alpha_9$-$\alpha_{10}$-G-$\alpha_{12}$-D-V (SEQ ID NO: 312), where: $\alpha_3$ is T, S, Q, M, or A; $\alpha_4$ is R, L, or V; $\alpha_5$ is V, E, A, G, I, D, or M; $\alpha_6$ is R, L, H, G, Q, or T; $\alpha_7$ is G or R; $\alpha_8$ is A, L, E, or G; $\alpha_9$ is V, I, M, F, R, or L; $\alpha_{10}$ is Y, H, F, or S; and $\alpha_{12}$ is T, L, H, or N.

In some aspects, if $\alpha_9$ is M, then either $\alpha_3$ is not T, $\alpha_4$ is not L, $\alpha_5$ is not V, $\alpha_6$ is not R, $\alpha_7$ is not G, $\alpha_8$ is not A, $\alpha_{10}$ is not Y, $\alpha_{12}$ is not T, or combinations thereof.

In some aspects, $\alpha_9$ is V, I, F, R, or L.

In some aspects, $\alpha_6$ is L, H, G, Q, or T.

In some aspects, $\alpha_3$ is not T. In some aspects, $\alpha_4$ is not L. In some aspects, $\alpha_5$ is not V. In some aspects, $\alpha_6$ is not R. In some aspects, $\alpha_7$ is not G. In some aspects, $\alpha_8$ is not A. In some aspects, $\alpha_9$ is not M. In some aspects, $\alpha_{10}$ is not Y. In some aspects, $\alpha_{12}$ is not T.

5.8.2. Chothia CDR-H2 Consensus Sequences

In some embodiments, the antibody comprises a Chothia CDR-H2 sequence defined by the consensus sequence $\beta_1$-$\beta_2$-D-$\beta_4$-S-$\beta_6$ (SEQ ID NO: 313), where: $\beta_1$ is W or S; $\beta_2$ is Y, D, or H; $\beta_4$ is G or A; and $\beta_6$ is N, I, D, H, K, or R.

In some aspects, $\beta_1$ is W.

In some aspects, $\beta_6$ is I.

In some aspects, $\beta_1$ is not S. In some aspects, $\beta_2$ is not Y. In some aspects, $\beta_4$ is not G. In some aspects, $\beta_6$ is not N or I.

5.8.3. Chothia CDR-H1 Consensus Sequences

In some embodiments, the antibody comprises a Chothia CDR-H1 sequence defined by the consensus sequence G-F-$\delta_3$-F-$\delta_5$-$\delta_6$-$\delta_7$ (SEQ ID NO: 314), where: $\delta_3$ is T, N, S, A, or D; $\delta_5$ is S, G, D, or A; $\delta_6$ is S or D; and $\delta_7$ is Y, H, or F.

In some aspects, $\delta_3$ is N, S, A, or D.

In some aspects, $\delta_3$ is not T. In some aspects, $\delta_5$ is not S. In some aspects, $\delta_6$ is not S. In some aspects, $\delta_7$ is not Y.

5.8.4. Kabat CDR-H2 Consensus Sequences

In some embodiments, the antibody comprises a Kabat CDR-H2 sequence defined by the consensus sequence V-$\gamma_2$-$\gamma_3$-$\gamma_4$-D-$\gamma_6$-S-$\gamma_8$-$\gamma_9$-$\gamma_{10}$-Y-A-$\gamma_{13}$-S-V-K-G (SEQ ID NO: 315), where: $\gamma_2$ is I, T, or V; $\gamma_3$ is W or S; $\gamma_4$ is Y, D, or H; $\gamma_6$ is G or A; $\gamma_8$ is N, I, D, H, K, or R; $\gamma_9$ is K, E, R, S, T, or D; $\gamma_{10}$ is Y, I, V, K, or N; and $\gamma_{13}$ is D or G.

In some aspects, $\gamma_9$ is E, R, S, T, or D.

In some aspects, $\gamma_2$ is not I. In some aspects, $\gamma_3$ is not S or W. In some aspects, $\gamma_4$ is not Y. In some aspects, $\gamma_6$ is not G. In some aspects, $\gamma_8$ is not N or I. In some aspects, $\gamma_9$ is not K. In some aspects, $\gamma_{10}$ is not Y. In some aspects, $\gamma_{13}$ is not D.

In some embodiments, the antibody comprises a Kabat CDR-H2 sequence defined by the consensus sequence V-$\sigma_2$-W-$\sigma_4$-D-$\sigma_6$-S-$\sigma_8$-$\sigma_9$-$\sigma_{10}$-Y-A-$\sigma_{13}$-S-V-K-G (SEQ ID NO: 316), where: $\sigma_2$ is I, T, or V; $\sigma_4$ is Y, D, or H; $\sigma_6$ is G or A; $\sigma_8$ is N, I, D, H, K, or R; $\sigma_9$ is K, E, R, S, T, or D; $\sigma_{10}$ is Y, I, V, K, or N; and $\sigma_{13}$ is D or G.

In some aspects, if $\sigma_2$ is I, then either $\sigma_4$ is not Y, $\sigma_6$ is not G, $\sigma_8$ is not N, $\sigma_9$ is not K, $\sigma_{10}$ is not Y, $\sigma_{13}$ is not D, or combinations thereof.

In some aspects, $\sigma_2$ is not I. In some aspects, $\sigma_3$ is not S or W. In some aspects, $\sigma_4$ is not Y. In some aspects, $\sigma_6$ is not G. In some aspects, $\sigma_8$ is not N or I. In some aspects, $\sigma_9$ is not K. In some aspects, $\sigma_{10}$ is not Y. In some aspects, $\sigma_{13}$ is not D.

5.8.5. Kabat CDR-H1 Consensus Sequences

In some embodiments, the antibody comprises a Kabat CDR-H1 sequence defined by the consensus sequence $\varepsilon_1$-$\varepsilon_2$-$\varepsilon_3$-M-H (SEQ ID NO: 317), where: $\varepsilon_1$ is S or D; $\varepsilon_2$ is Y, H, or F; and $\varepsilon_3$ is G or A.

In some aspects, $\varepsilon_1$ is D.

In some aspects, $\varepsilon_1$ is not S. In some aspects, $\varepsilon_2$ is not Y. In some aspects, $\varepsilon_3$ is not A or G.

5.8.6. CDR-L3 Consensus Sequences

In some embodiments, the antibody comprises a CDR-L3 sequence defined by the consensus sequence Q-$\Theta_2$-$\Theta_3$-$\Theta_4$-$\Theta_5$-$\Theta_6$-P-$\Theta_8$-T (SEQ ID NO: 318), where: $\Theta_2$ is Q or H; $\Theta_3$ is Y, H, Q, or N; $\Theta_4$ is N, Y, Q, H, or C; $\Theta_5$ is T, S, I, Y, P, L, or A; $\Theta_6$ is Y, T, W, or A; and $\Theta_8$ is L or P.

In some aspects, $\Theta_5$ is T, I, Y, P, L, or A.

In some aspects, $\Theta_2$ is not Q. In some aspects, $\Theta_3$ is not Y. In some aspects, $\Theta_4$ is not N. In some aspects, $\Theta_5$ is not S. In some aspects, $\Theta_6$ is not Y. In some aspects, $\Theta_8$ is not L.

5.8.7. CDR-L2 Consensus Sequences

In some embodiments, the antibody comprises a CDR-L2 sequence defined by the consensus sequence $\pi_1$-$\pi_2$-$\pi_3$-$\pi_4$-$\pi_5$-$\pi_6$-$\pi_7$ (SEQ ID NO: 319), where: $\pi_1$ is G, A, L, S, or N; $\pi_2$ is A, S, G, or R; $\pi_3$ is S, D, T, N, or R; $\pi_4$ is S, R, Y, Q, or L; $\pi_5$ is L or R; $\pi_6$ is Q or A; and $\pi_7$ is S, T, or I.

In some aspects, $\pi_7$ is S.

In some aspects, $\pi_1$ is not A. In some aspects, $\pi_2$ is not A. In some aspects, $\pi_3$ is not S. In some aspects, $\pi_4$ is not S. In some aspects, $\pi_5$ is not L. In some aspects, $\pi_6$ is not Q. In some aspects, $\pi_7$ is not S.

5.8.8. CDR-L1 Consensus Sequences

In some embodiments, the antibody comprises a CDR-L1 sequence defined by the consensus sequence R-A-$\mu_3$-Q-$\mu_5$-$\mu_6$-$\mu_7$-$\mu_8$-$\mu_9$-$\mu_{10}$-$\mu_{11}$-$\mu_{12}$ (SEQ ID NO: 320), where: $\mu_3$ is S or G; $\mu_5$ is G, S, D, or R; $\mu_6$ is V, I, or L; $\mu_7$ is S, G, F, A, or Y; $\mu_8$ is S, R, or G; $\mu_9$ is S, I, N, R, or nothing (i.e., not present); $\mu_{10}$ is W, Y, F, E, or D; $\mu_{11}$ is L or V; and $\mu_{12}$ is A, S, or G.

In some aspects, $\mu_7$ is G, F, A, or Y.

In some aspects, $\mu_3$ is not S. In some aspects, $\mu_5$ is not G. In some aspects, $\mu_6$ is not I. In some aspects, $\mu_7$ is not S. In some aspects, $\mu_8$ is not S. In some aspects, $\mu_9$ is present. In some aspects, $\mu_{10}$ is not W. In some aspects, $\mu_{11}$ is not L. In some aspects, $\mu_{12}$ is not A.

6. Thermostability

In some embodiments, the antibody is characterized by particular thermostability parameters. The thermostability of an antibody may be characterized by measuring its melting temperatures. The melting temperatures include Tm1 and Tm2. Tm1 represents the melting of the Fc domain of an IgG, while Tm2 represents the melting of the Fab domain of an IgG.

In some embodiments, the Tm2 of the antibody is at least 75° C., 75.5° C., 76° C., 76.5° C., 77° C., 77.5° C., 78° C., 78.5° C., or 79° C. In some embodiments, the Tm2 of the antibody is between about 75° C. and about 80° C. In some embodiments, the Tm2 of the antibody is between about 76° C. and about 79° C. In some embodiments, the Tm2 of the antibody is between about 77° C. and about 78° C. In some aspects, the Tm2s described above are for aglycosylated versions of the antibody.

In some embodiments, the Tm1 of the antibody is between about 59° C. and about 62.2° C. In some embodiments, the Tm1 of the antibody is less than 62.2° C. In some embodiments, the Tm1 of the antibody is less than 61° C. In some embodiments, the Tm1 of the antibody is less than 60° C. In some aspects, the Tm1s described above are for aglycosylated versions of the antibody.

7. Affinity

In some embodiments, the affinity of the antibody for CD74, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody conjugate is between about $10^{-9}$ M and $10^{-11}$ M. In some embodiments, the affinity of the antibody conjugate is between about $10^{-10}$ M and $10^{-11}$ M. In some embodiments, the affinity of the antibody is between about $1.08 \times 10^{-7}$ M and $9.57 \times 10^{-10}$ M. In some embodiments, the affinity of the antibody is $2.52 \times 10^{-10}$ M, or less. In some embodiments, the affinity of the antibody is about $2.52 \times 10^{-10}$ M. In some embodiments, the affinity of the antibody is about $3.54 \times 10^{-10}$ M. In some embodiments, the affinity of the antibody is between about $2.52 \times 10^{-10}$ M and about $3.54 \times 10^{-10}$ M. In some aspects, the $K_D$ is determined at 25° C.

In some embodiments the antibody has a $k_a$ of at least about $10^5$ $M^{-1} \times sec^{-1}$. In some embodiments the antibody has a $k_a$ of at least about $10^6$ $M^{-1} \times sec^{-1}$. In some embodiments the antibody has a $k_a$ of between about $10^5$ $M^{-1} \times sec^{-1}$ and about $10^6$ $M^{-1} \times sec^{-1}$. In some embodiments the antibody has a $k_a$ of between about $1.66 \times 10^5$ $M^{-1} \times sec^{-1}$ and about $1.07 \times 10^6$ $M^{-1} \times sec^{-1}$. In some embodiments the antibody has a $k_a$ of about $3.09 \times 10^5$ $M^{-1} \times sec^{-1}$, or more. In some embodiments the antibody has a $k_a$ of about $3.09 \times 10^5$ $M^{-1} \times sec^{-1}$. In some embodiments the antibody has a $k_a$ of about $3.38 \times 10^5$ $M^{-1} \times sec^{-1}$. In some embodiments the antibody has a $k_a$ between about $3.09 \times 10^5$ $M^{-1} \times sec^{-1}$ and about $3.38 \times 10^5$ $M^{-1} \times sec^{-1}$. In some aspects, the $k_a$ is determined at 25° C.

In some embodiments the antibody has a $k_a$ of about $10^{-4}$ $sec^{-1}$ or less. In some embodiments the antibody has a $k_a$ of about $10^{-5}$ $sec^{-1}$ or less. In some embodiments the antibody has a $k_a$ of between about $10^{-4}$ $sec^{-1}$ and about $10^{-5}$ $sec^{-1}$. In some embodiments the antibody has a $k_a$ of between about $2.35 \times 10^{-4}$ $sec^{-1}$ and about $7.10 \times 10^{-5}$ $sec^{-1}$. In some embodiments the antibody has a $k_a$ of about $7.77 \times 10^{-5}$ $sec^{-1}$, or less. In some embodiments the antibody has a $k_a$ of about $7.77 \times 10^{-5}$ sec 1. In some embodiments the antibody has a $k_a$ of about $1.20 \times 10^{-4}$ $sec^{-1}$. In some embodiments the antibody has a $k_a$ between about $1.20 \times 10^{-4}$ $sec^{-1}$ and about $7.77 \times 10^{-5}$ $sec^{-1}$. In some aspects, the $k_a$ is determined at 25° C.

8. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody conjugate.

9. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody conjugate-directed complement-mediated cytotoxicity (ADCC). Numerous substitutions or substitutions or deletions with altered effector function are known in the art.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.*, 1986, 83:7059-7063; Hellstrom et al., *Proc. Natl. Acad. Sci. U.S.A.*, 1985, 82:1499-1502; and Bruggemann et al., *J Exp. Med.*, 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J Immunol. Meth-* ods, 1996, 202:163-171; Cragg et al., *Blood,* 2003, 101: 1045-1052; and Cragg and Glennie, *Blood,* 2004, 103:2738-2743.

FcRn binding and in vivo clearance (half-life determination) can also be measured, for example, using the methods described in Petkova et al., *Intl. Immunol.,* 2006, 18:1759-1769.

10. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido and alkynyl. Modified amino acids are also described in, for example, WO 2013/185115 and WO 2015/006555, each of which is incorporated herein by reference in its entirety.

In certain embodiments, the amino acid residue is according to any of the following formulas:

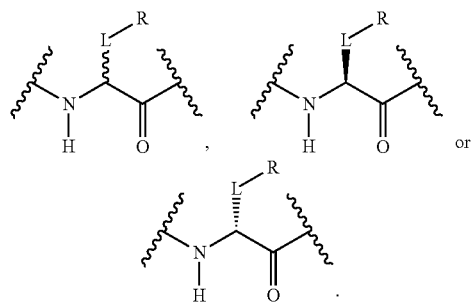

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^1NR^2R^3$, $R^1C(=O)R^2$, $R^1C(=O)OR^2$, $R^1N_3$, $R^1C(\equiv CH)$. In these embodiments, $R^1$ is selected from the group consisting of a bond, alkylene, heteroalkylene, arylene, heteroarylene. $R^2$ and $R^3$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2]cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

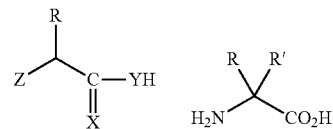

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, P and y amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

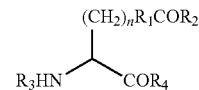

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

In some examples, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Comish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

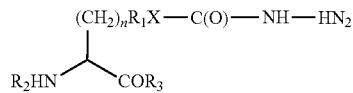

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

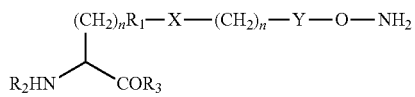

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, J. Org. Chem. 68: 8853-8858 (2003). Certain aminooxy-containing amino acids, such as L-2-amino-4-(aminooxy)butyric acid), have been isolated from natural sources (Rosenthal, G. et al., Life Sci. 60: 1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed.

Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

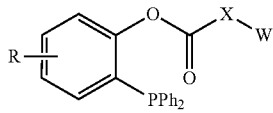

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

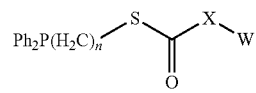

wherein n is 1-10; X can be O, N, S or not present, Ph is phenyl, and W is a water soluble polymer.

Exemplary alkyne-containing amino acids can be represented as follows:

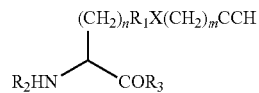

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one skilled in the art.

Exemplary azide-containing amino acids can be represented as follows:

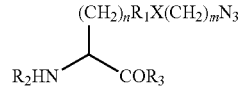

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, and p-azido-phenylalanine. One particularly useful non-natural amino acid is p-azido phenylalanine. This amino acid residue is known to those of skill in the art to facilitate Huisgen [3+2] cycloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the alpha carbon of the non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids having the structure of Formula (I):

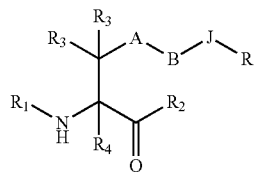

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl; J is

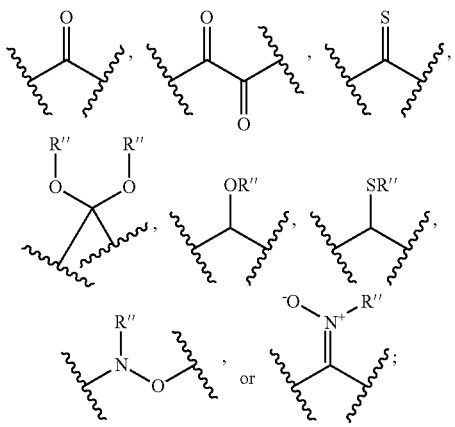

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R_3$ is H, B is present; and that when A is —$(CH_2)_4$— and each $R_3$ is H, B is not —$NHC(O)(CH_2CH_2)$—; and that when A and B are absent and each $R_3$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (I) are stable in aqueous solution for at least 1 month under mildly acidic conditions. In certain embodiments, compounds of Formula (I) are stable for at least 2 weeks under mildly acidic conditions. In certain embodiments, compound of Formula (I) are stable for at least 5 days under mildly acidic conditions. In certain embodiments, such acidic conditions are pH 2 to 8.

In certain embodiments of compounds of Formula (I), B is lower alkylene, substituted lower alkylene, —O-(alkylene or substituted alkylene)-, —C(R')=N—N(R')—, —N(R')CO—, —C(O)—, —C(R')=N—, —C(O)-(alkylene or substituted alkylene)-, —CON(R')-(alkylene or substituted alkylene)-, —S(alkylene or substituted alkylene)-, —S(O)(alkylene or substituted alkylene)-, or —$S(O)_2$(alkylene or substituted alkylene)-. In certain embodiments of compounds of Formula (I), B is —$O(CH_2)$—, —CH=N—, —CH=N—NH—, —$NHCH_2$—, —NHCO—, —C(O)—, —C(O)—$(CH_2)$—, —CONH—$(CH_2)$—, —$SCH_2$—, —S(=O)$CH_2$—, or —$S(O)_2CH_2$—. In certain embodiments of compounds of Formula (I), R is $C_{1-6}$ alkyl or cycloalkyl. In certain embodiments of compounds of Formula (I) R is —$CH_3$, —$CH(CH_3)_2$, or cyclopropyl. In certain embodiments of compounds of Formula (I), $R_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (I), $R_1$ is a resin, amino acid, polypeptide, or polynucleotide. In certain embodiments of compounds of Formula (I), $R_2$ is OH, O-methyl, O-ethyl, or O-t-butyl. In certain embodiments of compounds of Formula (I), $R_2$ is a resin, amino acid, polypeptide, or polynucleotide. In certain embodiments of compounds of Formula (I), $R_2$ is a polynucleotide. In certain embodiments of compounds of Formula (I), $R_2$ is ribonucleic acid (RNA). In certain embodiments of compounds of Formula (I), $R_2$ is tRNA. In certain embodiments of compounds of Formula (I), the tRNA specifically recognizes a selector codon. In certain embodiments of compounds of Formula (I) the selector codon is selected from the group consisting of an amber codon, ochre codon, opal codon, a unique codon, a rare codon, an unnatural codon, a five-base codon, and a four-base codon. In certain embodiments of compounds of Formula (I), $R_2$ is a suppressor tRNA.

In certain embodiments of compounds of Formula (I), is selected from the group consisting of: (i) A is substituted lower alkylene, $C_4$-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2N(R')$, —N(R')C(O)N(R')—, —N(R')C(S)N(R')—, —N(R')S(O)N(R')—, —N(R')$S(O)_2$N(R')—, —N(R')—N=, —C(R')=N—N(R')—, —C(R')=N—N=, —C(R')$_2$—N=N—, and —C(R')$_2$—N(R')—N(R')—; (ii) A is optional, and when present is substituted lower alkylene, $C_4$-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2N(R')$, —N(R')C(O)N(R')—, —N(R')C(S)N(R')—, —N(R')S(O)N(R')—, —N(R')$S(O)_2$N(R')—, —N(R')—N=, —C(R')=N—N(R')—, —C(R')=N—N=, —C(R')$_2$—N=N—, and —C(R')$_2$—N(R')—N(R')—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CSN(R')—, —CON(R')-(alkylene or substituted alkylene)-, —N(R')C(O)O—, —N(R')C(S)—, —S(O)N(R'), —$S(O)_2N(R')$, —N(R')C(O)N(R')—, —N(R')C(S)N(R')—, —N(R')S(O)N(R')—, —N(R')$S(O)_2$N(R')—, —N(R')—N=, —C(R')=N—N(R')—, —C(R')=N—N=, —C(R')$_2$—N=N—, and —C(R')$_2$—N(R')—N(R')—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2N(R')$, —N(R')C(O)N(R')—, —N(R')C(S)N(R')—, —N(R')S(O)N(R')—, —N(R')$S(O)_2$N(R')—, —N(R')—N=, —C(R')'N—N(R')—, —C(R')=N—N=, —C(R')$_2$—N=N—, and —C(R')$_2$—N(R')—N(R')—; J is

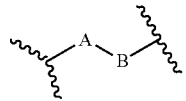

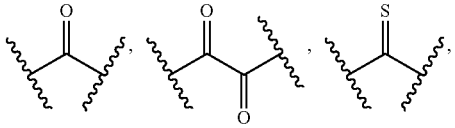

-continued

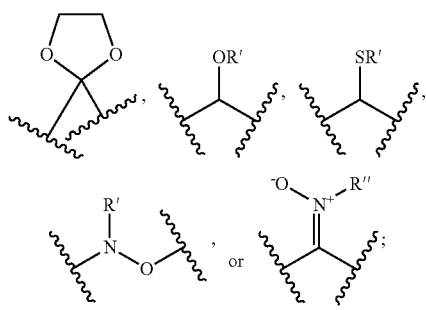

each R' is independently H, alkyl, or substituted alkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; and each $R_3$ and $R_4$ is independently H, halogen, lower alkyl, or substituted lower alkyl; and R is H, alkyl, substituted alkyl, cycloalkyl, or substituted cycloalkyl.

In certain embodiments, the non-natural amino acid can be according to formula XIX:

Formula XIX

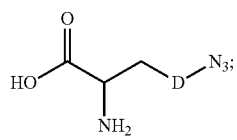

or a salt thereof, wherein: D is —Ar—$W_3$— or —$W_1$-$Y_1$—C(O)—$Y_2$—$W_2$—; Ar is

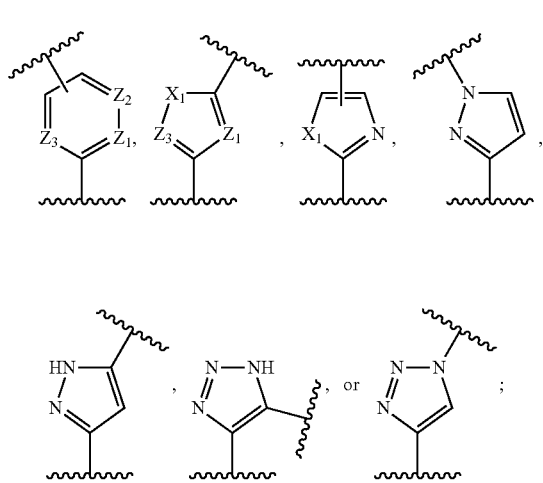

each of $W^1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—. In certain embodiments, the non-natural amino acid is according to formula XIXa:

Formula XIXa

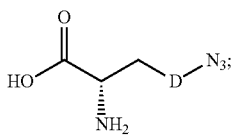

where D is a defined in the context of formula XIX. In certain embodiments, the non-natural amino acid is according formula XIXb:

Formula XIXb

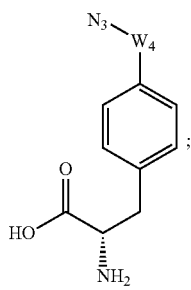

or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene. In particular embodiments, the non-natural amino acid is selected from the group consisting of.

(1)

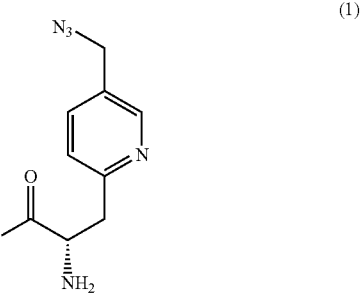

(2)

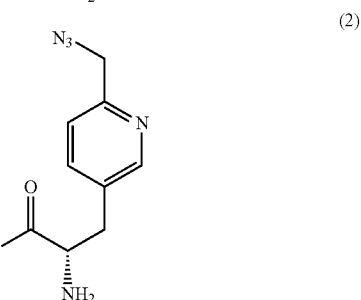

(3)

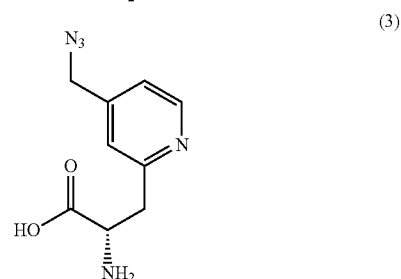

-continued
(4)
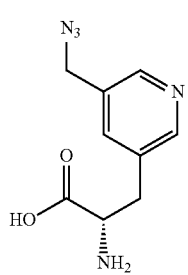
(5)
(6)
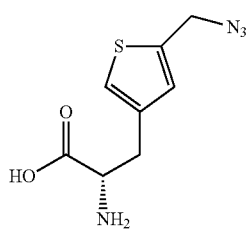
(7)
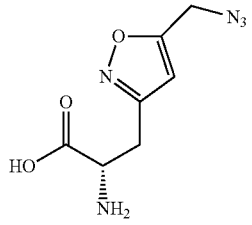
(8)
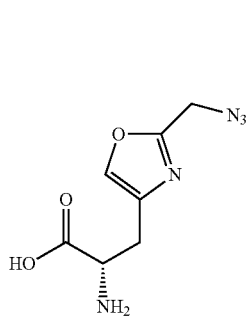
(9)
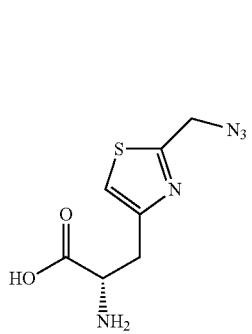
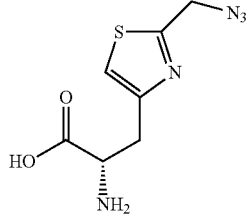
-continued
(10)
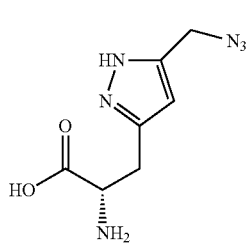
(11)
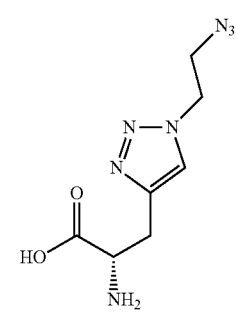
(12)
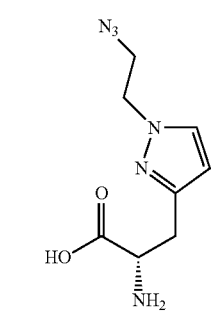
(13)
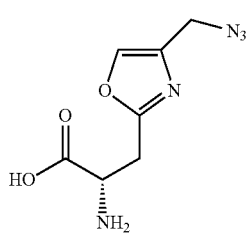
(14)
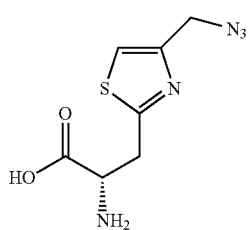
(15)
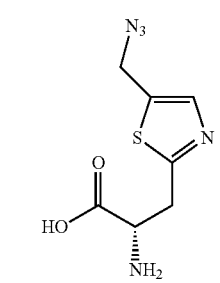

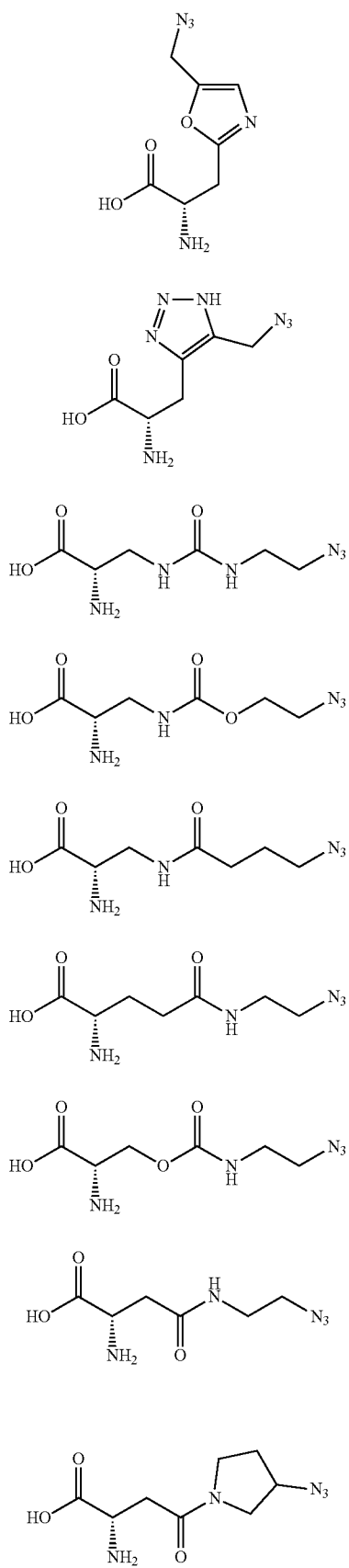
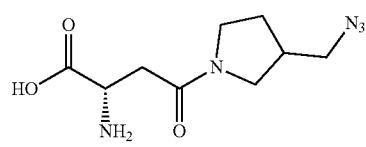
(25)
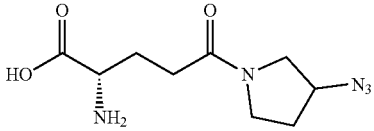
(26)
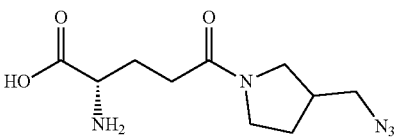
(27)
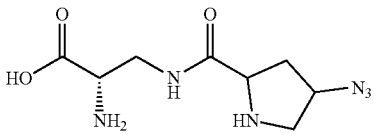
(28)
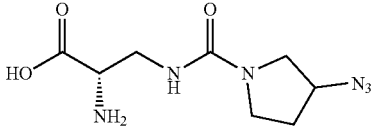
(29)
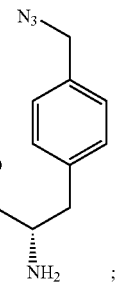
(30)
; and
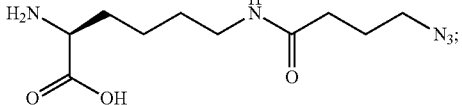
(40)
or a salt thereof. Such non-natural amino acids may be in the form of a salt, or may be incorporated into a non-natural amino acid polypeptide, polymer, polysaccharide, or a polynucleotide and optionally post translationally modified.
In certain embodiments, the modified amino acid is according to formula I:
Formula I
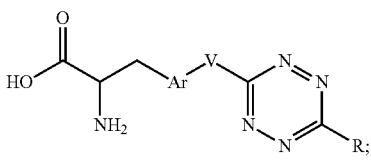

or a salt thereof, wherein Ar is:

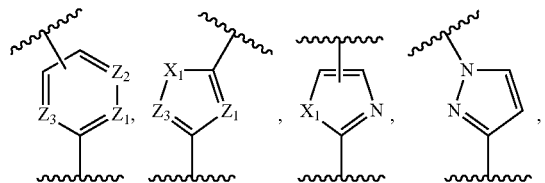

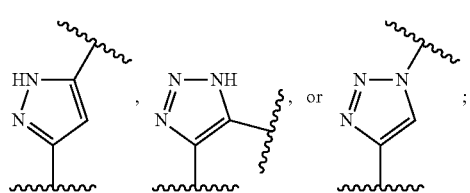

V is a single bond, lower alkylene, or —W$_1$-W$_2$—; one of W$_1$ and W$_2$ is absent or lower alkylene, and the other is —NH—, —O—, or —S—; each X$_1$ is independently —NH—, —O—, or —S—; one of Z$_1$, Z$_2$, and Z$_3$ is —CH— or —N— and the others of Z$_1$, Z$_2$, and Z$_3$ are each independently —CH—; and R is lower alkyl. In certain embodiments, when Ar is

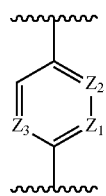

and V is —NH—, then one of Z$_1$, Z$_2$, and Z$_3$ is —N—. In certain embodiments, V is a single bond, —NH—, or —CH$_2$NH—.

In certain embodiments, Ar is

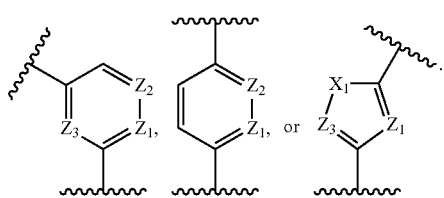

and Z$_1$, Z$_2$, Z$_3$ and X$_1$ are as defined in the context of formula I. In certain embodiments according to this paragraph, V is —W$_1$-W$_2$—; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, Z$_1$ is N. In certain embodiments according to this paragraph, Z$_2$ is N. In certain embodiments according to this paragraph, Z$_3$ is N. In certain embodiments according to this paragraph, Z$_1$ is CH, Z$_3$ is CH and X$_1$ is S.

In certain embodiments, Ar is

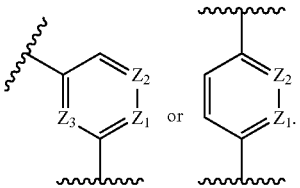

and Z$_1$, Z$_2$, and Z$_3$ are as defined in the context of formula I. In certain embodiments according to this paragraph, V is —W$_1$-W$_2$—; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, Z$_1$ is N. In certain embodiments according to this paragraph, Z$_2$ is N. In certain embodiments according to this paragraph, Z$_3$ is N.

In certain embodiments, Ar is

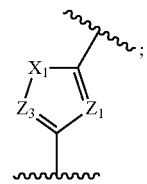

and Z$_1$, Z$_3$ and X$_1$ are as defined in the context of formula I. In certain embodiments according to this paragraph, V is —W$_1$-W$_2$—; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, Z$_1$ is N. In certain embodiments according to this paragraph, Z$_3$ is N. In certain embodiments according to this paragraph, Z$_1$ is CH, Z$_3$ is CH and X$_1$ is S.

In certain embodiments, the modified amino acid is according to formula Ia:

Formula Ia

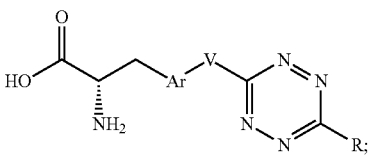

where Ar, V, and R are defined in the context of formula I.

In an embodiment, compounds of either of formulas I and Ia are provided wherein V is a single bond. In another embodiment, compounds of either of formulas I and Ia are provided wherein V is —NH—. In another embodiment, compounds of either of formulas I and Ia are provided wherein V is —CH$_2$NH—.

In certain embodiments, the modified amino acid is according to formula II:

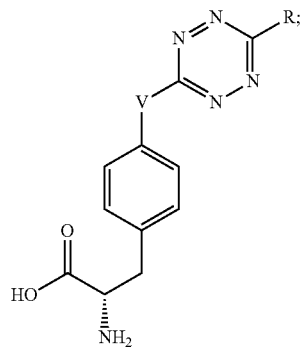

Formula II or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond or —CH₂NH—; and R is methyl.

In certain embodiments, the modified amino acid is according to formula III:

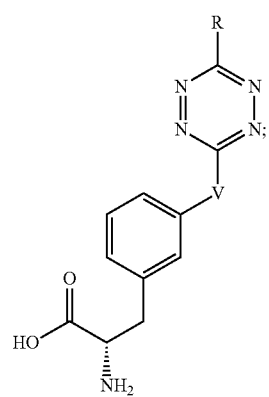

Formula III or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula IV:

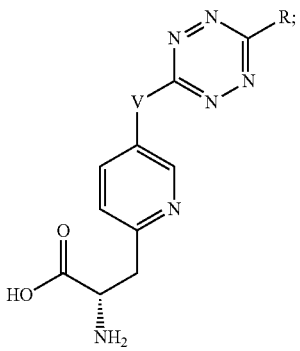

Formula IV or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula V:

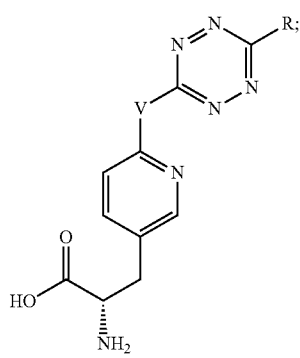

Formula V or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula VI:

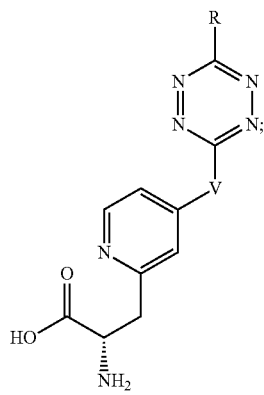

Formula VI or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula VII:

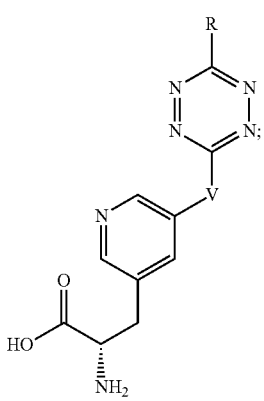

Formula VII or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula VIII:

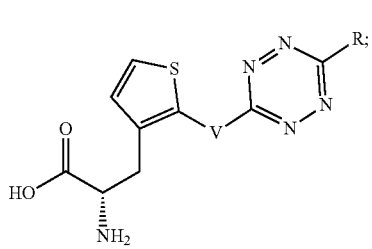

Formula VIII or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to formula IX:

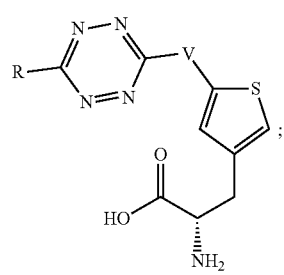

Formula IX or a salt thereof, wherein V and R are as defined in Formula I. In certain embodiments according to this paragraph, V is —W₁-W₂—; one of W₁ and W₂ is absent or —CH₂—, and the other is —NH—, —O—, or —S—. In certain embodiments, V is a single bond, —NH—, or —CH₂NH—. In certain embodiments, V is a single bond, —NH—, or —CH₂NH—; and R is methyl.

In certain embodiments, the modified amino acid is according to any of formulas 51-60:

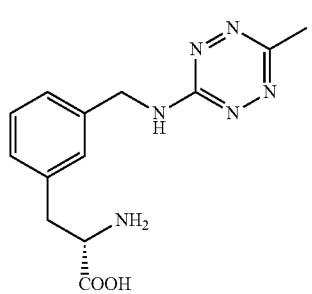

(51)

(52) 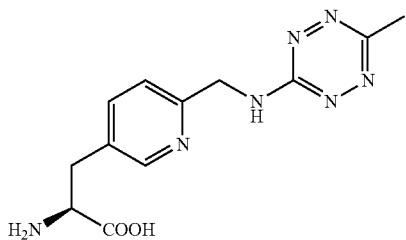

(53) 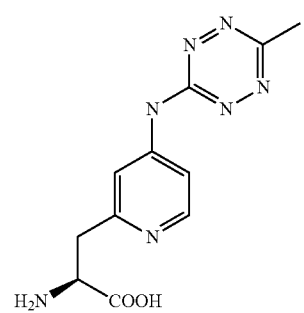

(54) 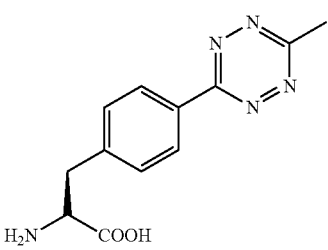

(55) 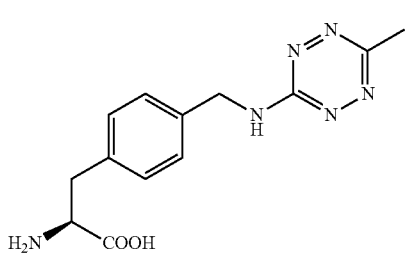

(56) 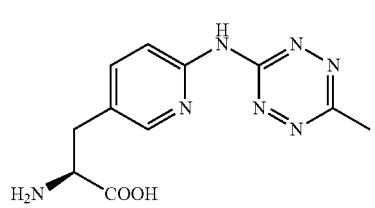

(57) 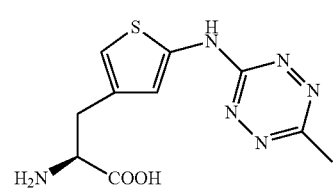

(58) 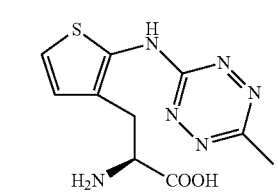

(59) 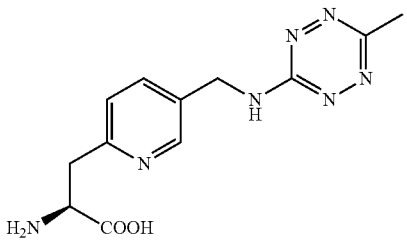

(60) 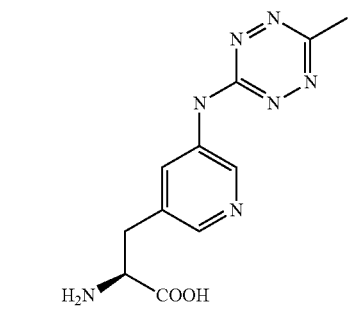

or a salt thereof.

In certain embodiments, the non-natural amino acid is selected from the group consisting of compounds 30, 53, 56, 59, and 60 above. In certain embodiments, the non-natural amino acid is compound 30. In certain embodiments, the non-natural amino acid is compound 56.

11. Preparation of Antibody Conjugates

11.1. Antigen Preparation

The CD74 antigen to be used for production of antibodies may be intact CD74 or a fragment of CD74. Other forms of CD74 useful for generating antibodies will be apparent to those skilled in the art.

11.2. Monoclonal Antibodies

Monoclonal antibodies may be obtained, for example, using the hybridoma method first described by Kohler et al., Nature, 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., Monoclonal Antibodies: Principles and Practice 3$^{rd}$ ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

11.3. Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370.

11.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573, 905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

11.5. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Exemplary conditions are described in the examples below.

12. Vectors, Host Cells, and Recombinant Methods

The invention also provides isolated nucleic acids encoding anti-CD74 antibody conjugates, vectors and host cells comprising the nucleic acids, and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-CD74 antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans,* and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium,* and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-CD74 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs,* 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.,* 1983, 62:1-13). Protein G is useful for all mouse isotypes and for human γ3 (Guss et al., *EMBO J.,* 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5-4.5, generally performed at low salt concentrations (e.g., from about 0-0.25 M salt).

13. Pharmaceutical Compositions and Methods of Administration

The antibody conjugates provided herein can be formulated into pharmaceutical compositions using methods available in the art and those disclosed herein. Any of the antibody conjugates provided herein can be provided in the appropriate pharmaceutical composition and be administered by a suitable route of administration.

The methods provided herein encompass administering pharmaceutical compositions comprising at least one antibody provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences.*

In clinical practice the pharmaceutical compositions or antibody conjugates provided herein may be administered by any route known in the art. In certain embodiments, a pharmaceutical composition or antibody provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmacopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising an antibody, since water can facilitate the degradation of some antibody conjugates.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more excipients that reduce the rate by which an antibody will decompose. Such antibody conjugates, which are referred to herein as "stabilizers," include, but are not limited to, antioxidants such as ascorbic acid, pH buffers, or salt buffers.

13.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibody conjugates disclosed herein can also be incorporated into the parenteral dosage forms.

13.2. Dosage and Unit Dosage Forms

In human therapeutics, the doctor will determine the posology which he considers most appropriate according to a preventive or curative treatment and according to the age, weight, stage of the infection and other factors specific to the subject to be treated.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibody conjugates provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

14. Therapeutic Applications

For therapeutic applications, the antibody conjugates of the invention are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The antibody conjugates provided herein may be useful for the treatment of any disease or condition involving upregulation of CD74. Upregulation of CD74 expression has been observed in cancers and autoimmune disease (Borghese et al., *Exp. Op. Ther. Targets,* 2011, 15:237-251, incorporated by reference in its entirety), as well as in infection (Hofman et al., *Modern Pathology,* 2007, 20:974-989, incorporated by reference in its entirety) and inflammatory conditions (Vera et al., *Exp. Biol. & Med.,* 2008, 233:620-626, incorporated by reference in its entirety). CD74 is known to be expressed at moderate to high levels in multiple myeloma. Burton et al., *Clin. Cancer Res.,* 2004, 10:6606-6611, incorporated by reference in its entirety. CD74 expression is also known to be a key factor associated with the progression of pancreatic cancer. Zhang et al., *Hepatobiliary Pancreat. Dis. Int.,* 2014, 13:81-86, incorporated by reference in its entirety.

In certain aspects, the antibody conjugates provided herein are useful for the treatment of one or more B cell malignancies. The B cell malignancy can be any B cell malignancy known to the practitioner of skill. These include B-cell malignancies described in the Revised European-American Lymphoma classification system (REAL) and those described in Harris et al., 1994, Blood 84:1361-1392 and Armitage & Weisenburger, 1998, J. Clin. Oncol. 16:2780-2795, each incorporated by reference in its entirety. In certain embodiments, the B cell malignancy is selected from the group consisting of diffuse large B-cell lymphoma (DLBCL), follicular lymphoma, marginal zone B-cell lymphoma (MZL), mucosa-associated lymphatic tissue lymphoma (MALT), small lymphocytic lymphoma, mantle cell lymphoma (MCL). In certain embodiments, the DLBCL is selected from the group consisting of primary mediastinal (thymic) large B cell lymphoma, T cell/histiocyte-rich large B-cell lymphoma, primary cutaneous diffuse large B-cell lymphoma, leg type (primary cutaneous DLBCL, leg type), EBV positive diffuse large B-cell lymphoma of the elderly, diffuse large B-cell lymphoma associated with inflammation. In certain embodiments the B-cell malignancy is selected from the group consisting of Burkitt's lymphoma, lymphoplasmacytic lymphoma, Waldenstrom's macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHV8-associated multicentric Castleman's disease, B-cell lymphoma (unclassifiable with features intermediate between diffuse large B-cell lymphoma and Burkitt lymphoma), and B-cell lymphoma (unclassifiable with features intermediate between diffuse large B-cell lymphoma and classical Hodgkin lymphoma). In certain embodiments, the malignancy is selected from Hodgkin's lymphoma, classic Hodgkin's lymphoma, and nodular lymphocyte predominant Hodgkin's lymphoma. In certain embodiments, the malignancy is non-Hodgkin's lymphoma.

In certain aspects, the antibody conjugates provided herein are useful for the treatment of one or more leukemias. In certain embodiments, the leukemia is acute leukemia. In certain embodiments, the leukemia is chronic leukemia. In certain embodiments, the leukemia is selected from the group consisting of acute lymphoblastic leukemia (ALL), chronic lymphocytic leukemia (CLL), acute myelogenous leukemia (AML), chronic myelogenous leukemia (CML), and hairy cell leukemia (HCL).

15. Diagnostic Applications

In some embodiments, the antibody conjugates provided herein are used in diagnostic applications. For example, an ant-CD74 antibody may be useful in assays for CD74 protein. In some aspects the antibody can be used to detect the expression of CD74 in various cells and tissues. These assays may be useful, for example, diagnosing cancer, infection and autoimmune disease.

In some diagnostic applications, the antibody may be labeled with a detectable moiety. Suitable detectable moieties include, but are not limited to radioisotopes, fluorescent labels, and enzyme-substrate labels. In another embodiment of the invention, the anti-CD74 antibody need not be labeled, and the presence thereof can be detected using a labeled antibody which specifically binds to the anti-CD74 antibody.

16. Affinity Purification Reagents

The antibody conjugates of the invention may be used as affinity purification agents. In this process, the antibody conjugates may be immobilized on a solid phase such a resin or filter paper, using methods well known in the art. The immobilized antibody is contacted with a sample containing the CD74 protein (or fragment thereof) to be purified, and thereafter the support is washed with a suitable solvent that will remove substantially all the material in the sample except the CD74 protein, which is bound to the immobilized antibody. Finally, the support is washed with another suitable solvent, such as glycine buffer, pH 5.0, that will release the CD74 protein from the antibody.

17. Kits

In some embodiments, an antibody of the present invention can be provided in a kit, i.e., a packaged combination of reagents in predetermined amounts with instructions for performing a procedure. In some embodiments, the procedure is a diagnostic assay. In other embodiments, the procedure is a therapeutic procedure.

EXAMPLES

Example 1: Production and Purification of Anti-CD74 Antibodies

Antibodies were expressed in an Xpress CF™ reaction as described previously with the following modifications. The cell free extract for this work were created from an OmpT sensitive RF 1 attenuated *E. coli* strain engineered to over-express *E. coli* DsbC and FkpA as well as an orthogonal tRNA containing the CUA anti-codon for decoding the Amber Stop Codon. Extract was treated with 75 μM iodo-acetamide for 45 min at RT (20° C.) and added to a premix containing all other components, except for IgG heavy and light chain DNA. The final concentration in the protein synthesis reaction was 30% (v/v) cell extract, 2 mM para-azidomethylphenylalanine (pAMF) (RSP Amino Acids), 5 uM engineered pAMF-specific amino-acyl tRNA synthetase (FRS variant), 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP, 1 μg/mL antiCD74 light chain DNA, and 4 μg/mL antiCD74 heavy chain DNA. Site directed mutagenesis was used to introduce an amber stop codon (TAG) into the nucleotide sequence to encode for the pAMF non-natural amino acid at positions S7 and F404 (light and heavy chains respectively, kabat numbering). Cell free reactions were initiated by addition of plasmid DNA and incubated at 30° C. for 16 h in 100×10 mm petri dishes containing 10 mL.

The anti-CD74 cell free reactions were clarified by centrifugation at 10,000 rpm's for 30 minutes. The clarified supernatant was applied to Protein A MabSelect SuRe (GE Healthcare) with standard wash and low pH elution. Impurities such as aggregates were removed via preparative SEC (Sepax SRT-10C) equilibrated in 50 mM sodium phosphate, 200 mM arginine, pH 6.5. Final formulation of the sample was done in Dulbecco's Phosphate Buffered Saline (1×DPBS).

Example 2: Production of Anti-CD74 Antibodies with Non-Natural Amino Acids

Antibodies were prepared having non-natural amino acids at positions heavy chain residues 404, 241, and 222, according to the EU number scheme, and at light chain residue 7, according to the Kabat or Chothia numbering scheme. One antibody comprised residue (56), above, at position 404, and four antibodies comprised residue (30), above, at each of positions 404, 241, 222 (heavy chain) and 7 (light chain). The starting heavy chain was according to SEQ ID NO:236, and the starting light chain was according to SEQ ID NO:256.

Figure 2B:
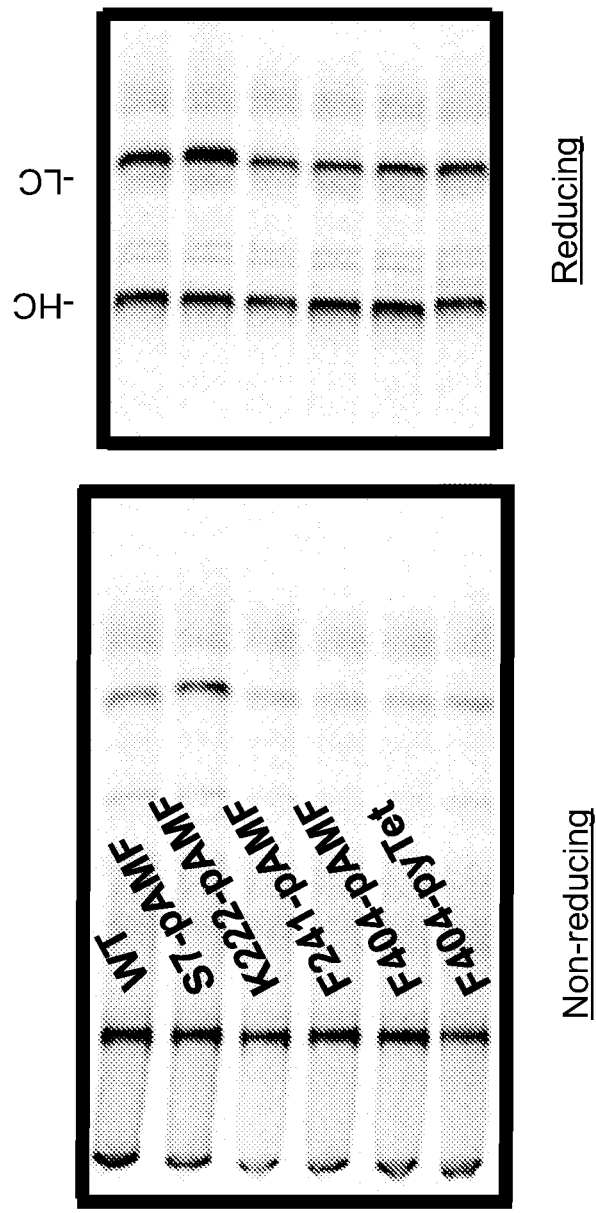
FIG. 2B provides SDS-PAGE analysis of the antibodies under non-reducing and reducing conditions.

Each antibody was expressed at a total yield of at least 400 mg/L as shown in FIG. 2A, and intact IgG were detected by SDS-PAGE as shown in FIG. 2B.

Example 3: Production of Antibody-PEG$_4$-Maytansine Conjugate

Purified anti-CD74 IgG containing modified amino acid residue (30) (i.e. para-azido-methyl-L-phenylalanine, or pAMF) at EU position 404 in its heavy chains was obtained according to Example 2. The anti-CD74 IgG was conjugated to a cytotoxic agent, maytansine, using a strained cyclooctyne reagent to yield Conjugate A.

In brief, DBCO-PEG$_4$-maytansine (ACME Bioscience; Palo Alto, Calif.) according to the following:

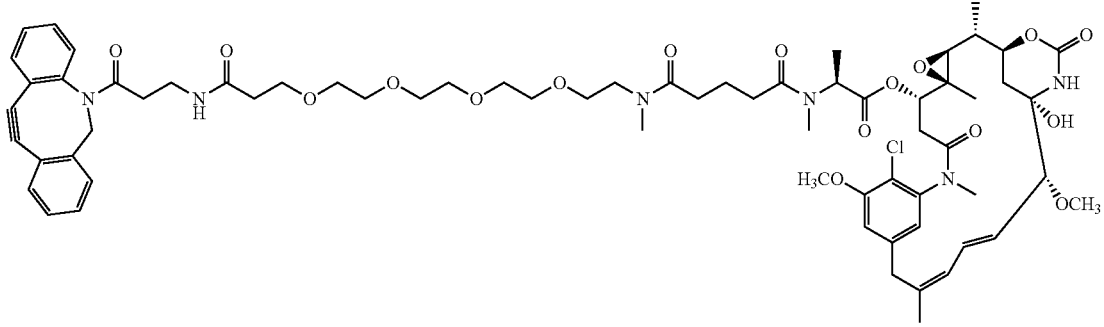 [SMILES: COc1cc2cc(c1Cl)N(C)C(=O)C[C@H](OC(=O)[C@H](C)N(C)C(=O)CCCC(=O)N(C)CCOCCOCCOCCOCCC(=O)NCCC(=O)N1Cc3ccccc3C#Cc3ccccc31)[C@]1(C)O[C@H]1[C@H](C)[C@@H]1C[C@@](O)(NC(=O)O1)[C@H](OC)/C=C/C=C(/C)C2]

was dissolved in DMSO to a final concentration of 5 mM. The compound was added to 1 mg/mL purified protein in PBS at a drug to antibody molar ratio of 12 to 1. The reaction mixture was incubated at RT (20° C.) for 17 hours. Excess free drug was removed by Zeba plate (Thermo Scientific) equilibrated in PBS.

DAR analysis was done by MALDI-TOF (Bruker AutoFlex Speed). The conjugated protein was reduced for 10 min at 37° C. with 10 mM TCEP in water and diluted to a final concentration of 50 µg/mL in 30% acetonitrile, 0.1% trifluoroacetic acid. Samples were combined 1:1 with S-DHB MALDI matrix (50 mg/mL in 50% acetonitrile, 0.10% trifluoroacetic acid) and 1 uL was applied to the MALDI target and dried under vacuum. Each MALDI spectra was accumulated for 5000 shots at full laser power in linear mode and the final DAR analysis was calculated by comparing the relative peak heights for conjugated and unconjugated masses for both the heavy and light chains.

By peak intensity, MALDI-TOF showed a drug to antibody ratio (DAR) of 3.92. Conjugate A, as two regioisomers:

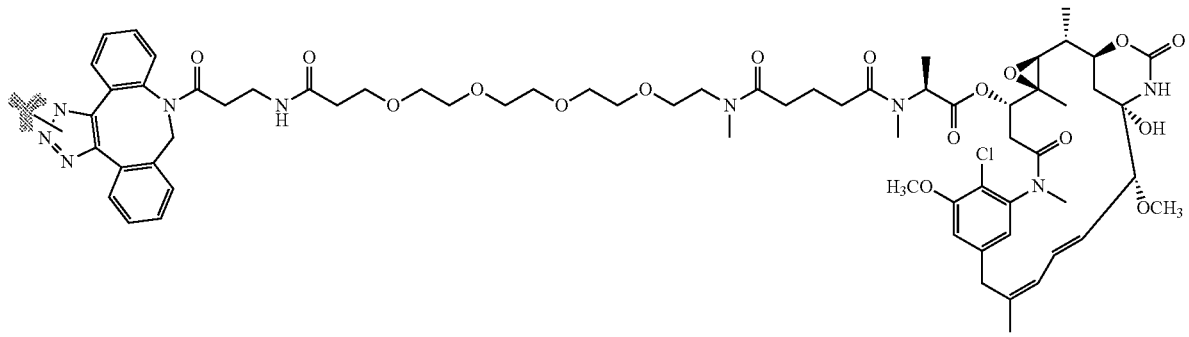

Example 4: Production of Antibody Conjugates

Purified anti-CD74 IgG containing modified amino acid residue 30 according to Example 2 was conjugated to maytansine, hemiasterlin, amanitin, MMAF, and MMAE linker-payload precursors to yield several anti-CD74-linker-payload conjugates designated Conjugates B-F.

Conjugate B was prepared following a protocol consistent with Example 3 with the following PEG$_4$-maytansine precursor:

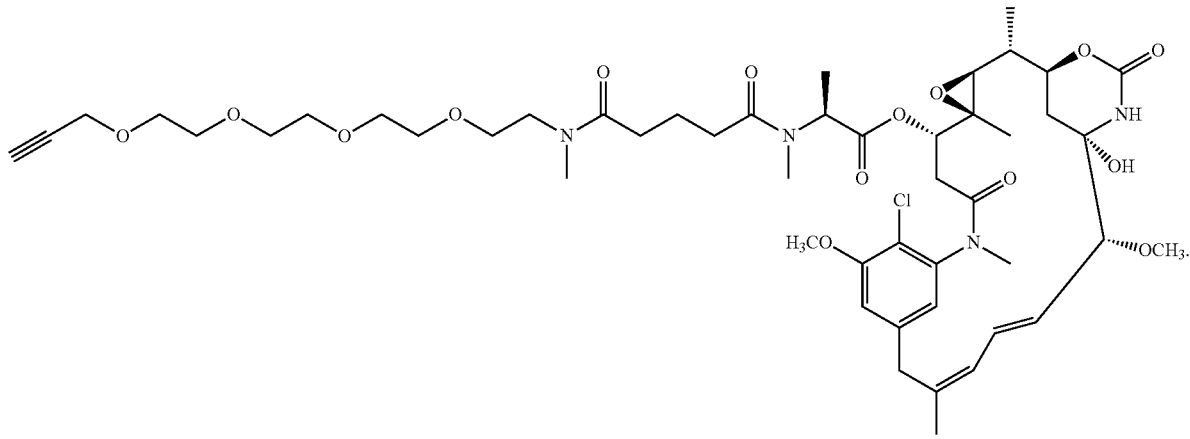 [SMILES: C#CCOCCOCCOCCOCCN(C)C(=O)CCCC(=O)N(C)[C@@H](C)C(=O)O[C@H]1CC(=O)N(C)c2cc(cc(OC)c2Cl)C/C(C)=C\C=C\[C@@H](OC)[C@@]2(O)C[C@H](OC(=O)N2)[C@@H](C)[C@@H]2O[C@@]12C]

Conjugate B has the following structure, or a regioisomer thereof:
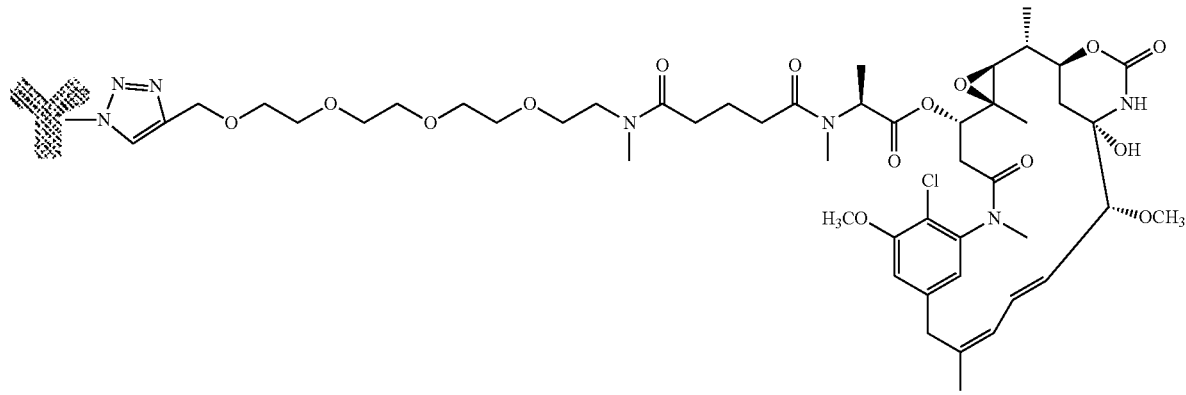 [SMILES: COc1cc2cc(c1Cl)N(C)C(=O)C[C@H](OC(=O)[C@H](C)N(C)C(=O)CCCC(=O)N(C)CCOCCOCCOCCOCc1cn(C)nn1)[C@]1(C)O[C@H]1[C@H](C)[C@@H]1C[C@@](O)(NC(=O)O1)[C@H](OC)/C=C/C=C(/C)C2]
Conjugate C was prepared with the following val-cit-PAB-hemiasterlin precursor as described in U.S. application No. 62/110,390, filed Jan. 30, 2015, entitled Hemiasterlin Derivatives for Conjugation and Therapy, incorporated by reference herein:
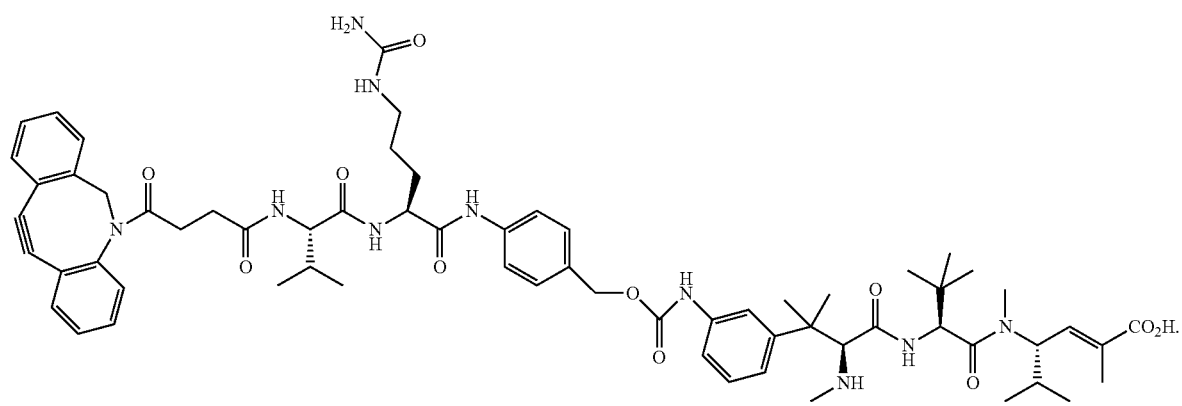 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](CCCNC(N)=O)NC(=O)[C@@H](NC(=O)CCC(=O)N3Cc4ccccc4C#Cc4ccccc43)C(C)C)cc2)c1]
Conjugate C has the following structure, shown as two regioisomers:
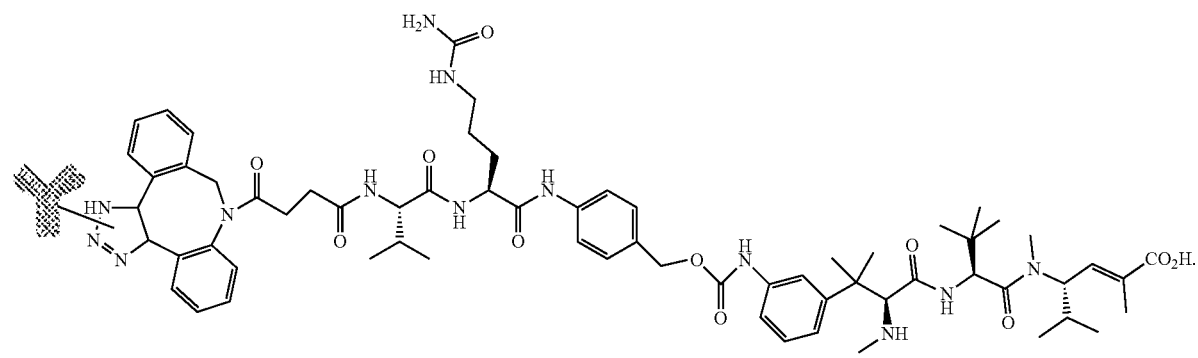

Conjugate D was prepared with the following linker-amanitin precursor:

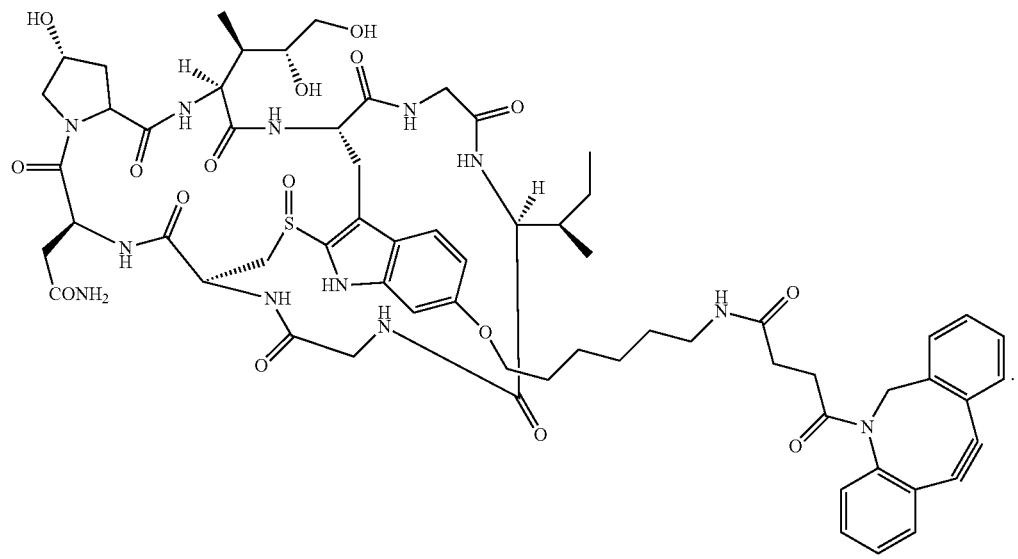 [SMILES: CC[C@@H](C)[C@@H]1NC(=O)CNC(=O)[C@@H]2Cc3c([nH]c4cc(OCCCCCCNC(=O)CCC(=O)N5Cc6ccccc6C#Cc6ccccc65)ccc34)S(=O)C[C@@H](NC(=O)CNC1=O)C(=O)N[C@@H](CC(N)=O)C(=O)N1C[C@H](O)CC1C(=O)N[C@@H]([C@@H](C)[C@@H](O)CO)C(=O)N2]

Conjugate D was prepared via O-alkylation of α-amanitin (BioTrend LLC, Destin, Fla.) with tert-butyl (6-bromohexyl)carbamate, followed by cleavage of the Boc protecting group and acylation with DBCO succinate. Conjugate D has the following structure, shown as two regioisomers:

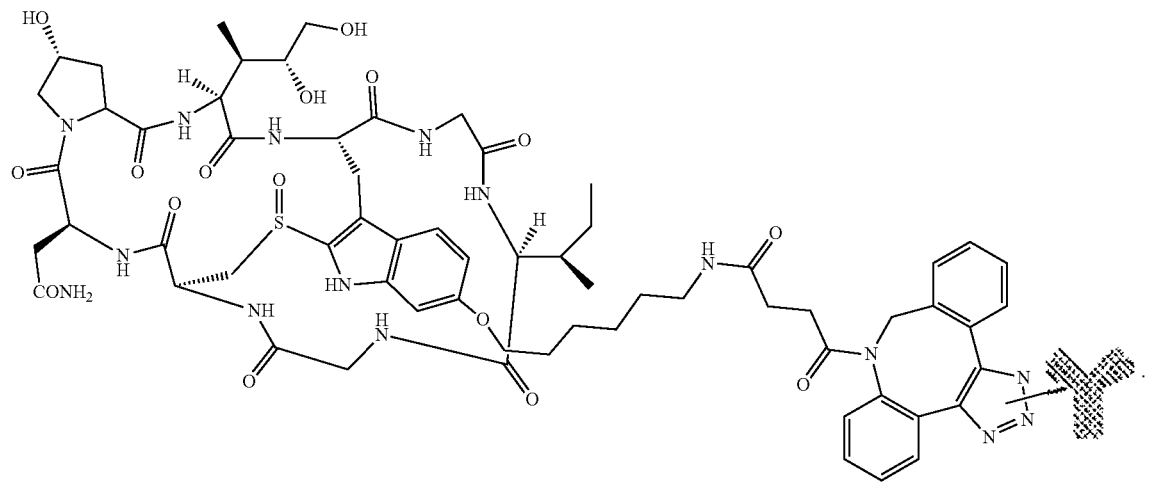

Conjugate E was prepared with the following PEG$_4$-MMAF precursor:

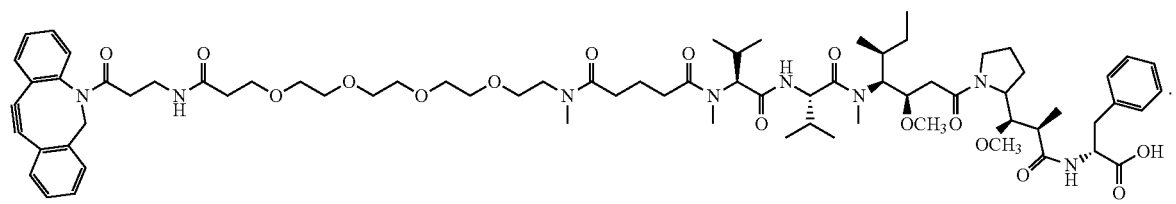 [SMILES: CC[C@H](C)[C@@H]([C@@H](CC(=O)N1CCCC1[C@H](OC)[C@@H](C)C(=O)N[C@H](Cc1ccccc1)C(=O)O)OC)N(C)C(=O)[C@@H](NC(=O)[C@H](C(C)C)N(C)C(=O)CCCC(=O)N(C)CCOCCOCCOCCOCCC(=O)NCCC(=O)N1Cc2ccccc2C#Cc2ccccc21)C(C)C]

Conjugate E was prepared via acylation of MMAF (Doronina, S. et al 2003 *Nat Biotechnol* 21, 778-84) adapting the basic method outlined for Conjugate A. Conjugate E has the following structure, shown as two regioisomers:

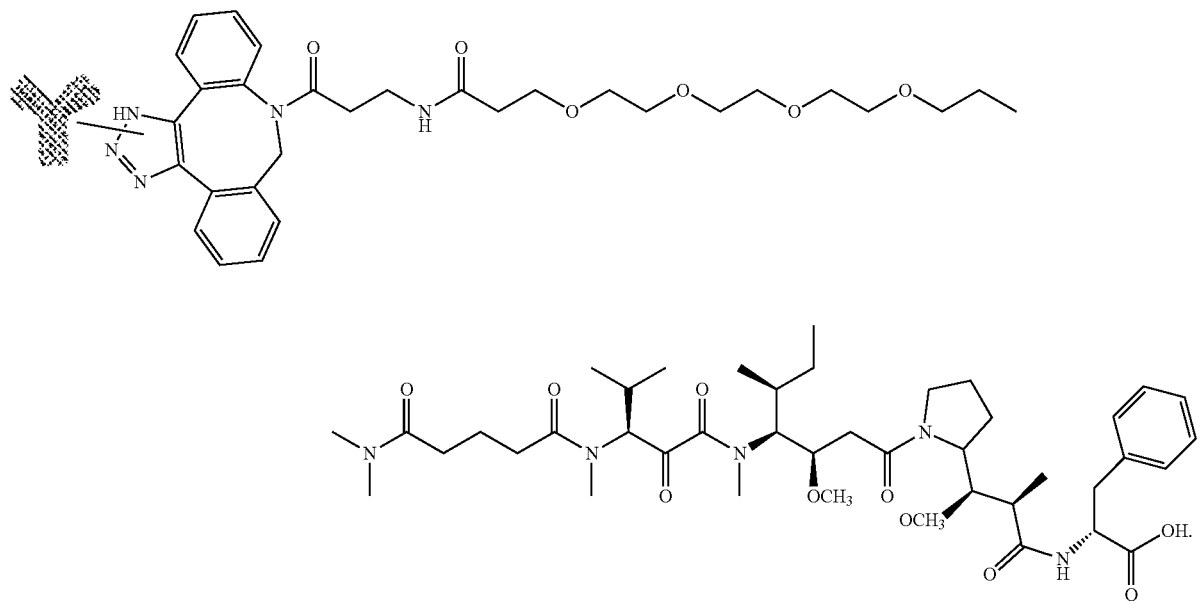

Conjugate F was prepared with the following PEG$_4$-MMAF precursor:

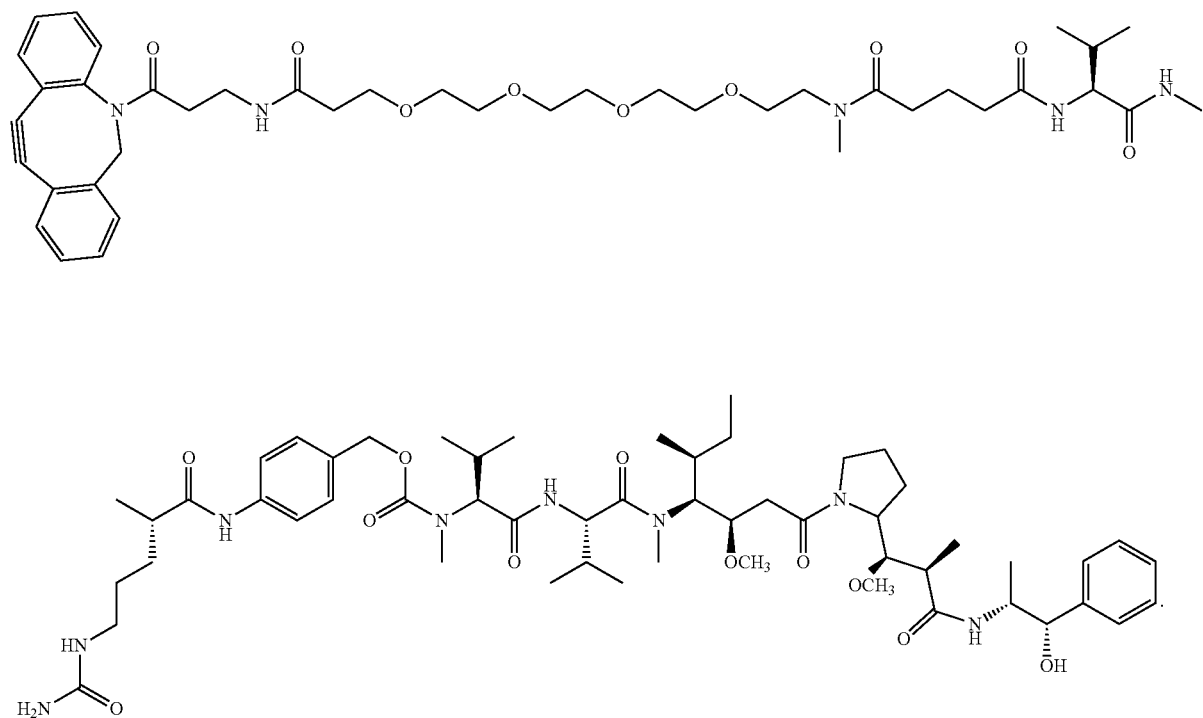

Conjugate F was prepared by modification of the method described in Doronina, S. et al 2003 *Nat Biotechnol* 21, 778-84. Conjugate F has the following structure, shown as two regioisomers:

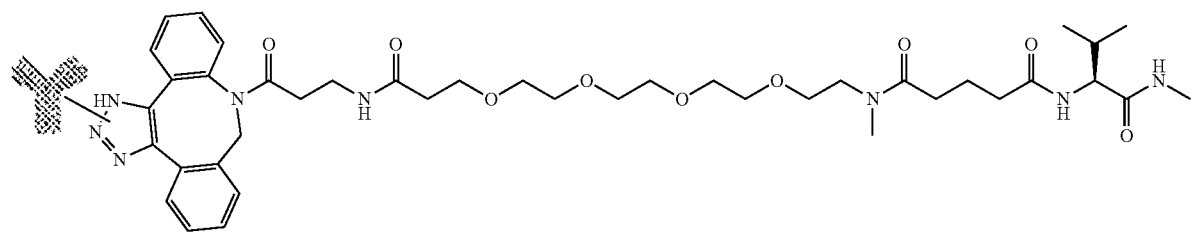

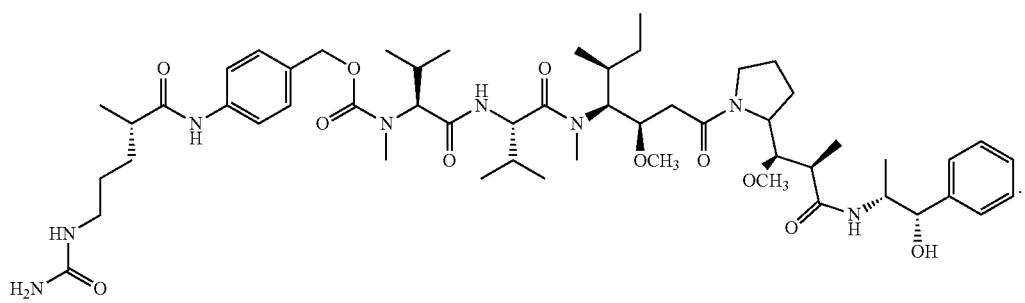

Expression of each conjugate was measured by absorbance at 280 nm, and the extent of conjugation was measured by MALDI-TOF. Control was the unconjugated antibody of Example 3. The data is summarized in the following table:

| Conjugate | mg/mL (A280) | DAR | Buffer |
|---|---|---|---|
| Control | 17.6 | | PBS |
| A | 1.90 | 1.94 | PBS + 0.2 mM pAMF |
| B | 2.10 | 1.96 | PBS + 0.2 mM pAMF |
| C | 2.10 | 1.88 | PBS + 0.2 mM pAMF |
| D | 2.04 | 1.95 | PBS + 0.2 mM pAMF |
| E | 1.73 | 1.91 | PBS + 0.2 mM pAMF |
| F | 1.79 | 1.73 | PBS + 0.2 mM pAMF |

Example 5: Cell Binding and Cell Killing

Conjugate A was evaluated for the ability to bind and kill cells expressing CD74 by the methods below. Cell lines tested included B-lymphoma, multiple myeloma, and leukemia cells. Controls included unconjugated anti-CD74 antibody and free linker-drug (DIBCO-PEG$_4$-maytansine).

Cell Binding Assay

Cell lines were maintained in RPMI, high glucose (Cellgro-Mediatech; Manassas, Va.) supplemented with 20% heat-inactivated fetal bovine serum (Hyclone; Thermo Scientific; Waltham, Mass.), 2 mM glutamax (Invitrogen; Carlsbad, Calif.) and 1×Pencillin/streptomycin (Cellgro-Mediatech; Manassas, Va.). Cells were harvested and re-suspended in FACS buffer (DPBS buffer supplemented with 1% bovine serum albumin). A total of 200,000 cells per well were incubated on ice with serial dilutions of anti-CD74 antibody without conjugation for 60 minutes. Cells were washed twice with ice-cold FACS buffer and incubated with 5 ug/ml Alexa 647 labeled donkey anti-human IgG antibody (Jackson Immune-Research) on ice for another 60 mins. Unstained cells and cells stained with secondary antibody alone were used as controls. Samples were then washed twice using FACS buffer and analyzed using a BD FACS Canto system. Mean fluorescence intensities were fitted using non-linear regression analysis with one site specific binding equation on GraphPad Prism. Data was expressed as geometric mean fluorescent intensity vs. antibody concentration in nM.

Cell Killing Assay

Cytotoxicity effects of the free drug linkers and conjugates were measured with a cell proliferation assay. A total of 12500 cells in a volume of 25 μl were seeded in a 384-well flat bottom white polystyrene plate on the day of assay. Free drug-linkers and conjugates were formulated at 2× starting concentration (1000 nM for free drug linkers and 100 nM for ADCs) in RPMI medium and filtered through MultiScreen HTS 96-Well Filter Plates (Millipore). Filter sterilized samples were serial diluted (1:3) under sterile conditions and added into treatment wells. Plates were cultured at 37° C. in a CO$_2$ incubator for 72 hrs. For cell viability measurement, 30 μl of Cell Titer-Glo® reagent (Promega Corp.) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response, variable slope, 4 parameter fit equation using GraphPad Prism. Data was expressed as % relative cell viability vs. dose of free drug-linker or conjugate in nM.

Results for Conjugate A are summarized in the following Table 2:

TABLE 2

Results for Conjugate A

| | | Cell Binding | | Cell Killing Activity | | | |
| | | anti-CD74 | | Conjugate A | | Free Linker-Drug | |
| Diseases | Cell Lines Tested | Bmax | Kd (nM) | Span (%) | IC50 (nM) | Span (%) | IC50 (nM) |
| --- | --- | --- | --- | --- | --- | --- | --- |
| B-Lymphoma | RPMI-6666 (HL) | 3879 | 2.3 | 84 | 1.0 | 85 | ~13 |
|  | SU-DHL-6 (NHL) | 1565 | 2.0 | 98 | 0.6 | 98 | 15.0 |
| Multiple Myeloma | ARD (MM) | 190 | 2.6 | 38 | 8.6 | 40 | ~34 |
|  | ARP-1 (MM) | 341 | 2.8 | 74 | 9.0 | 77 | 17.0 |
|  | RPMI-8226 (MM) | 119 | 3.6 | NK | NK | NK | 18.0 |
|  | OPM-2 (MM) | NB | NB | NK | NK | NK | 24.0 |
| Leukemia | BDCM (AML) | 3059 | 4.5 | 74 | 4.6 | 76 | 13.0 |
|  | SUP-B15 (ALL) | 680 | 3.5 | 64 | 3.0 | 65 | 11.0 |
|  | JVM-13 (CLL) | 447 | 2.5 | 58 | 1.5 | 65 | 25.0 |
|  | K562 (CML) | NB | NB | NK | NK | NK | 60.0 |

NK = no killing

NB = no binding

Example 6: Cell Binding and Cell Killing

Each of Conjugates A-F was evaluated for the ability to bind and kill cells expressing CD74. Cell lines tested included B-lymphoma, multiple myeloma, and leukemia cells. Controls included unconjugated anti-CD74 antibody. The results are summarized in the following Table 3:

TABLE 3

Results for Conjugates A-F

| | | Cell Binding | | Cell Killing Activity (Conjugate) | | | | | | | | | | | |
| | | anti-CD74 | | A | | B | | C | | D | | E | | F | |
| Disease | Cell Lines Tested | Bmax | Kd (nM) | IC50 (nM) | Span (%) | IC50 (nM) | Span (%) | IC50 (nM) | Span (%) | IC50 (nM) | Span (%) | IC50 (nM) | Span (%) | IC50 (nM) | Span (%) |
| --- | --- | --- | --- | --- | --- | --- | --- | --- | --- | --- | --- | --- | --- | --- | --- |
| B-Lymphoma | RPMI-6666 (HL) | 3879 | 2.3 | 1.0 | 85 | 1.3 | 89 | 0.9 | 84 | 4.3 | 69 | 1.5 | 80 | 0.7 | 82 |
|  | SU-DHL-6 (NHL) | 1565 | 2.0 | 0.6 | 98 | 1.3 | 98 | 0.3 | 97 | 0.7 | 99 | 0.5 | 98 | 0.3 | 97 |
| Multiple Myeloma | ARD (MM) | 190 | 2.6 | 8.6 | 40 | 31.0 | 53 | 26.0 | 74 | 7.1 | 25 | 18.0 | 20 | 16.0 | 73 |
|  | ARP-1 (MM) | 341 | 2.8 | 9.0 | 77 | 16.0 | 82 | 7.6 | 87 | 1.7 | 91 | 6.0 | 71 | 4.2 | 93 |
|  | RPMI-8226 (MM) | 119 | 3.6 | NK | NK | 51.0 | 41 | 17.0 | 43 | NK | NK | NK | NK | 20.0 | 31 |
|  | OPM-2 (MM) | NB | NB | NK | NK | NK | NK | NK | NK | NK | NK | NK | NK | NK | NK |
| Leukemia | BDCM (AML) | 3059 | 4.5 | 4.6 | 76 | 15.0 | 95 | 1.1 | 89 | 2.2 | 84 | 3.3 | 78 | 1.4 | 94 |
|  | SUP-B15 (ALL) | 680 | 3.5 | 3.0 | 65 | 5.7 | 72 | 2.8 | 68 | 2.4 | 74 | 2.5 | 58 | 3.7 | 65 |
|  | JVM-13 (CLL) | 447 | 2.5 | 1.5 | 65 | 2.0 | 69 | 0.9 | 54 | 6.8 | 73 | 7.8 | 47 | 5.0 | 59 |
|  | K562 (CML) | NB | NB | NK | NK | NK | NK | NK | NK | NK | NK | NK | NK | NK | NK |

Example 7: Evaluation of In Vivo Anti-Tumor Activity in a Mouse Multiple Myeloma Model A study was carried out to investigate the in vivo anti-tumor efficacy of an anti-CD74 antibody-drug conjugate in a human multiple myeloma model (disseminated). Conjugate A (Example 3) was evaluated in animals inoculated with ARP-1 multiple myeloma cells. ARP-1 (and isogenic cell lines ARD-1 and CAG) were established from bone marrow aspirates of a patient with multiple myeloma patient (Kwong, K. Characterization of an Isogenic Model System for KDM6A/UTX Loss in Multiple Myeloma. (2013), incorporated herein by reference in its entirety).

Protocol. Female CB17 SCID (severe combined immunodeficiency) were inoculated with ARP-1 cells via tail vein injection. Prior to tumor cell inoculation, animals were pre-treated with 0.4 mg/mouse Fludarabine and 2 mg/mouse Cyclophosphamide (intraperitoneal injection). Randomization and treatment was initiated 14 days post tumor inoculation. Treatment groups are outlined in Table 4. All test articles were formulated in 10 mM citrate pH 6.0, 10% sucrose and diluted with PBS. Animals were administered with the designated test article four times every 7 days (q7dx4) by intravenous injection. Untreated animals did not receive chemo pre-treatment and were not inoculated with ARP-1 cells. Body weights were monitored twice per week. When vehicle control animals reached the study endpoint (euthanized due to large, palpable internal tumors), three animals from the Group 2 and Group 3 were euthanized for necropsy and bone marrow harvest (from tibia and femur) for flow cytometry. The remaining animals in treated groups were monitored for up to 3 months after start of treatment.

TABLE 4

Treatment groups

| Group | Treatment | DAR | Dose (mg/kg) | Route | N |
|---|---|---|---|---|---|
| 1 | Vehicle (PBS) | — | — | IV | 10 |
| 2 | Conjugate A | 1.97 | 3 | IV | 10 |
| 3 | Untreated | — | — | — | 3 |

Bone marrow cells from mouse femur and tibia were pooled and assessed for CD138 expression using the Alexa Fluor 647 mouse anti-human CD138 clone MI15 (BD Biosciences #562097) according to the manufacturer's protocol. Direct immunofluorescence flow cytometric analysis was performed using an LSRII flow cytometer and FACS Diva Software. Data was analyzed using Flowjo (Tree Star, Inc., Ashland, Oreg.).

Body weight, tissue volume, or tissue weights at study endpoint, were analyzed using a one-way analysis of variance (ANOVA) with Dunnett's multiple comparison test. A probability of less than 5% ($p<0.05$) was considered as significant.

Figure 3B:
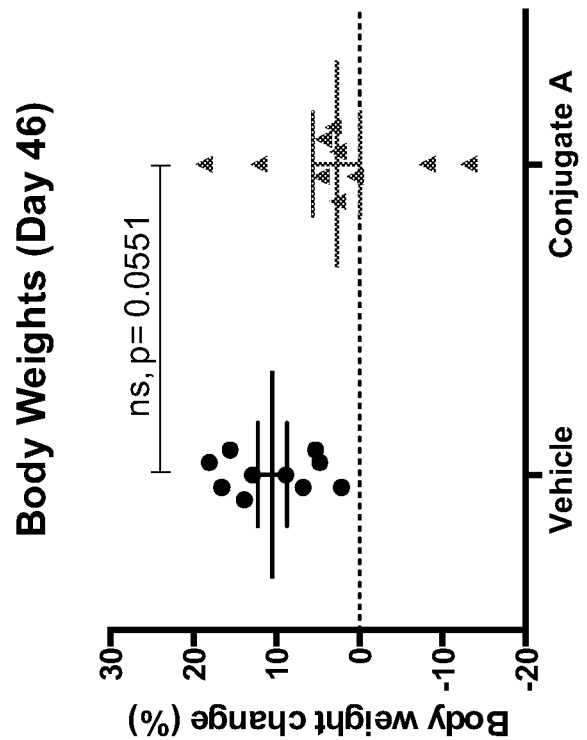
FIG. 3B provides a scatter plot of the individual body weight data for each experimental group on day 46 of post-tumor cell inoculation.
Figure 3A:
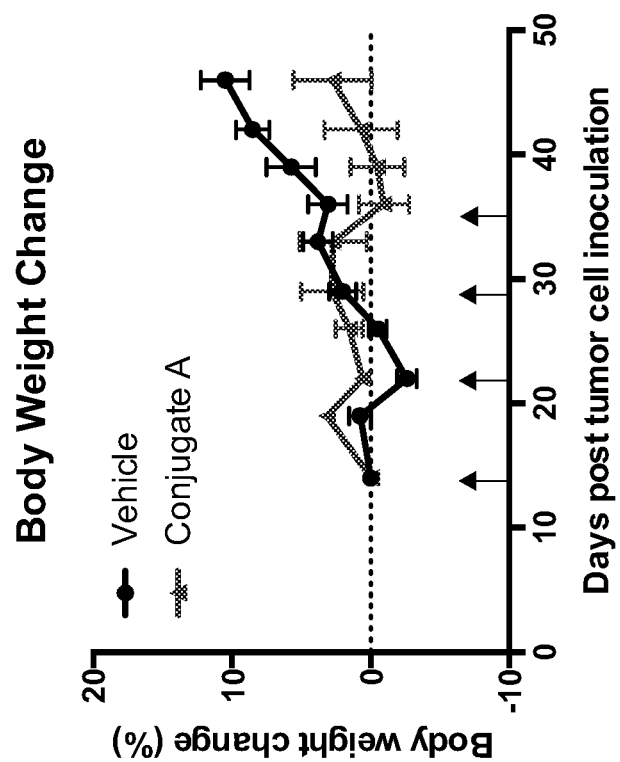
FIG. 3A is a plot illustrating body weight change (BWC) as a function of time in a disseminated ARP-1 multiple myeloma model after administration of an anti-CD74 antibody-drug conjugate as disclosed herein.

Results. Multiple myeloma cells, ARP-1, were inoculated intravenously into CB17 SCID mice and treated with 3 mg/kg Conjugate A (q7dx4). Study endpoint was characterized by noteworthy body weight change, formation of large palpable internal tumors, and moribundity. FIG. 3A shows steady weight gain (increase in BWC) in vehicle control animals starting on approximately day 25 post tumor inoculation, and subsequent development of distended abdomens by day 35. On day 49, vehicle control animals were euthanized based on clinical endpoints and palpable tumors in the abdomen. No meaningful change in body weight (FIG. 3A), enlarged abdomen, or signs of distress were observed in groups treated with Conjugate A. The BWC on the last recorded day for vehicle control group (day 46) was trending toward significant (Conjugate A, $p=0.0551$) compared to vehicle control (FIG. 3B).

Figure 4A:
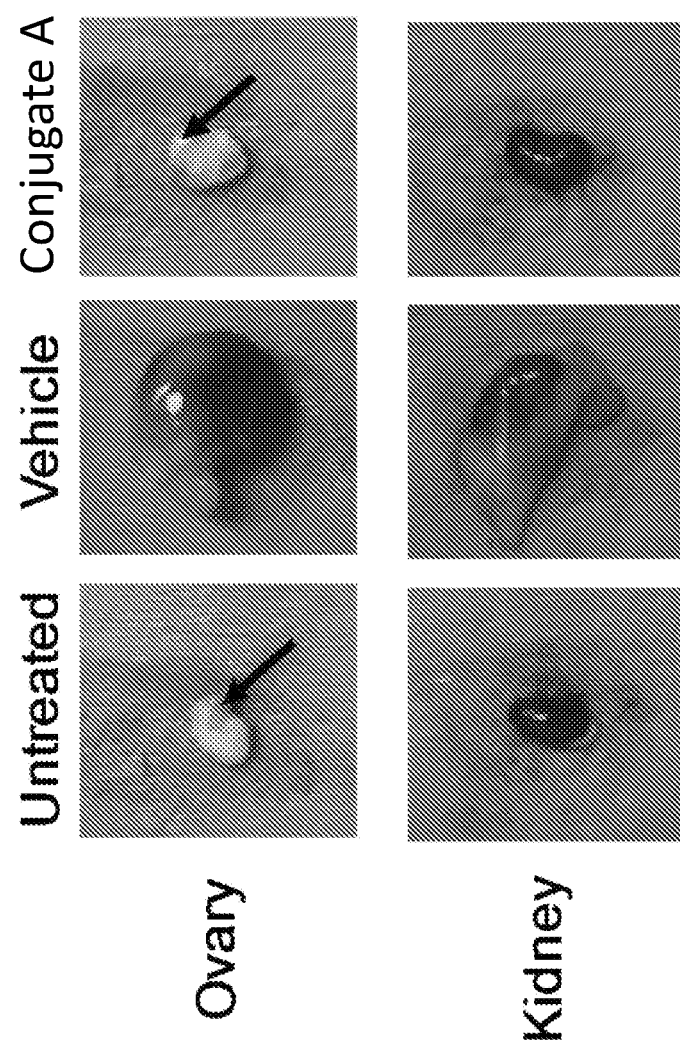
FIG. 4A includes images of resulting tumor masses formed in and around ovaries and kidneys from a disseminated ARP-1 multiple myeloma model after administration of an anti-CD74 antibody-drug conjugate as disclosed herein.
Figure 4B:
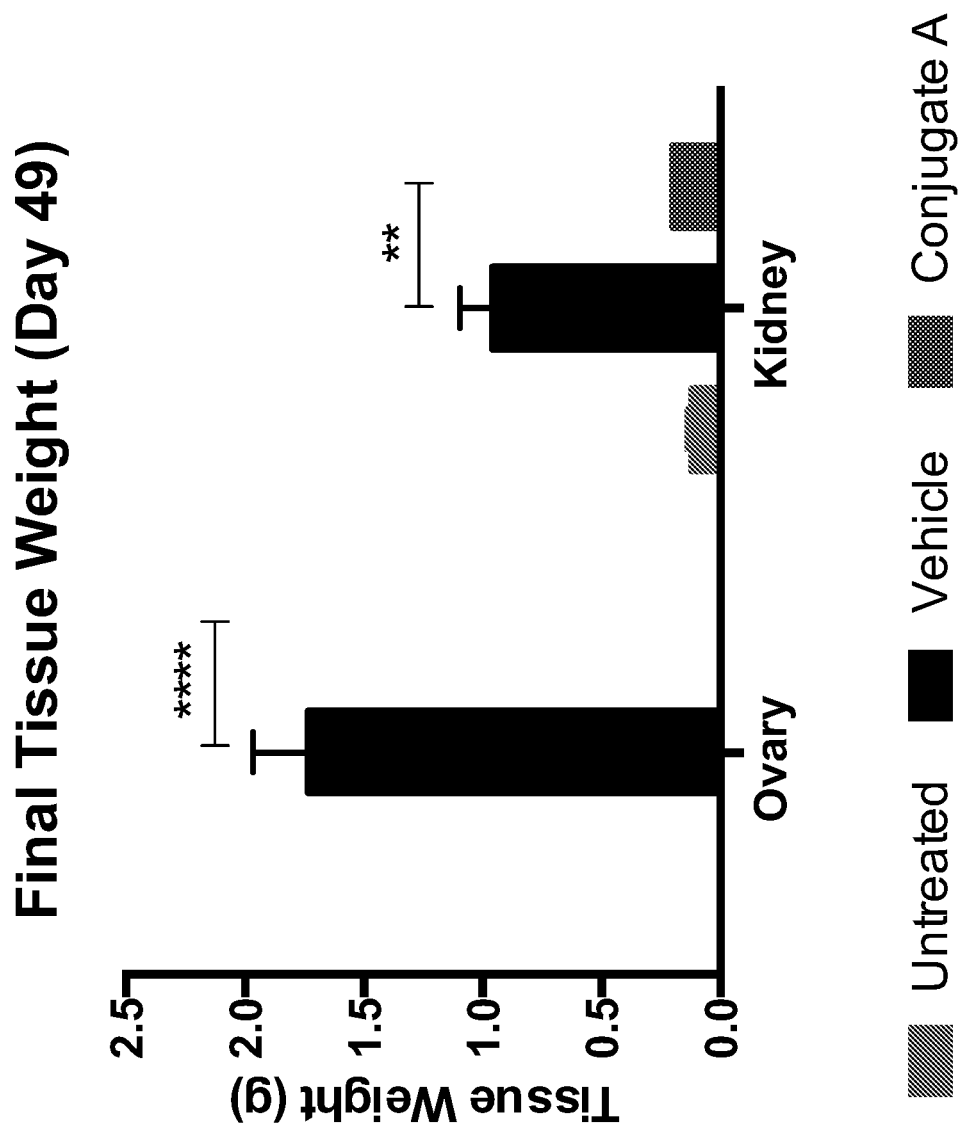
FIG. 4B provides a bar graph of the final tumor tissue weight for each experimental group.
Figure 5A:
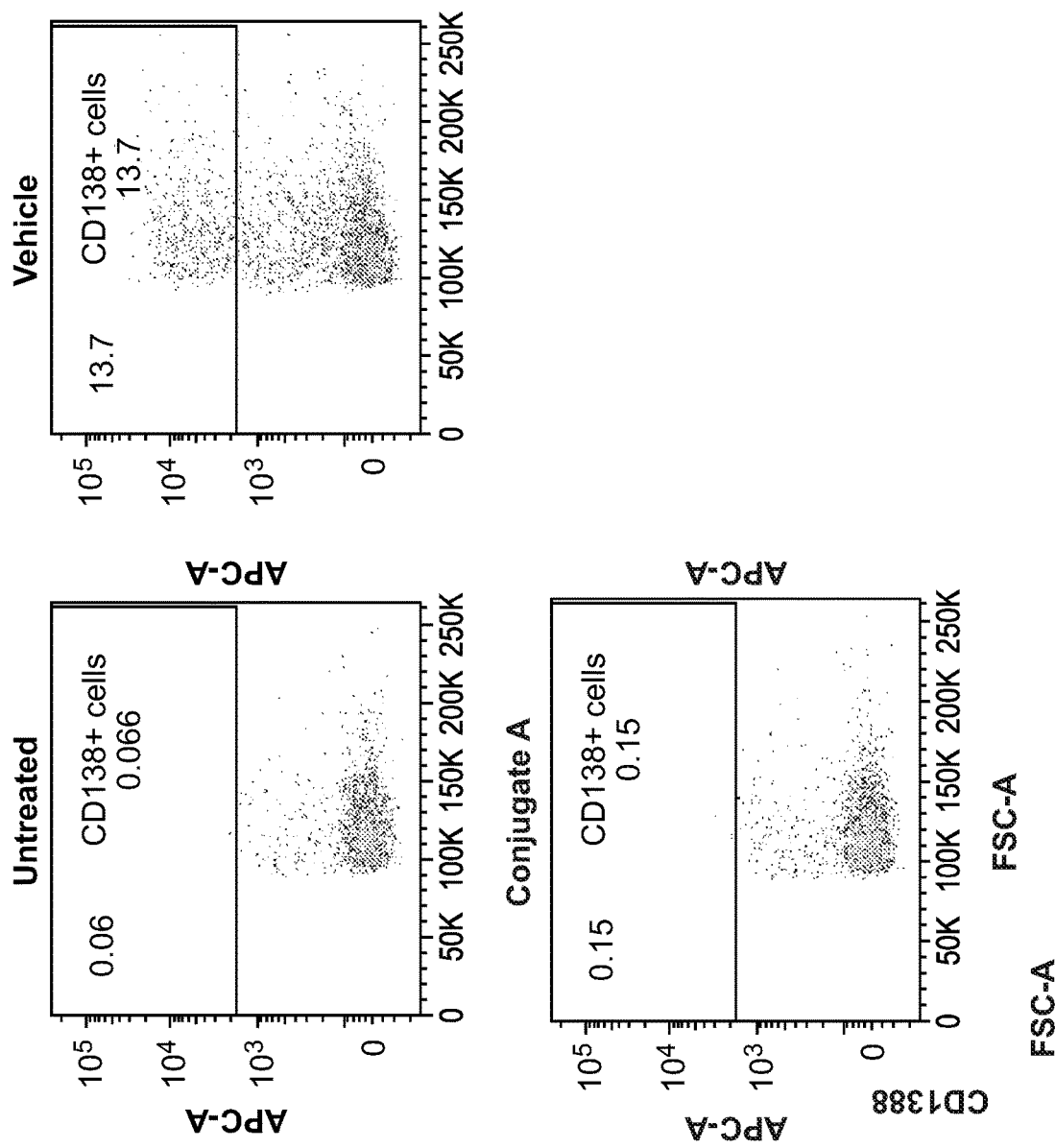
FIG. 5A provides representative flow cytometry dot plots for percentage of human CD138 positive ARP-1 myeloma cells present in the bone marrow (femur and tibia) after administration of an anti-CD74 antibody-drug conjugate as disclosed herein.
Figure 5B:
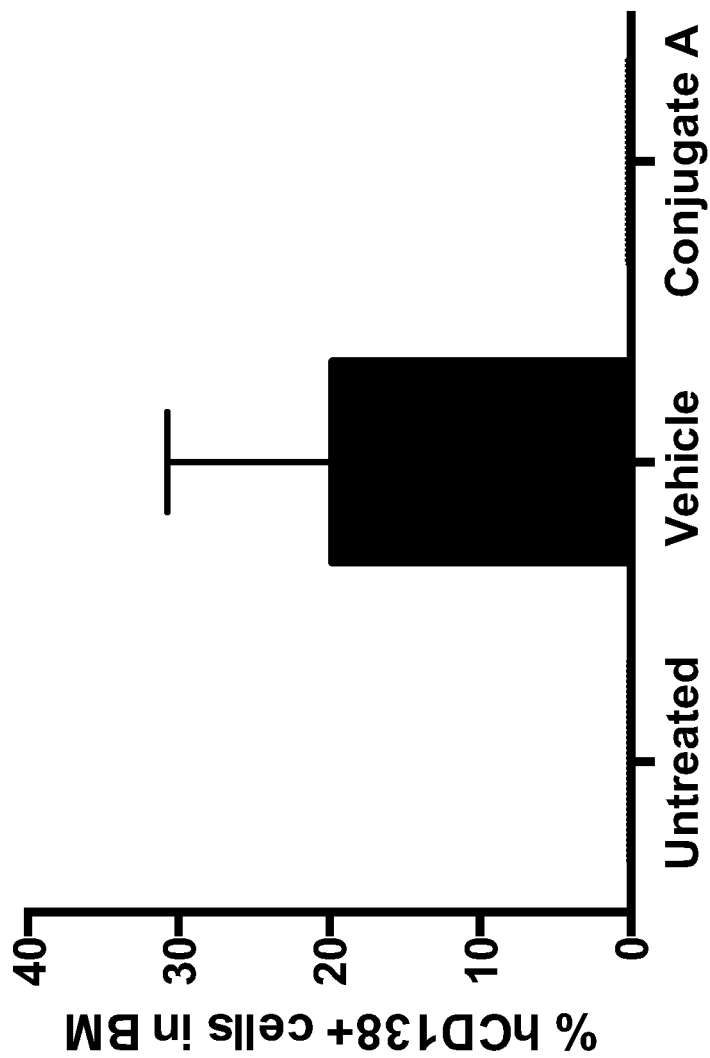
FIG. 5B provides the flow cytometry data as a bar graph of the percentage of human CD138 positive ARP-1 myeloma cells for each experimental group.

Gross pathological analysis of vehicle control animals revealed large tumor masses in and around the ovaries and/or kidneys (FIGS. 4A, 4B). Formation of internal tumors likely accounts for distended abdomens and increase in body weight observed in vehicle control group. A subset of animals from groups treated with Conjugate A (n=3 per group) were harvested for anatomical examination and flow cytometry. FIGS. 4A and 4B show that kidney and ovaries from both groups that received CD74 ADC treatment looked phenotypically normal, and had comparable tissue weights to untreated age-matched control animals (which did not receive cells or treatment). Tumor burden was also assessed by measuring the percentage of human CD138 positive ARP-1 myeloma cells present in the bone marrow (femur and tibia). CD138 is a specific surface antigen for multiple myeloma and plasma cells in the bone marrow (Chilosi, M. et al. "CD138/syndecan-1: A useful immunohistochemical marker of normal and neoplastic plasma cells on routine trephine bone marrow biopsies." *Mod. Pathol. Off J. U. S. Can. Acad. Pathol. Inc* 12, 1101-1106 (1999), incorporated herein by reference in its entirety). The vehicle control group showed high tumor burden, while treatment with Conjugate A substantially inhibited ARP-1 growth in the bone marrow (FIGS. 5A, 5B). Bone marrow isolated from untreated age-matched controls looked similar to the Conjugate A-treated group. Cumulatively, these results demonstrate that Conjugate A abrogated tumor burden.

Remaining animals in the Conjugate A treatment group (n=6-7 per group) continued to be monitored for disease progression after the first round of treatment. Treatment with Conjugate A similarly delayed weight gain for approximately 20 days, followed by a steady increase in weight starting at approximately day 70 or 35 days after the last dose. By day 82 (45 days after last treatment), some animals developed distended abdomens and large tumor mass around ovaries and/or kidneys. A subset of animals from the treatment group (n=3) received a second round of Conjugate A treatment starting on day 82. Apparent stabilization of weight gain was observed, suggesting prevention of disease progression.

Results from this study show that Conjugate A attenuated body weight increase and reduced tumor burden (in bone marrow and for internal tumors) with similar potency and duration of response in animals inoculated with ARP-1 multiple myeloma cells.

Example 8: Further Studies of In Vivo Anti-Tumor Activity in a Mouse Multiple Myeloma Model A study was carried out to investigate the in vivo anti-tumor efficacy of an anti-CD74 antibody-drug conjugate in a human multiple myeloma model (disseminated). Conjugate A (Example 3) was evaluated in animals inoculated with MM.1 S multiple myeloma cells.

Protocol. Female NOD SCID gamma (NSG) mice 8 weeks of age were inoculated with multiple myeloma MM.1S cells into the tail vein. Randomization by body weight and start of treatment was initiated 11 days post tumor inoculation. Treatment groups are outlined in Table 5. Test articles were formulated in 10 mM citrate, pH 6.0, 10% sucrose and diluted in PBS for administration. Animals were administered with Conjugate A every 7 days for 3 weeks (q7dx3) by intravenous (IV) injection. For each group, a subset of animals was used for bone marrow harvest and analysis (n=3) and the remaining animals (n=5) were monitored for survival. Survival endpoint was characterized by >20% body weight loss and clinical signs including lethargy, hind limb paralysis or moribundity. On day 32 (3 weeks after start of treatment), 3 animals from each group were randomly chosen to be euthanized for bone marrow harvest (pooled from tibia and femur) for flow cytometry. On day 129 (~4 months after start of treatment), all surviving animals were euthanized and bone marrow was harvested (pooled from tibia and femur) for flow cytometry.

TABLE 5

List of Treatment Groups

| Group | Treatment | Dose (mg/kg) | Dosing frequency | Route | N |
|---|---|---|---|---|---|
| 1 | Vehicle control | na | q7dx3 | IV | 8 |
| 2 | Conjugate A | 3 | q7dx3 | IV | 8 |
| 3 | Conjugate A | 10 | q7dx3 | IV | 8 |

Body weights were monitored at least twice per week for up to 129 days. All graphs are presented as mean±standard error of the mean (SEM) versus days post-treatment start.

Percent body weight change (BWC) is calculated relative to weight on the day of treatment. Substantial toxicity was defined as a >20% decrease in animal weight, at which point affected animals are euthanized.

Bone marrow cells from mouse femur and tibia were pooled and assessed for human CD138 expression using the Alexa Fluor 647 mouse anti-human CD138 clone MI15 (BD Biosciences #562097) according to the manufacturer's protocol. CD138 is a specific surface antigen for MM and plasma cells in the bone marrow (Chilosi, M. et al. (1999), supra). Direct immunofluorescence flow cytometric analysis was performed using an LSRII flow cytometer and FACS Diva Software. Data was analyzed using Flowjo (Tree Star, Inc., Ashland, Oreg.).

Human CD138+ cells in the bone marrow on day 32 was analyzed using one-way analysis of variance (ANOVA) with a Dunnett's adjustment at 0.05 significance level. Data from MM.1s positive control were excluded from analysis. A probability of less than 5% ($p<0.05$) was considered as significant.

Figure 6B:
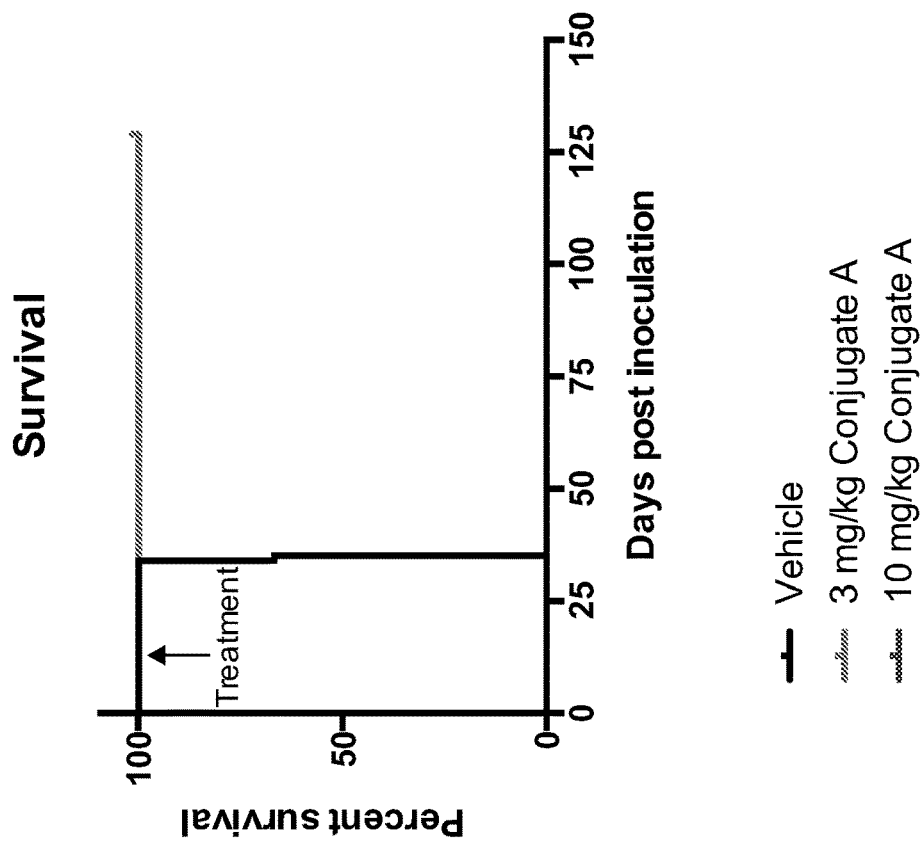
FIG. 6B provides a Kaplan-Meier survival plot (right) in the multiple myeloma model for each treatment group.
Figure 6A:
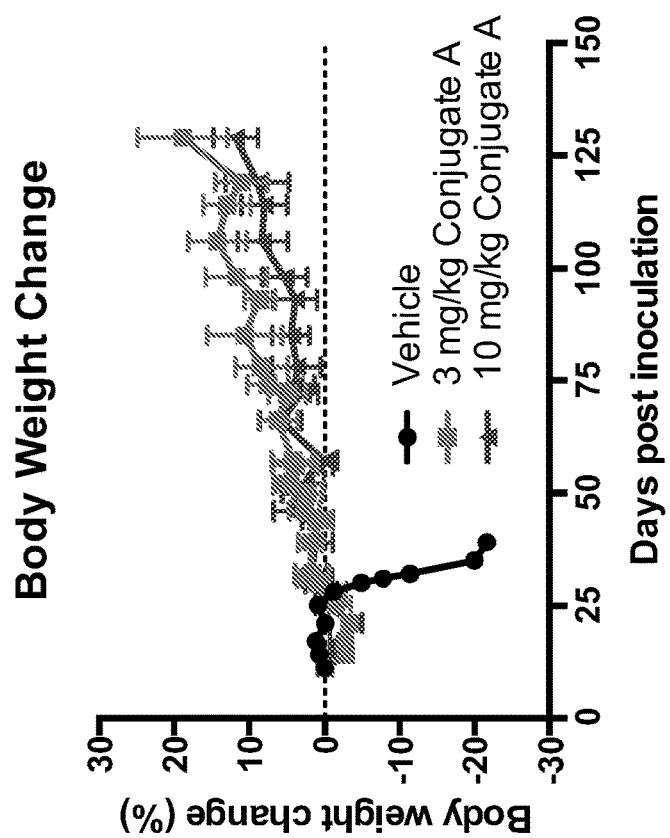
FIG. 6A shows body weight change (BWC) as a function of time in a disseminated MM.1S multiple myeloma model after administration of an anti-CD74 antibody-drug conjugate as disclosed herein.

Results. Multiple myeloma MM.1S cells were inoculated intravenously into NSG mice and treated with vehicle, 3 mg/kg or 10 mg/kg Conjugate A (q7dx3) starting on day 11 post-tumor inoculation. The survival study endpoint criteria included body weight change greater than 20% and clinical signs of moribundity. FIG. 6A shows body weight loss in vehicle control animals starting approximately on day 28 post tumor inoculation. Body weight loss was accompanied by hunched posture, hind-limb paralysis and severe lethargy. The mean survival for the vehicle group was 35 days, while treatment with 3 or 10 mg/kg Conjugate A resulted in 100% survival with all animals showing no sign of disease on day 129 post inoculation (FIG. 6B).

Figure 6C:
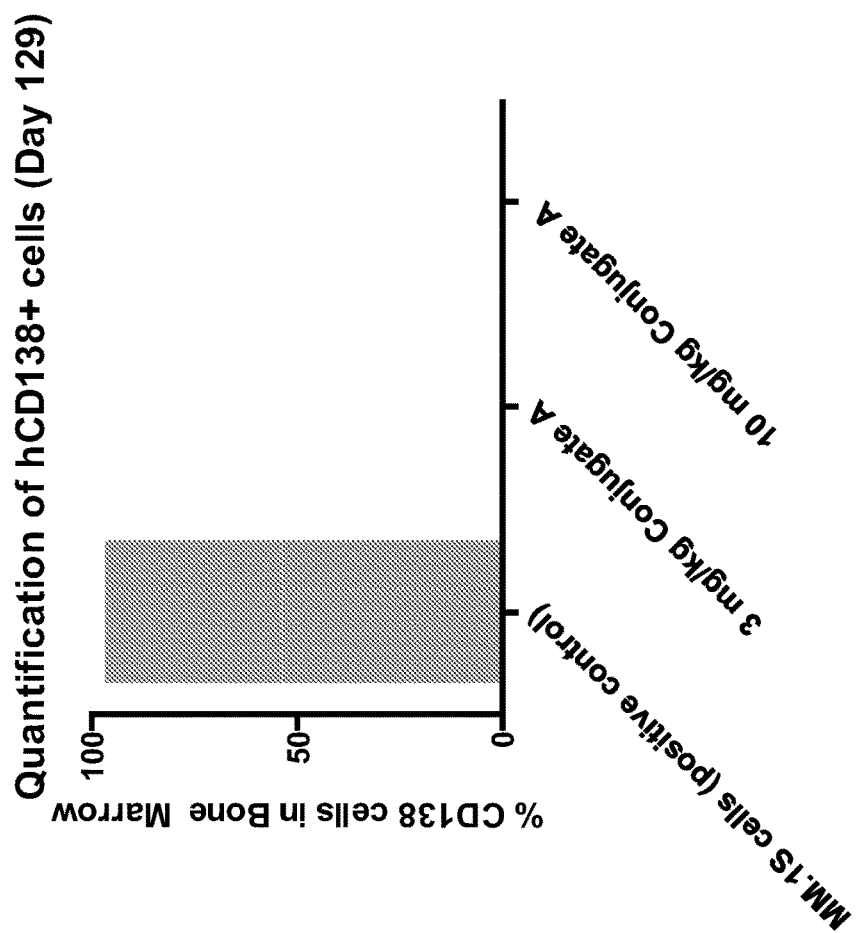
FIG. 6C illustrates bar charts of the percentage of human CD138 positive MM.1S myeloma cells present in the bone marrow on day 32 post-tumor inoculation for each experimental group after administration of an anti-CD74 antibody-drug conjugate as disclosed herein.
Figure 6D:
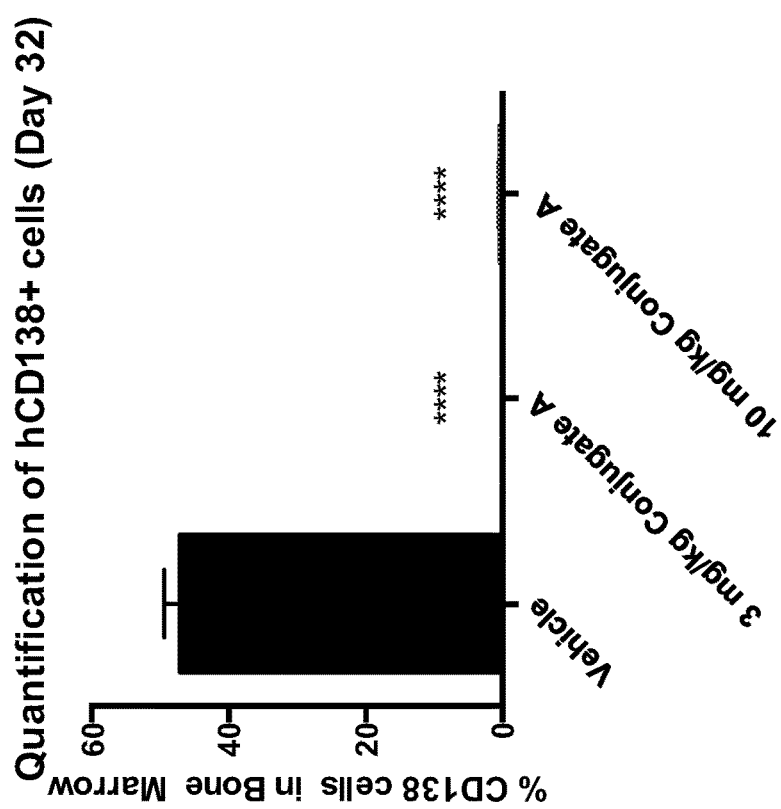
FIG. 6D illustrates bar charts of the percentage of human CD138 positive MM.1S myeloma cells present in the bone marrow on day 129 post-tumor inoculation for the experimental groups after administration of anti-CD74 antibody-drug conjugates as disclosed herein.

On day 32, tumor burden was assessed by measuring the percentage of hCD138+ myeloma cells in the bone marrow. FIG. 6C shows that both doses of Conjugate A significantly reduced tumor burden compared to high tumor burden (~50%) in the vehicle control group. After approximately 4 months (Day 129), no hCD138+ cells were detected in the bone marrow of animals treated with 3 and 10 mg/kg Conjugate A (FIG. 6D). Both data sets on day 32 and day 129 included bone marrow from non-inoculated negative control animals (no cells or treatment) and MM.1S cells as a positive control. As expected, the non-inoculated group and MM.1S cells had low and high hCD138+, respectively.

Results from this study show that 3 or 10 mg/kg Conjugate A (q7dx3) eradicated disease based on 100% survival and absence of hCD138+ in the bone marrow approximately 4 months after initiation of treatment in the disseminated MM.1 S model.

Example 9: Evaluation of In Vivo Anti-Tumor Activity in a Mouse Non-Hodgkin's Lymphoma (NHL) Model A study was carried out to investigate the in vivo anti-tumor efficacy of an anti-CD74 antibody-drug conjugate in a human non-Hodgkin's lymphoma ("NHL") model. Conjugate A (Example 3) was evaluated in the animals bearing established subcutaneous SU-DHL-6 NHL tumors (diffuse large B-cell lymphoma). Treatment with Conjugate A significantly delayed growth of NHL tumors SU-DHL-6.

Protocol. Female CB17 SCID mice 9 weeks of age were anesthetized with isoflurane and implanted subcutaneously into the right flank with a 1:1 mixture of SU-DHL-6 cells and matrigel. Randomization, enrollment into treatment groups, and start of treatment was initiated approximately 14 days post implantation. Treatment groups are outlined in Table 6. All test articles were formulated in 10 mM citrate pH 6.0, 9% sucrose and diluted in PBS. Body weight and tumor size were monitored twice per week until mean of control treated tumors were >1000 $mm^3$ or end of study. Animal body weights included the tumor weight. Percent body weight change (BWC) is calculated relative to weight on the day of treatment. No samples were collected at the end of study.

TABLE 6

Treatment groups

| Group | Treatment | DAR | Dose (mg/kg) | Dosing frequency | Route | N |
|---|---|---|---|---|---|---|
| 1 | Vehicle | — | — | q7d × 3 | IV | 7 |
| 2 | Conjugate A | 1.97 | 10 | q7d × 3 | IV | 7 |

Tumor size on day 18 post-tumor implantation (last day control animals were on study) was analyzed using a one-way analysis of variance (ANOVA) with Dunnett's multiple comparison test. A probability of less than 5% ($p<0.05$) was considered as significant.

Figure 7B:
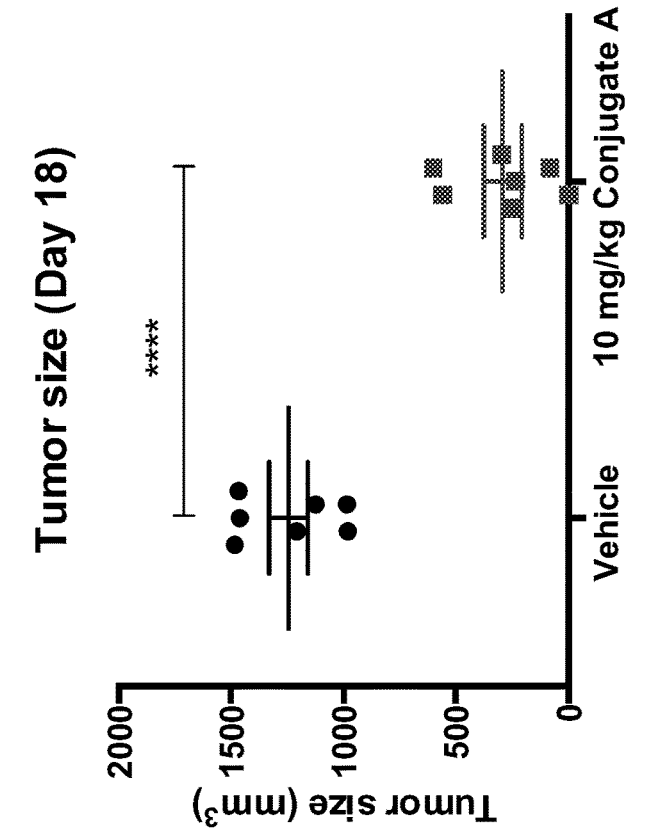
FIG. 7B provides a scatter plot of individual tumor size on day 18 for each experimental group in the non-Hodgkin's lymphoma model after administration of the anti-CD74 antibody-drug conjugate.
Figure 7A:
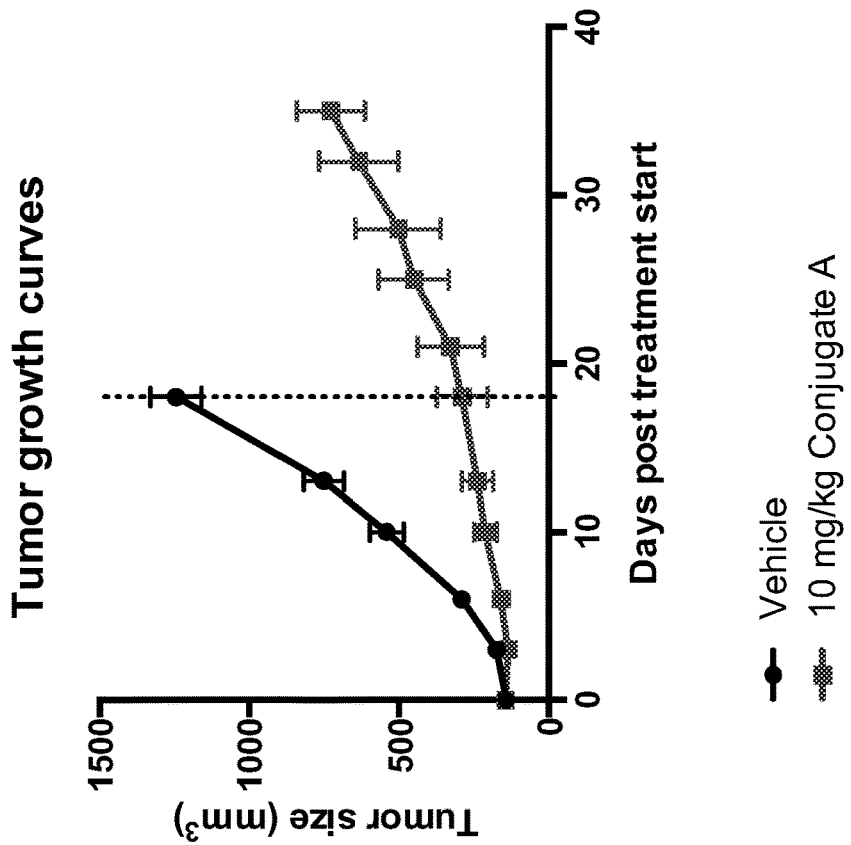
FIG. 7A provides a tumor growth curve as a function of time in a non-Hodgkin's lymphoma model after administration of an anti-CD74 antibody-drug conjugate as disclosed herein.
Figure 8:
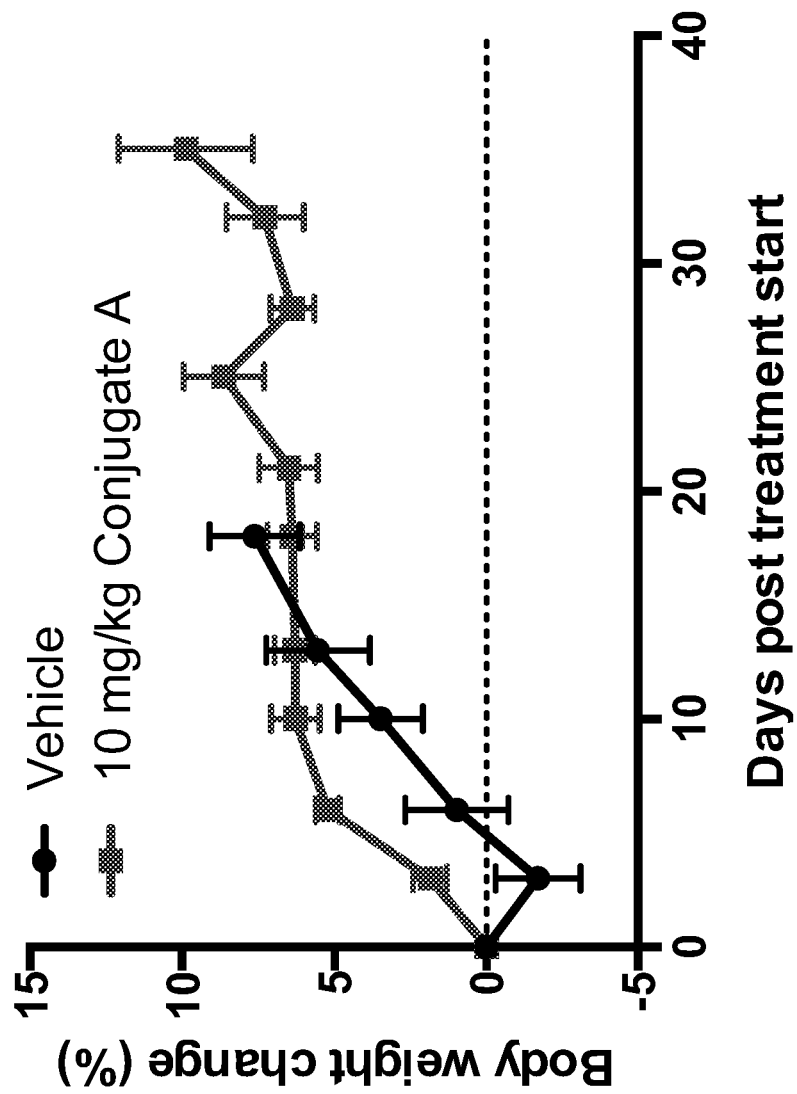
FIG. 8 provides a plot of body weight change (BWC) as a function of time in a non-Hodgkin's lymphoma animal model after administration of anti-CD74 antibody-drug conjugates as disclosed herein.

Results. In this study, NHL cells SU-DHL-6 were implanted subcutaneously into CB17 SCID mice and treated with 10 mg/kg Conjugate A. Efficacy results from a repeat dosing regimen (q7dx3) is presented in FIG. 7A and FIG. 7B. Treatment with Conjugate A (q7dx3) significantly inhibited SU-DHL-6 tumor growth, and resulted in ~80% tumor growth inhibition compared to control on day 18 (**** $p<0.0001$, Table 6). It was noted that there was some continued growth of SU-DHL-6 tumors in the presence of treatment with Conjugate A. In addition, treatment with Conjugate A was well tolerated and did not exhibit any toxicity based on the absence of significant effects on animal body weights (FIG. 8).

TABLE 6

Statistical comparison of tumor size on day 18 versus vehicle control

| Group compared to vehicle (1246 $mm^3$ on day 21) | Average final tumor size on day 18 | Significant? | Adjusted p value |
|---|---|---|---|
| 10 mg/kg Conjugate A | 291 $mm^3$ | Yes | <0.0001 |

Results from this study show that Conjugate A is significantly efficacious in slowing SU-DHL-6 tumor growth.

Example 10: Sequences

Table 7 provides sequences referred to herein.

TABLE 7

Sequences.

| SEQ ID NO | Molecule | Region | Scheme | Sequence |
|---|---|---|---|---|
| 1 | 1251-B08 | CDR-H1 | Chothia | GFNFSDY |
| 2 | 1193-C08 | CDR-H1 | Chothia | GFTFNNN |
| 3 | 1193-E06b | CDR-H1 | Chothia | GFTFNNT |
| 4 | 1193-H04b | CDR-H1 | Chothia | GFTFTSS |
| 5 | 1198-A01 | CDR-H1 | Chothia | GFTFSDY |
| 6 | 1198-B10 | CDR-H1 | Chothia | GFNISGS |
| 7 | 1198-D03 | CDR-H1 | Chothia | GFNINNY |
| 8 | 1198-D04 | CDR-H1 | Chothia | GFNINNY |
| 9 | 1251-A02 | CDR-H1 | Chothia | GFAFSDH |
| 10 | 1251-A03 | CDR-H1 | Chothia | GFAFSDH |
| 11 | 1251-A06 | CDR-H1 | Chothia | GFDFSSY |
| 12 | 1193-B06 | CDR-H1 | Chothia | GFTFTGN |
| 13 | 1251-B09 | CDR-H1 | Chothia | GFNFSDY |
| 14 | 1251-B10 | CDR-H1 | Chothia | GFNFSSH |
| 15 | 1251-C03 | CDR-H1 | Chothia | GFNFSSY |
| 16 | 1251-D02 | CDR-H1 | Chothia | GFSFASH |
| 17 | 1251-D06 | CDR-H1 | Chothia | GFSFGSY |
| 18 | 1251-D09 | CDR-H1 | Chothia | GFSFSSY |
| 19 | 1251-E06 | CDR-H1 | Chothia | GFTFDSY |
| 20 | 1251-F06 | CDR-H1 | Chothia | GFTFSSF |
| 21 | 1251-F07 | CDR-H1 | Chothia | GFTFSSH |
| 22 | 1251-G02 | CDR-H1 | Chothia | GFTFSSY |
| 23 | 1445-A03 | CDR-H1 | Chothia | GFNISGY |
| 24 | 1445-B09 | CDR-H1 | Chothia | GFNITGT |
| 25 | 1447-D11 | CDR-H1 | Chothia | GFTFNNT |
| 26 | 1447-E08 | CDR-H1 | Chothia | GFTFNDT |
| 27 | 1447-F11 | CDR-H1 | Chothia | GFTFDNT |
| 28 | 1447-G01 | CDR-H1 | Chothia | GFTFNTS |
| 29 | VH11-[19] | CDR-H1 | Chothia | GFTFSSY |
| 30 | VHS-[7] | CDR-H1 | Chothia | GFTFSSY |
| 31 | VH6-[11] | CDR-H1 | Chothia | GFTFSSY |
| 32 | VH8-[15] | CDR-H1 | Chothia | GFTFSSY |
| 33 | 1251-B08 | CDR-H1 | Kabat | DYGMH |
| 34 | 1193-C08 | CDR-H1 | Kabat | NNWMS |
| 35 | 1193-E06b | CDR-H1 | Kabat | NTDMS |
| 36 | 1193-H04b | CDR-H1 | Kabat | SSWMS |

TABLE 7-continued

Sequences.

| SEQ ID NO | Molecule | Region | Scheme | Sequence |
|---|---|---|---|---|
| 37 | 1198-A01 | CDR-H1 | Kabat | DYDMS |
| 38 | 1198-B10 | CDR-H1 | Kabat | GSWIH |
| 39 | 1198-D03 | CDR-H1 | Kabat | NYDIH |
| 40 | 1198-D04 | CDR-H1 | Kabat | NYDIH |
| 41 | 1251-A02 | CDR-H1 | Kabat | DHGMH |
| 42 | 1251-A03 | CDR-H1 | Kabat | DHGMH |
| 43 | 1251-A06 | CDR-H1 | Kabat | SYGMH |
| 44 | 1193-B06 | CDR-H1 | Kabat | GNWMS |
| 45 | 1251-B09 | CDR-H1 | Kabat | DYGMH |
| 46 | 1251-B10 | CDR-H1 | Kabat | SHGMH |
| 47 | 1251-C03 | CDR-H1 | Kabat | SYGMH |
| 48 | 1251-D02 | CDR-H1 | Kabat | SHGMH |
| 49 | 1251-D06 | CDR-H1 | Kabat | SYGMH |
| 50 | 1251-D09 | CDR-H1 | Kabat | SYGMH |
| 51 | 1251-E06 | CDR-H1 | Kabat | SYGMH |
| 52 | 1251-F06 | CDR-H1 | Kabat | SFGMH |
| 53 | 1251-F07 | CDR-H1 | Kabat | SHGMH |
| 54 | 1251-G02 | CDR-H1 | Kabat | SYGMH |
| 55 | 1445-A03 | CDR-H1 | Kabat | GYYIH |
| 56 | 1445-B09 | CDR-H1 | Kabat | GTGIH |
| 57 | 1447-D11 | CDR-H1 | Kabat | NTDMS |
| 58 | 1447-E08 | CDR-H1 | Kabat | DTDMS |
| 59 | 1447-F11 | CDR-H1 | Kabat | NTDMS |
| 60 | 1447-G01 | CDR-H1 | Kabat | TSDMS |
| 61 | VH11-[19] | CDR-H1 | Kabat | SYGMH |
| 62 | VHS-[7] | CDR-H1 | Kabat | SYAMH |
| 63 | VH6-[11] | CDR-H1 | Kabat | SYAMH |
| 64 | VH8-[15] | CDR-H1 | Kabat | SYAMH |
| 65 | 1251-B08 | CDR-H1 | Kabat | WYDGSI |
| 66 | 1193-C08 | CDR-H2 | Chothia | NGDDGY |
| 67 | 1193-H04b | CDR-H2 | Chothia | NGSGGA |
| 68 | 1193-H04b | CDR-H2 | Chothia | NGYNGI |
| 69 | 1198-A01 | CDR-H2 | Chothia | AQDGSY |
| 70 | 1198-B10 | CDR-H2 | Chothia | YPDDGD |
| 71 | 1198-D03 | CDR-H2 | Chothia | DPYNGA |
| 72 | 1198-D04 | CDR-H2 | Chothia | DPYNGT |
| 73 | 1251-A02 | CDR-H2 | Chothia | WYDGSH |
| 74 | 1251-A03 | CDR-H2 | Chothia | WYDGSH |

TABLE 7-continued

Sequences.

| SEQ ID NO | Molecule | Region | Scheme | Sequence |
|---|---|---|---|---|
| 75 | 1251-A06 | CDR-H2 | Chothia | WDDGSD |
| 76 | 1193-B06 | CDR-H2 | Chothia | YGTSGA |
| 77 | 1251-B09 | CDR-H2 | Chothia | WYDGSR |
| 78 | 1251-B10 | CDR-H2 | Chothia | WHDGSD |
| 79 | 1251-C03 | CDR-H2 | Chothia | WYDGSI |
| 80 | 1251-D02 | CDR-H2 | Chothia | WDDGSD |
| 81 | 1251-D06 | CDR-H2 | Chothia | WYDGSK |
| 82 | 1251-D09 | CDR-H2 | Chothia | WYDASI |
| 83 | 1251-E06 | CDR-H2 | Chothia | WYDGSN |
| 84 | 1251-F06 | CDR-H2 | Chothia | WYDGSN |
| 85 | 1251-F07 | CDR-H2 | Chothia | WDDGSN |
| 86 | 1251-G02 | CDR-H2 | Chothia | WHDGSK |
| 87 | 1445-A03 | CDR-H2 | Chothia | SPTGGY |
| 88 | 1445-B09 | CDR-H2 | Chothia | TPYNGT |
| 89 | 1447-D11 | CDR-H2 | Chothia | NGSGGS |
| 90 | 1447-E08 | CDR-H2 | Chothia | NGAGGA |
| 91 | 1447-F11 | CDR-H2 | Chothia | NGSGGV |
| 92 | 1447-G01 | CDR-H2 | Chothia | NGSGGA |
| 93 | VH11-[19] | CDR-H2 | Chothia | WYDGSN |
| 94 | VH5-[7] | CDR-H2 | Chothia | SYDGSN |
| 95 | VH6-[11] | CDR-H2 | Chothia | SYDGSI |
| 96 | VH8-[15] | CDR-H2 | Chothia | SYDGSN |
| 97 | 1251-B08 | CDR-H2 | Kabat | VIWYDGSISYYADSVKG |
| 98 | 1193-C08 | CDR-H2 | Kabat | IINGDDGYTYYADRVKG |
| 99 | 1193-E06b | CDR-H2 | Kabat | IINGSGGATNYADSVKG |
| 100 | 1193-H04b | CDR-H2 | Kabat | IINGYNGITYYADSVKG |
| 101 | 1198-A01 | CDR-H2 | Kabat | FIAQDGSYKYYVDSVKG |
| 102 | 1198-B10 | CDR-H2 | Kabat | YIYPDDGDTYYADSVKG |
| 103 | 1198-D03 | CDR-H2 | Kabat | NIDPYNGATYYADSVKG |
| 104 | 1198-D04 | CDR-H2 | Kabat | NIDPYNGTTYYADSVKG |
| 105 | 1251-A02 | CDR-H2 | Kabat | VIWYDGSHKIYADSVKG |
| 106 | 1251-A03 | CDR-H2 | Kabat | VIWYDGSHKIYADSVKG |
| 107 | 1251-A06 | CDR-H2 | Kabat | VIWDDGSDRYYADSVKG |
| 108 | 1193-B06 | CDR-H2 | Kabat | IIYGTSGATYYADSVKG |
| 109 | 1251-B09 | CDR-H2 | Kabat | VTWYDGSREYYADSVKG |
| 110 | 1251-B10 | CDR-H2 | Kabat | VIWHDGSDKYYADSVKG |
| 111 | 1251-C03 | CDR-H2 | Kabat | VIWYDGSIKNYADSVKG |
| 112 | 1251-D02 | CDR-H2 | Kabat | VIWDDGSDRYYADSVKG |

TABLE 7-continued

Sequences.

| SEQ ID NO | Molecule | Region | Scheme | Sequence |
|---|---|---|---|---|
| 113 | 1251-D06 | CDR-H2 | Kabat | VVWYDGSKTIYADSVKG |
| 114 | 1251-D09 | CDR-H2 | Kabat | VIWYDASIRKYAGSVKG |
| 115 | 1251-E06 | CDR-H2 | Kabat | VIWYDGSNKVYADSVKG |
| 116 | 1251-F06 | CDR-H2 | Kabat | VIWYDGSNEYYADSVKG |
| 117 | 1251-F07 | CDR-H2 | Kabat | VIWDDGSNEVYADSVKG |
| 118 | 1251-G02 | CDR-H2 | Kabat | VIWHDGSKDYYADSVKG |
| 119 | 1445-A03 | CDR-H2 | Kabat | EISPTGGYTYYADSVKG |
| 120 | 1445-B09 | CDR-H2 | Kabat | IITPYNGTTNYADSVKG |
| 121 | 1447-D11 | CDR-H2 | Kabat | VINGSGGSSNYADSVKG |
| 122 | 1447-E08 | CDR-H2 | Kabat | MINGAGGASFYADSVRG |
| 123 | 1447-F11 | CDR-H2 | Kabat | IINGSGGVTNYADSVRG |
| 124 | 1447-G01 | CDR-H2 | Kabat | IINGSGGATNYADSVKG |
| 125 | VH11-[19] | CDR-H2 | Kabat | VIWYDGSNKYYADSVKG |
| 126 | VH5-[7] | CDR-H2 | Kabat | VISYDGSNKYYADSVKG |
| 127 | VH6-[11] | CDR-H2 | Kabat | VISYDGSIKYYADSVKG |
| 128 | VH8-[15] | CDR-H2 | Kabat | VISYDGSNKYYADSVKG |
| 129 | 1251-B08 | CDR-H3 | K/C | GGTVEHGAVYGTDV |
| 130 | 1193-C08 | CDR-H3 | K/C | VALGRPRRFDY |
| 131 | 1193-E06b | CDR-H3 | K/C | FENEWEVSMDY |
| 132 | 1193-H04b | CDR-H3 | K/C | PSAPGARRFDY |
| 133 | 1198-A01 | CDR-H3 | K/C | SKLFRAGQFDY |
| 134 | 1198-B10 | CDR-H3 | K/C | EGSHNLDKMDY |
| 135 | 1198-D03 | CDR-H3 | K/C | VLWGFWAPFDY |
| 136 | 1198-D04 | CDR-H3 | K/C | VPWGFWAPFDY |
| 137 | 1251-A02 | CDR-H3 | K/C | GGSLAGGAVYGTDV |
| 138 | 1251-A03 | CDR-H3 | K/C | GGSLAGGAVYGTDV |
| 139 | 1251-A06 | CDR-H3 | K/C | GGTRVLGAIHGTDV |
| 140 | 1193-B06 | CDR-H3 | K/C | PSMSGSRGFDY |
| 141 | 1251-B09 | CDR-H3 | K/C | GGTLVHGALYGNDV |
| 142 | 1251-B10 | CDR-H3 | K/C | GGTRVLGAVYGLDV |
| 143 | 1251-C03 | CDR-H3 | K/C | GGALMRGEFSGHDV |
| 144 | 1251-D02 | CDR-H3 | K/C | GGTRVLGAIHGTDV |
| 145 | 1251-D06 | CDR-H3 | K/C | GGTLVRGAVYGLDV |
| 146 | 1251-D09 | CDR-H3 | K/C | GGTVERGAIYGTDV |
| 147 | 1251-E06 | CDR-H3 | K/C | GGMVGQGAMFGLDV |
| 148 | 1251-F06 | CDR-H3 | K/C | GGSLVTRGVYGLDV |
| 149 | 1251-F07 | CDR-H3 | K/C | GGTRIRGLRYGTDV |
| 150 | 1251-G02 | CDR-H3 | K/C | GGQLDHGAIYGLDV |

TABLE 7-continued

Sequences.

| SEQ ID NO | Molecule | Region | Scheme | Sequence |
|---|---|---|---|---|
| 151 | 1445-A03 | CDR-H3 | K/C | EHGLVYGQPMDY |
| 152 | 1445-B09 | CDR-H3 | K/C | GGYGYYYPPFDY |
| 153 | 1447-D11 | CDR-H3 | K/C | YETEWEVSLDY |
| 154 | 1447-E08 | CDR-H3 | K/C | FENQWEVTFDY |
| 155 | 1447-F11 | CDR-H3 | K/C | YESEWEVSLDY |
| 156 | 1447-G01 | CDR-H3 | K/C | YENEMEVSMDY |
| 157 | VH11-[19] | CDR-H3 | K/C | GGTLVRGAMYGTDV |
| 158 | VHS-[7] | CDR-H3 | K/C | GRYYGSGSYSSYFDY |
| 159 | VH6-[11] | CDR-H3 | K/C | GREITSQNIVILLDY |
| 160 | VH8-[15] | CDR-H3 | K/C | GREITSQNIVILLDY |
| 161 | 1337-A09 | CDR-L1 | K/C | RASQGIGSWLA |
| 162 | 1193-C08 | CDR-L1 | K/C | RASQSVSSNYLA |
| 163 | 1193-E06b | CDR-L1 | K/C | RASQSVSSSYLA |
| 164 | 1193-H04b | CDR-L1 | K/C | RASQSVSSSYLA |
| 165 | 1275-C10 | CDR-L1 | K/C | RASQGVSSWLA |
| 166 | 1275-D01 | CDR-L1 | K/C | RASQGIGRWLA |
| 167 | 1275-D10 | CDR-L1 | K/C | RASQGVFSWLA |
| 168 | 1275-G02 | CDR-L1 | K/C | RASQGLGSFLA |
| 169 | 1337-A04 | CDR-L1 | K/C | RASQDIGRWVA |
| 170 | 1337-A05 | CDR-L1 | K/C | RASQGIGRWVA |
| 171 | 1337-A06 | CDR-L1 | K/C | RASQDIGSWVA |
| 172 | 1337-A07 | CDR-L1 | K/C | RASQGISSWVA |
| 173 | 1337-A08 | CDR-L1 | K/C | RASQDIGSWVA |
| 174 | 1193-B06 | CDR-L1 | K/C | RAGQSVSSSYLA |
| 175 | 1337-A10 | CDR-L1 | K/C | RASQGISSWVA |
| 176 | 1447-D11 | CDR-L1 | K/C | RASQSVSSSYLA |
| 177 | 1447-E08 | CDR-L1 | K/C | RASQRVAGIDLS |
| 178 | 1447-F11 | CDR-L1 | K/C | RASQSVYRSYLA |
| 179 | 1447-G01 | CDR-L1 | K/C | RASQSVSSRELG |
| 180 | VL-5[23] & VL6-[26] | CDR-L1 | K/C | RASQGISSWLA |
| 181 | 1337-A09 | CDR-L2 | K/C | AADRLQS |
| 182 | 1193-C08 | CDR-L2 | K/C | GASSRAT |
| 183 | 1193-E06b | CDR-L2 | K/C | GASSRAT |
| 184 | 1193-H04b | CDR-L2 | K/C | GASSRAT |
| 185 | 1275-C10 | CDR-L2 | K/C | SARYLQS |
| 186 | 1275-D01 | CDR-L2 | K/C | GRSSLQS |
| 187 | 1275-D10 | CDR-L2 | K/C | NATQLQS |
| 188 | 1275-G02 | CDR-L2 | K/C | LGNLLQI |

TABLE 7-continued

Sequences.

| SEQ ID NO | Molecule | Region | Scheme | Sequence |
|---|---|---|---|---|
| 189 | 1337-A04 | CDR-L2 | K/C | GASSLQS |
| 190 | 1337-A05 | CDR-L2 | K/C | GADRLQS |
| 191 | 1337-A06 | CDR-L2 | K/C | GADRLQS |
| 192 | 1337-A07 | CDR-L2 | K/C | GASRLQS |
| 193 | 1337-A08 | CDR-L2 | K/C | ASDSLQS |
| 194 | 1193-B06 | CDR-L2 | K/C | GASSRAT |
| 195 | 1337-A10 | CDR-L2 | K/C | GSSRLQS |
| 196 | 1447-D11 | CDR-L2 | K/C | GASSRAT |
| 197 | 1447-E08 | CDR-L2 | K/C | GASSRAT |
| 198 | 1447-F11 | CDR-L2 | K/C | GASSRAT |
| 199 | 1447-G01 | CDR-L2 | K/C | GASSRAT |
| 200 | VL-5[23] & VL6-[26] | CDR-L2 | K/C | AASSLQS |
| 201 | 1337-A09 | CDR-L3 | K/C | QQYHTYPLT |
| 202 | 1193-C08 | CDR-L3 | K/C | QQHYTTPPT |
| 203 | 1193-E06b | CDR-L3 | K/C | QQHYTTPPT |
| 204 | 1193-H04b | CDR-L3 | K/C | QQHYTTPPT |
| 205 | 1275-C10 | CDR-L3 | K/C | QQYNLYPLT |
| 206 | 1275-D01 | CDR-L3 | K/C | QQYNIYPLT |
| 207 | 1275-D10 | CDR-L3 | K/C | QQYYYYPLT |
| 208 | 1275-G02 | CDR-L3 | K/C | QQYNAYPLT |
| 209 | 1337-A04 | CDR-L3 | K/C | QQYNTYPLT |
| 210 | 1337-A05 | CDR-L3 | K/C | QQYNSYPLT |
| 211 | 1337-A06 | CDR-L3 | K/C | QQYNSYPLT |
| 212 | 1337-A07 | CDR-L3 | K/C | QQYHTYPLT |
| 213 | 1337-A08 | CDR-L3 | K/C | QQYNSYPLT |
| 214 | 1193-B06 | CDR-L3 | K/C | QQHYTTPPT |
| 215 | 1337-A10 | CDR-L3 | K/C | QQYNTYPLT |
| 216 | 1447-D11 | CDR-L3 | K/C | QHNQPTPPT |
| 217 | 1447-E08 | CDR-L3 | K/C | QQHNTTPPT |
| 218 | 1447-F11 | CDR-L3 | K/C | QQHQTAPPT |
| 219 | 1447-G01 | CDR-L3 | K/C | QQQCSWPPT |
| 220 | VL-5[23] & VL6-[26] | CDR-L3 | K/C | QQYNSYPLT |
| 221 | 1193-B06 | scFv | | EVQLLESGGGLVQPGGSLRLSCAASGFTF TGNWMSWVRQAPGKGLEWVGIIYGTSGAT YYADSVKGRFTISRDNSKNTLYLQMNSLR AEDTAVYYCAKPSMSGSRGFDYWGQGTLV TVSSGGGGSGGGGSGGGGSEIVLTQSPGT LSLSPGERATLSCRAGQSVSSSYLAWYQQ KPGQAPRLLIYGASSRATGIPDRFSGSGS GTDFTLTISRLEPEDFAVYYCQQHYTTPP TFGQGTKVEIK |

TABLE 7-continued

Sequences.

| SEQ ID NO | Molecule | Region | Scheme | Sequence |
|---|---|---|---|---|
| 222 | 1193-C08 | scFv | | EVQLLESGGGLVQPGGSLRLSCAASGFTF NNNWMSWVRQAPGKGLEWVGIINGDDGYT YYADRVKGRFTIIRDNSKNTLYLQMNSLR AEDTAVYYCAKVALGRPRRFDYWGQGTLV TVSSGGGGSGGGGSGGGGSEIVLTQSPGT LSLTPGERATLSCRASQSVSSNYLAWYQQ KPGQAPRLLIYGASSRATGIPDRFSGSGS GTDFTLTISRLEPEDFAMYYCQHYTTPP TFGQGTKVEIK |
| 223 | 1193-E06b | scFv | | EVQLLESGGGLVQPGGSLRLSCAASGFTF NNTDMSWVRQAPGKGLEWVGIINGSGGAT NYADSVKGRFTISRDNSKNTLYLQMNSLR AEDTAVYYCAKFENEWEVSMDYWGQGTLV TVSSGGGGSGGGGSGGGGSEIVLTQSPGT LSLSPGERATLSCRASQSVSSSYLAWYQQ KPGQAPRLLIYGASSRATGIPDRFSGSGS GTDFTLTISRLEPEDFAVYYCQQHYTTPP TFGQGTKVEIK |
| 224 | 1193-H04b | scFv | | EVQLLESGGGLVQPGGSLRLSCAASGFTF TSSWMSWVRQAPGKGLEWVGIINGYNGIT YYADSVKGRFTISRDNSKNTLYLQMNSLR AEDTAVYYCAKPSAPGARRFDYWGQGTLV TVSSGGGGSGGGGSGGGGSEIVLTQSPGT LSLSPGEATLSCRASQSVSSSYLAWYQQR PGQAPRLLIYGASSRATGIPDRFSGSGSG TDFTLTISRLEPEDFAVYYCQQHYTTPPT FGQGTKVEIK |
| 225 | 1447-D11 | scFv | | EVQLLESGGGLVQPGGSLRLSCAASGFTF NNTDMSWVRQAPGKGLEWVGVINGSGGSS NYADSVKGRFTISRDNSKNTLYLQMNSLR AEDTAVYYCAKYETEWEVSLDYWGQGTLV TVSSGGGGSGGGGSGGGGSEIVLTQSPGT LSLSPGERATLSCRASQSVSSSYLAWYQQ KPGQAPRLLIYGASSRATGIPDRFSGSGS GTDFTLTISRLEPEDFAVYYCQHNQPTPP TFGQGTKVEIK |
| 226 | 1447-E08 | scFv | | EVQLLESGGGLVQPGGSLRLSCAASGFTF NDTDMSWVRQAPGKGLEWVGMINGAGGAS FYADSVRGRFTISRDNSKNTLYLQMNSLR AEDTAVYYCAKFENQWEVTFDYWGQGTLV TVSSGGGGSGGGGSGGGGSEIVLTQSPGT LSLSPGERATLSCRASQRVAGIDLSWYQQ KPGQAPRLLIYGASSRATGIPDRFSGSGS GTDFTLTISRLEPEDFAVYYCQQHNTTPP TFGQGTKVEIK |
| 227 | 1447-F11 | scFv | | EVQLLESGGGLVQTGGSLRLSCAASGFTF DNTDMSWVRQAPGKGLEWVGIINGSGGVT NYADSVRGRFTISRDNSKNTLYLQMNSLR AEDTAVYYCAKYESEWEVSLDYWGQGTLV TVSSGGGGSGGGGSGGGGSEIVLTQSPGT LSLSPGERATLSCRASQSVYRSYLAWYQQ KPGQAPRLLIYGASSRATGIPDRFSGSGS GTDFTLTISRLEPEDFAVYYCQQHQTAPP TFGQGTKVEIK |
| 228 | 1447-G01 | scFv | | EVQLLESGGGLVQPGGSLRLSCAASGFTF NTSDMSWVRQAPGKGLEWVGIINGSGGAT NYADSVKGRFTISRDNSKNTLYLQMNSLR AEDTAVYYCAKYENEMEVSMDYWGQGTLV TVSSGGGGSGGGGSGGGGSEIVLTQSPGT LSLSPGERATLSCRASQSVSSRELGWYQQ KPGQAPRLLIYGASSRATGIPDRFSGSGS GTDFTLTISRLEPEDFAVYYCQQQCSWPP TFGQGTKVEIK |
| 229 | 1251-B08-g_1337-A09-g scFv-Fc | scFv-Fc | | QVQLVESGGGVVQPGRSLRLSCAASGFNF SDYGMHWVRQAPGKGLEWVAVIWYDGSIS YYADSVKGRFTISRDNSKNTLYLQMNSLR AEDTAVYYCARGGTVEHGAVYGTDVWGQG TTVTVSSGGGGSGGGGSGGGGSDIQMTQS PSSVSASVGDRVTITCRASQGIGSWLAWY |

TABLE 7-continued

Sequences.

| SEQ ID NO | Molecule | Region | Scheme | Sequence |
|---|---|---|---|---|
| | | | | QQKPGKAPKLLIYAADRLQSGVPSRFSGS GSGTDFTLTISSLQPEDFATYYCQQYHTY PLTEGGGTKVEIKAAGSDQEPKSSDKTHT CPPCSAPELLGGSSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSRDELTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 230 | 1198-A01 | VH | | EVQLVESGGGLVQPGGSLRLSCAASGFTF SDYDMSWVRQAPGKGLEWVGFIAQDGSYK YYVDSVKGRFTISRDNAKNSLYLQMNSLR AEDTAVYYCARSKLFRAGQFDYWGQGTLV TVSS |
| 231 | 1198-B10 | VH | | EVQLVESGGGLVQPGGSLRLSCAASGENI SGSWIHWVRQAPGKGLEWVGYIYPDDGDT YYADSVKGRFTISADTSKNTAYLQMNSLR AEDTAVYYCAREGSHNLDKMDYWGQGTLV TVSS |
| 232 | 1198-D03 | VH | | EVQLVESGGGLVQPGGSLRLSCAASGENI NNYDIHWVRQAPGKGLEWVANIDPYNGAT YYADSVKGRFTISADTSKNTAYLQMNSLR AEDTAVYYCARVLWGFWAPFDYWGQGTLV TVSS |
| 233 | 1198-D04 | VH | | EVQLVESGGGLVQPGGSLRLSCAASGENI NNYDIHWVRQAPGKGLEWVANIDPYNGTT YYADSVKGRFTISADTSKNTAYLQMNSLR AEDTAVYYCARVPWGFWAPFDYWGQGTLV TVSS |
| 234 | 1251-A02 | VH | | QVQLVESGGGVVQPGRSLRLSCAASGFAF SDHGMHWVRQAPDKGLEWVAVIWYDGSHK IYADSVKGRFTISRDNSKNTLYLQMNSLR AEDTAVYYCARGGSLAGGAVYGTDVWGQG TTVTVSS |
| 235 | 1251-A03 | VH | | QVQLVESGGGVVQPGRSLRLSCAASGFAF SDHGMHWVRQAPDKGLEWVAVIWYDGSHK IYADSVKGRFTISRDNSKNTLYLQMNSLR AEDTAVYYCARGGSLAGGAVYGTDVWGQG TTVTVSS |
| 236 | 1251-808-g | VH | | QVQLVESGGGVVQPGRSLRLSCAASGFNF SDYGMHWVRQAPGKGLEWVAVIWYDGSIS YYADSVKGRFTISRDNSKNTLYLQMNSLR AEDTAVYYCARGGTVEHGAVYGTDVWGQG TTVTVSS |
| 237 | 1251-A06-g | VH | | QVQLVESGGGVVQPGRSLRLSCAASGFDF SSYGMHWVRQAPGKGLEWVAVIWDDGSDR YYADSVKGRFTISRDNSKNTLYLQMNSLR AEDTAVYYCARGGTRVLGAIHGTDVWGQG TTVTVSS |
| 238 | 1251-B08 | VH | | QVQLVESGGGVVQPGRSLRLSCAASGFNF SDYGMHWVRQAPDKGLEWVAVIWYDGSIS YYADSVKGRFTISRDNSKNTLYLQMNSLR AEDTAVYYCARGGTVEHGAVYGTDVWGQG ATVTVSS |
| 239 | 1251-A06 | VH | | QVQLVESGGGVVQPGRSLRLSCAASGFDF SSYGMHWVRQAPDKGLEWVAVIWDDGSDR YYADSVKGRFTISRDNSKNTLYLQMNSLR AEDTAVYYCARGGTRVLGAIHGTDVWGQG TTVTVSS |

TABLE 7-continued

Sequences.

| SEQ ID NO | Molecule | Region | Scheme | Sequence |
|---|---|---|---|---|
| 240 | 1251-B09 | VH | | QVQLVESGGGVVQPGRSLRLSCAASGFNFSDYGMHWVRQAPDKGLEWVAVTWYDGSREYYADSVKGRFTISRDNSKNTLYLQMNSLRAEDTAVYYCARGGTLVHGALYGNDVWGQGTTVTVSS |
| 241 | 1251-B10 | VH | | QVQLVESGGGVVQPGRSLRLSCAASGFNFSSHGMHWVRQAPDKGLEWVAVIWHDGSDKYYADSVKGRFTISRDNSKNTLYLQMNSLRAEDTAVYYCARGGTRVLGAVYGLDVWGQGTTVTVSS |
| 242 | 1251-C03 | VH | | QVQLVESGGGVVQPGRSLRLSCAASGFNFSSYGMHWVRQAPDKGLEWVAVIWYDGSIKNYADSVKGRFTISRDNSKNTLYLQMNSLRAEDTAVYYCARGGALMRGEFSGHDVWGQGTTVTVSS |
| 243 | 1251-D02 | VH | | QVQLVESGGGVVQPGRSLRLSCAASGFSFASHGMHWVRQAPDKGLEWVAVIWDDGSDRYYADSVKGRFTISRDNSKNTLYLQMNSLRAEDTAVYYCARGGTRVLGAIHGTDVWGQGTTVTVSS |
| 244 | 1251-D06 | VH | | QVQLVESGGGVVQPGRSLRLSCAASGFSFGSYGMHWVRQAPDKGLEWVAVVWYDGSKTIYADSVKGRFTISRDNSKNTLYLQMNSLRAEDTAVYYCARGGTLVRGAVYGLDVWGQGTTVTVSS |
| 245 | 1251-D09 | VH | | QVQLVESGGGVVQPGRSLRLSCAASGFSFSSYGMHWVRQAPDKGLEWVAVIWYDASIRKYAGSVKGRFTISRDNSKNTLYLQMNSLRAEDTAVYYCARGGTVERGAIYGTDVWGQGTTVTVSS |
| 246 | 1251-E06 | VH | | QVQLVESGGGVVQPGRSLRLSCAASGFTFDSYGMHWVRQAPDKGLEWVAVIWYDGSNKVYADSVKGRFTISRDNSKNTLYLQMNSLRAEDTAVYYCARGGMVGQGAMFGLDVWGQGTTVTVSS |
| 247 | 1251-F06 | VH | | QVQLVESGGGVVQPGRSLRLSCAASGFTFSSFGMHWVRQAPDKGLEWVAVIWDGSNEYYADSVKGRFTISRDNSKNTLYLQMNSLRAEDTAVYYCARGGSLVTRGVYGLDVWGQGTTVTVSS |
| 248 | 1251-F07 | VH | | QVQLVESGGGVVQPGRSLRLSCAASGFTFSSHGMHWVRQAPDKGLEWVAVIWDDGSNEVYADSVKGRFTISRDNSKNTLYLQMNSLRAEDTAVYYCARGGTRIRGLRYGTDVWGQGTTVTVSS |
| 249 | 1251-G02 | VH | | QVQLVESGGGVVQPGRSLRLSCAASGFTFSSYGMHWVRQAPDKGLEWVAVIWHDGSKDYYADSVKGRFTISRDNSKNTLYLQMNSLRAEDTAVYYCARGGQLDHGAIYGLDVWGQGTTVTVSS |
| 250 | 1445-A03 | VH | | EVQLVESGGGLVQPGGSLRLSCAASGENISGYYTHWVRQAPGKGLEWVAEISPTGGYTYYADSVKGRFTISADTSKNTAYLQMNSLRAEDTAVYYCAREHGLVYGQPMDYWGQGTLVTVSS |
| 251 | 1445-B09 | VH | | EVQLVESGGGLVQPGGSLRLSCAASGENITGTGIHWVRQAPGKGLEWVGIITPYNGTTNYADSVKGRFTISADTSKNTAYLQMNSLRAEDTAVYYCARGGYGYYYPPFDYWGQGTLVTVSS |

TABLE 7-continued

Sequences.

| SEQ ID NO | Molecule | Region | Scheme | Sequence |
|---|---|---|---|---|
| 252 | VH11-[19] | VH | | QVQLVESGGGVVQPGRSLRLSCAASGFTFSSYGMHWVRQAPDKGLEWVAVIWYDGSNKYYADSVKGRFTISRDNSKNTLYLQMNSLRAEDTAVYYCARGGTLVRGAMYGTDVWGQGTTVTVSS |
| 253 | VH5-[7] | VH | | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCASGRYYGSGSYSSYFDYWGQGTLVTVSS |
| 254 | VH6-[11] | VH | | QVQLVESGGGVVQPGRSLRLSCAASGFTFSSYAMHWVRQAPGKGLEWVAVISYDGSIKYYADSVKGRFTISRDNSKNTLYLQMNSLRVEDTAVFYCARGREITSQNIVILLDYWGQGTLVTVTS |
| 255 | VH8-[15] | VH | | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARGREITSQNIVILLDYWGQGTLVTVSS |
| 256 | 1337-A09-g | VL | | DIQMTQSPSSVSASVGDRVTITCRASQGIGSWLAWYQQKPGKAPKLLIYAADRLQSGVPSRFSGSGSGTDFTLTISSLQPEDFATYYCQQYHTYPLTFGGGTKVEIK |
| 257 | 1275-C10-g | VL | | DIQMTQSPSSVSASVGDRVTITCRASQGVSSWLAWYQQKPGKAPKLLIYSARYLQSGVPSRFSGSGSGTDFTLTISSLQPEDFATYYCQQYNLYPLTFGGGTKVEIK |
| 258 | 1275-D01 | VL | | DIQMTQSPSSLSASVGDRVTITCRASQGIGRWLAWYQQKPEKAPKSLIYGRSSLQSGVPSRFSGSGSGTDFTLTISSLQPEDFATYYCQQYNIYPLTFGGGTKVEIK |
| 259 | 1275-D10 | VL | | DIQMTQSPSSLSASVGDRVTITCRASQGVFSWLAWYQQKPEKAPKSLIYNATQLQSGVPSRFSGSGSGTDFTLTISSLQPEDFATYYCQQYYYPLTFGGGTKVEIK |
| 260 | 1275-G02 | VL | | DIQMTQSPSSLSASVGDRVTITCRASQGLGSFLAWYQQKPEKAPKSLIYLGNLLQIGVPSRFSGSGSGTDFTLTISSLQPEDFATYYCQQYNAYPLTFGGGTKVEIK |
| 261 | 1337-A04 | VL | | DIQMTQSPSSLSASVGDRVTITCRASQDIGRWVAWYQQKPEKAPKSLIYGASSLQSGVPSRFSGSGSGTDFTLTISSLQPEDFATYYCQQYNTYPLTFGGGTKVEIK |
| 262 | 1337-A05 | VL | | DIQMTQSPSSLSASVGDRVTITCRASQGIGRWVAWYQQKPEKAPKSLIYGADRLQSGVPSRFSGSGSGTDFTLTISSLQPEDFATYYCQQYNSYPLTFGGGTKVEIK |
| 263 | 1337-A06 | VL | | DIQMTQSPSSLSASVGDRVTITCRASQDIGSWVAWYQQKPEKAPKSLIYGADRLQSGVPSRFSGSGSGTDFTLTISSLQPEDFATYYCQQYNSYPLTFGGGTKVEIK |
| 264 | 1337-A07-g | VL | | DIQMTQSPSSVSASVGDRVTITCRASQGISSWVAWYQQKPGKAPKLLIYGASRLQSGVPSRFSGSGSGTDFTLTISSLQPEDFATYYCQQYHTYPLTFGGGTKVEIK |
| 265 | 1337-A07 | VL | | DIQMTQSPSSLSASVGDRVTITCRASQGISSWVAWYQQKPEKAPKSLIYGASRLQSGVPSRFSGSGSGTDFTLTISSLQPEDFATYYCQQYHTYPLTFGGGTKVEIK |

TABLE 7-continued

Sequences.

| SEQ ID NO | Molecule | Region | Scheme | Sequence |
|---|---|---|---|---|
| 266 | 1337-A08 | VL | | DIQMTQSPSSLSASVGDRVTITCRASQDIGSWVAWYQQKPEKAPKSLIYASDSLQSGVPSRFSGSGSGTDFTLTISSLQPEDFATYYCQQYNSYPLTFGGGTKVEIK |
| 267 | 1337-A09 | VL | | DIQMTQSPSSLSASVGDRVTITCRASQGIGSWLAWYQQKPEKAPKSLIYAADRLQSGVPSRFSGSGSGTDFTLTISSLQPEDFATYYCQQYHTYPLTFGGGTKVEIK |
| 268 | 1275-C10 | VL | | DIQMTQSPSSLSASVGDRVTITCRASQGVSSWLAWYQQKPEKAPKSLIYSARYLQSGVPSRFSGSGSGTDFTLTISSLQPEDFATYYCQQYNLYPLTFGGGTKVEIK |
| 269 | 1337-A10 | VL | | DIQMTQSPSSLSASVGDRVTITCRASQGISSWVAWYQQKPEKAPKSLIYGSSRLQSGVPSRFSGSGSGTDFTLTISSLQPEDFATYYCQQYNTYPLTFGGGTKVEIK |
| 270 | 1337-A10-g | VL | | DIQMTQSPSSVSASVGDRVTITCRASQGISSWVAWYQQKPGKAPKLLIYGSSRLQSGVPSRFSGSGSGTDFTLTISSLQPEDFATYYCQQYNTYPLTFGGGTKVEIK |
| 271 | VL5-[23] | VL | | DIQMTQSPSSLSASVGDRVTITCRASQGISSWLAWFQQKPEKAPKSLIYAASSLQSGVPSRFSGSGSGTDFTLTISSLQPEDFATYYCQQYNSYPLTFGGGTKVEIK |
| 272 | VL6-[26] | VL | | DIQMTQSPSSLSASVGDRVTITCRASQGISSWLAWYQQKPEKAPKSLIYAASSLQSGVPSRFSGSGSGTDFTLTISSLQPEDFATYYCQQYNSYPLTFGGGTKVEIK |
| 273 | 1193-B06 | VH | | EVQLLESGGGLVQPGGSLRLSCAASGFTFTGNWMSWVRQAPGKGLEWVGIIYGTSGATYYADSVKGRFTISRDNSKNTLYLQMNSLRAEDTAVYYCAKPSMSGSRGFDYWGQGTLVTVSS |
| 274 | 1193-C08 | VH | | EVQLLESGGGLVQPGGSLRLSCAASGFTFNNNWMSWVRQAPGKGLEWVGIINGDDGYTYYADRVKGRFTIIRDNSKNTLYLQMNSLRAEDTAVYYCAKVALGRPRRFDYWGQGTLVTVSS |
| 275 | 1193-E06b | VH | | EVQLLESGGGLVQPGGSLRLSCAASGFTFNNTDMSWVRQAPGKGLEWVGIINGSGGATNYADSVKGRFTISRDNSKNTLYLQMNSLRAEDTAVYYCAKFENEWEVSMDYWGQGTLVTVSS |
| 276 | 1193-H04b | VH | | EVQLLESGGGLVQPGGSLRLSCAASGFTFTSSWMSWVRQAPGKGLEWVGIINGYNGITYYADSVKGRFTISRDNSKNTLYLQMNSLRAEDTAVYYCAKPSAPGARRFDYWGQGTLVTVSS |
| 277 | 1447-D11 | VH | | EVQLLESGGGLVQPGGSLRLSCAASGFTFNNTDMSWVRQAPGKGLEWVGVINGSGGSSNYADSVKGRFTISRDNSKNTLYLQMNSLRAEDTAVYYCAKYETEWEVSLDYWGQGTLVTVSS |
| 278 | 1447-E08 | VH | | EVQLLESGGGLVQPGGSLRLSCAASGFTFNDTDMSWVRQAPGKGLEWVGMINGAGGASFYADSVRGRFTISRDNSKNTLYLQMNSLRAEDTAVYYCAKFENQWEVTFDYWGQGTLVTVSS |
| 279 | 1447-F11 | VH | | EVQLLESGGGLVQTGGSLRLSCAASGFTFDNTDMSWVRQAPGKGLEWVGIINGSGGVTNYADSVRGRFTISRDNSKNTLYLQMNSLRAEDTAVYYCAKYESEWEVSLDYWGQGTLVTVSS |

TABLE 7-continued

Sequences.

| SEQ ID NO | Molecule | Region | Scheme | Sequence |
|---|---|---|---|---|
| 280 | 1447-G01 | VH | | EVQLLESGGGLVQPGGSLRLSCAASGFTF NTSDMSWVRQAPGKGLEWVGIINGSGGAT NYADSVKGRFTISRDNSKNTLYLQMNSLR AEDTAVYYCAKYENEMEVSMDYWGQGTLV TVSS |
| 281 | 1193-B06 | VL | | EIVLTQSPGTLSLSPGERATLSCRAGQSV SSSYLAWYQQKPGQAPRLLIYGASSRATG IPDRFSGSGSGTDFTLTISRLEPEDFAVY YCQQHYTTPPTFGQGTKVEIK |
| 282 | 1193-C08 | VL | | EIVLTQSPGTLSLTPGERATLSCRASQSV SSNYLAWYQQKPGQAPRLLIYGASSRATG IPDRFSGSGSGTDFTLTISRLEPEDFAMY YCQQHYTTPPTFGQGTKVEIK |
| 283 | 1193-E06b | VL | | EIVLTQSPGTLSLSPGERATLSCRASQSV SSSYLAWYQQKPGQAPRLLIYGASSRATG IPDRFSGSGSGTDFTLTISRLEPEDFAVY YCQQHYTTPPTFGQGTKVEIK |
| 284 | 1193-H04b | VL | | EIVLTQSPGTLSLSPGEATLSCRASQSVS SSYLAWYQQRPGQAPRLLIYGASSRATGI PDRFSGSGSGTDFTLTISRLEPEDFAVYY CQQHYTTPPTFGQGTKVEIK |
| 285 | 1447-D11 | VL | | EIVLTQSPGTLSLSPGERATLSCRASQSV SSSYLAWYQQKPGQAPRLLIYGASSRATG IPDRFSGSGSGTDFTLTISRLEPEDFAVY YCQHNQPTPPTFGQGTKVEIK |
| 286 | 1447-E08 | VL | | EIVLTQSPGTLSLSPGERATLSCRASQRV AGIDLSWYQQKPGQAPRLLIYGASSRATG IPDRFSGSGSGTDFTLTISRLEPEDFAVY YCQQHNTTPPTFGQGTKVEIK |
| 287 | 1447-F11 | VL | | EIVLTQSPGTLSLSPGERATLSCRASQSV YRSYLAWYQQKPGQAPRLLIYGASSRATG IPDRFSGSGSGTDFTLTISRLEPEDFAVY YCQQHQTAPPTFGQGTKVEIK |
| 288 | 1447-G01 | VL | | EIVLTQSPGTLSLSPGERATLSCRASQSV SSRELGWYQQKPGQAPRLLIYGASSRATG IPDRFSGSGSGTDFTLTISRLEPEDFAVY YCQQQCSWPPTFGQGTKVEIK |
| 289 | IgG1 Fc from scFv-Fc | | | AAGSDQEPKSSDKTHTCPPCSAPELLGGS SVFLFPPKPKDTLMISRTPEVTCVVVDVS HEDPEVKFNWYVDGVEVHNAKTKPREEQY NSTYRVVSVLTVLHQDWLNGKEYKCKVSN KALPAPIEKTISKAKGQPREPQVYTLPPS RDELTKNQVSLTCLVKGFYPSDIAVEWES NGQPENNYKTTPPVLDSDGSFFLYSKLTV DKSRWQQGNVFSCSVMHEALHNHYTQKSL SLSPGK |
| 290 | Trastuzumab LC | LC | | DIQMTQSPSSLSASVGDRVTITCRASQDV NTAVAWYQQKPGKAPKLLIYSASFLYSGV PSRFSGSRSGTDFTLTISSLQPEDFATYY CQQHYTTPPTFGQGTKVEIK |
| 291 | 1251-A06-(wt) | HC | | MQVQLVESGGGVVQPGRSLRLSCAASGFD FSSYGMHWVRQAPDKGLEWVAVIWDDGSD RYYADSVKGRFTISRDNSKNTLYLQMNSL RAEDTAVYYCARGGTRVLGAIHGTDVWGQ GTTVTVSSASTKGPSVFPLAPSSKSTSGG TAALGCLVEDYFPEPATVSWNSGALTSGV HTFPAVLQSSGLYSLSSVVTVPSSSLGTQ TYICNVNHKPSNTKVDKKVEPKSCDKTHT CPPCPAPELLGGPSVFLFPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD |

TABLE 7-continued

Sequences.

| SEQ ID NO | Molecule | Region | Scheme | Sequence |
|---|---|---|---|---|
| | | | | SDGSFFLYSKLTVDKSRWQQGNVFSCSVM HEALHNHYTQKSLSLSPGK |
| 292 | 1251-A06-(g) | HC | | MQVQLVESGGGVVQPGRSLRLSCAASGFD FSSYGMHWVRQAPGKGLEWVAVIWDDGSD RYYADSVKGRFTISRDNSKNTLYLQMNSL RAEDTAVYYCARGGTRVLGAIHGTDVWGQ GTTVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 293 | 1251-B08-(wt) | HC | | MQVQLVESGGGVVQPGRSLRLSCAASGFN FSDYGMHWVRQAPDKGLEWVAVIWYDGSI SYYADSVKGRFTISRDNSKNTLYLQMNSL RAEDTAVYYCARGGTVEHGAVYGTDVWGQ GATVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 294 | 1251-B08-(g) | HC | | MQVQLVESGGGVVQPGRSLRLSCAASGFN FSDYGMHWVRQAPGKGLEWVAVIWYDGSI SYYADSVKGRFTISRDNSKNTLYLQMNSL RAEDTAVYYCARGGTVEHGAVYGTDVWGQ GTTVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 295 | 1275-C10-(wt) | LC | | MDIQMTQSPSSLSASVGDRVTITCRASQG VSSWLAWYQQKPEKAPKSLIYSARYLQSG VPSRFSGSGSGTDFTLTISSLQPEDFATY YCQQYNLYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 296 | 1275-C10-(g) | LC | | MDIQMTQSPSSVSASVGDRVTITCRASQG VSSWLAWYQQKPGKAPKLLIYSARYLQSG VPSRFSGSGSGTDFTLTISSLQPEDFATY YCQQYNLYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 297 | 1337-A07-(wt) | LC | | MDIQMTQSPSSLSASVGDRVTITCRASQG ISSWVAWYQQKPEKAPKSLIYGASRLQSG VPSRFSGSGSGTDFTLTISSLQPEDFATY YCQQYHTYPLTEGGGTKVEIKRTVAAPSV |

TABLE 7-continued

Sequences.

| SEQ ID NO | Molecule | Region | Scheme | Sequence |
|---|---|---|---|---|
| | | | | FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 298 | 1337-A07-(g) | LC | | MDIQMTQSPSSVSASVGDRVTITCRASQG ISSWVAWYQQKPGKAPKLLIYGASRLQSG VPSRFSGSGSGTDFTLTISSLQPEDFATY YCQQYHTYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 299 | 1337-A09-(wt) | LC | | MDIQMTQSPSSLSASVGDRVTITCRASQG IGSWLAWYQQKPEKAPKSLIYAADRLQSG VPSRFSGSGSGTDFTLTISSLQPEDFATY YCQQYHTYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 300 | 1337-A09-(g) | LC | | MDIQMTQSPSSVSASVGDRVTITCRASQG IGSWLAWYQQKPGKAPKLLIYAADRLQSG VPSRFSGSGSGTDFTLTISSLQPEDFATY YCQQYHTYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 301 | 1337-A10-(wt) | LC | | MDIQMTQSPSSLSASVGDRVTITCRASQG ISSWVAWYQQKPEKAPKSLIYGSSRLQSG VPSRFSGSGSGTDFTLTISSLQPEDFATY YCQQYNTYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 302 | 1337-A10-(g) | LC | | MDIQMTQSPSSVSASVGDRVTITCRASQG ISSWVAWYQQKPGKAPKLLIYGSSRLQSG VPSRFSGSGSGTDFTLTISSLQPEDFATY YCQQYNTYPLTEGGGTKVEIKRTVAAPSV FIFPPSDEQLKSGTASVVCLLNNEYPREA KVQWKVDNALQSGNSQESVTEQDSKDSTY SLSSTLTLSKADYEKHKVYACEVTHQGLS SPVTKSFNRGEC |
| 303 | C-term His Tag | Tag | | GGSHHHHHH |
| 304 | HC Constant | HC Constant | | ASTKGPSVFPLAPSSKSTSGGTAALGCLV KDYFPEPVTVSWNSGALTSGVHTFPAVLQ SSGLYSLSSVVTVPSSSLGTQTYICNVNH KPSNTKVDKKVEPKSCDKTHTCPPCPAPE LLGGPSVFLEPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVY TLPPSREEMTKNQVSLTCLVKGFYPSDIA VEWESNGQPENNYKTTPPVLDSDGSFFLY SKLTVDKSRWQQGNVFSCSVMHEALHNHY TQKSLSLSPGK |
| 305 | LC Constant | LC Constant | | RTVAAPSVFIFPPSDEQLKSGTASVVCLL NNFYPREAKVQWKVDNALQSGNSQESVTE QDSKDSTYSLSSTLTLSKADYEKHKVYAC EVTHQGLSSPVTKSFNRGEC |
| 306 | 1251-A03 | HC | | MQVQLVESGGGVVQPGRSLRLSCAASGFA FSDHGMHWVRQAPDKGLEWVAVIWYDGSH KIYADSVKGRFTISRDNSKNTLYLQMNSL RAEDTAVYYCARGGSLAGGAVYGTDVWGQ GTTVTVSSASTKGPSVFPLAPSSKSTSGG TAALGCLVKDYFPEPVTVSWNSGALTSGV |

TABLE 7-continued

Sequences.

| SEQ ID NO | Molecule | Region | Scheme | Sequence |
|---|---|---|---|---|
| | | | | HTFPAVLQSSGLYSLSSVVTVPSSSLGTR TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 307 | 1251-B09 | HC | | MQVQLVESGGGVVQPGRSLRLSCAASGFN FSDYGMHWVRQAPDKGLEWVAVTWYDGSR EYYADSVKGRFTISRDNSKNTLYLQMNSL RAEDTAVYYCARGGTLVHGALYGNDVWGQ GTTVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 308 | 1251-B10 | HC | | MQVQLVESGGGVVQPGRSLRLSCAASGFN FSSHGMHWVRQAPDKGLEWVAVIWHDGSD KYYADSVKGRFTISRDNSKNTLYLQMNSL RAEDTAVYYCARGGTRVLGAVYGLDVWGQ GTTVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSSTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 309 | Fc Constant | Fc Constant | | AAGSDQEPKSSDKTHTCPPCSAPELLGGS SVFLEPPKPKDTLMISRTPEVTCVVVDVS HEDPEVKFNWYVDGVEVHNAKTKPREEQY NSTYRVVSVLTVLHQDWLNGKEYKCKVSN KALPAPIEKTISKAKGQPREPQVYTLPPS RDELTKNQVSLTCLVKGFYPSDIAVEWES NGQPENNYKTTPPVLDSDGSFFLYSKLTV DKSRWQQGNVFSCSVMHEALHNHYTQKSL SLSPGK |
| 310 | 1251-A06 HC | HC | | MQVQLVESGGGVVQPGRSLRLSCAASGFD FSSYGMHWVRQAPDKGLEWVAVIWDDGSD RYYADSVKGRFTISRDNSKNTLYLQMNSL RAEDTAVYYCARGGTRVLGAIHGTDVWGQ GTTVTVSSASTKGPSVFPLAPSSKSTSGG TAALGCLVKDYFPEPVTVSWNSGALTSGV HTFPAVLQSSGLYSLSSVVTVPSSSLGTQ TYICNVNHKPSNTKVDKKVEPKSCDKTHT CPPCPAPELLGGPSVFLEPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVYTLPPSREEMTKNQVSLTCLVK GFYPSDIAVEWESNGQPENNYKTTPPVLD SDGSFFLYSKLTVDKSRWQQGNVFSCSVM HEALHNHYTQKSLSLSPGK |
| 311 | 1251-F07 HC | HC | | MQVQLVESGGGVVQPGRSLRLSCAASGFT FSSHGMHWVRQAPDKGLEWVAVIWDDGSN EVYADSVKGRFTISRDNSKNTLYLQMNSL RAEDTAVYYCARGGTRIRGLRYGTDVWGQ |

TABLE 7-continued

Sequences.

| SEQ ID NO | Molecule | Region | Scheme | Sequence |
|---|---|---|---|---|
| | | | | GTTVTVSSASTKGPSVFPLAPSSKSTSGG<br>TAALGCLVKDYFPEPVTVSWNSGALTSGV<br>HTFPAVLQSSGLYSLSSVVTVPSSSLGTQ<br>TYICNVNHKPSNTKVDKKVEPKSCDKTHT<br>CPPCPAPELLGGPSVFLEPPKPKDTLMIS<br>RTPEVTCVVVDVSHEDPEVKFNWYVDGVE<br>VHNAKTKPREEQYNSTYRVVSVLTVLHQD<br>WLNGKEYKCKVSNKALPAPIEKTISKAKG<br>QPREPQVYTLPPSREEMTKNQVSLTCLVK<br>GFYPSDIAVEWESNGQPENNYKTTPPVLD<br>SDGSFFLYSKLTVDKSRWQQGNVFSCSVM<br>HEALHNHYTQKSLSLSPGK |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:
1. An antibody conjugate comprising an antibody that specifically binds to CD74 linked site-specifically to at least one payload moiety, wherein the antibody comprises a non-natural amino acid at a site selected from the group consisting of HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, and HC-S70,
  wherein the payload moiety is covalently linked to the non-natural amino acid directly or via a linker,
  and wherein the antibody comprises three heavy chain CDRs and three light chain CDRs of a $V_H$-$V_L$ pair selected from the group consisting of:
    a. the $V_H$ region SEQ ID NO: 236 and the $V_L$ region SEQ ID NO: 256;
    b. the $V_H$ region SEQ ID NO: 236 and the $V_L$ region SEQ ID NO: 257;
    c. the $V_H$ region SEQ ID NO: 236 and the $V_L$ region SEQ ID NO: 265;
    d. the $V_H$ region SEQ ID NO: 236 and the $V_L$ region SEQ ID NO: 264;
    e. the $V_H$ region SEQ ID NO: 236 and the $V_L$ region SEQ ID NO: 267;
    f. the $V_H$ region SEQ ID NO: 236 and the $V_L$ region SEQ ID NO: 268;
    g. the $V_H$ region SEQ ID NO: 236 and the $V_L$ region SEQ ID NO: 269;
    h. the $V_H$ region SEQ ID NO: 236 and the $V_L$ region SEQ ID NO: 270;
    i. the $V_H$ region SEQ ID NO: 237 and the $V_L$ region SEQ ID NO: 256;
    j. the $V_H$ region SEQ ID NO: 237 and the $V_L$ region SEQ ID NO: 257;
    k. the $V_H$ region SEQ ID NO: 237 and the $V_L$ region SEQ ID NO: 265;
    l. the $V_H$ region SEQ ID NO: 237 and the $V_L$ region SEQ ID NO: 264;
    m. the $V_H$ region SEQ ID NO: 237 and the $V_L$ region SEQ ID NO: 267;
    n. the $V_H$ region SEQ ID NO: 237 and the $V_L$ region SEQ ID NO: 268;
    o. the $V_H$ region SEQ ID NO: 237 and the $V_L$ region SEQ ID NO: 269;
    p. the $V_H$ region SEQ ID NO: 237 and the $V_L$ region SEQ ID NO: 270;
    q. the $V_H$ region SEQ ID NO: 238 and the $V_L$ region SEQ ID NO: 256;
    r. the $V_H$ region SEQ ID NO: 238 and the $V_L$ region SEQ ID NO: 257;
    s. the $V_H$ region SEQ ID NO: 238 and the $V_L$ region SEQ ID NO: 265;
    t. the $V_H$ region SEQ ID NO: 238 and the $V_L$ region SEQ ID NO: 264;
    u. the $V_H$ region SEQ ID NO: 238 and the $V_L$ region SEQ ID NO: 267;
    v. the $V_H$ region SEQ ID NO: 238 and the $V_L$ region SEQ ID NO: 268;
    w. the $V_H$ region SEQ ID NO: 238 and the $V_L$ region SEQ ID NO: 269;
    x. the $V_H$ region SEQ ID NO: 238 and the $V_L$ region SEQ ID NO: 270;
    y. the $V_H$ region SEQ ID NO: 239 and the $V_L$ region SEQ ID NO: 256;
    z. the $V_H$ region SEQ ID NO: 239 and the $V_L$ region SEQ ID NO: 257;
    aa. the $V_H$ region SEQ ID NO: 239 and the $V_L$ region SEQ ID NO: 265;
    bb. the $V_H$ region SEQ ID NO: 239 and the $V_L$ region SEQ ID NO: 264;
    cc. the $V_H$ region SEQ ID NO: 239 and the $V_L$ region SEQ ID NO: 267;
    dd. the $V_H$ region SEQ ID NO: 239 and the $V_L$ region SEQ ID NO: 268;
    ee. the $V_H$ region SEQ ID NO: 239 and the $V_L$ region SEQ ID NO: 269;
    ff. the $V_H$ region SEQ ID NO: 239 and the $V_L$ region SEQ ID NO: 270;
    gg. the $V_H$ region SEQ ID NO: 235 and the $V_L$ region SEQ ID NO: 256;
    hh. the $V_H$ region SEQ ID NO: 240 and the $V_L$ region SEQ ID NO: 256; and
    ii. the $V_H$ region SEQ ID NO: 241 and the $V_L$ region SEQ ID NO: 256; and
  wherein the conjugate is according to any of formulas 101a-104b:

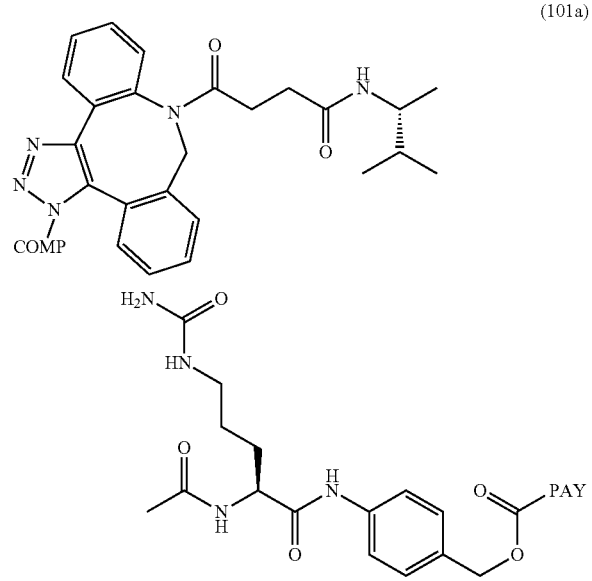

(101a)

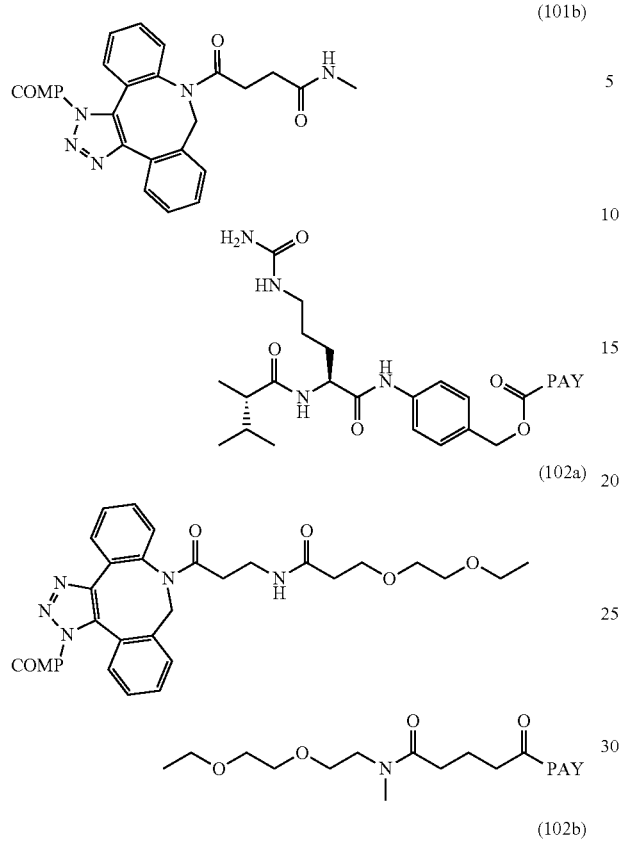
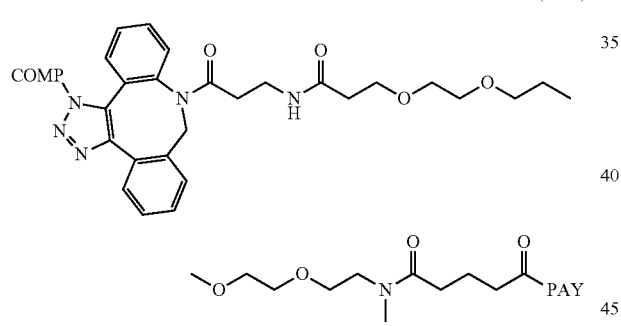
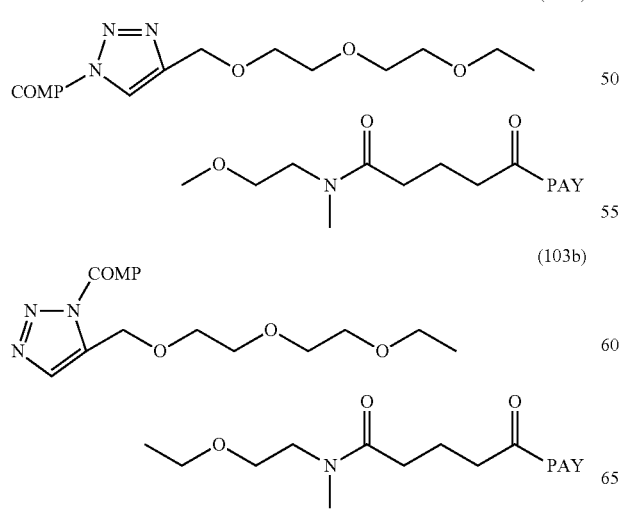

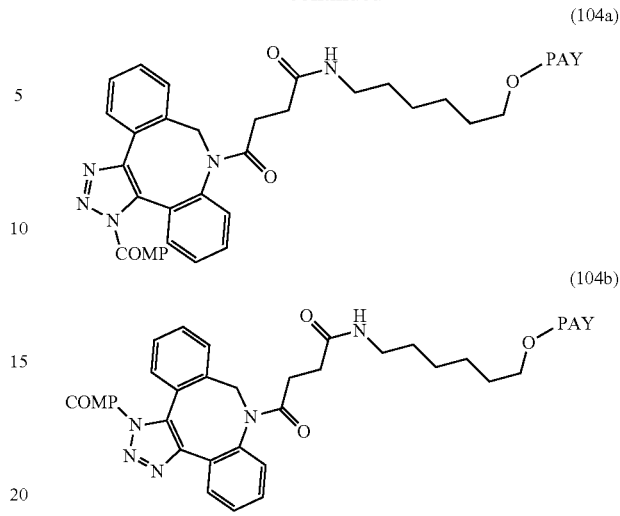

wherein COMP is the non-natural amino acid residue of the antibody and PAY is a payload moiety.

2. The antibody conjugate of claim 1, wherein the non-natural amino acid is selected from the group consisting of p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, L-Dopa, fluorinated phenylalanine, isopropyl-L-phenylalanine, p-azido-L-phenylalanine, p-azidomethyl-L-phenylalanine, compound 56:

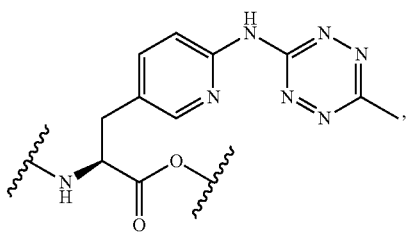 [SMILES: *N[C@@H](Cc1ccc(Nc2nnc(C)nn2)nc1)C(=O)O*]

compound 30:

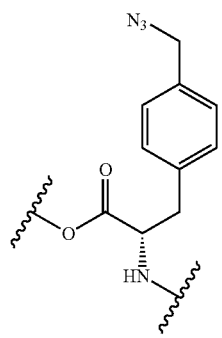 [SMILES: *N[C@@H](Cc1ccc(CN=[N+]=[N-])cc1)C(=O)O*]

p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and p-propargyloxy-phenylalanine.

3. The antibody conjugate of claim 2, wherein the antibody is linked to the payload moiety via a linker that is hydrolytically stable.

4. The antibody conjugate of claim 2, wherein the antibody is linked to the payload moiety via a linker that is cleavable.

5. The antibody conjugate of claim 2 wherein the non-natural amino acid residue is compound 30:

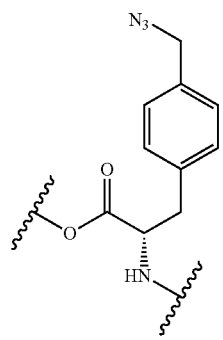 [SMILES: *N[C@@H](Cc1ccc(CN=[N+]=[N-])cc1)C(=O)O*]

or compound 56:

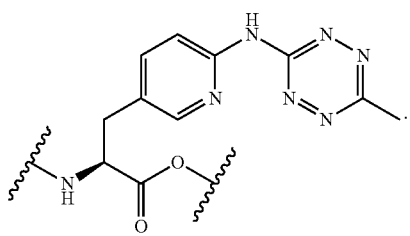 [SMILES: *N[C@@H](Cc1ccc(Nc2nnc(C)nn2)nc1)C(=O)O*]

6. The antibody conjugate of claim 1 wherein the payload moiety is selected from the group consisting of maytansines, hemiasterlins, amanitins, and auristatins.

7. The antibody conjugate of claim 6 wherein the payload moiety is selected from the group consisting of DM1, hemiasterlin, amanitin, MMAF, and MMAE.

8. The antibody conjugate of claim 1, wherein the antibody comprises:
  a. a $V_H$ comprising: a CDR-H1 comprising either one of SEQ ID NOs: 10 and 42; a CDR-H2 comprising either one of SEQ ID NOs: 74 and 106; and a CDR-H3 comprising SEQ ID NO: 138;
  b. $V_H$ comprising: a CDR-H1 comprising either one of SEQ ID NOs: 11 and 43; a CDR-H2 comprising either one of SEQ ID NOs: 75 and 107; and a CDR-H3 comprising SEQ ID NO: 139;
  c. a $V_H$ comprising: a CDR-H1 comprising either one of SEQ ID NOs: 1 and 33; a CDR-H2 comprising either one of SEQ ID NOs: 65 and 97; and a CDR-H3 comprising SEQ ID NO: 129;
  d. a $V_H$ comprising: a CDR-H1 comprising either one of SEQ ID NOs: 13 and 45; a CDR-H2 comprising either one of SEQ ID NOs: 77 and 109; and a CDR-H3 comprising SEQ ID NO: 141; or
  e. a $V_H$ comprising: a CDR-H1 comprising either one of SEQ ID NOs: 14 and 46; a CDR-H2 comprising either one of SEQ ID NOs: 78 and 110; and a CDR-H3 comprising SEQ ID NO: 142.

9. The antibody conjugate of claim 1, wherein the antibody comprises:
  a. a $V_L$ comprising: a CDR-L1 comprising SEQ ID NO: 165; a CDR-L2 comprising SEQ ID NO: 185; and a CDR-L3 comprising SEQ ID NO: 205;
  b. a $V_L$ comprising: a CDR-L1 comprising SEQ ID NO: 172; a CDR-L2 comprising SEQ ID NO: 192; and a CDR-L3 comprising SEQ ID NO: 212;
  c. a $V_L$ comprising: a CDR-L1 comprising SEQ ID NO: 161; a CDR-L2 comprising SEQ ID NO: 181; and a CDR-L3 comprising SEQ ID NO: 201; or
  d. a $V_L$ comprising: a CDR-L1 comprising SEQ ID NO: 175; a CDR-L2 comprising SEQ ID NO: 195; and a CDR-L3 comprising SEQ ID NO: 215.

10. The antibody conjugate of claim 1, wherein the antibody comprises:
  a. the $V_H$ region SEQ ID NO: 236, and the $V_L$ region SEQ ID NO: 256;
  b. the $V_H$ region SEQ ID NO: 236, and the $V_L$ region SEQ ID NO: 257;
  c. the $V_H$ region SEQ ID NO: 236, and the $V_L$ region SEQ ID NO: 265;
  d. the $V_H$ region SEQ ID NO: 236, and the $V_L$ region SEQ ID NO: 264;
  e. the $V_H$ region SEQ ID NO: 236, and the $V_L$ region SEQ ID NO: 267;
  f. the $V_H$ region SEQ ID NO: 236, and the $V_L$ region SEQ ID NO: 268;
  g. the $V_H$ region SEQ ID NO: 236, and the $V_L$ region SEQ ID NO: 269;
  h. the $V_H$ region SEQ ID NO: 236, and the $V_L$ region SEQ ID NO: 270;
  i. the $V_H$ region SEQ ID NO: 237, and the $V_L$ region SEQ ID NO: 256;
  j. the $V_H$ region SEQ ID NO: 237, and the $V_L$ region SEQ ID NO: 257;
  k. the $V_H$ region SEQ ID NO: 237, and the $V_L$ region SEQ ID NO: 265;
  l. the $V_H$ region SEQ ID NO: 237, and the $V_L$ region SEQ ID NO: 264;
  m. the $V_H$ region SEQ ID NO: 237, and the $V_L$ region SEQ ID NO: 267;
  n. the $V_H$ region SEQ ID NO: 237, and the $V_L$ region SEQ ID NO: 268;
  o. the $V_H$ region SEQ ID NO: 237, and the $V_L$ region SEQ ID NO: 269;
  p. the $V_H$ region SEQ ID NO: 237, and the $V_L$ region SEQ ID NO: 270
  q. the $V_H$ region SEQ ID NO: 238, and the $V_L$ region SEQ ID NO: 256;
  r. the $V_H$ region SEQ ID NO: 238, and the $V_L$ region SEQ ID NO: 257;
  s. the $V_H$ region SEQ ID NO: 238, and the $V_L$ region SEQ ID NO: 265;
  t. the $V_H$ region SEQ ID NO: 238, and the $V_L$ region SEQ ID NO: 264;
  u. the $V_H$ region SEQ ID NO: 238, and the $V_L$ region SEQ ID NO: 267;
  v. the $V_H$ region SEQ ID NO: 238, and the $V_L$ region SEQ ID NO: 268;
  w. the $V_H$ region SEQ ID NO: 238, and the $V_L$ region SEQ ID NO: 269;
  x. the $V_H$ region SEQ ID NO: 238, and the $V_L$ region SEQ ID NO: 270;
  y. the $V_H$ region SEQ ID NO: 239, and the $V_L$ region SEQ ID NO: 256;
  z. the $V_H$ region SEQ ID NO: 239, and the $V_L$ region SEQ ID NO: 257;
  aa. the $V_H$ region SEQ ID NO: 239, and the $V_L$ region SEQ ID NO: 265;
  bb. the $V_H$ region SEQ ID NO: 239, and the $V_L$ region SEQ ID NO: 264;

cc. the $V_H$ region SEQ ID NO: 239, and the $V_L$ region SEQ ID NO: 267;
dd. the $V_H$ region SEQ ID NO: 239, and the $V_L$ region SEQ ID NO: 268;
ee. the $V_H$ region SEQ ID NO: 239, and the $V_L$ region SEQ ID NO: 269;
ff. the $V_H$ region SEQ ID NO: 239, and the $V_L$ region SEQ ID NO: 270;
gg. the $V_H$ region SEQ ID NO: 235, and the $V_L$ region SEQ ID NO: 256;
hh. the $V_H$ region SEQ ID NO: 240, and the $V_L$ region SEQ ID NO: 256; or ii. the $V_H$ region SEQ ID NO: 241, and the $V_L$ region SEQ ID NO: 256.

11. The antibody conjugate of claim 10, wherein the antibody comprises a non-natural amino acid at site HC-F404 according to the EU numbering scheme of Kabat.

12. The antibody conjugate of claim 11, wherein the non-natural amino acid is para-azidomethylphenylalanine or p-azidomethyl-L-phenylalanine.

13. The antibody conjugate of claim 12, wherein the antibody conjugate has the formula of (102b):

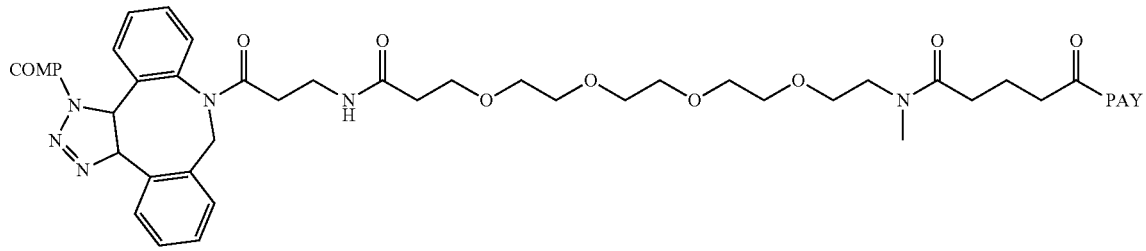

wherein COMP is the non-natural amino acid residue of the antibody and PAY is DM1.

14. The antibody conjugate of claim 13, wherein the antibody conjugate has the structure of Conjugate A:

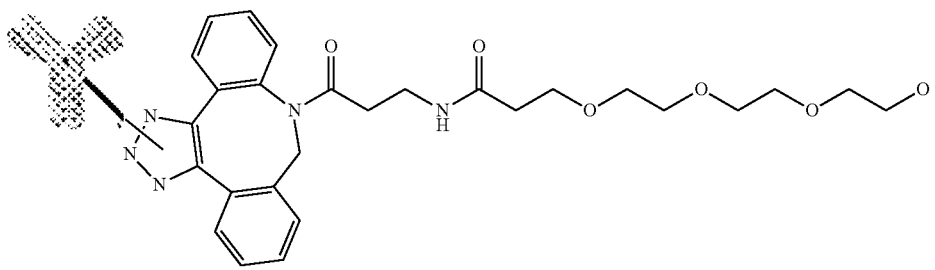

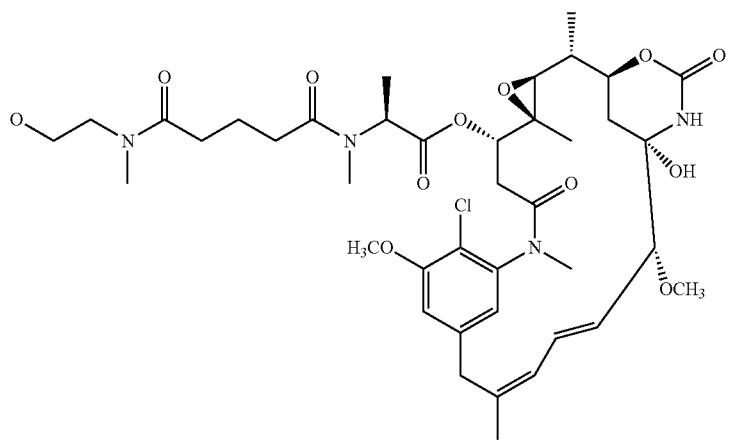

and the antibody comprises a $V_H$ region comprising SEQ ID NO: 236 and a $V_L$ region comprising SEQ ID NO: 256.

15. The antibody conjugate of claim 1, further comprising at least one constant region domain.

16. The antibody conjugate of claim 15, wherein the constant region comprises a sequence selected from SEQ ID NOs: 304-305.

17. The antibody conjugate of claim 1, wherein the antibody is a monoclonal antibody.

18. The antibody conjugate of claim 1, wherein the antibody is an IgA, an IgD, an IgE, an IgG, or an IgM.

19. The antibody conjugate of claim 1, wherein the antibody is humanized or human.

20. The antibody conjugate of claim 1, wherein the antibody is aglycosylated.

21. The antibody conjugate of claim 1, wherein the antibody is an antibody fragment.

22. The antibody conjugate of claim 21, wherein the antibody fragment is selected from an Fv fragment, a Fab fragment, a F(ab')$_2$ fragment, a Fab' fragment, an scFv (sFv) fragment, and an scFv-Fc fragment.

23. The antibody conjugate of claim 22, wherein the antibody is an scFv fragment that comprises a sequence selected from SEQ ID NOs: 221-228.

24. The antibody conjugate of claim 22, wherein the antibody is an scFv-Fc fragment that comprises SEQ ID NO: 229.

25. The antibody conjugate of claim 1, wherein the Tm2 of the antibody is at least 75° C., 75.5° C., 76° C., 76.5° C., 77° C., 77.5° C., 78° C., 78.5° C., or 79° C.

26. The antibody conjugate of claim 1, wherein the Tm1 of the antibody is less than 61° C. or less than 60° C.

27. A kit comprising an antibody conjugate of claim 1, and instructions for use of the antibody conjugate.

28. A pharmaceutical composition comprising the antibody conjugate of claim 1 and a pharmaceutically acceptable carrier.

29. A method of treating a disease or condition in a subject in need thereof, wherein the disease or condition is a CD-74 expressing cancer, comprising administering to the subject an effective amount of an antibody conjugate of claim 1.

* * * * *